(12) United States Patent
Su

(10) Patent No.: US 9,404,081 B2
(45) Date of Patent: Aug. 2, 2016

(54) PYRUVATE KINASE ACTIVATORS FOR USE IN THERAPY

(75) Inventor: Shin-San Michael Su, Newton, MA (US)

(73) Assignee: AGIOS PHARMACEUTICALS, INC., Cambridge, MA (US)

( * ) Notice: Subject to any disclaimer, the term of this patent is extended or adjusted under 35 U.S.C. 154(b) by 90 days.

(21) Appl. No.: 14/115,292

(22) PCT Filed: May 3, 2012

(86) PCT No.: PCT/US2012/036413
§ 371 (c)(1),
(2), (4) Date: Jan. 24, 2014

(87) PCT Pub. No.: WO2012/151452
PCT Pub. Date: Nov. 8, 2012

(65) Prior Publication Data
US 2014/0155408 A1  Jun. 5, 2014

Related U.S. Application Data

(60) Provisional application No. 61/482,166, filed on May 3, 2011.

(51) Int. Cl.
| | | |
|---|---|---|
| *A61K 31/535* | (2006.01) | |
| *C07D 471/04* | (2006.01) | |
| *C12N 5/078* | (2010.01) | |
| *A61K 31/4965* | (2006.01) | |
| *A61K 31/497* | (2006.01) | |
| *C07D 215/36* | (2006.01) | |
| *C07D 401/12* | (2006.01) | |
| *C07D 405/12* | (2006.01) | |
| *C07D 413/12* | (2006.01) | |
| *C07D 417/12* | (2006.01) | |
| *C07D 451/02* | (2006.01) | |

(52) U.S. Cl.
CPC ............ *C12N 5/0641* (2013.01); *A61K 31/497* (2013.01); *A61K 31/4965* (2013.01); *C07D 215/36* (2013.01); *C07D 401/12* (2013.01); *C07D 405/12* (2013.01); *C07D 413/12* (2013.01); *C07D 417/12* (2013.01); *C07D 451/02* (2013.01)

(58) Field of Classification Search
CPC ............................ A61K 31/535; C07D 471/04
USPC ......................... 514/234.2; 544/127
See application file for complete search history.

(56) References Cited

U.S. PATENT DOCUMENTS

| | | | |
|---|---|---|---|
| 5,834,485 A | 11/1998 | Dyke et al. | |
| 5,965,559 A | 10/1999 | Faull et al. | |
| 5,965,569 A | 10/1999 | Camps Garcia et al. | |
| 6,313,127 B1 | 11/2001 | Waterson et al. | |
| 8,785,450 B2 | 7/2014 | Salituro et al. | |
| 8,889,667 B2 | 11/2014 | Salituro et al. | |
| 2003/0095958 A1 | 5/2003 | Bhisetti et al. | |
| 2003/0207882 A1 | 11/2003 | Stocker et al. | |
| 2008/0214495 A1 | 9/2008 | Alstermark et al. | |
| 2010/0331307 A1 | 12/2010 | Salituro et al. | |

FOREIGN PATENT DOCUMENTS

| | | |
|---|---|---|
| CN | 101296909 A | 10/2008 |
| WO | 9630343 A1 | 10/1996 |
| WO | 97/28128 A1 | 8/1997 |
| WO | 97/28129 A1 | 8/1997 |
| WO | 9744322 A1 | 11/1997 |
| WO | 9948490 A1 | 9/1999 |
| WO | 0119788 A2 | 3/2001 |
| WO | 0119798 A2 | 3/2001 |
| WO | 0164642 A2 | 9/2001 |
| WO | 0164643 A2 | 9/2001 |
| WO | 02100822 A1 | 12/2002 |
| WO | 2004089470 A2 | 10/2004 |
| WO | 2005120474 A2 | 12/2005 |
| WO | 2006034341 A2 | 3/2006 |
| WO | 2006-038594 A1 | 4/2006 |
| WO | 2007003934 A2 | 1/2007 |
| WO | 2007023186 A1 | 3/2007 |
| WO | 2008/050168 A1 | 5/2008 |
| WO | 2008052190 A2 | 5/2008 |
| WO | 2008073670 A2 | 6/2008 |
| WO | 2010105243 | 9/2010 |
| WO | 2010/129596 | 11/2010 |
| WO | 2010130638 A1 | 11/2010 |
| WO | 2011002817 A1 | 1/2011 |
| WO | 2011032169 A2 | 3/2011 |
| WO | 2011047432 A1 | 4/2011 |
| WO | 2011109441 A1 | 9/2011 |
| WO | 2012069503 A1 | 5/2012 |
| WO | 2012/092442 A1 | 7/2012 |
| WO | 2012151452 | 11/2012 |

OTHER PUBLICATIONS

Beutler et al. "Elevated Pyruvate Kinase Activity in Patients with Hemolytic Anemia Due to Red Cell Pyruvate Kinase 'Deficiency'" The American Journal of Medicine (1987) vol. 83, pp. 899-904.
International Preliminary Report for related application No. PCT/US2011/067752 dated Apr. 11, 2013.
International Search Report and Written Opinion for International Application No. PCT/US2012/036412 dated Jul. 6, 2012.
International Search Report and Written Opinion for International Application No. PCT/US2012/036413 dated Jul. 6, 2012.
International Search Report dated Mar. 5, 2012 for related international application No. PCT/US2011/067752.
International Search Report for PCT/US10/040486 dated Sep. 1, 2010.

(Continued)

*Primary Examiner* — Raymond Henley, III

(57) ABSTRACT

Described herein are methods for using compounds that activate pyruvate kinase.

25 Claims, No Drawings

(56) References Cited

OTHER PUBLICATIONS

Pan et al. "Research Status of Pyruvate Deficiency" Chinese Journal of Hematology (1999) vol. 20, No. 4, pp. 223.

Petz et al. "Increased IgG Molecules Bound to the Surface of Red Blood Cells of Patients With Sickle Cell Anemia" Blood (1984) vol. 64, No. 1, pp. 301-304.

Supplementary Search Report for EP10794668 Mailed Oct. 18, 2012.

Charache et al. "Effect of 2,3-Diphosphoglycerate on Oxygen Affinity of Blood in Sickle Cell Anemia" Journal of Clinical Investigation (1970) vol. 49, pp. 806-812.

International Preliminary Report on Patentability for PCT/US2010/040486 dated Jan. 12, 2012.

STN Tokyo, Registry No. 1001833-18-6, Entered STN on Feb. 6, 2008, Chemical Abstracts Index Name "1,4-Benzodioxin-6-sulfonamide, 2,3-dihydro-N-[4- [(4-methyl-l-piperazinyl)carbonyl]phenyl]-".

STN Tokyo, Registry No. 1030142-35-8, Entered STN on Jun. 24, 2008, Chemical Abstracts Index Name "1,4-Benzodioxin-6-sulfonamide, 2,3-dihydro-N-[4-[[4-[(5-methyl-3-isoxazolyl)methyl]-l-piperazinyl]carbonyl]phenyl]-".

STN Tokyo, Registry No. 1031531-78-8, Entered STN on Jun. 29, 2008 Chemical Abstracts Index Name "1,4-Benzodioxin-6-sulfonamide, N-4[4-[(4-acetyl-1-piperazinyl)carbonyl]phenyl]-2,3-dihydro-".

STN Tokyo, Registry No. 1057928-35-4, Entered STN on Oct. 7, 2008, Chemical Abstracts Index Name "1,4-Benzodioxin-6-sulfonamide, 2,3-dihydro-N-[4-[[4-(2-pyridinyl)-l-piperazinyl]carbonyl]phenyl]-".

STN Tokyo, Registry No. 1240875-006, entered STN on Sep. 14, 2010, Chemical Abstracts Index Name "1,4-Benzodioxin-6-sulfonamide, 2,3-dihydro-N-[4-[[4-(2-pyrimidinyl)-1-piperazinyl]carbonyl]phenyl]-".

STN Tokyo, Registry No. 748791-86-8, Entered STN on Sep. 21, 2004, Chemical Abstracts Index Name "1,4-Benzodioxin-6-sulfonamide, N-[4-[[4-(2-furanylcarbonyl)-1-piperazinyl]carbonyl]phenyl]-2,3-dihydro-".

STN Tokyo, Registry No. 878469-24-0, Entered STN on Mar. 29, 2006, Chemical Abstracts Index Name "1,4-Benzodioxin-6-sulfonamide, 2,3-dihydro-N-[[4-(2-pyrimidinyl)-1-piperazinyl]carbonyl]phenyl]-".

STN Tokyo, Registry No. 878474-39-6, Entered STN on Mar. 29, 2006, Chemical Abstracts Index Name "1,4-Benzodioxin-6-sulfonamide, 2,3-dihydro-N-[4[(4-phenyl-1-piperazinyl)carbonyl]phenyl]-".

STN Tokyo, Registry No. 878590-33-1, Entered STN on Mar. 30, 2006, Chemical Abstracts Index Name "1,4-Benzodioxin-6-sulfonamide, 2,3-dihydro-N-[4-{{4-(tetrahydro-2-furanyl)methyl]-1-piperazinyl]carbonyl]phenyl]-".

STN Tokyo, Registry No. 878943-66-9 Entered STN on Apr. 2, 2006, Chemical Abstracts Index Name "1,4-Benzodioxin-6-sulfonamide, 3,4-dihydro-N-[[4-(2-pyrimidinyl1)-1-piperazinyl)carbonyl]phenyl]-".

STN Tokyo, Registry No. 878956-06-0, Entered STN on Apr. 2, 2006, Chemical Abstracts Index Name "1,4-Benzodioxin-6-sulfonamide, N-[4-[[4-(cyclopropylcarbonyl)-1-piperazinyl]carbonyl]phenyl]-2,3-dihydro-".

STN Tokyo, Registry No. 9200679-46-5, Entered STN on Feb. 13, 2007, Chemical Abstracts Index Name "1,4-Benzodioxin-6-sulfonamide, 2,3-dihydro-N-[4-[[4-(4-pyridinyl)-1-piperazinyl]carbonyl]phenyl]-".

STN Tokyo, Registry No. 920822-52-2, Entered STN on Feb. 14, 2007, Chemical Abstracts Index Name "1,4-Benzodioxin-6-sulfonamide, N-[4-[[4-(4-fluoropheyl)-1-piperazinyl]carbonyl]phenyl]-2,3dihydro-".

STN Tokyo, Registry No. 920824-56-2, Entered STN on Feb. 14, 2007, Chemical Abstracts Index Name "1,4-Benzodioxin-6-sulfonamide, 2,3-dihydro-N-[4-[[4-(3-thienylmethyl)-1-piperazinyl]carbonyl]phenyl]-".

STN Tokyo, Registry No. 920847-34-3, Entered STN on Feb. 14, 2007, Chemical Abstracts Index Name "1,4-Benzodioxin-6-sulfonamide, 2,3-dihydro-N-[4-[[4-(2-methylphenyl)-1-piperazinyl]carbonyl]phenyl]-".

STN Tokyo, Registry No. 920875-39-4, Entered STN on Feb. 14, 2007, Chemical Abstracts Index Name "1,4-Benzodioxin-6-sulfonamide, 2,3-dihydro-N-[4-[[4-(2-hydroxyphenyl)-1-piperazinyl]carbonyl]phenyl]-".

STN Tokyo, Registry No. 920902-88-1, Entered STN on Feb. 14, 2007, Chemical Abstracts Index Name "1,4-Benzodioxin-6-sulfonamide, 2,3-dihydro-N-[4-[[4-(2-thienylmethyl)-l-piperazinyl]carbonyl]phenyl]-".

STN Tokyo, Registry No. 920921-09-1 Entered STN on Feb. 14, 2007, Chemical Abstracts Index Name "2H-1, 5-Benzodioxepin-7-sulfonamide, 3,4-dihydro-N-[4-[[4-(2pyridinyl)-1-piperazinyl]carbonyl]phenyl]-".

STN Tokyo, Registry No. 920924-42-1, Entered STN on Feb. 14, 2007, Chemical Abstracts Index Name "1,4-Benzodioxin-6-sulfonamide, 2,3-dihydro-N-[4-[[4-(2-pyridinylmethyl)-1-piperazinyl]carbonyl]phenyl]-".

STN Tokyo, Registry No. 941220-77-5, Entered STN on Jul. 4, 2007, Chemical Abstracts Index Name "2H-1, 5-Benzodioxepin-7-sulfonamide, 3,4-dihydro-N-[4-[(4-methyl-l-piperazinyl)carbonyl]phenyl]-".

US 9,404,081 B2

PYRUVATE KINASE ACTIVATORS FOR USE IN THERAPY

CLAIM OF PRIORITY

This application is a national stage application under 35 U.S.C. §371 of International Application No. PCT/US2012/036413, filed May 3, 2012, and published as International Publication No. WO 2012/151452 on Nov. 8, 2012, which claims priority from U.S. Ser. No. 61/482,166, filed May 3, 2011. The contents of each of these applications is incorporated herein by reference in its entirety.

BACKGROUND

Pyruvate kinase deficiency (PKD) is one of the most common enzyme defects in erythrocytes in human due to autosomal recessive mutations of the PKLR gene (Zanella, A., et al., *Br J Haematol* 2005, 130 (1), 11-25). It is also the most frequent enzyme mutation in the central glycolytic pathway and only second to glucose-6 phosphate dehydrogenase (G6PD) deficiency (Kedar, P., et al., *Clin Genet* 2009, 75 (2), 157-62) of the hexose monophosphate shunt.

Human erythrocytes are unique in that they anucleate when mature. Immature erythrocytes have nuclei but during early erythropoiesis prior to becoming circulating reticulocytes they extrude nuclei as well as other organelles such as mitochondria, endoplasmic reticulum, and golgi aparatus, in order to make room for oxygen-carrying hemoglobin. As a result of lacking mitochondria, mature red blood cells do not utilize any of the oxygen they transport to economically synthesize adenosine triphosphate (ATP) as other normal differentiated cells do. Instead, red blood cells depend entirely on anaerobic glycolysis to cycle nicotinamide adenine dinucleotide ($NAD^+$) and to make ATP, an essential energy source largely used to drive ATPase-dependent $K^+/Na^+$ and $Ca^{2+}$ pumps, in order to maintain cell membrane integrity and pliability as they navigate through blood vessels. In PKD disorder, two major distinctive metabolic abnormalities are ATP depletion and concomitant increase of 2,3-diphosphoglycerate consistent with accumulation of upper glycolytic intermediates. Moreover, one of the consequences of decreased ATP and pyruvate level is lowered lactate level leading to inability to regenerate $NAD^+$ through lactate dehydrogenase for further use in glycolysis. The lack of ATP disturbs the cation gradient across the red cell membrane, causing the loss of potassium and water, which causes cell dehydration, contraction, and crenation, and leads to premature destruction and diminished lifetime of the red blood cells (RBCs). Such defective RBCs are destroyed in the spleen, and excessive hemolysis rate in the spleen leads to the manifestation of hemolytic anemia. The exact mechanism by which PKD sequesters newly matured RBCs in the spleen to effectively shorten overall half-lives of circulating RBCs is not yet clear, but recent studies suggest that metabolic dysregulation affects not only cell survival but also the maturation process resulting in ineffective erythropoiesis (Aizawa, S. et al., *Exp Hematol* 2005, 33 (11), 1292-8).

Pyruvate kinase catalyzes the transfer of a phosphoryl group from phosphoenolpyruvate (PEP) to ADP, yielding one molecule of pyruvate and one molecule of ATP. The enzyme has an absolute requirement for $Mg^{2+}$ and $K^+$ cations to drive catalysis. PK functions as the last critical step in glycolysis because it is an essentially irreversible reaction under physiological conditions. In addition to its role of synthesizing one of the two ATP molecules from the metabolism of glucose to pyruvate, pyruvate kinase is also an important cellular metabolism regulator. It controls the carbon flux in lower-glycolysis to provide key metabolite intermediates to feed biosynthetic processes, such as pentose-phosphate pathway among others, in maintaining healthy cellular metabolism. Because of these critical functions, pyruvate kinase is tightly controlled at both gene expression and enzymatic allostere levels. In mammals, fully activated pyruvate kinase exists as a tetrameric enzyme. Four different isozymes (M1, M2, L and R) are expressed from two separate genes. Erythrocyte-specific isozyme PKR is expressed from the PKLR gene ("L gene") located on chromosome 1q21. This same gene also encodes the PKL isozyme, which is predominately expressed in the liver. PKLR consists of 12 exons with exon 1 is erythroid-specific whereas exon 2 is liver-specific. The two other mammalian isozymes PKM1 and PKM2 are produced from the PKM gene ("M gene") by alternative splicing events controlled by hnRNP proteins. The PKM2 isozyme is expressed in fetal tissues and in adult proliferating cells such as cancer cells. Both PKR and PKM2 are in fact expressed in proerythroblasts. However, upon erythroid differentiation and maturation, PKM2 gradually is decreased in expression and progressively replaced by PKR in mature erythrocytes.

Clinically, hereditary PKR deficiency disorder manifests as non-spherocytic hemolytic anemia. The clinical severity of this disorder range from no observable symptoms in fully-compensated hemolysis to potentially fatal severe anemia requiring chronic transfusions and/or splenectomy at early development or during physiological stress or serious infections. Most affected individuals who are asymptomatic, paradoxically due to enhanced oxygen-transfer capacity, do not require any treatment. However, for some of the most severe cases, while extremely rare population-wise with estimated prevalence of 51 per million (Beutler, E. *Blood* 2000, 95 (11), 3585-8), there is no disease-modifying treatment available for these patients other than palliative care (Tavazzi, D. et al., *Pediatr Ann* 2008, 37 (5), 303-10). These hereditary non-spherocytic hemolytic anemia (HNSHA) patients present a clear unmet medical need.

Heterogenous genetic mutations in PKR lead to dysregulation of its catalytic activity. Since the initial cloning of PKR and report of a single point mutation $Thr^{384}$>Met associated with a HNSHA patient (Kanno, H. et al., *Proc Natl Acad Sci USA* 1991, 88 (18), 8218-21), there are now nearly 200 different reported mutations associated with this disease reported worldwide (Zanella, A. et al., *Br J Haematol* 2005, 130 (1), 11-25; Kedar, P., et al., *Clin Genet.* 2009, 75 (2), 157-62; Fermo, E. et al., *Br J Haematol* 2005, 129 (6), 839-46; Pissard, S. et al., *Br J Haematol* 2006, 133 (6), 683-9). Although these mutations represent wide range genetic lesions that include deletional and transcriptional or translational abnormalities, by far the most common type is missense mutation in the coding region that one way or another affects conserved residues within domains that are structurally important for optimal catalytic function of PKR. The pattern of mutation prevalence seems to be unevenly distributed toward specific ethnic backgrounds. For instance, the most frequent codon substitutions reported for North American and European patients appear to be $Arg^{486}$>Trp and $Arg^{510}$>Gln, while mutations $Arg^{479}$>His, $Arg^{490}$>Trp and $Asp^{331}$>Gly were more frequently found in Asian patients (Kedar, P., et al., *Clin Genet* 2009, 75 (2), 157-62).

SUMMARY

The present invention provides a method for increasing lifetime of the red blood cells (RBCs) in need thereof comprising contacting blood with an effective amount of (1) a compound disclosed herein or a pharmaceutically acceptable salt thereof; (2) a composition comprising a compound disclosed herein or a salt thereof and a carrier; or (3) a pharmaceutical composition comprising a compound disclosed herein or a pharmaceutically acceptable salt thereof, and a pharmaceutically acceptable carrier.

The present invention further provides a method for regulating 2,3-diphosphoglycerate levels in blood in need thereof comprising contacting blood with an effective amount of (1) a compound disclosed herein or a pharmaceutically acceptable salt thereof; (2) a composition comprising a compound disclosed herein or a salt thereof and a carrier; or (3) a pharmaceutical composition comprising a compound disclosed herein or a pharmaceutically acceptable salt thereof, and a pharmaceutically acceptable carrier.

The present invention also provides a method for treating hereditary non-spherocytic hemolytic anemia comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating sickle cell anemia comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating hemolytic anemia (e.g., chronic hemolytic anemia caused by phosphoglycerate kinase deficiency, Blood Cells Mol Dis, 2011; 46(3):206) comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating thalassemia (e.g., beta-thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), or anemia of chronic diseases comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating diseases or conditions that are associated with increased 2,3-diphosphoglycerate levels (e.g., liver diseases (Am J Gastroenterol, 1987; 82(12):1283) and Parkinson's (J. Neurol, Neurosurg, and Psychiatry 1976, 39:952) comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

Compounds and compositions described herein are activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the emzyme. Examples of such mutations are described in Valentini et al, JBC 2002. Some examples of the mutants that are activated by the compounds described herein include G332S, G364D, T384M, G37E, R479H, R479K, R486W, R532W, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Example 1. Compounds described herein are also activators of wild type PKR.

In an embodiment, to increase the lifetime of the red blood cells, a compound, composition or pharmaceutical composition described herein is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the rate of release of 2,3-DPG from the blood. A decrease in the level of 2,3-DPG concentration induces a leftward shift of the oxygen-hemoglobin dissociation curve and shifts the allosteric equilibribrium to the R, or oxygenated state, thus producing a therapeutic inhibition of the intracellular polymerization that underlies sickling by increasing oxygen affinity due to the 2,3-DPG depletion, thereby stabilizing the more soluble oxy-hemoglobin. Accordingly, in one embodiment, compounds and pharmaceutical compositions described herein are useful as antisickling agents. In another embodiment, to regulate 2,3-diphosphoglycerate, a compound, composition or pharmaceutical composition described herein is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes).

Described herein are compounds of Formula I that activate pyruvate kinase R (PKR), wild type and/or mutant enzymes (such as those described herein), and pharmaceutically acceptable salts, solvates, and hydrates thereof:

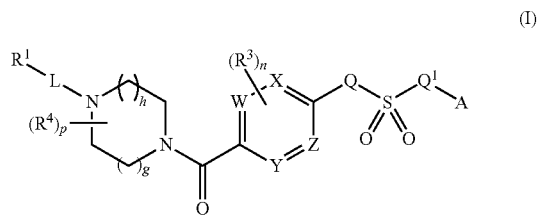

(I)

wherein:

W, X, Y and Z are each independently selected from CH or N;

Q and $Q^1$ are independently selected from a bond or $NR^b$;

A is optionally substituted bicyclic aryl or optionally substituted bicyclic heteroaryl;

L is a bond, —C(O)—, —$(CR^cR^c)_m$—, —C(O)—, —$(CR^cR^c)_m$—OC(O)—, —$(CR^cR^c)_m$—C(O)—, —$NR^bC(S)$—, or —$NR^bC(O)$— (wherein the point of the attachment to $R^1$ is on the left-hand side);

$R^1$ is selected from alkyl, carbocycle, aryl, heteroaryl, and heterocyclyl; each of which is substituted with 0-5 occurrences of $R^d$;

each $R^3$ is independently selected from halo, haloalkyl, alkyl, hydroxyl and —$OR^a$, or two adjacent $R^3$ taken together with the carbon atoms to which they are attached form an optionally substituted heterocyclyl;

each $R^4$ is independently selected from halo, haloalkyl, alkyl, hydroxyl, =O, —$OR^a$, and phenyl, or two $R^4$ taken together with the carbon atoms to which they are attached form a carbocycle;

each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted carbocycle;

each $R^d$ is independently selected from halo, haloalkyl, haloalkoxy, alkyl, alkynyl, nitro, cyano, hydroxyl, —$C(O)R^a$, —$OC(O)R^a$, —$C(O)R^a$, —$SR^a$, —$NR^aR^b$ and —$OR^a$, or two $R^d$ taken together with the carbon atoms to which they are attached form an optionally substituted heterocyclyl;

n is 0, 1, or 2;
m is 1, 2 or 3;
h is 0, 1, 2;
g is 0, 1 or 2;
the sum of g+h is equal to or greater than 2; and
p is 0, 1 or 2; and provided that the compound of formula (I) is not N-[3-[(3,5-dimethoxyphenyl)amino]-2-quinoxalinyl]-4-[(4-methyl-1-piperazinyl)carbonyl]-benzenesulfonamide;

N-[4-[[4-(2-furanylmethyl)-1-piperazinyl]carbonyl]phenyl]-2,3-dihydro-2-oxo-1H-benzimidazole-5-sulfonamide;

2,3-dihydro-2-oxo-N-[4-[[4-(2,2,2-trifluoroethyl)-1-piperazinyl]carbonyl]phenyl]-1H-benzimidazole-5-sulfonamide;

2,3-dihydro-N-[4-[[4-(4-nitrophenyl)-1-piperazinyl]carbonyl]phenyl]-2-oxo-1H-benzimidazole-5-sulfonamide;

N-[4-[[4-(2-ethoxyphenyl)-1-piperazinyl]carbonyl]phenyl]-2,3-dihydro-2-oxo-1H-benzimidazole-5-sulfonamide;

2,3-dihydro-2-oxo-N-[4-[[4-(3-thienylmethyl)-1-piperazinyl]carbonyl]phenyl]-1H-benzimidazole-5-sulfonamide;

N-[4-[[4-(2,3-dimethylphenyl)-1-piperazinyl]carbonyl]phenyl]-2,3-dihydro-2-oxo-1H-benzimidazole-5-sulfonamide;

2,3-dihydro-N-[4-[[4-(2-hydroxyphenyl)-1-piperazinyl]carbonyl]phenyl]-2-oxo-1H-benzimidazole-5-sulfonamide;

4-[4-[[(2,3-dihydro-2-oxo-1H-benzimidazol-5-yl)sulfonyl]amino]benzoyl]-1-piperazinecarboxylic acid ethyl ester;

N-[4-[(4-acetyl-1-piperazinyl)carbonyl]phenyl]-2,3-dihydro-2-oxo-1H-benzimidazole-5-sulfonamide;

N-[4-[[4-(4-fluorophenyl)-1-piperazinyl]carbonyl]phenyl]-2,3-dihydro-2-oxo-1H-benzimidazole-5-sulfonamide;

2,3-dihydro-2-oxo-N-[4-[(4-phenyl-1-piperazinyl)carbonyl]phenyl]-1H-benzimidazole-5-sulfonamide; or 2,3-dihydro-2-oxo-N-[4-[[4-(2-pyridinyl)-1-piperazinyl]carbonyl]phenyl]-1H-benzimidazole-5-sulfonamide.

Also provided are pharmaceutical compositions comprising a compound of Formula I or a pharmaceutically acceptable salt thereof and a pharmaceutically acceptable carrier.

The details of construction and the arrangement of components set forth in the following description or illustrated in the drawings are not meant to be limiting. Embodiments can be practiced or carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

The term "halo" or "halogen" refers to any radical of fluorine, chlorine, bromine or iodine.

The term "alkyl" refers to a monovalent hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. In certain aspects, the term "alkyl" refers to a monovalent hydrocarbon chain that may be a straight chain or branched chain, containing 1 to 6 carbon atoms. In other aspects, the term "alkyl" refers to a monovalent hydrocarbon chain that may be a straight chain or branched chain, containing 1 to 4 carbon atoms.

The term "haloalkyl" refers to an alkyl in which one or more hydrogen atoms are replaced by halo, and includes alkyl moieties in which all hydrogens have been replaced by halo (e.g., perfluoroalkyl).

The term "alkenyl" refers to a monovalent straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. In certain aspects, the term "alkenyl" refers to a monovalent straight or branched hydrocarbon chain containing 2-6 carbon atoms and having one or more double bonds. In other aspects, the term "alkenyl" refers to a monovalent straight or branched hydrocarbon chain containing 2-4 carbon atoms and having one or more double bonds.

The term "alkynyl" refers to a monovalent straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The terms "alkylamino" and "dialkylamino" refer to —NH(alkyl) and —NH(alkyl)$_2$ radicals respectively.

The term "aralkylamino" refers to a —NH(aralkyl) radical.

The term "alkylaminoalkyl" refers to a (alkyl)NH-alkyl-radical.

The term "dialkylaminoalkyl" refers to a (alkyl)$_2$N-alkyl-radical.

The term "mercapto" refers to an —SH radical.

The term "thioalkoxy" refers to an —S-alkyl radical.

The term "thioaryloxy" refers to an —S-aryl radical.

The term "alkoxy" refers to an —O-alkyl radical.

The term "aryl" refers to a monocyclic, bicyclic, or tricyclic aromatic hydrocarbon ring system. Examples of aryl moieties include, but are not limited to, phenyl, naphthyl, and anthracenyl.

The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "carbocyclyl" refers to a non-aromatic, monocyclic, bicyclic, or tricyclic hydrocarbon ring system. Carbocyclyl groups include fully saturated ring systems (e.g., cycloalkyls), and partially saturated ring systems.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). Examples of cycloalkyl moieties include, but are not limited to, cyclopropyl, cyclohexyl, methylcyclohexyl, adamantyl, and norbornyl.

The term "heteroaryl" refers to a fully aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms selected independently from N, O, or S if monocyclic, bicyclic, or tricyclic, respectively).

The term "heterocyclyl" refers to a nonaromatic, 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heteroatom may optionally be the point of attachment of the heterocyclyl substituent. Examples of heterocyclyl include, but are not limited to, tetrahydrofuranyl, tetrahydropyranyl, piperidinyl, morpholino, pyrrolinyl, pyrimidinyl, and pyrrolidinyl.

Bicyclic and tricyclic ring systems containing one or more heteroatoms and both aromatic and non-aromatic rings are considered to be heterocyclyl groups according to the present definition. Such bicyclic or tricyclic ring systems may be alternately characterized as being an aryl or a heteroaryl fused to a carbocyclyl or heterocyclyl, particularly in those instances where the ring bound to the rest of the molecule is required to be aromatic.

The terms "heteroarylalkyl" and "heteroaralkyl", as used herein, refers to an alkyl group substituted with a heteroaryl group.

The term "heterocyclylalkyl", as used herein, refers to an alkyl group substituted with a heterocyclyl group.

The term "acyl" refers to an alkylcarbonyl, carbocyclecarbonyl, arylcarbonyl, heterocyclylcarbonyl, or heteroarylcarbonyl substituent, any of which may be further substituted (e.g., by one or more substituents).

All ring systems (i.e, aryl, heteroaryl, carbocyclyl, cycloalkyl, heterocyclyl, etc.) or ring system portions of groups (e.g., the aryl portion of an aralkyl group) are optionally substituted at one or more substitutable carbon atoms with substituents including: halo, —C≡N, $C_1$-$C_4$ alkyl, =O, $C_3$-$C_7$ carbocyle (e.g., cycloalkyl), $C_1$-$C_4$ alkyl, —OH, —O—($C_1$-$C_4$ alkyl), —SH, —S—($C_1$-$C_4$ alkyl), —($C_1$-$C_4$ alkyl)-N($R^{b'}$)($R^{b'}$), —N($R^{b'}$)($R^{b'}$), —O—($C_1$-$C_4$ alkyl)-N($R^{b'}$)($R^{b'}$), —($C_1$-$C_4$ alkyl)-O—($C_1$-$C_4$ alkyl)-N($R^{b'}$)($R^{b'}$), —C(O)—O($R^{b'}$), —OC(O)($R^{b'}$), —O—C(O)—O($R^{b'}$), —C(O)—N($R^{b'}$)($R^{b'}$), —N($R^{b'}$)—C(O)$R^{b'}$, —N($R^{b'}$)C(O)N($R^{b'}$)($R^{b'}$), —N($R^{b'}$)—S(O)$_{1-2}$$R^{b'}$, —S(O)$_{1-2}$N($R^{b'}$)($R^{b'}$), —N($R^{b'}$)S(O)$_{1-2}$N($R^{b'}$)($R^{b'}$), —($C_1$-$C_4$ alkyl)-C(O)—N($R^{b'}$)($R^{b'}$), —O-(heteroaryl), —O-(heterocycle), —O-phenyl, -heteroaryl, -heterocycle, and -phenyl, wherein:

each $R^{b'}$ is independently selected from hydrogen, —$C_1$-$C_4$ alkyl, carbocycle, carbocyclylalkyl, aryl, aralkyl, heteroaryl, heteroaralkyl, heterocyclyl, or heterocyclylalkyl; or two $R^{b'}$ are taken together with the nitrogen atom to which they are bound to form a 4- to 8-membered saturated heterocycle optionally comprising one additional heteroatom selected from N, S, S(=O), S(=O)$_2$, and O, any alkyl substituent is optionally further substituted with one or more of —OH, —O—($C_1$-$C_4$ alkyl), halo, —NH$_2$, —NH($C_1$-$C_4$ alkyl), or —N($C_1$-$C_4$ alkyl)$_2$; and any carbon atom on a phenyl, carbocycle (e.g., cycloalkyl), heteroaryl or heterocycle substituent is optionally further substituted with one or more of —($C_1$-$C_4$ alkyl), —($C_1$-$C_4$ fluoroalkyl), —OH, —O—($C_1$-$C_4$ alkyl), —O—($C_1$-$C_4$ fluoroalkyl), halo, —NH$_2$, —NH($C_1$-$C_4$ alkyl), or —N($C_1$-$C_4$ alkyl)$_2$.

All heterocyclyl ring systems (and any heterocyclyl substituents on any ring system) are optionally substituted on one or more any substitutable nitrogen atom with —$C_1$-$C_4$ alkyl, oxo, fluoro-substituted $C_1$-$C_4$ alkyl, or acyl.

The term "substituted" refers to the replacement of a hydrogen atom by another group.

The term "oxo" refers to an oxygen atom, which forms a carbonyl when attached to carbon, an N-oxide when attached to nitrogen, and a sulfoxide or sulfone when attached to sulfur.

The term "activator" as used herein means an agent that (measurably) increases the activity of wild type pyruvate kinase R (wtPKR) or causes wild type pyruvate kinase R (wt PKR) activity to increase to a level that is greater than wt PKR's basal levels of activity or an agent that (measurably) increases the activity of a mutant pyruvate kinase R (mPKR) or causes mutant pyruvate kinase R (mPKR) activity to increase to a level that is greater than that mutant PKR's basal levels of activity, for examples, to a level that is 20%, 40%, 50%, 60%, 70%, 80%, 90% or 100% of the activity of wild type PKR.

Compounds

Described herein are compounds and compositions that activate wild type PKR and/or mutant PKRs such as those described herein. In one embodiment, provided is a compound of formula (I) or a pharmaceutically acceptable salt thereof, or a pharmaceutical composition comprising a compound of formula (I) or a pharmaceutically acceptable salt thereof:

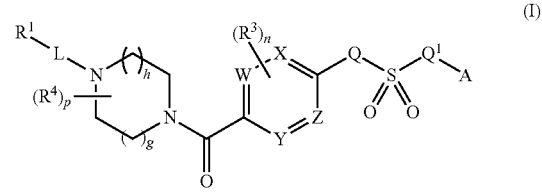

(I)

wherein: W, X, Y and Z are each independently selected from CH or N;

Q and $Q^1$ are independently selected from a bond or $NR^b$;

A is optionally substituted bicyclic aryl or optionally substituted bicyclic heteroaryl;

L is a bond, —C(O)—, —($CR^cR^c$)$_m$—, —C(O)—, —($CR^c$ $R^c$)$_m$—OC(O)—, —($CR^cR^c$)$_m$—C(O)—, —$NR^b$C(S)—, or —$NR^b$C(O)— (wherein the point of the attachment to $R^1$ is on the left-hand side);

$R^1$ is selected from alkyl, carbocycle, aryl, heteroaryl, and heterocyclyl; each of which is substituted with 0-5 occurrences of $R^d$;

each $R^3$ is independently selected from halo, haloalkyl, alkyl, hydroxyl and —$OR^a$, or two adjacent $R^3$ taken together with the carbon atoms to which they are attached form an optionally substituted heterocyclyl;

each $R^4$ is independently selected from halo, haloalkyl, alkyl, hydroxyl, =O, —$OR^a$ and phenyl, or two $R^4$ taken together with the carbon atoms to which they are attached form a bridged, fused or spyro-fused carbocycle, an aryl or a heterocyclyl;

each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, haloalkoxy, alkyl, alkynyl, nitro, cyano, hydroxyl, —C(O)R$^a$, —OC(O)R$^a$, —C(O)OR$^a$, —SR$^a$, —NR$^a$R$^b$ and —OR$^a$, or two $R^d$ taken together with the carbon atoms to which they are attached form an optionally substituted heterocyclyl;

n is 0, 1, or 2;

m is 1, 2 or 3;

h is 0, 1, 2;

g is 0, 1 or 2;

the sum of g+h is equal to or greater than 2; and p is 0, 1 or 2; and provided that the compound of formula (I) is not N-[3-[(3,5-dimethoxyphenyl)amino]-2-quinoxalinyl]-4-[(4-methyl-1-piperazinyl)carbonyl]-benzenesulfonamide;

N-[4-[[4-(2-furanylmethyl)-1-piperazinyl]carbonyl]phenyl]-2,3-dihydro-2-oxo-1H-benzimidazole-5-sulfonamide;

2,3-dihydro-2-oxo-N-[4-[[4-(2,2,2-trifluoroethyl)-1-piperazinyl]carbonyl]phenyl]-1H-benzimidazole-5-sulfonamide;

2,3-dihydro-N-[4-[[4-(4-nitrophenyl)-1-piperazinyl]carbonyl]phenyl]-2-oxo-1H-benzimidazole-5-sulfonamide;

N-[4-[[4-(2-ethoxyphenyl)-1-piperazinyl]carbonyl]phenyl]-2,3-dihydro-2-oxo-1H-benzimidazole-5-sulfonamide;

2,3-dihydro-2-oxo-N-[4-[[4-(3-thienylmethyl)-1-piperazinyl]carbonyl]phenyl]-1H-benzimidazole-5-sulfonamide;

N-[4-[[4-(2,3-dimethylphenyl)-1-piperazinyl]carbonyl]phenyl]-2,3-dihydro-2-oxo-1H-benzimidazole-5-sulfonamide;

2,3-dihydro-N-[4-[[4-(2-hydroxyphenyl)-1-piperazinyl]carbonyl]phenyl]-2-oxo-1H-benzimidazole-5-sulfonamide;

4-[4-[[(2,3-dihydro-2-oxo-1H-benzimidazol-5-yl)sulfonyl]amino]benzoyl]-1-piperazinecarboxylic acid ethyl ester;

N-[4-[(4-acetyl-1-piperazinyl)carbonyl]phenyl]-2,3-dihydro-2-oxo-1H-benzimidazole-5-sulfonamide;

N-[4-[[4-(4-fluorophenyl)-1-piperazinyl]carbonyl]phenyl]-2,3-dihydro-2-oxo-1H-benzimidazole-5-sulfonamide;

2,3-dihydro-2-oxo-N-[4-[(4-phenyl-1-piperazinyl)carbonyl]phenyl]-1H-benzimidazole-5-sulfonamide; or 2,3-dihydro-2-oxo-N-[4-[[4-(2-pyridinyl)-1-piperazinyl]carbonyl]phenyl]-1H-benzimidazole-5-sulfonamide.

In certain embodiments of a compound of formula (I) or a pharmaceutically acceptable salt thereof p is 1 or 2. In one aspect of this embodiment, p is 2 and the compound has the formula Ia:

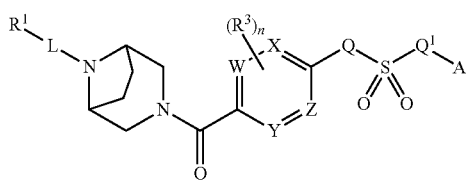

(Ia)

or formula Ib:

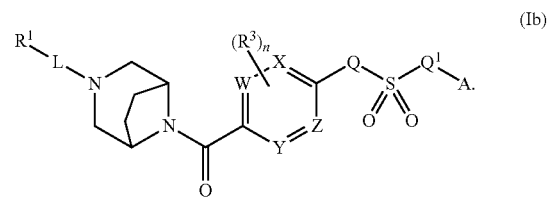

(Ib)

In an alternate aspect of this embodiment, p is 1 or 2; and each $R^4$ is independently selected from (S)-alkyl, (R)-alkyl, (S)-phenyl, and (R)-phenyl. In an even more specific aspect of this embodiment, g is 1, h is 1; p is 1 or 2; and each $R^4$ is independently selected from (S)-methyl, (R)-methyl, (S)-ethyl, (R)-ethyl, (S)-isopropyl, (R)-isopropyl, (S)-phenyl, and (R)-phenyl. In still another alternate aspect, p is 2 and the two $R^4$ taken together with the carbon atoms to which they are attached form a phenyl ring that is fused to the piperazine ring.

In certain embodiments of a compound of formula (I) or a pharmaceutically acceptable salt thereof n is 1 or 2.

In certain embodiments of a compound of formula (I) or a pharmaceutically acceptable salt thereof, A is an optionally substituted bicyclic heteroaryl. In an aspect A is

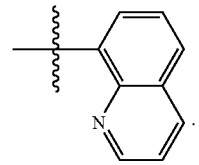 [SMILES: *c1cccc2cccnc12]

In some embodiments, g is 1 or 2; h is 1 or 2; and g+h is 2 or 3. In one aspect of this embodiment g+h=2. In an alternate aspect of this embodiment, g+h=3.

In some embodiments, W, X, Y, Z and the carbons to which they are attached form a phenyl ring.

In some embodiments, W, X, Y, Z and the carbons to which they are attached form a pyridyl ring. In one aspect of this embodiment W, X and Y are CH and Z is N. In an alternate aspect X, Y and Z are CH and W is N.

In some embodiments, W, X, Y, Z and the carbon atoms to which they are attached form a pyrimidyl ring.

In some embodiments, W, X, Y, Z and the carbon atoms to which they are attached form a pyridazinyl ring.

In some embodiments the ring comprising W, X, Y and Z is unsubstituted (i.e., n is 0). In some embodiments, the ring comprising W, X, Y and Z is monosubstituted (i.e., n is 1).

In some embodiments where n is 1, $R^3$ is selected from fluoro, chloro methyl, ethyl, $CF_3$, methoxy, and $OCF_3$.

In some embodiments, Q is NR$^b$ and Q$^1$ is a bond. In some aspects of these embodiments, $R^b$ is methyl. In other aspects of these embodiments, $R^b$ is hydrogen (H).

In some embodiments, L is a bond.

In some embodiments, L is —(CR$^c$R$^c$)$_m$— and m is 1. In some aspects of these embodiments, each $R^c$ is hydrogen. In other aspects of these embodiments, one $R^c$ is methyl and the other $R^c$ is hydrogen. In some aspects of these embodiments, one $R^c$ is —$CF_3$ and one $R^c$ is hydrogen. In some aspects of these embodiments, both $R^c$ are methyl. In some aspects of these embodiments, two $R^c$ taken together with the carbon to which they are attached form a cyclopropyl, cyclobutyl, cyclopentyl or cyclohexyl.

In some embodiments, L is ethyl or n-propyl.

In some embodiments, L is —C(O)—.

In some embodiments, L is -O—C(O)—.

In some embodiments, L is —(CR$^c$R$^c$)$_m$—C(O)— and m is 1. In some aspects of these embodiments, each R$^c$ is hydrogen. In some aspects of these embodiments, one R$^c$ is methyl and one R$^c$ is hydrogen. In some aspects of these embodiments, both R$^c$ are methyl.

In some embodiments, L is —(CR$^c$R$^c$)$_m$—O—C(O)— and m is 1 or 2. In some aspects of these embodiments, each R$^c$ is hydrogen.

In some embodiments, L is selected from bond, —C(O)—, —OC(O)—, —CH$_2$—OC(O)—, —(CH$_2$)$_2$—OC(O)—, —C(CH$_3$)$_2$—C(O)—, —CH$_2$—, —(CH$_2$)$_2$—, —(CH$_2$)$_3$—, —CH(CH$_3$)—, —CH(CF$_3$)—, —C(CH$_3$)$_2$—, —CHD-, —CD$_2$-,

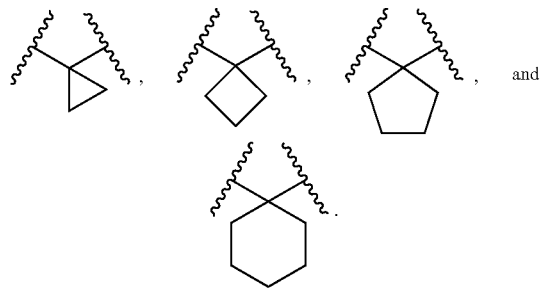

In some embodiments, R$^1$ is selected from methyl, ethyl, isopropyl, cyclopropyl, cyclobutyl, cyclopentyl, cyclohexyl, phenyl, pyridin-2-yl, pyridin-3-yl, pyridin-4-yl, 1,2,3-thiadiazol-5-yl, 1,2,3-thiadiazol-4-yl, thiazol-4-yl, thiazol-5-yl, 1H-imidazol-4-yl, 1H-imidazol-2-yl, 1H-pyrazol-3-yl, 1H-pyrazol-4-yl, 1H-pyrazol-5-yl, pyrazin-2-yl, oxazol-4-yl, isoxazol-5-yl, tetrahydrofuran-2-yl, tetrahydrofuran-3-yl, tetrahydro-2H-pyran-4-yl, tetrahydro-2H-pyran-3-yl, and tetrahydro-2H-pyran-2-yl.

In certain embodiments R$^1$ is substituted with one or more substituents independently selected from fluoro, chloro, methyl, CF$_3$, and methoxy.

Compounds described herein are useful as activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the emzyme. Examples of such mutations are described in Valentini et al, JBC 2002. Some examples of the mutants that are activated by the compounds described herein include G332S, G364D, T384M, G37E, R479H, R479K, R486W, R532W, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Example 18. Compounds described herein are also useful as activators of wild type PKR.

In an embodiment, to increase the lifetime of the red blood cells, a compound, composition or pharmaceutical composition described herein is added directly to whole blood or packed cells extracorporeally or be provided to the patient directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the rate of release of 2,3-DPG from the blood. A decrease in the level of 2,3-DPG concentration induces a leftward shift of the oxygen-hemoglobin dissociation curve and shifts the allosteric equilibribrium to the R, or oxygenated state, thus producing a therapeutic inhibition of the intracellular polymerization that underlies sickling by increasing oxygen affinity due to the 2,3-DPG depletion, thereby stabilizing the more soluble oxy-hemoglobin. Accordingly, in one embodiment, compounds and pharmaceutical compositions described herein are useful as antisickling agents. In another embodiment, to regulate 2,3-diphosphoglycerate, a compound, composition or pharmaceutical composition described herein is added directly to whole blood or packed cells extracorporeally or be provided to the patient directly (e.g., by i.p., i.v., i.m., oral, inhalation (aerosolized delivery), transdermal, sublingual and other delivery routes).

A compound described herein may be an activator of a PKR, for example, a wild type (wt) or mutated PKR (e.g., R510Q, R532W, OR T384W). Exemplary compounds are shown in Table 1. As shown in Table 1, A refers to a compound that has a % activation at 1 μM of from 1 to 100. B refers to an a compound that has a % activation at 1 μM of from 101 to 500. C refers a compound that has a % activation at 1 μM of >500.

In Table 1, a compound described herein may also have an AC50 of wild type PKR, PKR R532W, PKR T384W, PKR G332S, PKR G364D, PKR G37E and/or PKR R479H. AA refers to an AC50 less than 100 nM, BB refers to an AC50 from 101 nM to 500 nM and CC refers to an AC50 greater than 500 nM.

TABLE 1

| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| [structure] | B | B | B | B | | AA | | | | |

TABLE 1-continued

| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| | B | B | B | B | | | | | | |
| | B | B | B | B | | | | | | |
| | B | B | B | B | | | | | | |
| | B | B | B | B | | | | | | |
| | A | B | B | B | | | | | | |
| | A | B | A | B | | | | | | |

TABLE 1-continued

| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| *structure* | A | A | B | B | | | | | | |
| *structure* | B | B | B | B | | | | | | |
| *structure* | B | A | B | B | | | | | | |
| *structure* | B | B | B | B | AA | | CC | | | |
| *structure* | A | B | B | B | CC | | CC | | | |
| *structure* | B | B | A | A | | | | | | |

TABLE 1-continued
| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| 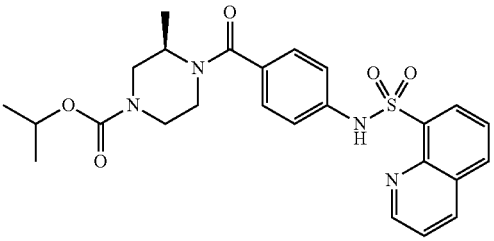 [SMILES: CC(C)OC(=O)N1CCN(C(=O)c2ccc(NS(=O)(=O)c3cccc4cccnc34)cc2)[C@H](C)C1] | B | B | B | B | AA | CC | AA | | | |
| 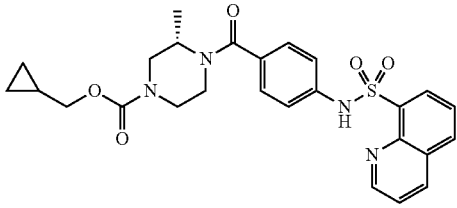 [SMILES: C[C@H]1CN(C(=O)OCC2CC2)CCN1C(=O)c1ccc(NS(=O)(=O)c2cccc3cccnc23)cc1] | A | B | B | B | | | | | | |
| 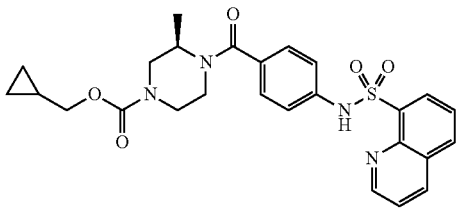 [SMILES: C[C@@H]1CN(C(=O)OCC2CC2)CCN1C(=O)c1ccc(NS(=O)(=O)c2cccc3cccnc23)cc1] | A | B | A | A | | | | | | |
| 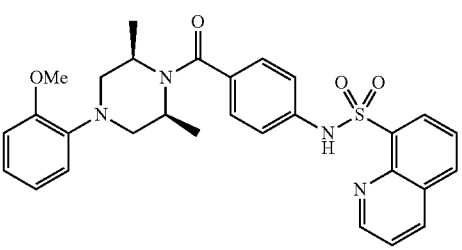 [SMILES: COc1ccccc1N1C[C@@H](C)N(C(=O)c2ccc(NS(=O)(=O)c3cccc4cccnc34)cc2)[C@@H](C)C1] | B | B | B | B | | | | | | |
| 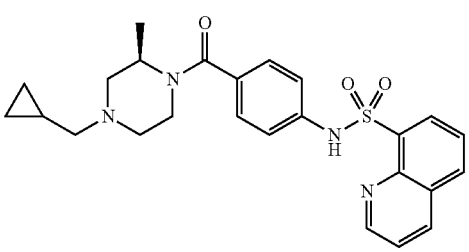 [SMILES: C[C@@H]1CN(CC2CC2)CCN1C(=O)c1ccc(NS(=O)(=O)c2cccc3cccnc23)cc1] | B | A | B | B | | | | | | |
| 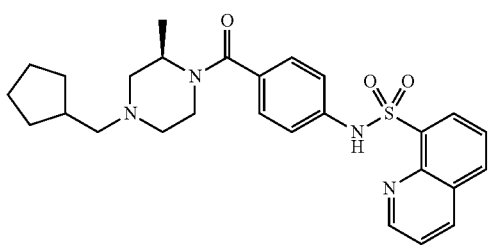 [SMILES: C[C@@H]1CN(CC2CCCC2)CCN1C(=O)c1ccc(NS(=O)(=O)c2cccc3cccnc23)cc1] | A | A | B | A | | | | | | |

TABLE 1-continued
| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| 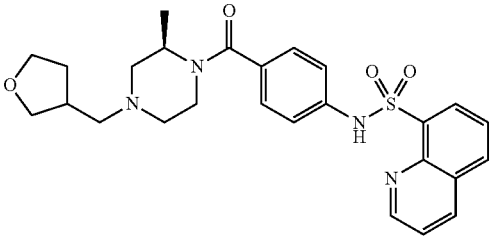 [SMILES: C[C@@H]1CN(CC2CCOC2)CCN1C(=O)c1ccc(NS(=O)(=O)c2cccc3cccnc23)cc1] | B | B | B | B | | | | | | |
| 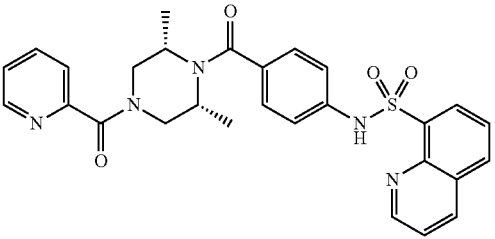 [SMILES: C[C@@H]1CN(C(=O)c2ccccn2)C[C@H](C)N1C(=O)c1ccc(NS(=O)(=O)c2cccc3cccnc23)cc1] | A | A | A | B | | | | | | |
| 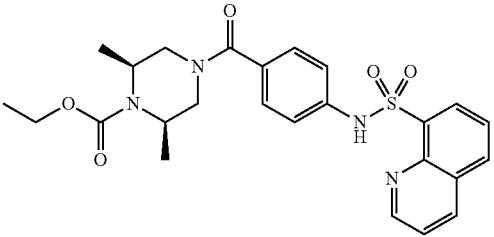 [SMILES: CCOC(=O)N1[C@H](C)CN(C(=O)c2ccc(NS(=O)(=O)c3cccc4cccnc34)cc2)C[C@@H]1C] | B | B | B | B | | | | | | |
| 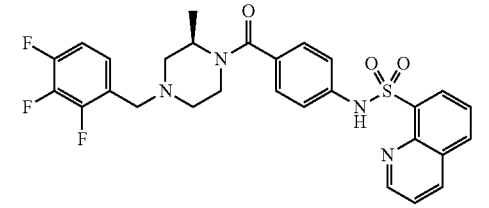 [SMILES: C[C@@H]1CN(Cc2ccc(F)c(F)c2F)CCN1C(=O)c1ccc(NS(=O)(=O)c2cccc3cccnc23)cc1] | B | A | B | A | | | | | | |
| 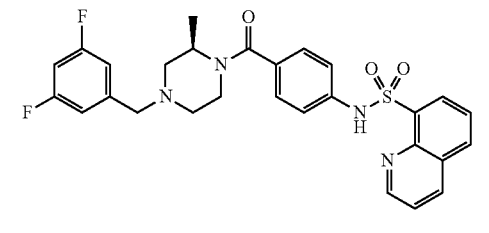 [SMILES: C[C@@H]1CN(Cc2cc(F)cc(F)c2)CCN1C(=O)c1ccc(NS(=O)(=O)c2cccc3cccnc23)cc1] | A | A | A | A | | | | | | |
| 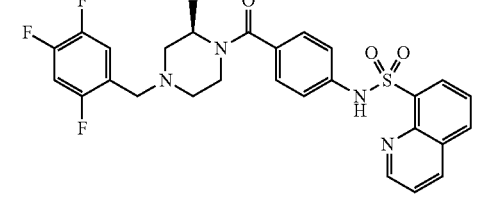 | A | A | A | A | | | | | | |

TABLE 1-continued

| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| *structure* | A | A | A | A | | | | | | |
| *structure* | A | A | A | A | | | | | | |
| *structure* | A | A | A | A | | | | | | |
| *structure* | A | A | A | A | | | | | | |
| *structure* | A | B | A | B | | | | | | |
| *structure* | A | B | A | B | | | | | | |
| *structure* | B | B | B | B | | | | | | |

TABLE 1-continued

| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| (tetrahydrofurfuryl carbamate piperazine benzamide quinoline sulfonamide) | A | A | A | B | | | | | | |
| (cyclopentyl carbamate piperazine benzamide quinoline sulfonamide) | B | B | B | B | | | | | | |
| (2,3-dimethoxybenzyl piperazine benzamide quinoline sulfonamide) | A | B | B | B | | | | | | |
| (4-fluorobenzyl piperazine benzamide quinoline sulfonamide) | A | B | B | B | | | | | | |
| (2,3,4-trifluorobenzyl piperazine benzamide quinoline sulfonamide) | A | B | B | B | | | | | | |
| (1-(4-fluorophenyl)ethyl piperazine benzamide quinoline sulfonamide) | B | B | B | B | | | | | | |
| (4-fluorobenzyl ethyl-piperazine benzamide quinoline sulfonamide) | A | B | B | B | | | | | | |

TABLE 1-continued

| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| | B | B | B | B | | | | | | |
| | B | B | B | B | | | | | | |
| 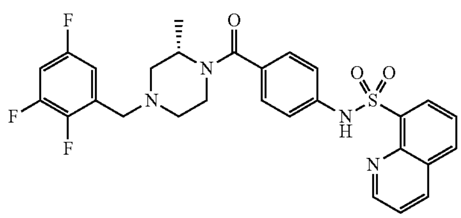 [SMILES: C[C@H]1CN(Cc2cc(F)cc(F)c2F)CCN1C(=O)c1ccc(NS(=O)(=O)c2cccc3cccnc23)cc1] | A | A | B | B | | | | | | |
| | B | B | A | B | | | | | | |
| | B | A | A | B | | | | | | |
| | B | A | B | B | | | | | | |

TABLE 1-continued

| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| [2,3,6-trifluorobenzyl piperazine structure] | A | A | B | B | | | | | | |
| [3,5-difluorobenzyl piperazine structure] | B | A | B | B | | | | | | |
| [2-fluorobenzyl piperazine structure] | A | B | B | B | | | | | | |
| [cyclopropylmethyl piperazine structure] | A | B | A | B | | | | | | |
| [2,4,5-trifluorobenzyl piperazine structure] | A | A | B | A | | | | | | |
| [2,3-dimethoxybenzyl piperazine structure] | A | A | B | B | | | | | | |

TABLE 1-continued

| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| (structure) | B | B | A | B | | | | | | |
| (structure) | B | B | B | B | AA | CC | AA | AA | BB | AA |
| (structure) | A | B | A | A | | | | | | |
| (structure) | B | A | A | A | | | | | | |
| (structure) | B | B | B | B | | | | | | |
| (structure) | B | B | A | B | | | | | | |

TABLE 1-continued

| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| | B | A | B | B | | | | | | |
| | A | B | A | A | | | | | | |
| | A | A | A | A | | | | | | |
| | A | A | B | A | | | | | | |
| | A | A | A | A | | | | | | |
| | B | A | B | A | | | | | | |

TABLE 1-continued

| Structure | Act. % 510Q | Act, % 532W | Act. % 384W | Act. % WT | PKR WT AC50 (µM) | PKR R510Q AC50 (µM) | PKR R532W AC50 (µM) | PKR T384W AC50 (µM) | PKR G364D AC50 (µM) | PKR R479H AC50 (µM) |
|---|---|---|---|---|---|---|---|---|---|---|
| | B | A | B | A | | | | | | |
| | B | A | A | A | | | | | | |
| | A | A | A | B | | | | | | |
| | A | A | A | A | | | | | | |
| | A | A | A | A | | | | | | |
| | A | B | B | B | | | | | | |

TABLE 1-continued

| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| | A | B | B | A | | | | | | |
| | A | A | A | A | | | | | | |
| 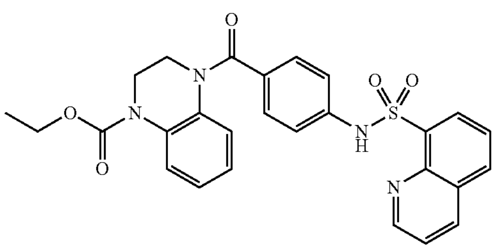 [SMILES: CCOC(=O)N1CCN(C(=O)c2ccc(NS(=O)(=O)c3cccc4cccnc34)cc2)c2ccccc21] | B | B | A | B | | | | | | |
| | A | A | A | A | | | | | | |
| | A | B | B | B | | | | | | |
| | A | B | B | B | | | | | | |

TABLE 1-continued
| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| 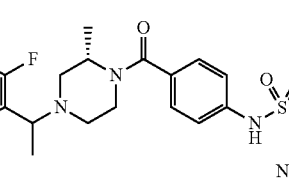 | B | B | A | B | | | | | | |
| 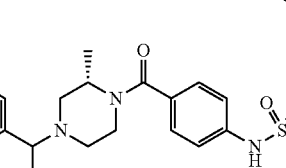 | A | B | B | B | | | | | | |
| 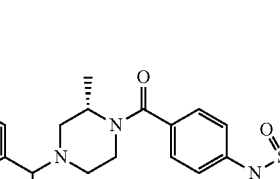 | A | A | A | A | | | | | | |
| 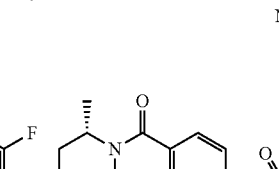 | B | B | B | B | | | | | | |
| 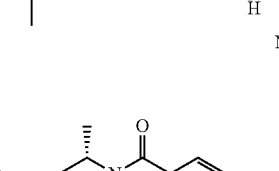 | B | B | B | B | | | | | | |
| 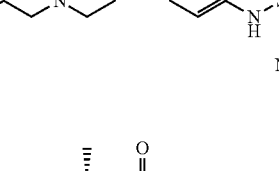 | A | B | A | A | | | | | | |
| 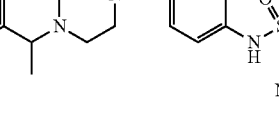 | A | B | B | B | | | | | | |

TABLE 1-continued
| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| 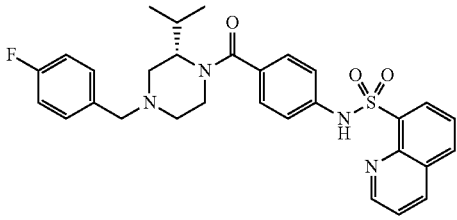 [SMILES: CC(C)[C@H]1CN(Cc2ccc(F)cc2)CCN1C(=O)c1ccc(NS(=O)(=O)c2cccc3cccnc23)cc1] | A | A | B | A | | | | | | |
| 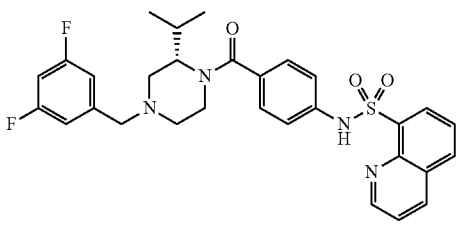 [SMILES: CC(C)[C@H]1CN(Cc2cc(F)cc(F)c2)CCN1C(=O)c1ccc(NS(=O)(=O)c2cccc3cccnc23)cc1] | A | A | B | A | | | | | | |
| 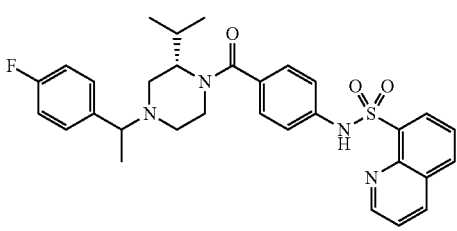 [SMILES: CC(C)[C@H]1CN(C(C)c2ccc(F)cc2)CCN1C(=O)c1ccc(NS(=O)(=O)c2cccc3cccnc23)cc1] | A | B | B | B | | | | | | |
| 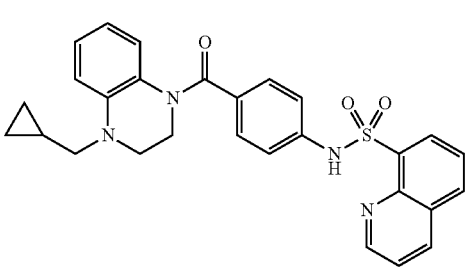 [SMILES: O=C(c1ccc(NS(=O)(=O)c2cccc3cccnc23)cc1)N1CCN(CC2CC2)c2ccccc21] | A | B | B | B | | | | | | |
| 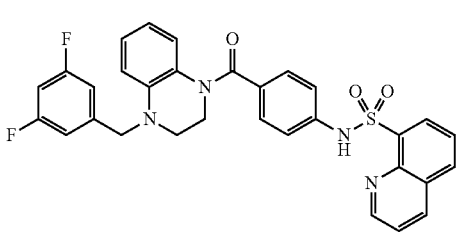 [SMILES: O=C(c1ccc(NS(=O)(=O)c2cccc3cccnc23)cc1)N1CCN(Cc2cc(F)cc(F)c2)c2ccccc21] | A | B | B | B | | | | | | |
| 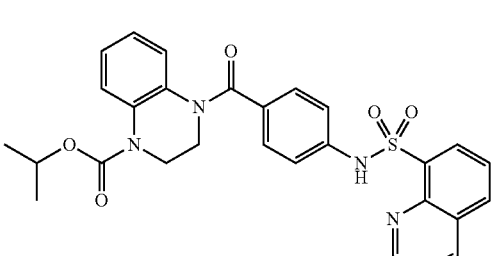 | A | A | A | A | | | | | | |

TABLE 1-continued
| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| 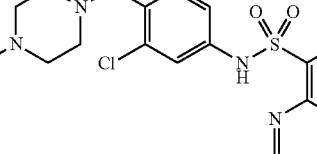 | A | A | A | A | | | | | | |
| 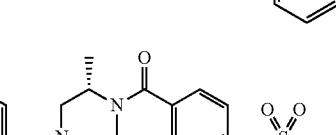 | B | B | A | A | | | | | | |
| 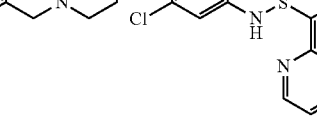 | A | A | A | A | | | | | | |
| 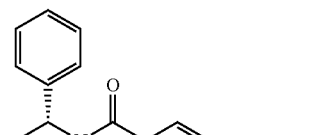 | B | A | A | A | | | | | | |
| 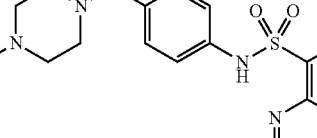 | B | A | A | A | | | | | | |
| 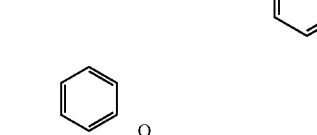 | A | A | A | A | | | | | | |

TABLE 1-continued

| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| | A | B | A | A | | | | | | |
| | A | B | B | A | | | | | | |
| | A | A | A | A | | | | | | |
| | A | B | B | A | | | | | | |
| 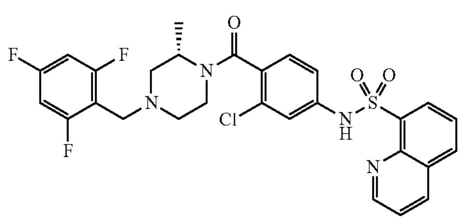 [SMILES: C[C@H]1CN(Cc2c(F)cc(F)cc2F)CCN1C(=O)c1ccc(NS(=O)(=O)c2cccc3cccnc23)cc1Cl] | B | A | B | B | | | | | | |
| | A | A | B | B | | | | | | |

TABLE 1-continued

| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| | A | B | B | B | | | | | | |
| | A | B | B | B | | | | | | |
| | A | B | B | A | | | | | | |
| | A | B | B | B | | | | | | |
| 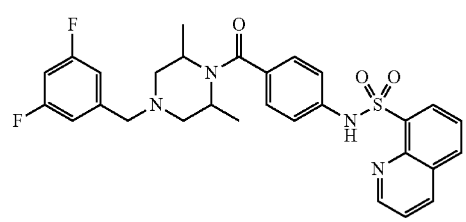 [SMILES: CC1CN(Cc2cc(F)cc(F)c2)CC(C)N1C(=O)c1ccc(NS(=O)(=O)c2cccc3cccnc23)cc1] | B | B | A | A | | | | | | |
| | A | B | B | B | | | | | | |

TABLE 1-continued
| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| 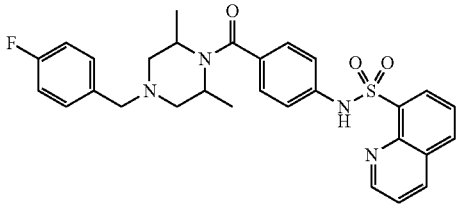 [SMILES: CC1CN(Cc2ccc(F)cc2)CC(C)N1C(=O)c1ccc(NS(=O)(=O)c2cccc3cccnc23)cc1] | A | B | A | A | | | | | | |
| 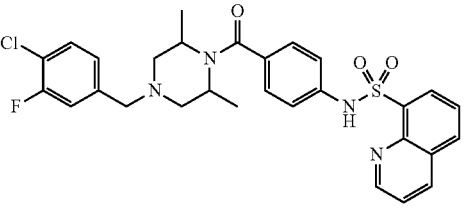 [SMILES: CC1CN(Cc2ccc(Cl)c(F)c2)CC(C)N1C(=O)c1ccc(NS(=O)(=O)c2cccc3cccnc23)cc1] | B | A | B | B | | | | | | |
| 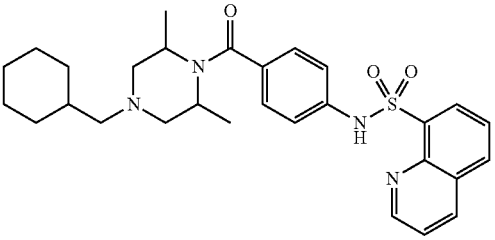 [SMILES: CC1CN(CC2CCCCC2)CC(C)N1C(=O)c1ccc(NS(=O)(=O)c2cccc3cccnc23)cc1] | B | B | B | B | | | | | | |
| 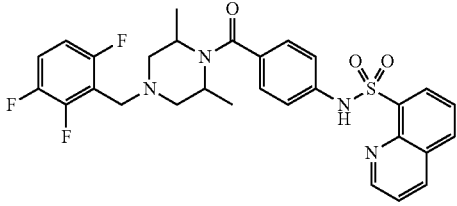 [SMILES: CC1CN(Cc2c(F)ccc(F)c2F)CC(C)N1C(=O)c1ccc(NS(=O)(=O)c2cccc3cccnc23)cc1] | A | B | A | A | | | | | | |
| 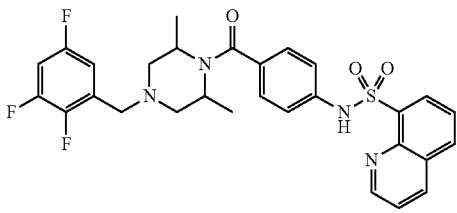 [SMILES: CC1CN(Cc2cc(F)cc(F)c2F)CC(C)N1C(=O)c1ccc(NS(=O)(=O)c2cccc3cccnc23)cc1] | B | B | B | B | | | | | | |
| 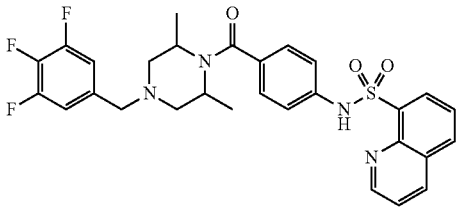 [SMILES: CC1CN(Cc2cc(F)c(F)c(F)c2)CC(C)N1C(=O)c1ccc(NS(=O)(=O)c2cccc3cccnc23)cc1] | A | B | A | A | | | | | | |

TABLE 1-continued
| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| 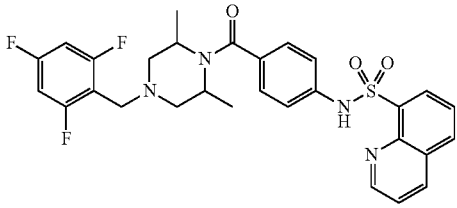 [SMILES: CC1CN(Cc2c(F)cc(F)cc2F)CC(C)N1C(=O)c1ccc(NS(=O)(=O)c2cccc3cccnc23)cc1] | B | B | A | B | | | | | | |
| 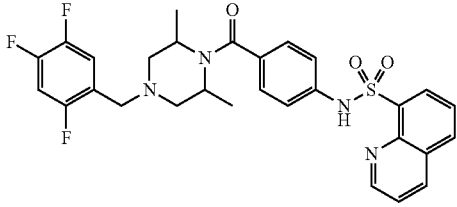 [SMILES: CC1CN(Cc2cc(F)c(F)cc2F)CC(C)N1C(=O)c1ccc(NS(=O)(=O)c2cccc3cccnc23)cc1] | B | A | A | B | | | | | | |
| 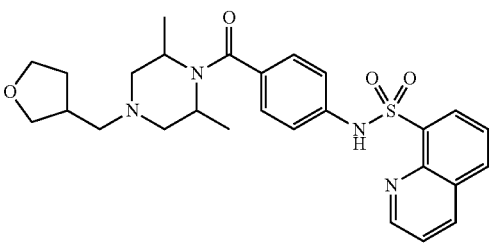 [SMILES: CC1CN(CC2CCOC2)CC(C)N1C(=O)c1ccc(NS(=O)(=O)c2cccc3cccnc23)cc1] | B | A | A | A | | | | | | |
| 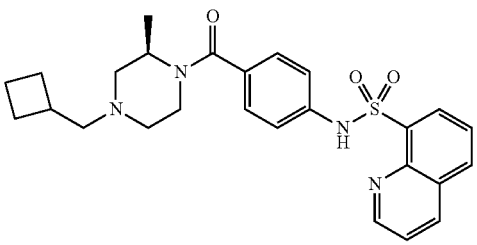 [SMILES: C[C@@H]1CN(CC2CCC2)CCN1C(=O)c1ccc(NS(=O)(=O)c2cccc3cccnc23)cc1] | B | B | A | B | | | | | | |
| 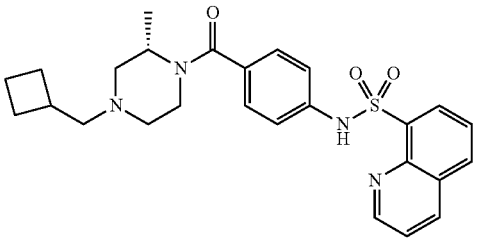 [SMILES: C[C@H]1CN(CC2CCC2)CCN1C(=O)c1ccc(NS(=O)(=O)c2cccc3cccnc23)cc1] | B | B | B | B | | | | | | |
| 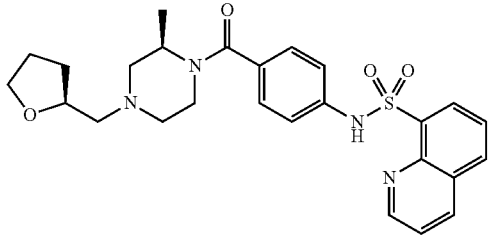 [SMILES: C[C@@H]1CN(C[C@@H]2CCCO2)CCN1C(=O)c1ccc(NS(=O)(=O)c2cccc3cccnc23)cc1] | B | B | B | B | | | | | | |

TABLE 1-continued

| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| | A | B | B | B | | | | | | |
| | B | B | B | B | | | | | | |
| | A | A | B | B | | | | | | |
| | B | B | B | B | | | | | | |
| | B | A | B | B | | | | | | |
| | B | A | A | B | | | | | | |

TABLE 1-continued

| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
| | B | B | B | B | | | | | | |
| | B | B | B | A | | | | | | |
| | B | B | B | B | | | | | | |
| | B | A | B | A | | | | | | |
| | B | B | B | B | | | | | | |
| 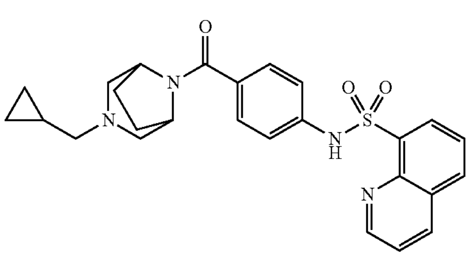 [SMILES: O=C(c1ccc(NS(=O)(=O)c2cccc3cccnc23)cc1)N1C2CCC1CN(CC1CC1)C2] | A | B | B | B | | | | | | |

TABLE 1-continued

| Structure | Act. % 510Q | Act, % 532W | Act. % 384W | Act. % WT | PKR WT AC50 (μM) | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|---|---|---|---|---|
|  | B | A | B | B | AA | BB | AA | AA |  | AA |
|  | B | A | B | A | AA | BB | AA | AA |  | AA |

In certain embodiments, the compound of Formula I is selected from any one of the compounds set forth in the Examples, Table 2 or Table 3.

TABLE 2

| Cmpd # | Structure |
|---|---|
| 217 | 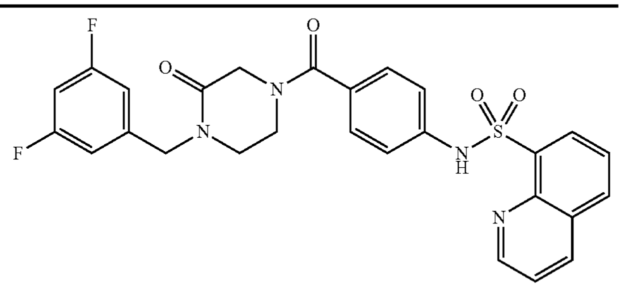 |
| 183 | 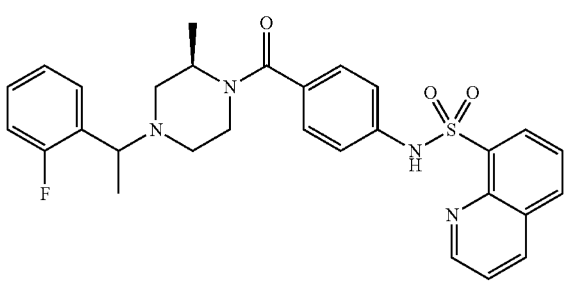 [SMILES: CC(c1ccccc1F)N1CCN(C(=O)c2ccc(NS(=O)(=O)c3cccc4cccnc34)cc2)[C@H](C)C1] |
| 167 | 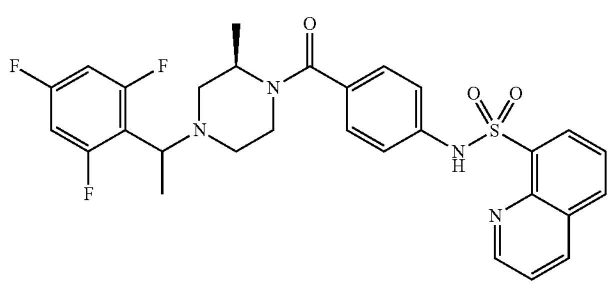 [SMILES: CC(c1c(F)cc(F)cc1F)N1CCN(C(=O)c2ccc(NS(=O)(=O)c3cccc4cccnc34)cc2)[C@H](C)C1] |

TABLE 2-continued

| Cmpd # | Structure |
|---|---|
| 165 | 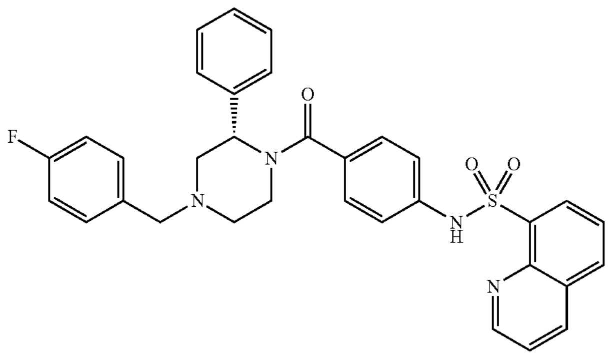 [SMILES: O=C(c1ccc(NS(=O)(=O)c2cccc3cccnc23)cc1)N1CCN(Cc2ccc(F)cc2)C[C@@H]1c1ccccc1] |
| 173 | 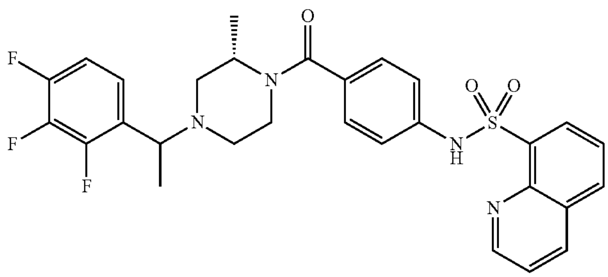 [SMILES: CC(c1ccc(F)c(F)c1F)N1CCN(C(=O)c2ccc(NS(=O)(=O)c3cccc4cccnc34)cc2)[C@@H](C)C1] |
| 181 | 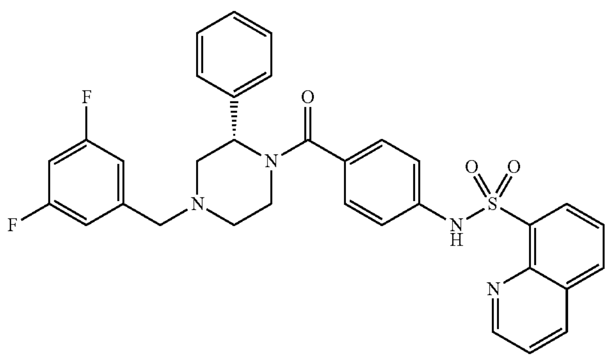 [SMILES: O=C(c1ccc(NS(=O)(=O)c2cccc3cccnc23)cc1)N1CCN(Cc2cc(F)cc(F)c2)C[C@@H]1c1ccccc1] |
| 170 | 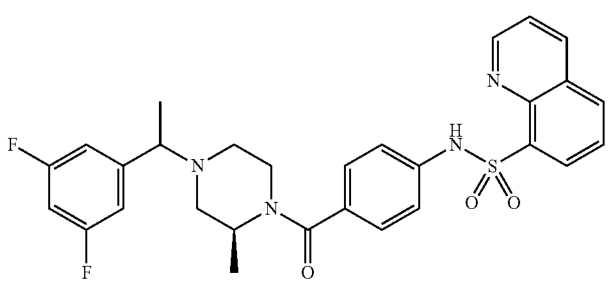 [SMILES: CC(c1cc(F)cc(F)c1)N1CCN(C(=O)c2ccc(NS(=O)(=O)c3cccc4cccnc34)cc2)[C@@H](C)C1] |
| 166 | 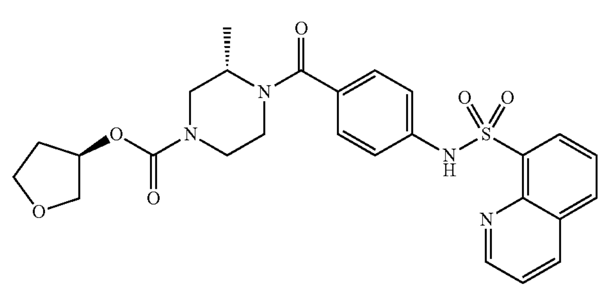 |

TABLE 2-continued
| Cmpd # | Structure |
|---|---|
| 171 | 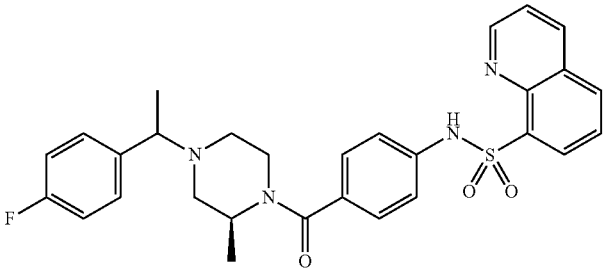 [SMILES: CC(c1ccc(F)cc1)N1CCN(C(=O)c2ccc(NS(=O)(=O)c3cccc4cccnc34)cc2)[C@@H](C)C1] |
| 100 | 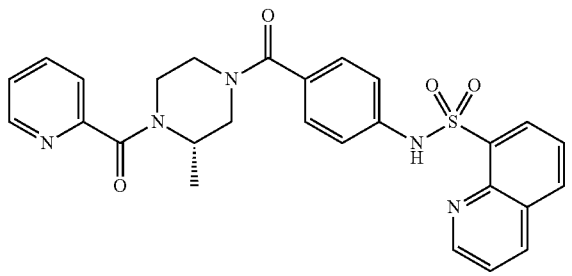 [SMILES: C[C@H]1CN(C(=O)c2ccc(NS(=O)(=O)c3cccc4cccnc34)cc2)CCN1C(=O)c1ccccn1] |
| 182 | 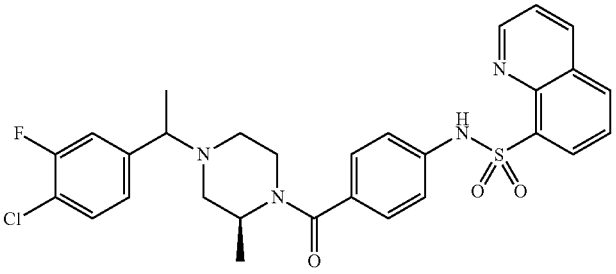 [SMILES: CC(c1ccc(Cl)c(F)c1)N1CCN(C(=O)c2ccc(NS(=O)(=O)c3cccc4cccnc34)cc2)[C@@H](C)C1] |
| 214 | 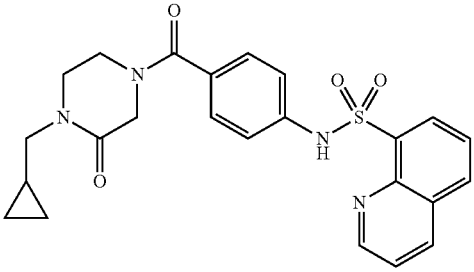 [SMILES: O=C1CN(C(=O)c2ccc(NS(=O)(=O)c3cccc4cccnc34)cc2)CCN1CC1CC1] |
| 101 | 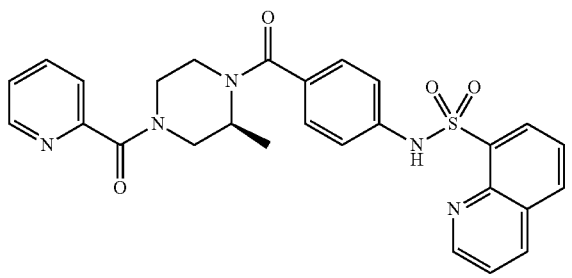 [SMILES: C[C@H]1CN(C(=O)c2ccccn2)CCN1C(=O)c1ccc(NS(=O)(=O)c2cccc3cccnc23)cc1] |

TABLE 2-continued

| Cmpd # | Structure |
|---|---|
| 177 | 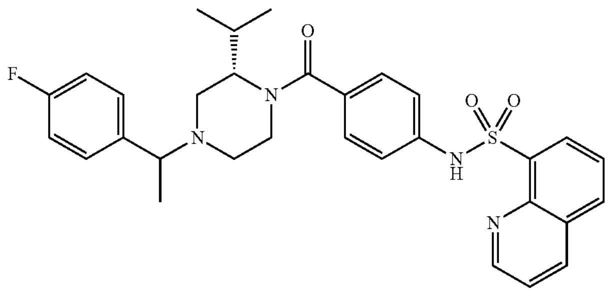 [SMILES: CC(C)[C@H]1CN(C(C)c2ccc(F)cc2)CCN1C(=O)c1ccc(NS(=O)(=O)c2cccc3cccnc23)cc1] |
| 175 | 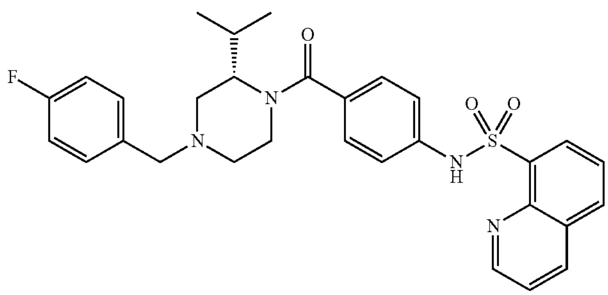 [SMILES: CC(C)[C@H]1CN(Cc2ccc(F)cc2)CCN1C(=O)c1ccc(NS(=O)(=O)c2cccc3cccnc23)cc1] |
| 176 | 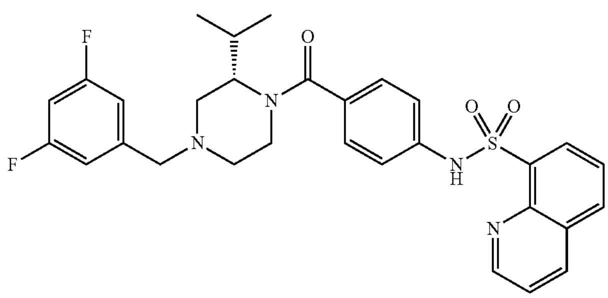 [SMILES: CC(C)[C@H]1CN(Cc2cc(F)cc(F)c2)CCN1C(=O)c1ccc(NS(=O)(=O)c2cccc3cccnc23)cc1] |
| 102 | 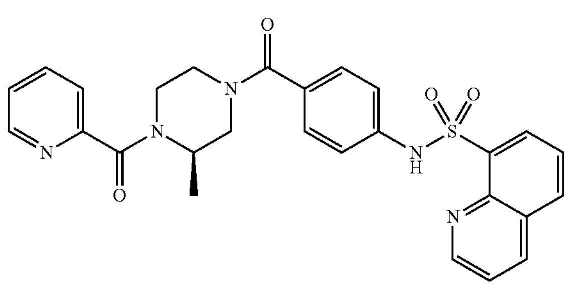 [SMILES: C[C@@H]1CN(C(=O)c2ccc(NS(=O)(=O)c3cccc4cccnc34)cc2)CCN1C(=O)c1ccccn1] |
| 103 | 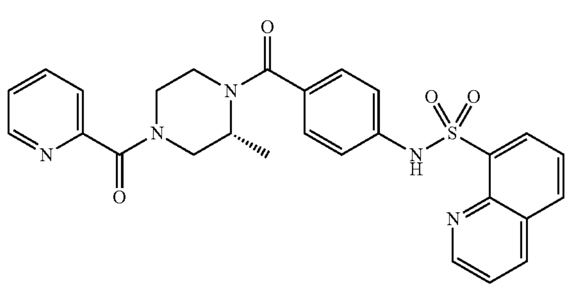 [SMILES: C[C@@H]1CN(C(=O)c2ccccn2)CCN1C(=O)c1ccc(NS(=O)(=O)c2cccc3cccnc23)cc1] |

TABLE 2-continued

| Cmpd # | Structure |
|---|---|
| 168 | 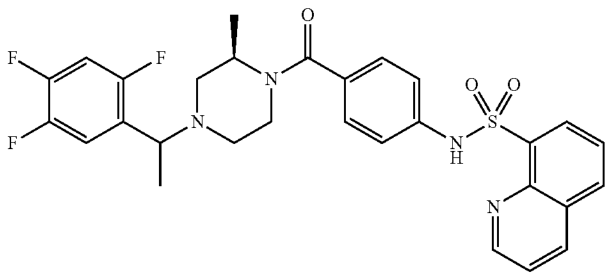 [SMILES: CC(c1cc(F)c(F)cc1F)N1CCN(C(=O)c2ccc(NS(=O)(=O)c3cccc4cccnc34)cc2)[C@H](C)C1] |
| 178 | 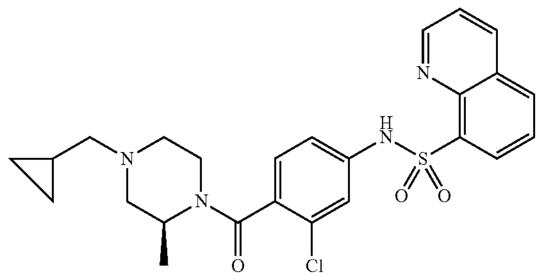 [SMILES: C[C@H]1CN(CC2CC2)CCN1C(=O)c1ccc(NS(=O)(=O)c2cccc3cccnc23)cc1Cl] |
| 180 | 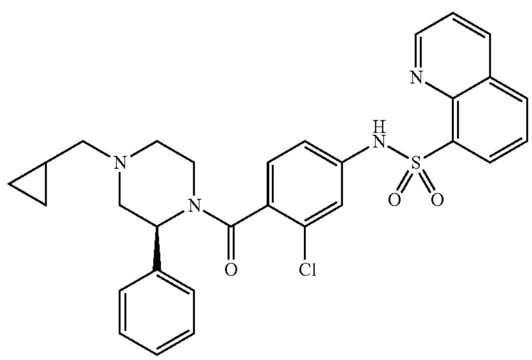 [SMILES: O=C(c1ccc(NS(=O)(=O)c2cccc3cccnc23)cc1Cl)N1CCN(CC2CC2)C[C@@H]1c1ccccc1] |
| 169 | 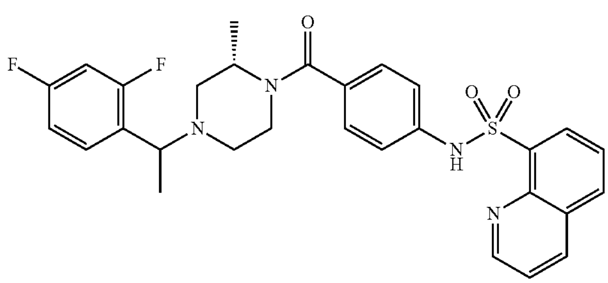 [SMILES: CC(c1ccc(F)cc1F)N1CCN(C(=O)c2ccc(NS(=O)(=O)c3cccc4cccnc34)cc2)[C@@H](C)C1] |
| 172 | 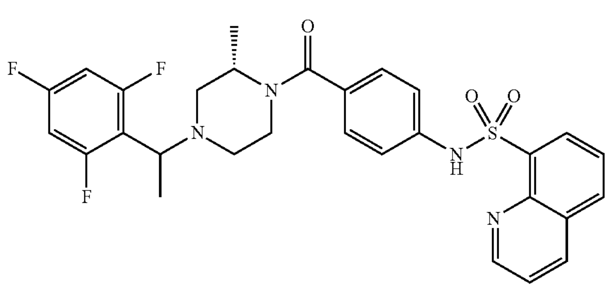 [SMILES: CC(c1c(F)cc(F)cc1F)N1CCN(C(=O)c2ccc(NS(=O)(=O)c3cccc4cccnc34)cc2)[C@@H](C)C1] |

TABLE 2-continued
| Cmpd # | Structure |
|---|---|
| 174 | 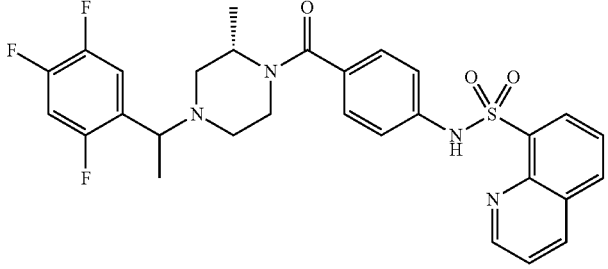 [SMILES: CC(c1cc(F)c(F)cc1F)N1CCN(C(=O)c2ccc(NS(=O)(=O)c3cccc4cccnc34)cc2)[C@@H](C)C1] |
| 179 | 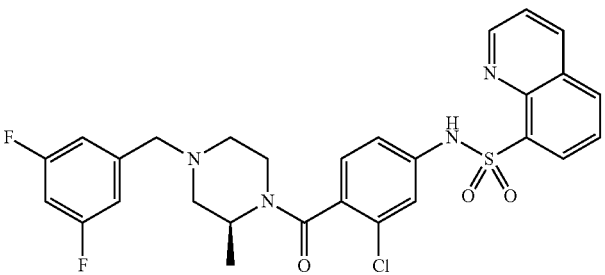 [SMILES: C[C@H]1CN(Cc2cc(F)cc(F)c2)CCN1C(=O)c1ccc(NS(=O)(=O)c2cccc3cccnc23)cc1Cl] |
| 209 | 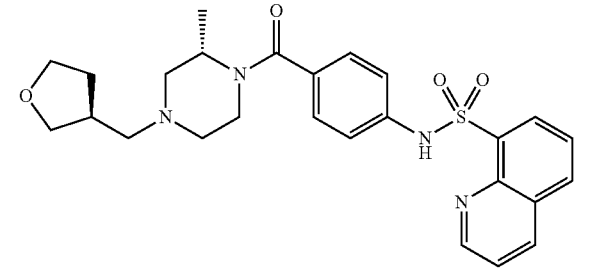 [SMILES: C[C@H]1CN(C[C@@H]2CCOC2)CCN1C(=O)c1ccc(NS(=O)(=O)c2cccc3cccnc23)cc1] |
| 210 | 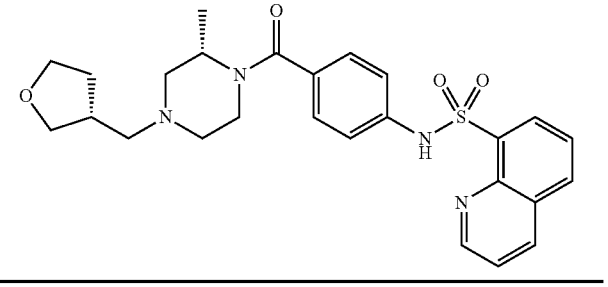 |
TABLE 3
| Cmpd # | Structure |
|---|---|
| 405 | 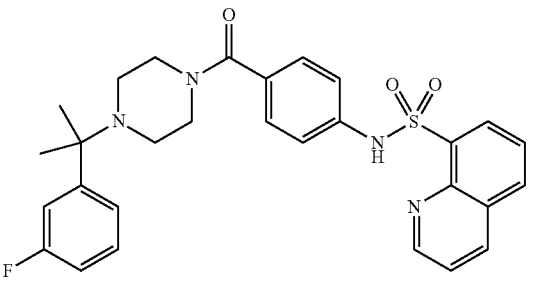 [SMILES: CC(C)(c1cccc(F)c1)N1CCN(C(=O)c2ccc(NS(=O)(=O)c3cccc4cccnc34)cc2)CC1] |

TABLE 3-continued

| Cmpd # | Structure |
|---|---|
| 364 | 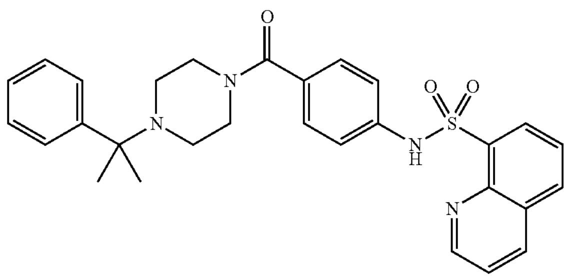 [SMILES: CC(C)(c1ccccc1)N1CCN(C(=O)c2ccc(NS(=O)(=O)c3cccc4cccnc34)cc2)CC1] |
| 372 | 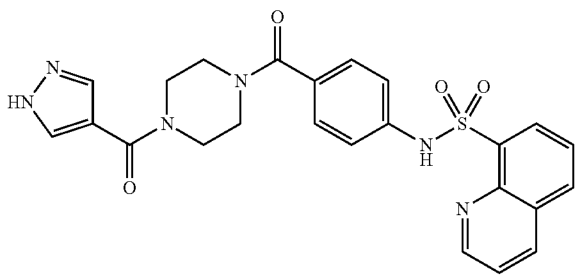 [SMILES: O=C(c1ccc(NS(=O)(=O)c2cccc3cccnc23)cc1)N1CCN(C(=O)c2cn[nH]c2)CC1] |
| 410 | 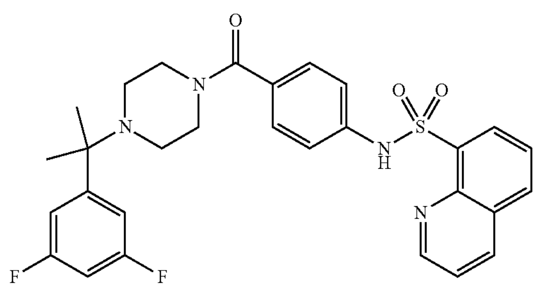 [SMILES: CC(C)(c1cc(F)cc(F)c1)N1CCN(C(=O)c2ccc(NS(=O)(=O)c3cccc4cccnc34)cc2)CC1] |
| 363 | 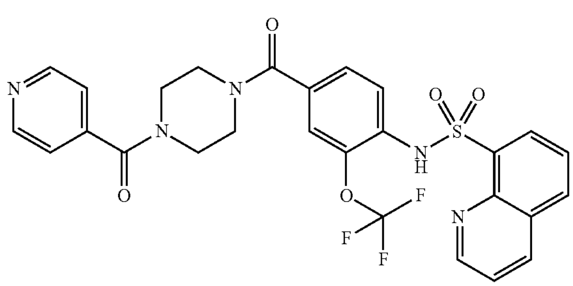 [SMILES: O=C(c1ccncc1)N1CCN(C(=O)c2ccc(NS(=O)(=O)c3cccc4cccnc34)c(OC(F)(F)F)c2)CC1] |
| 454 | 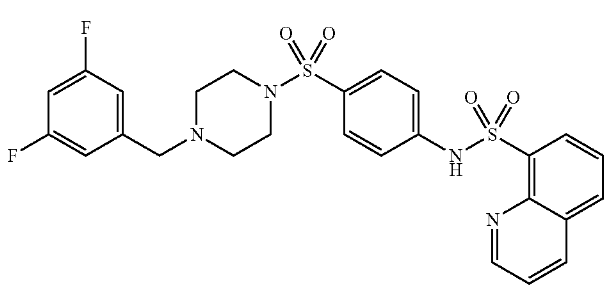 [SMILES: O=S(=O)(Nc1ccc(S(=O)(=O)N2CCN(Cc3cc(F)cc(F)c3)CC2)cc1)c1cccc2cccnc12] |

TABLE 3-continued

| Cmpd # | Structure |
|---|---|
| 456 | 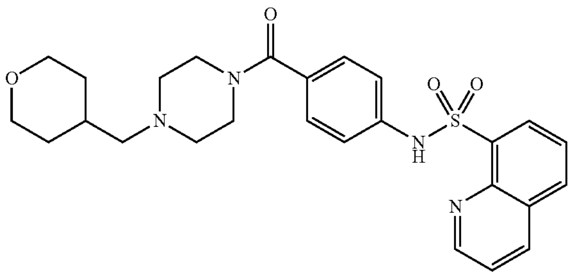 [SMILES: O=C(c1ccc(NS(=O)(=O)c2cccc3cccnc23)cc1)N1CCN(CC2CCOCC2)CC1] |
| 458 | 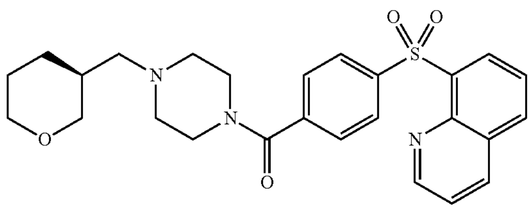 [SMILES: O=C(c1ccc(S(=O)(=O)c2cccc3cccnc23)cc1)N1CCN(C[C@@H]2CCCOC2)CC1] |
| 460 | 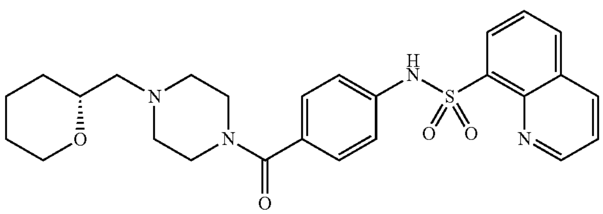 [SMILES: O=C(c1ccc(NS(=O)(=O)c2cccc3cccnc23)cc1)N1CCN(C[C@H]2CCCCO2)CC1] |
| 462 | 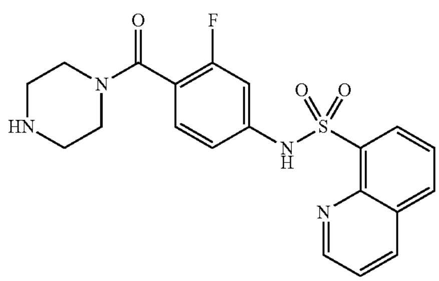 [SMILES: O=C(c1ccc(NS(=O)(=O)c2cccc3cccnc23)cc1F)N1CCNCC1] |
| 361 | 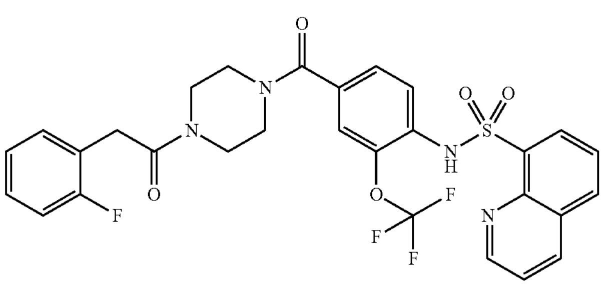 [SMILES: O=C(Cc1ccccc1F)N1CCN(C(=O)c2ccc(NS(=O)(=O)c3cccc4cccnc34)c(OC(F)(F)F)c2)CC1] |
| 455 | 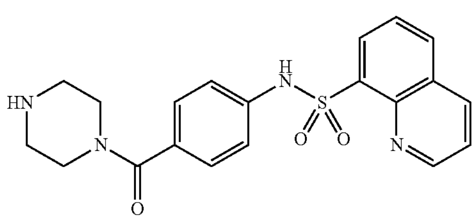 [SMILES: O=C(c1ccc(NS(=O)(=O)c2cccc3cccnc23)cc1)N1CCNCC1] |

TABLE 3-continued
| Cmpd # | Structure |
|---|---|
| 457 | 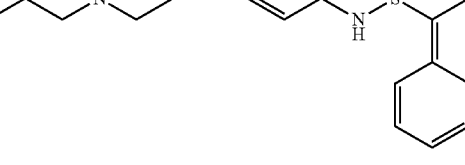 |
| 459 | 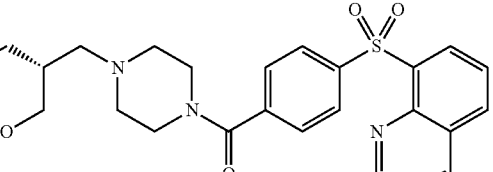 |
| 461 | 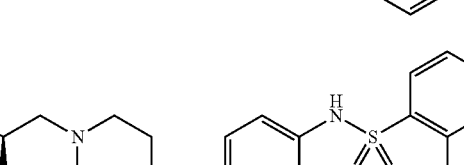 |
| 383 | 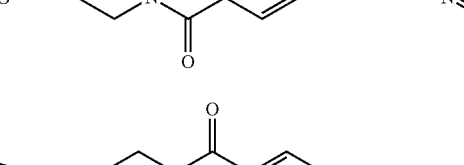 |
| 362 | 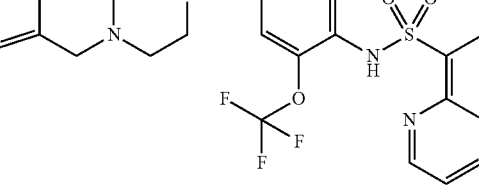 |
| 300 | 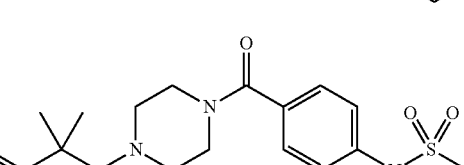 |

TABLE 3-continued

| Cmpd # | Structure |
|---|---|
| 360 | 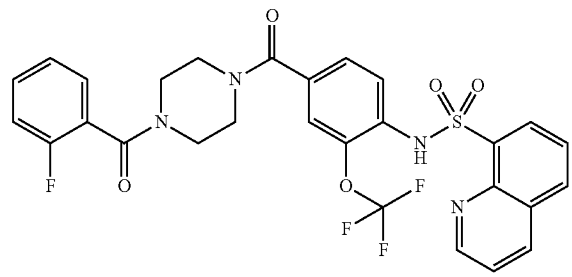 [SMILES: O=C(c1ccc(NS(=O)(=O)c2cccc3cccnc23)c(OC(F)(F)F)c1)N1CCN(C(=O)c2ccccc2F)CC1] |
| 326 | 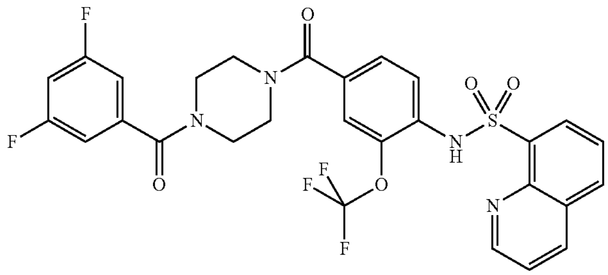 [SMILES: O=C(c1cc(F)cc(F)c1)N1CCN(C(=O)c2ccc(NS(=O)(=O)c3cccc4cccnc34)c(OC(F)(F)F)c2)CC1] |

The compounds described herein can be made using a variety of synthetic techniques as set forth in the Examples. As can be appreciated by the skilled artisan, methods of synthesizing additional compounds of the formulae herein will be evident to those of ordinary skill in the art by appropriate modifications of the exemplified schemes. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds provided herein may contain one or more asymmetric centers and thus occur as racemates and racemic mixtures, single enantiomers, individual diastereomers and diastereomeric mixtures. All such isomeric forms of these compounds are expressly included within the scope. Unless otherwise indicated when a compound is named or depicted by a structure without specifying the stereochemistry and has one or more chiral centers, it is understood to represent all possible stereoisomers of the compound. The compounds provided herewith may also contain linkages (e.g., carbon-carbon bonds) or substituents that can restrict bond rotation, e.g. restriction resulting from the presence of a ring or double bond. Accordingly, all cis/trans and E/Z isomers are expressly included.

The compounds provided herein (e.g. of Formula I) may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like. The compounds provided herein may also be represented in multiple tautomeric forms, in such instances, expressly includes all tautomeric forms of the compounds described herein, even though only a single tautomeric form may be represented (e.g., alkylation of a ring system may result in alkylation at multiple sites; all such reaction products are expressly included). All such isomeric forms of such compounds are expressly included.

The compounds provided herein include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

The compounds provided herein may be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Certain activator compounds useful as PKR wild type and/ or mutant activators are those that demonstrate specificity and activation of PKR enzyme (wild type and/or a mutant enzyme) in the absence of FBP to a level greater than that of 10, 15, 20, 25, 30, 35, 40, 45, 50, 55, 60, 65, 70, 75, 80, 85, 90, 95, 99, or 100% in the presence of FBP.

Methods of Treatment

In one embodiment, provided is a method for treating or preventing a disease, condition or disorder as described herein (e.g., treating) comprising administering a compound, a pharmaceutically acceptable salt of a compound or pharmaceutical composition comprising a compound described herein (e.g., a compound of formula (I), (I-a), (II), in Examples, Table 1 or Table 2).

The compounds and compositions described herein can be administered to cells in culture, e.g. in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second therapeutic agent to a subject, e.g., a patient, or application or administration of the compound to an isolated tissue or cell, e.g., cell line, from a subject, e.g., a patient, who has a disorder (e.g., a disorder as described herein), a symptom of a disorder, with the purpose to cure, heal, alleviate, relieve, alter, remedy, ameliorate, improve or affect the disorder, or one or more symptoms of the disorder.

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, the term "prevent" is defined as the application or administration of a compound, alone or in combination with, a second therapeutic agent to a subject, e.g., a patient, or application or administration of the compound to an isolated tissue or cell, e.g., cell line, from a subject, e.g., a patient, who has a predisposition toward a disorder, with the purpose to prevent the occurrence of at least one symptom of the disorder or to delay onset of at least one symptom of the disorder).

As used herein, an amount of a compound effective to prevent a disorder, or a "a prophylactically effective amount" of the compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound provided herewith, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions provided herewith may be administered orally, parenterally, by inhalation spray, topically, rectally, nasally, buccally, vaginally or via an implanted reservoir, preferably by oral administration or administration by injection. The pharmaceutical compositions provided herewith may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions provided herewith may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions provided herewith may also be administered in the form of suppositories for rectal administration. These compositions can be prepared by mixing a compound provided herewith with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions provided herewith may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions provided herewith comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with the compounds provided herewith in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination provided herewith may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Patient Selection and Monitoring

The compounds described herein can activate mutant PKRs. Accordingly, a patient and/or subject can be selected for treatment using a compound described herein by first evaluating the patient and/or subject to determine whether the subject carries a mutation in PKR (for examples, one of the mutations as described herein), and if the subject is determined to be carrying a mutation in PKR thus is in need of activation of the activity of the mutant PKR, then optionally administering to the subject a compound described herein. A subject can be evaluated as carrying a mutation in PKR using methods known in the art.

EXAMPLES

In the synthesis examples set forth below, certain compounds have specified stereochemistry at one or more positions. These compounds were prepared using the indicated scheme either using the appropriate chirally pure reagents or were separated from a racemate produced by the indicated scheme using an appropriate chiral separation column, such as a Chiralpak AD-H column (250×4.6 mm) 5 μM column, eluting with 0.05% diethyl amine in hexane/isopropanol (75: 25 v/v) with a flow rate of 2 ml/min with absorbance monitored at 220 nm. The chiral HPLC elution conditions set forth above can be easily modified by those of skill in the art to optimize separation for various chiral compounds of this invention.

Example 1

Preparation of Compounds of Formula Ic

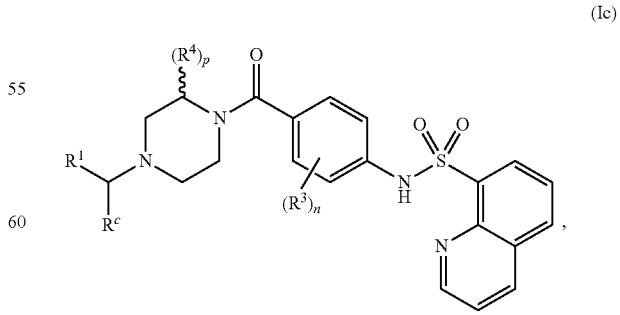

wherein $R^1$ is aryl or cyclopropyl; $R^c$ is methyl or $CF_3$; $R^3$ is alkyl and n is 0 or 1.

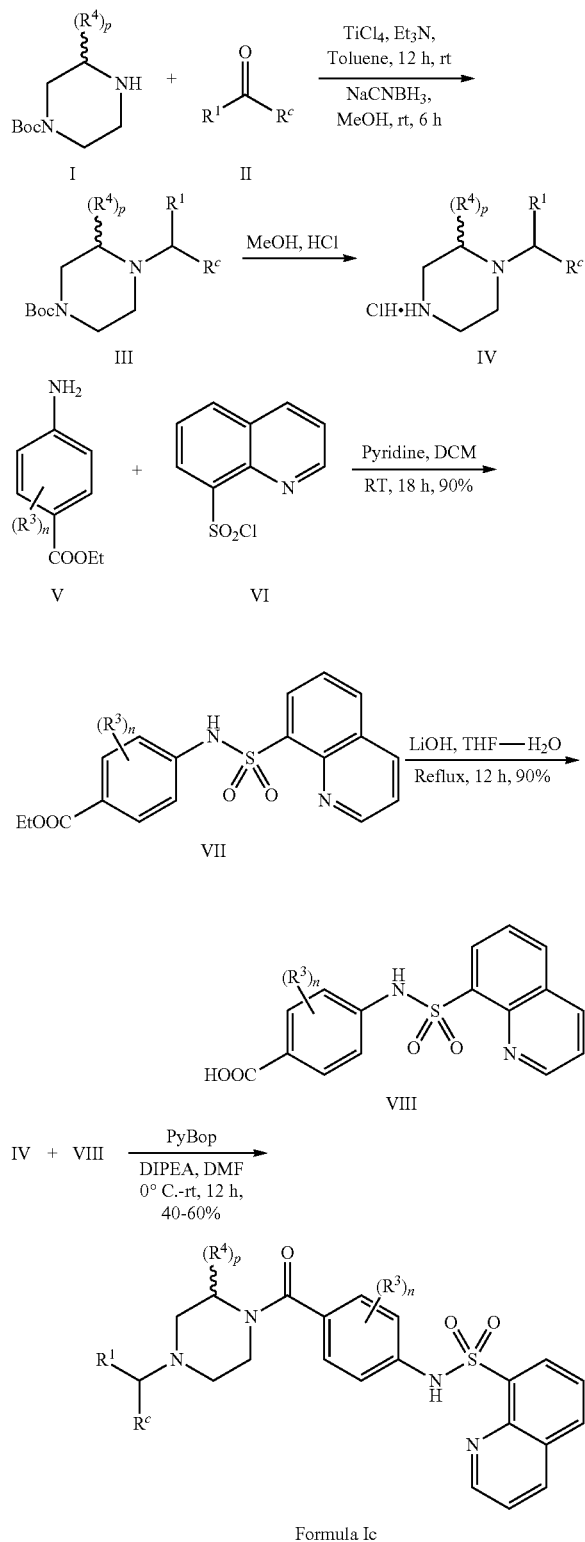

Formula Ic $R^1$ = Aryl, Cyclopropyl
$R^c$ = Me, $CF_3$
$R^4$ = Me, Et, isopropyl
p = 0 or 1

Synthesis of Intermediate IV

To a stirred solution of aryl ketones II (17 mmol) in 10 ml of dichloromethane were added optionally substituted tert-butyl piperazine-1-carboxylate I (16 mmol), $Et_3N$ (48 mmol) and 1 M $TiCl_4$ (8 mmol) at room temperature, followed by stiffing the reaction mixture at room temperature for 18 h. To the reaction mixture was added a solution of $NaBH_3CN$ (48 mmol) in MeOH (5 ml) at room temperature, followed by stirring the reaction mixture at room temperature for 6 h. Ethyl acetate and saturated aqueous $NaHCO_3$ solution were added to the reaction mixture. The insoluble material obtained was filtered off using celite. The ethyl acetate layer was separated, washed with brine, dried over anhydrous $MgSO_4$ and filtered. The filtrate was concentrated in vacuum and the crude compound was taken for the next step without purification. The compound obtained from this step was dissolved in 10 ml of Methanolic HCl and stirred the reaction mixture for 2 h at room temperature. The mixture was concentrated under vacuum to leave intermediate IV as solid. The obtained solid was neutralized with base to get a free base which was used for the next step (45-60% over two steps).

Synthesis of ethyl 4-(quinoline-8-sulfonamido)benzoate (VII)

To a solution of amine V (16 gm, 96.85 mmol) in a mixture (1:1) of DCM and pyridine, sulfonyl chloride VI (27.56 gm, 121.07 mmol) was added at room temperature under $N_2$ atmosphere. The resulting mixture was allowed to stir for 16 hrs. After completion of reaction, the crude mixture was diluted with DCM, washed with water followed by 1N HCl. The organic layer was then dried over $Na_2SO_4$ and concentrated under reduced pressure to afford intermediate VII in 98% yields (34 gm).

Synthesis of 4-(quinoline-8-sulfonamido)benzoic acid (VIII)

To a solution of sulfonamide VII (34 gm, 95.5 mmol) in THF and water (1:1), LiOH (20 gm, 47.66 mmol) was added and the resulting mixture was allowed to stir at 80° C. overnight. After completion of reaction, the crude mixture was washed with EtOAc. The aqueous layer was acidified with citric acid and filtered. Thus obtained solid was washed with $Et_2O$ and azeotroped by toluene, under reduced pressure to afford acid VIII (30 gm, 95.8% yield) which was taken forward for the next step without further purification.

Synthesis of Compounds of Formula I According to Scheme 1

To a solution of acid VIII (1 mmol) in DMF (2 ml), PyBoP (Benzotriazole-1-yl-oxy-tris-(dimethylamino)-phosphonium hexafluorophosphate) (0.78 gm, 1.5 mmol) was added at 0° C. and allowed to stir for 5 minutes. Then amine IV (1 mmol) was added to the reaction mixture at the same temperature under $N_2$ atmosphere and stirred overnight at room temperature. After completion of reaction, mixture was diluted with water and extracted with EtOAc. The organic layer was washed with water, dried over $Na_2SO_4$, and evaporated under reduced pressure. The residue was purified by column chromatography (silica gel, 60-120 mesh; MeOH-DCM, 2:8) to afford product IX in 40-66% yield.

The above procedure was used to produce the following compounds of Formula Ic using the appropriate aryl ketone II and the appropriate optionally substituted tert-butyl piperazine-1-carboxylate I.

(S)—N-(4-(4-(1-phenylethyl)piperazine-1-carbonyl)phenyl)quinoline-8-sulfonamide (Compound 387)

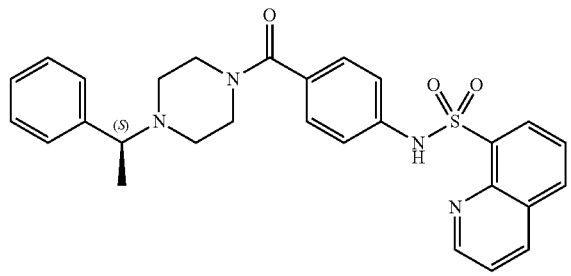

¹H NMR (400 MHz, CDCl₃) δ: 1.3 (d, 3H), 2.2-2.4 (m, 4H), 3.2-3.4 (m, 2H), 3.5 (m, 1H), 3.6-3.8 (m, 2H), 5.3 (s, 1H), 7.0-7.4 (m, 8H), 7.5-7.65 (m, 2H), 8.0 (d, 1H), 8.38 (m, 2H), 8.55 (s, 1H), 9.0 (m, 1H); HPLC Purity: 99.31%; Mass (M+1): 477.40.

N-(4-(4-(1-(3,5-difluorophenyl)ethyl)piperazine-1-carbonyl)phenyl)quinoline-8-sulfonamide (Compound 331)

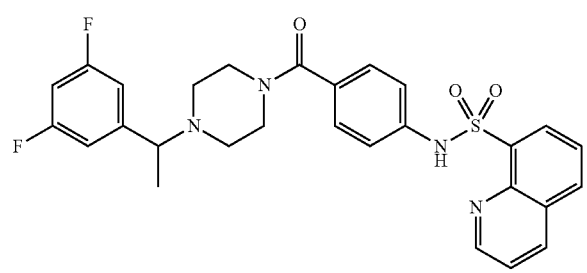

¹H NMR (400 MHz, DMSOd₆) δ: 1.3 (d, 3H), 2.2-2.4 (m, 4H), 3.2-3.5 (m, 2H), 3.6 (m, 1H), 7.0 (m, 4H), 7.2-7.4 (m, 3H), 7.6 (m, 2H), 8.2-8.4 (m, 3H), 9.1 (m, 1H), 10.2 (bs, 1H); HPLC Purity: 91.96%; Mass (M+1): 537.10.

N-(4-(4-(1-(3-chloro-4-fluorophenyl)ethyl)piperazine-1-carbonyl)phenyl)quinoline-8-sulfonamide (Compound 332)

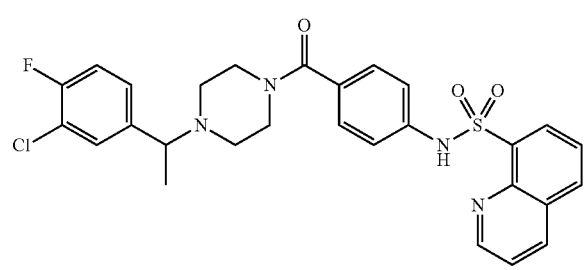 [SMILES: CC(c1ccc(F)c(Cl)c1)N1CCN(C(=O)c2ccc(NS(=O)(=O)c3cccc4cccnc34)cc2)CC1]

¹H NMR (400 MHz, DMSOd₆) δ: 1.2 (d, 3H), 1.3 (m, 1H), 2.2-2.5 (m, 6H), 3.1-3.4 (m, 2H), 7.0 (m, 4H), 7.2-7.4 (m, 3H), 7.8 (m, 2H), 8.2-8.4 (m, 3H), 9.1 (m, 1H), 10.2 (bs, 1H); HPLC Purity: 93.02%; Mass (M+1): 575.10.

N-(4-(4-(1-(2,3,4-trifluorophenyl)ethyl)piperazine-1-carbonyl)phenyl)quinoline-8-sulfonamide (Compound 403)

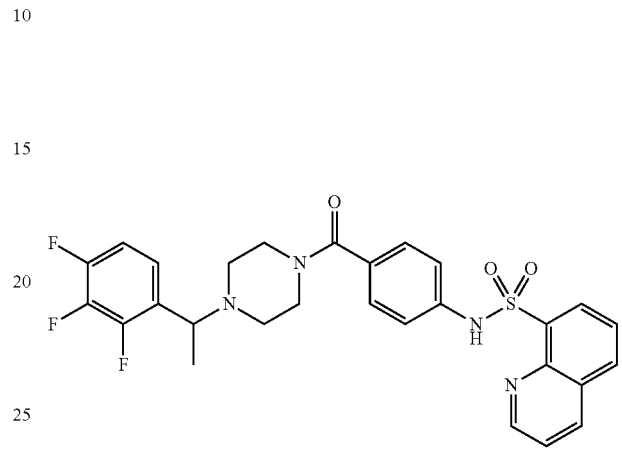

¹H NMR (400 MHz, CDCl₃) δ: 1.2 (d, 3H), 1.4 (m, 1H), 2.2-2.7 (m, 4H), 3.0-3.6 (m, 4H), 7.0-7.25 (m, 6H), 7.55-7.6 (m, 2H), 8.2-8.25 (d, 1H), 8.4 (m, 1H), 8.5-8.55 (d, 1H), 9.1 (m, 1H); HPLC Purity: 99.46%; Mass (M+1): 555.45.

N-(4-(4-(1-(2,3,6-trifluorophenyl)ethyl)piperazine-1-carbonyl)phenyl)quinoline-8-sulfonamide (Compound 404)

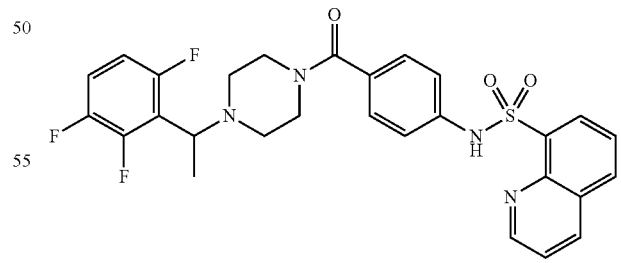

¹H NMR (400 MHz, DMSO-d₆) δ: 1.35 (d, 3H), 1.4 (m, 1H), 2.2-2.7 (m, 4H), 3.0-3.6 (m, 4H), 7.0-7.25 (m, 5H), 7.4

(m, 1H), 7.78-7.8 (m, 2), 8.25-8.3 (d, 1H), 8.4 (m, 1H), 8.5-8.55 (d, 1H), 9.1 (m, 1H), 10.4 (s, 1H); HPLC Purity: 98.97%; Mass (M+1): 555.1.

N-(4-(4-(1-(2,6-difluorophenyl)ethyl)piperazine-1-carbonyl)phenyl)quinoline-8-sulfonamide (Compound 357)

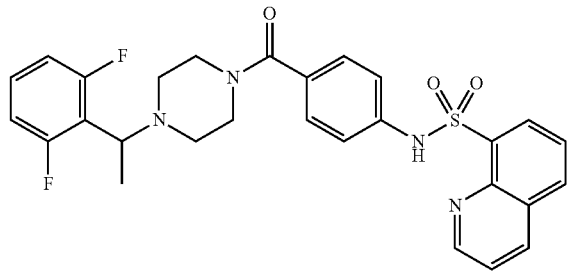 [SMILES: CC(c1c(F)cccc1F)N1CCN(C(=O)c2ccc(NS(=O)(=O)c3cccc4cccnc34)cc2)CC1]

$^1$H NMR (400 MHz, CDCl$_3$) δ: 1.3 (s, 3H), 2.2-2.5 (m, 4H), 3.0-3.4 (m, 2H), 3.5-3.8 (m, 2H), 7.0-7.2 (m, 6H), 7.4 (m, 1H), 8.2-8.6 (m, 3H), 8.3 (m, 2H), 8.6 (m, 1H), 9.0 (m, 1H) 10.4 (s, 1H); HPLC Purity: 98.29%; Mass (M+1): 537.20.

N-(4-(4-(1-(pyridin-3-yl)ethyl)piperazine-1-carbonyl)phenyl)quinoline-8-sulfonamide (Compound 370)

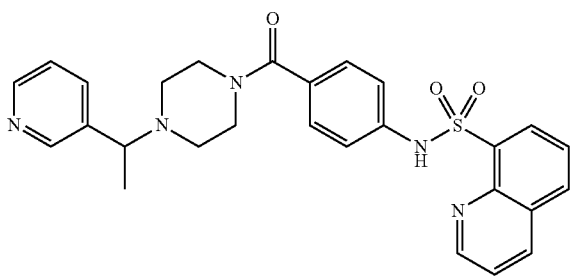 [SMILES: CC(c1cccnc1)N1CCN(C(=O)c2ccc(NS(=O)(=O)c3cccc4cccnc34)cc2)CC1]

$^1$H NMR (400 MHz, DMSO-d$_6$) δ: 1.3 (d, 3H), 2.2-2.2.4 (m, 4H), 3.2-3.6 (m, 4H), 3.5 (m, 1H), 7.1 (m, 4H), 7.3 (m, 1H), 7.7 (m, 3H), 8.3-8.5 (m, 5H), 9.0 (m, 1H), 10.0 (s, 1H); HPLC Purity: 98.12%; Mass (M+1): 502.40.

N-(4-(4-(1-(2,4,5-trifluorophenyl)ethyl)piperazine-1-carbonyl)phenyl)quinoline-8-sulfonamide (Compound 395)

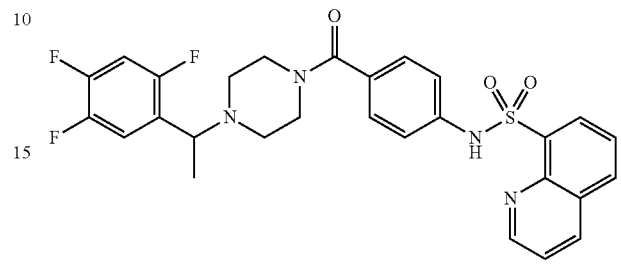

$^1$H NMR (400 MHz, DMSO-d$_6$) δ: 1.4 (d, 3H), 2.2-2.4 (m, 2H), 3.0-3.8 (m, 4H), 3.90 (q, 1H), 7.0-7.2 (m, 6H), 7.6-7.69 (m, 2H), 8.2-8.6 (m, 3H), 9.0 (m, 1H), 10.46 (bs, 1H); HPLC Purity: 96.86%; Mass (M+1): 555.50.

N-(4-(4-(1-(2,3,5-trifluorophenyl)ethyl)piperazine-1-carbonyl)phenyl)quinoline-8-sulfonamide (Compound 396)

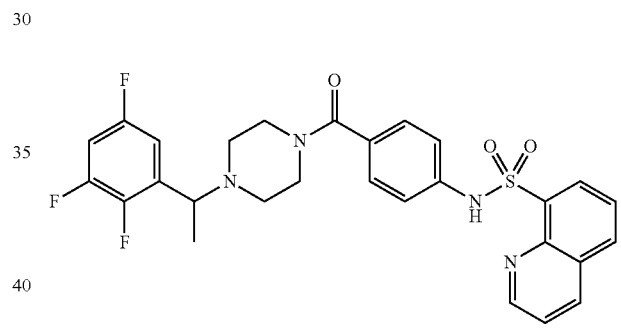

$^1$H NMR (400 MHz, DMSO-d$_6$) δ: 1.25 (d, 3H), 2.2-2.4 (m, 4H), 3.1-3.7 (m, 4H), 3.90 (q, 1H), 7.0-7.2 (m, 5H), 7.4 (m, 1H), 7.6-7.69 (m, 2H), 8.2-8.6 (m, 3H), 9.0 (m, 1H), 10.46 (bs, 1H); HPLC Purity: 96.86%; Mass (M+1): 555.50.

N-(4-(4-(1-(2,4,6-trifluorophenyl)ethyl)piperazine-1-carbonyl)phenyl)quinoline-8-sulfonamide (Compound 397)

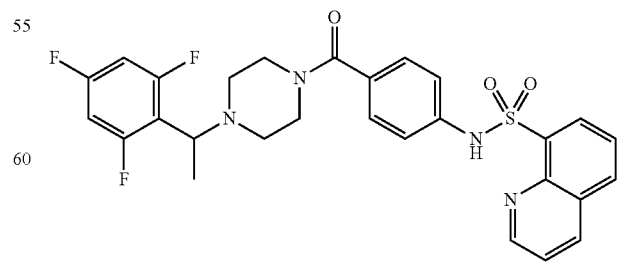

$^1$H NMR (400 MHz, DMSO-d$_6$) δ: 1.4 (s, 3H), 2.0-2.4 (m, 4H), 3.0-3.6 (m, 2H), 3.90 (m, 1H), 7.0-7.2 (m, 6H), 7.6-7.69

(m, 2H), 8.2-8.6 (m, 3H), 9.0 (m, 1H), 10.46 (bs, 1H); HPLC Purity: 99.97%; Mass (M+1): 555.50.

N-(4-(4-(1-(3,4,5-trifluorophenyl)ethyl)piperazine-1-carbonyl)phenyl)quinoline-8-sulfonamide (Compound 398)

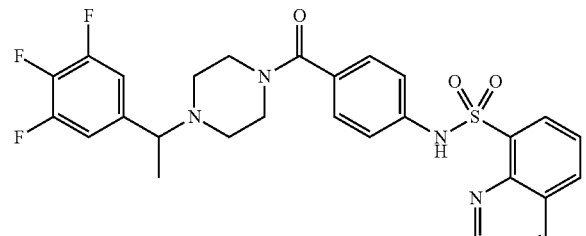

¹H NMR (400 MHz, DMSO-d₆) δ: 1.4 (s, 3H), 2.0-2.4 (m, 4H), 3.0-3.6 (m, 4H), 3.90 (m, 1H), 7.0-7.2 (m, 6H), 7.6-7.69 (m, 2H), 8.2-8.6 (m, 3H), 9.0 (m, 1H), 10.46 (bs, 1H); HPLC Purity: 95.10%; Mass (M+1): 555.45.

N-(4-(4-(1-cyclopropylethyl)piperazine-1-carbonyl)phenyl)quinoline-8-sulfonamide (Compound 442)

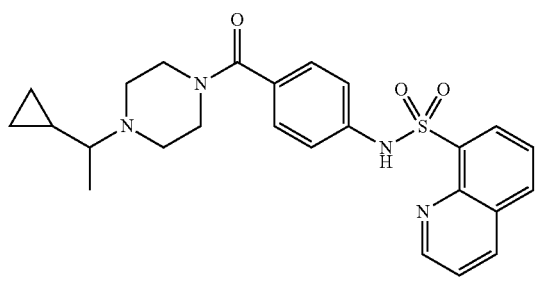

¹H NMR (400 MHz, DMSO-d₆) δ: 1.6 (d, 3H), 2.1-2.2 (m, 2H), 2.21-2.4 (m, 4H), 2.99-3.6 (m, 8H), 7.0-7.2 (m, 4H), 7.6-7.8 (m, 2H), 8.2-8.6 (m, 3H), 9.1-9.2 (m, 1H) 10.41 (bs, 1H); HPLC Purity: 99.49%; Mass (M+1): 465.3.

(R)—N-(4-(4-(1-phenylethyl)piperazine-1-carbonyl)phenyl)quinoline-8-sulfonamide (Compound 388)

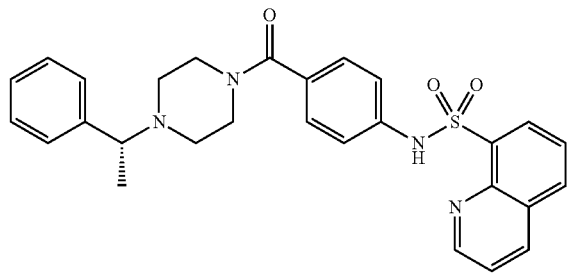 [SMILES: C[C@H](c1ccccc1)N1CCN(C(=O)c2ccc(NS(=O)(=O)c3cccc4cccnc34)cc2)CC1]

¹H NMR (400 MHz, CDCl₃) δ: 1.3 (d, 3H), 2.2-2.4 (m, 4H), 3.2-3.8 (m, 4H), 3.5 (m, 1H), 5.3 (s, 1H), 7.0-7.4 (m, 8H), 7.55-7.65 (m, 2H), 8.0 (d, 1H), 8.38-8.4 (m, 2H), 8.55 (s, 1H), 9.0 (m, 1H); HPLC Purity: 98.51%; Mass (M+1): 501.20.

N-(4-(4-(2,2,2-trifluoro-1-(4-fluorophenyl)ethyl)piperazine-1-carbonyl)phenyl)quinoline-8-sulfonamide (Compound 351)

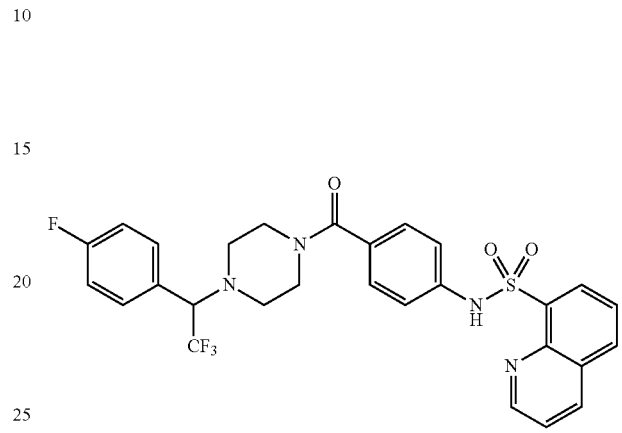

¹H NMR (400 MHz, CDCl₃) δ: 2.2 (m, 4H), 3.2 (m, 2H), 3.7 (m, 2H), 4.7 (m, 1H), 7.0 (m, 4H), 7.4-7.6 (m, 4H), 7.7 (m, 2H), 8.2-8.4 (m, 3H), 9.0 (m, 1H); HPLC Purity: 97.49%; Mass (M+1): 573.15.

N-(4-(4-(2,2,2-trifluoro-1-phenylethyl)piperazine-1-carbonyl)phenyl)quinoline-8-sulfonamide (Compound 358)

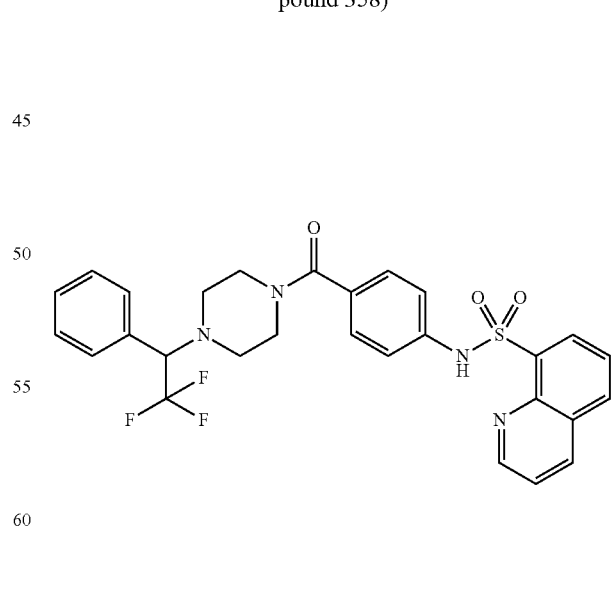

¹H NMR (400 MHz, CDCl₃) δ: 2.2-2.5 (m, 2H), 3.0-3.4 (m, 2H), 3.5-3.8 (m, 4H), 4.6 (m, 1H), 7.0 (m, 4H), 7.4 (m,

5H), 7.9 (m, 2H), 8.2-8.6 (m, 3H), 9.0 (m, 1H) 10.4 (s, 1H); HPLC Purity: 97.65%; Mass (M+1): 555.15.

N-(4-(4-(1-(2,4-dimethoxyphenyl)ethyl)piperazine-1-carbonyl)-2-(trifluoromethoxy)phenyl)quinoline-8-sulfonamide (Compound 333)

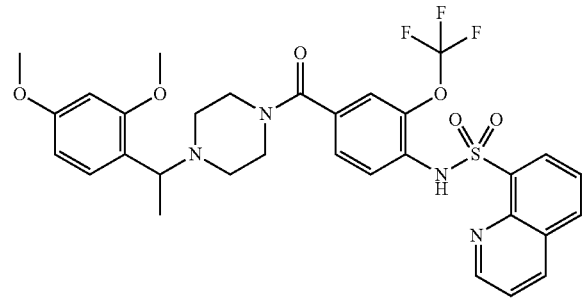 [SMILES: COc1ccc(C(C)N2CCN(C(=O)c3ccc(NS(=O)(=O)c4cccc5cccnc45)c(OC(F)(F)F)c3)CC2)c(OC)c1]

¹H NMR (400 MHz, DMSOd₆) δ: 2.2-2.5 (m, 4H), 3.2-3.6 (m, 4H), 3.8 (m, 6H), 6.5 (m, 2H), 7.2 (m, 3H), 7.5 (m, 1H), 7.8 (m, 2H), 8.3 (m, 2H), 8.6 (m, 1H), 9.0 (m, 1H), 10.0 (bs, 1H); HPLC Purity: 98.57%; Mass (M+1): 631.60.

N-(4-((2R)-4-(1-(4-fluorophenyl)ethyl)-2-methylpiperazine-1-carbonyl)phenyl)quinoline-8-sulfonamide (Compound 133)

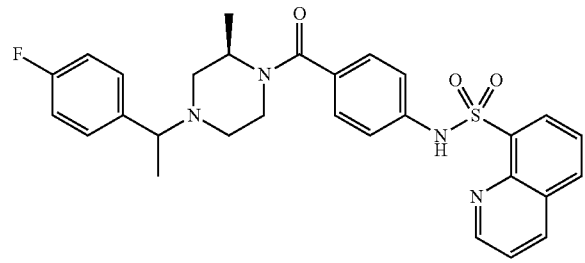 [SMILES: CC(c1ccc(F)cc1)N1CCN(C(=O)c2ccc(NS(=O)(=O)c3cccc4cccnc34)cc2)[C@H](C)C1]

¹H NMR (400 MHz, DMSO-d₆) δ: 0.9 (d, 3H), 1.0-1.12 (m, 1H), 1.13-1.3 (d, 3H), 1.4 (m, 1H), 1.99-2.1 (m, 2H), 2.8-3.6 (m, 4H), 7.0-7.2 (m, 5H), 7.22-7.4 (m, 2H), 7.6-7.8 (d, 2H), 8.25 (d, 1H), 8.4-8.5 (m, 2H), 9.1 (m, 1H), 10.4 (s, 1H); HPLC Purity: 99.93%; Mass (M+1): 533.55.

N-(4-((2R)-4-(1-(3,5-difluorophenyl)ethyl)-2-methylpiperazine-1-carbonyl)phenyl)quinoline-8-sulfonamide (Compound 135)

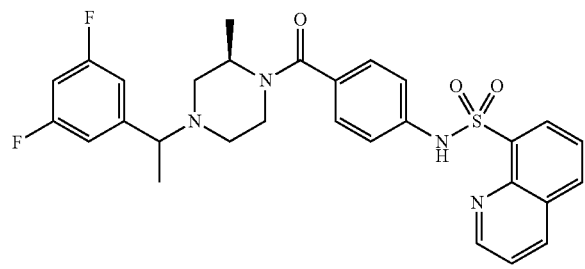 [SMILES: CC(c1cc(F)cc(F)c1)N1CCN(C(=O)c2ccc(NS(=O)(=O)c3cccc4cccnc34)cc2)[C@H](C)C1]

¹H NMR (400 MHz, DMSO-d₆) δ: 1.1-1.21 (d, 6H), 1.82-2.1 (m, 2H), 2.6 (m, 1H), 2.8-3.2 (m, 2H), 3.8-4.0 (m, 3H), 7.0-7.2 (m, 7H), 7.6-7.8 (d, 2H), 8.25 (d, 1H), 8.4-8.5 (m, 2H), 9.1 (m, 1H), 10.4 (s, 1H); HPLC Purity: 99.95%; Mass (M+1): 551.3.

N-(4-((2R)-4-(1-(4-chloro-2-fluorophenyl)ethyl)-2-methylpiperazine-1-carbonyl)phenyl)quinoline-8-sulfonamide (Compound 157)

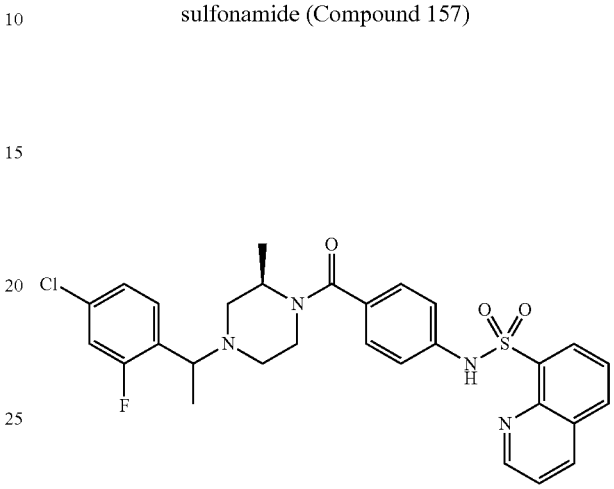

¹H NMR (400 MHz, DMSO-d₆) δ: 1.21 (d, 6H), 1.23-1.3 (m, 1H), 1.8-2.1 (m, 3H), 2.6-2.8 (m, 2H), 3.0-3.4 (m, 3H), 7.0-7.2 (m, 4H), 7.4-7.7 (m, 6H), 8.0 (d, 1H), 8.3-8.6 (m, 2H), 9.1 (m, 1H), 10.4 (s, 1H); HPLC Purity: 99.65%; Mass (M+1): 567.3.

N-(4-((2R)-2-methyl-4-(1-(3,4,5-trifluorophenyl)ethyl)piperazine-1-carbonyl)phenyl)quinoline-8-sulfonamide (Compound 158)

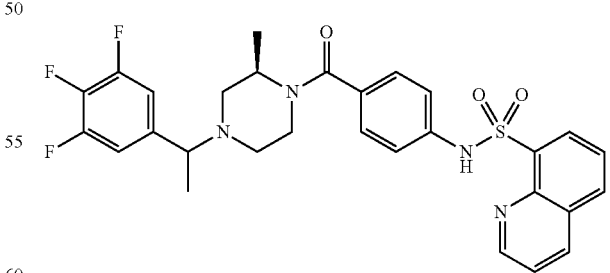

¹H NMR (400 MHz, DMSO-d₆) δ: 1.21 (d, 6H), 1.8-2.1 (m, 2H), 2.4-2.45 (m, 1H), 2.6-2.8 (m, 2H), 2.9-3.25 (m, 2H), 3.5-3.6 (m, 1H), 7.0-7.2 (m, 6H), 7.4-7.7 (m, 2H), 8.0 (d, 1H), 8.3-8.6 (m, 2H), 9.1 (m, 1H), 10.4 (s, 1H); HPLC Purity: 99.18%; Mass (M+1): 569.5.

N-(4-((2R)-4-(1-(2,6-difluorophenyl)ethyl)-2-methylpiperazine-1-carbonyl)phenyl)quinoline-8-sulfonamide (Compound 159)

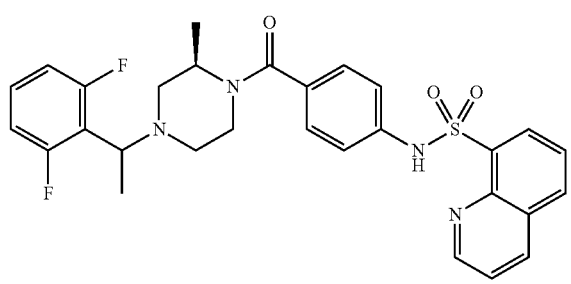 [SMILES: CC(c1c(F)cccc1F)N1CCN(C(=O)c2ccc(NS(=O)(=O)c3cccc4cccnc34)cc2)[C@H](C)C1]

¹H NMR (400 MHz, DMSO-d₆) δ: 1.1 (d, 3H), 1.24 (d, 3H), 1.8-2.0 (m, 2H), 2.6-2.8 (m, 1H), 3.4-3.6 (m, 3H), 3.8-4.0 (m, 2H), 7.0-7.2 (m, 5H), 7.4-7.7 (m, 4H), 8.0 (d, 1H), 8.3-8.6 (m, 2H), 9.1 (m, 1H), 10.4 (s, 1H); HPLC Purity: 99.18%; Mass (M+1): 569.5.

N-(4-((2R)-4-(1-(2,4-difluorophenyl)ethyl)-2-methylpiperazine-1-carbonyl)phenyl)quinoline-8-sulfonamide (Compound 160)

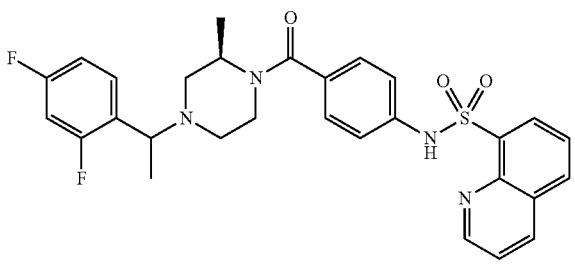 [SMILES: CC(c1ccc(F)cc1F)N1CCN(C(=O)c2ccc(NS(=O)(=O)c3cccc4cccnc34)cc2)[C@H](C)C1]

¹H NMR (400 MHz, DMSO-d₆) δ: 1.1 (d, 3H), 1.15 (d, 3H), 1.8-2.0 (m, 2H), 2.6-3.0 (m, 4H), 3.4-3.6 (m, 2H), 7.0-

7.4 (m, 5H), 7.41-7.7 (m, 3H), 8.0 (d, 1H), 8.3-8.6 (m, 2H), 9.1 (m, 1H), 10.4 (s, 1H); HPLC Purity: 99.18%; Mass (M+1): 551.3

N-(4-((2S)-4-(1-(3,5-difluorophenyl)ethyl)-2-ethylpiperazine-1-carbonyl)phenyl)quinoline-8-sulfonamide (Compound 161)

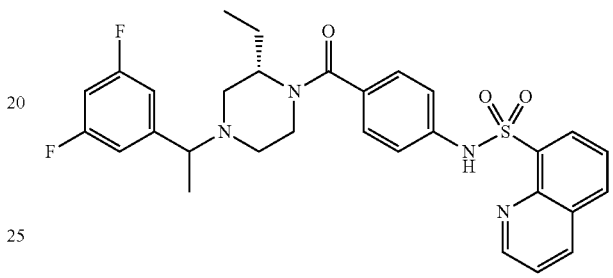

¹H NMR (400 MHz, DMSO-d₆) δ: 0.8 (t, 3H), 1.19 (d, 3H), 1.2 (m, 1H), 1.6-1.8 (m, 2H), 2.0-2.4 (m, 2H), 2.8-3.7 (m, 5H), 7.0-7.4 (m, 7H), 7.6-7.7 (m, 2H), 8.0 (d, 1H), 8.3-8.6 (m, 2H), 9.1 (m, 1H), 10.4 (s, 1H); HPLC Purity: 97.51%; Mass (M+1): 565.3

N-(4-((2S)-2-ethyl-4-(1-(3,4,5-trifluorophenyl)ethyl)piperazine-1-carbonyl)phenyl)quinoline-8-sulfonamide (Compound 162)

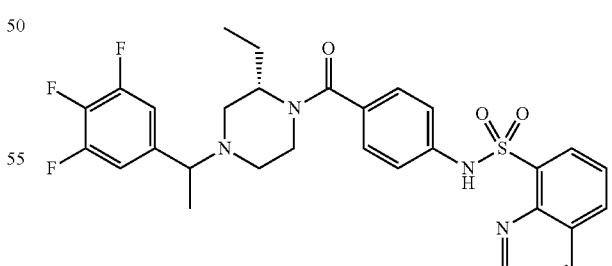

¹H NMR (400 MHz, DMSO-d₆) δ: 0.8 (t, 3H), 1.19 (d, 3H), 1.6-1.8 (m, 2H), 2.0-2.4 (m, 2H), 2.8-3.2 (m, 2H), 3.8-4.0 (m,

4H), 7.0-7.4 (m, 6H), 7.6-7.7 (m, 2H), 8.0 (d, 1H), 8.3-8.6 (m, 2H), 9.1 (m, 1H), 10.4 (s, 1H); HPLC Purity: 99.86%; Mass (M+1): 583.3

Example 2

Preparation of Compounds of Formula Id

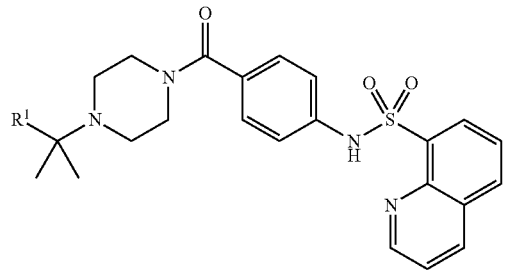

wherein $R^1$ is cyclopropyl or aryl.

Scheme 2

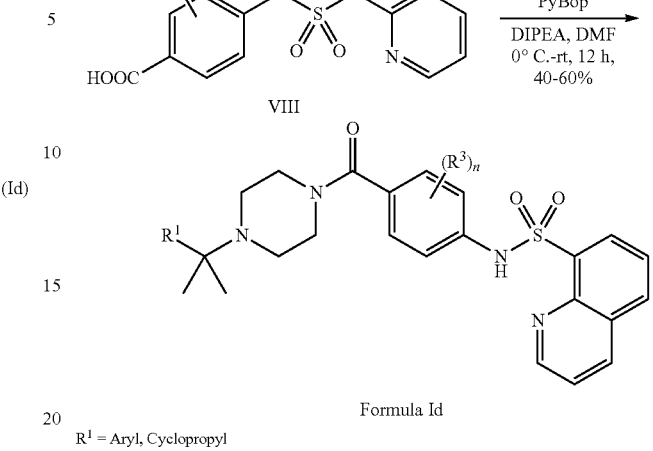

Formula Id $R^1$ = Aryl, Cyclopropyl

Synthesis of Intermediate XI

A solution of Aryl/Cycloalkyl methyl ketone X (1.6 mmol) in dry THF (10 ml) was cooled to −70° C. in $N_2$ atmosphere. Methylmagnesium bromide (8 mmol) in THF was added slowly at −70° C. and the reaction mixture stirred for 1 h under $N_2$ atmosphere. The reaction mixture was quenched with saturated $NH_4Cl$ and diluted with Ethyl acetate (20 ml) and Brine (20 ml). The organic layer was washed with water, dried over $Na_2SO_4$, and evaporated under reduced pressure. The residue was purified by column chromatography (silica gel, 60-120 mesh; EA-Hexane, 2:8) to afford product XI as an oil in 60-72% yield.

Synthesis of Intermediate XII

To a solution of Gemdimethyl alcohol XI (1.1 mmol) in dry DCM (10 ml) was added sodium azide (3.5 mmol) at room temperature under $N_2$ atmosphere. The reaction mixture was cooled to 0° C. and was added a solution of TFA (3 mmol) in DCM (1 ml). The reaction bath was allowed to warm up to room temperature and stirred further for 1 h at room temperature. The white precipitate formed was filtered and concentrated the solvent to get the desired azide which was used for the next step without purification (Yield 50-55%).

Synthesis of intermediate XIII

To a stirred solution of azide (1 mmol) in MeOH (5 ml) under $H_2$ atmosphere, was added 10% Pd/C (0.1 mmol) at room temperature. The reaction mixture stirred further for 3 h at room temperature and filtered through celite. The filtrate concentrated under reduced pressure to leave the amine which was used for the next step without purification (Yield 60%).

Synthesis of Intermediate XV

Tosyl Chloride (22 g, 0.114 moles, 3 eq) was dissolved in DCM (40 ml) at 0° C. with stirring. To this solution was added a solution of diethanol amine XIV (4 g, 0.038 moles, 1 eq) and triethylamine (17 ml, 0.114 moles, 3 eq) in DCM (20 ml) at 0° C. Stirring was continued for overnight at room temperature after the addition was completed. The precipitate generated from the reaction was filtered and the solutions was washed with water, dilute HCl, saturated NaHCO$_3$ and brine in turn, and dried (Na$_2$SO$_4$). The organic phase was concentrated under reduced pressure and purified by column chromatography (silica gel, 60-120 mess, 20% ethyl acetate in hexane) to give the intermediate XV as a white solid (9.8 g, 46%). $^1$H NMR (400 MHz, CDCl$_3$) 2.38 (s, 3H), 2.43 (s, 6H), 3.32-3.36 (m, 4H), 4.05-4.16 (m, 4H), 7.21-7.38 (m, 6H), 7.61-7.81 (m, 6H).

Synthesis of Intermediate XVI

To a solution of Tritosylate XV (1 g, 0.00176 moles, 1 eq) in 6 ml of DMF was added NaBr (0.93 g, 0.009 moles, 5 eq). The resulting suspension was stirred in an oil bath at 120° C. for 4 h. After cooling to room temperature, the reaction mixture was concentrated to about 2 ml. The viscous milky product was poured into rapidly stirred mixture of ice-water (30 ml) and extracted with ethyl acetate (30 ml). The organic phase was dried (Na$_2$SO$_4$) and concentrated under reduced pressure. The crude product was purified by column chromatography (silica gel, 60-120 mess, 10% ethyl acetate in hexane) to leave the product XVI as a pale yellow liquid (0.34 g, 51%) $^1$H NMR (400 MHz, CDCl$_3$) 2.41 (s, 3H), 3.44 (s, 8H), 7.38 (d, 4H), 7.76 (d, 4H)

Synthesis of Intermediate XVII

A mixture of dibromide XVI (0.150 g, 0.000389 moles, 1.1 eq) and amine XIII (0.000354 moles, 1 eq) and N,N-diisopropylethyl amine (0.15 ml) under nitrogen atmosphere was heated at 125° C. for 20 h. The reaction was allowed to cool to room temperature. The reaction mixture is extracted with water (10 ml), ethyl acetate (20 ml) and the organic phase was dried (Na$_2$SO$_4$) and concentrated under reduced pressure. The crude product was purified with column chromatography (silica gel, 60-120 mess, 20% ethyl acetate in hexane) to leave the product XVII as a pale yellow liquid (yield 55-60%)

Synthesis of Intermediate XVIII

To a mixture of compound N-tosylpiperazine derivative XVII (0.000398 moles, 1 eq) and 4-hydroxybenzoic acid (0.164 g, 0.00119 moles, 3 eq) was added hydrogen bromide solution (33 wt % in acetic acid, 1.8 ml) at room temperature. The reaction mixture was stirred under nitrogen atmosphere for 2 days at room temperature. Water (10 ml) was slowly added to the reaction mixture and the reaction mixture was continuously stirred for 2 h. A white precipitate was formed which was removed by filtration. The filter cake was washed with water (2×10 ml). The combined acidic aqueous washes were washed with toluene (20 ml). The aqueous phase was then cooled to 0° C. and basified with KOH pellets portion wise until pH>10, and extracted with toluene (20 ml) and ethyl acetate (2×20 ml). The combined organic phases were washed with brine, dried (Na$_2$SO$_4$), and concentrated under pressure to give the product XVIII as a pale yellow liquid which is used for the next step (Yield 90%)

Synthesis of Compounds of Formula Id

To a solution of acid VIII (1 mmol) in DMF (2 ml), PyBoP (Benzotriazole-1-yl-oxy-tris-(dimethylamino)-phosphonium hexafluorophosphate) (1.5 mmol) was added at 0° C. and allowed to stir for 5 minutes. Then Gem dimethyl piperizine XVIII (1 mmol) was added to the reaction mixture at the same temperature under N$_2$ atmosphere and stirred overnight at room temperature. After completion of reaction, mixture was diluted with water and extracted with EtOAc. The organic layer was washed with water, dried over Na$_2$SO$_4$, and evaporated under reduced pressure. The residue was purified by column chromatography (silica gel, 60-120 mesh; MeOH-DCM, 2:8) to afford product XIX in 35-55% yield.

The above procedure was used to produce the following compounds of Formula Id using the appropriate methyl ketone X and acid VIII intermediates.

N-(4-(4-(2-(2-fluorophenyl)propan-2-yl)piperazine-1-carbonyl)phenyl)quinoline-8-sulfonamide (Compound 409)

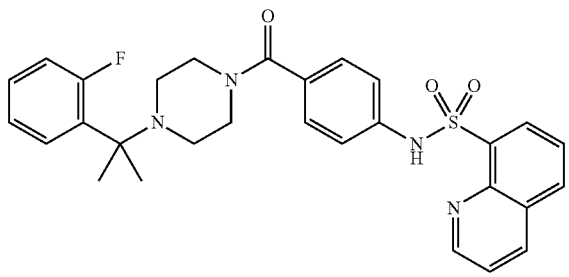 [SMILES: CC(C)(c1ccccc1F)N1CCN(C(=O)c2ccc(NS(=O)(=O)c3cccc4cccnc34)cc2)CC1]

$^1$H NMR (400 MHz, DMSO-d$_6$) δ: 1.22 (s, 6H), 2.2-2.4 (m, 4H), 2.99-3.2 (m, 2H), 3.4-3.6 (m, 2H), 7.0-7.2 (m, 5H), 7.22-7.4 (m, 3H), 7.6-7.8 (d, 2H), 8.25 (d, 1H), 8.4-8.5 (m, 2H), 9.1 (m, 1H), 10.4 (s, 1H); HPLC Purity: 96.19%; Mass (M+1): 535.05.

N-(4-(4-(2-phenylpropan-2-yl)piperazine-1-carbonyl)-2-(trifluoromethoxy)phenyl)quinoline-8-sulfonamide (Compound 340)

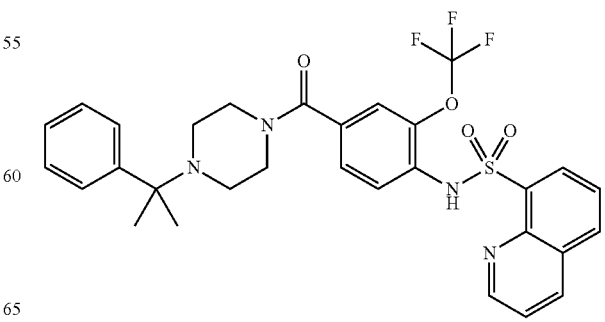

¹H NMR (400 MHz, DMSOd₆) δ: 1.2 (s, 6H), 2.2-2.4 (m, 4H), 3.1-3.6 (m, 4H), 7.2 (m, 5), 7.5 (m, 3H), 7.7 (m, 2H), 8.3 (m, 2H), 8.6 (m 1H), 9.0 (m, 1H); HPLC Purity: 97.72%; Mass (M+1): 599.4.

N-(3-methoxy-4-(4-(2-phenylpropan-2-yl)piperazine-1-carbonyl)phenyl)quinoline-8-sulfonamide (Compound 355)

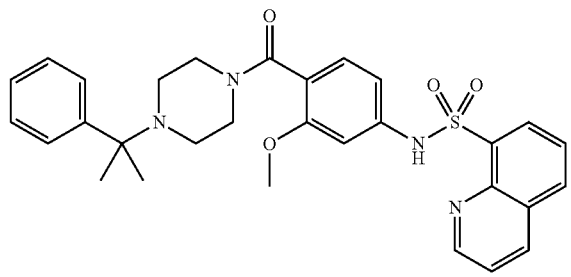 [SMILES: COc1cc(NS(=O)(=O)c2cccc3cccnc23)ccc1C(=O)N1CCN(C(C)(C)c2ccccc2)CC1]

¹H NMR (400 MHz, CDCl₃) δ: 3.4-3.7 (s, 6H), 2.1-2.4 (m, 4H), 3.0 (m, 4H), 4.5 (s, 3H), 6.6-6.9 (m, 3H), 7.1-7.5 (m, 5H), 7.7 (m, 2H), 8.2-8.4 (m, 3H), 9.0 (m, 1H) 10.4 (s, 1H); HPLC Purity: 95.72%; Mass (M+1): 545.3.

N-(2-methoxy-4-(4-(2-phenylpropan-2-yl)piperazine-1-carbonyl)phenyl)quinoline-8-sulfonamide (Compound 356)

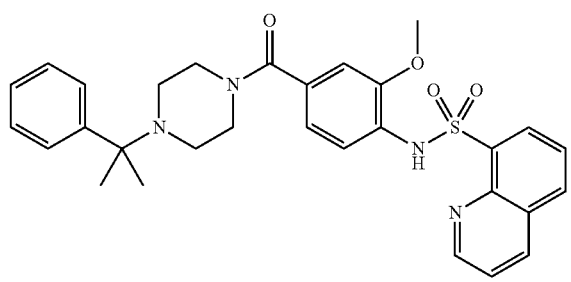 [SMILES: COc1cc(C(=O)N2CCN(C(C)(C)c3ccccc3)CC2)ccc1NS(=O)(=O)c1cccc2cccnc12]

¹H NMR (400 MHz, CDCl₃) δ: 1.3 (s, 6H), 2.2-2.5 (m, 4H), 3.2-3.7 (m, 7H), 6.8-7.1 (m, 2H), 7.0-7.4 (m, 6H), 7.6-7.8 (m, 2H), 8.3 (m, 2H), 8.6 (m, 1H), 9.0 (m, 2H); HPLC Purity: 94.22%; Mass (M+1): 544.66.

N-(4-(4-(2-cyclopropylpropan-2-yl)piperazine-1-carbonyl)phenyl)quinoline-8-sulfonamide (Compound 438)

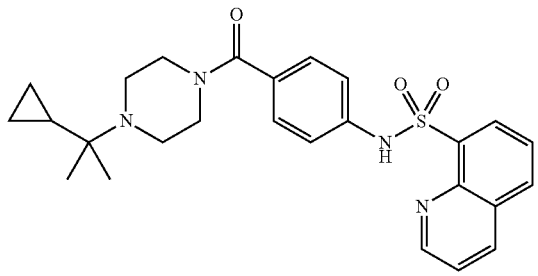 [SMILES: CC(C)(C1CC1)N1CCN(C(=O)c2ccc(NS(=O)(=O)c3cccc4cccnc34)cc2)CC1]

¹H NMR (400 MHz, DMSO-d₆) δ: 0.2-0.37 (m, 4H), 0.8 (s, 6H), 3.0-3.8 (m, 8H), 7.0-7.2 (m, 4H), 7.5-7.8 (m, 2H), 8.0-8.4 (m, 3H), 9.1-9.2 (m, 1H), 10.4 (s, 1H); HPLC Purity: 94.80%; Mass (M+1): 479.4.

N-(4-(4-(2-methyl-2-phenylpropanoyl)piperazine-1-carbonyl)-2-(trifluoromethoxy)phenyl)quinoline-8-sulfonamide (Compound 359)

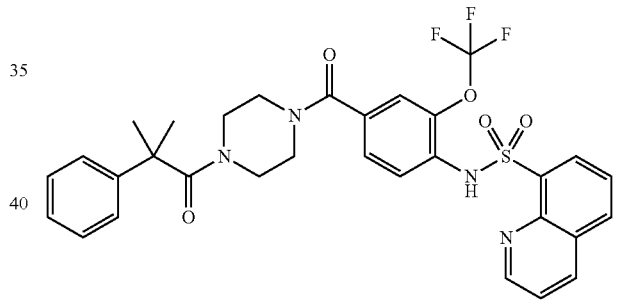

¹H NMR (400 MHz, CDCl₃) δ: 1.2 (m, 6H), 3.0-3.6 (m, 8H), 7.0-7.4 (m, 7H), 7.6 (m, 2H), 7.9 (m, 1H), 8.0-8.4 (m, 3H), 9.0 (m, 1H); HPLC Purity: 99.85%; Mass (M+1): 627.2.

Example 3

Preparation of Compounds of Formula Ie

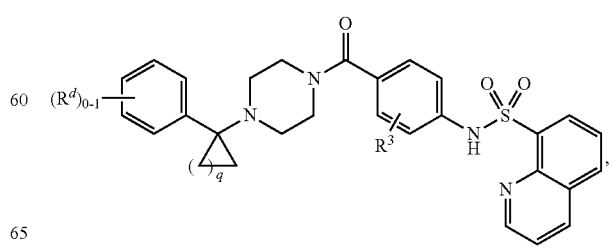

(Ie)

wherein $R^d$, when present, is aryl; $R^3$ is methoxy or $OCF_3$; and q is 1, 2, 3, or 4.

Scheme 3:

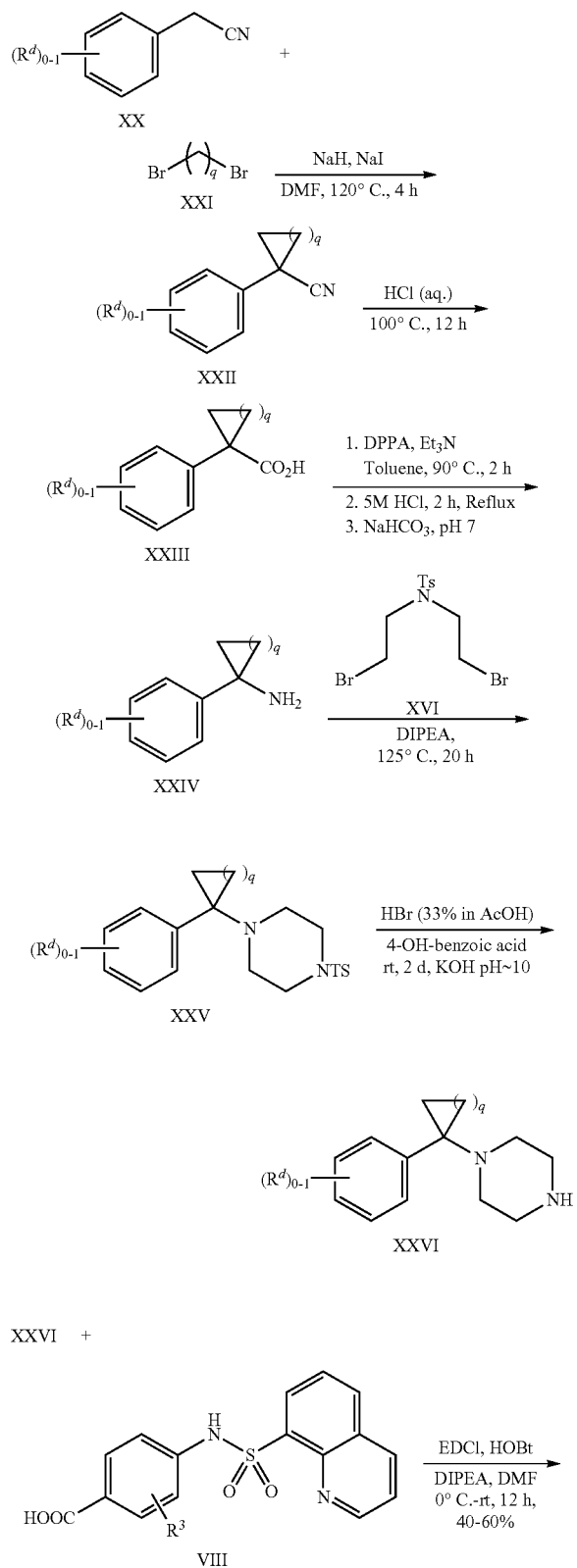

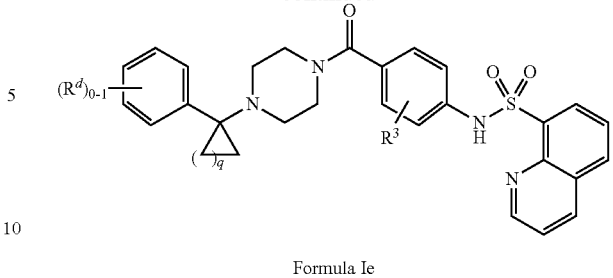

Formula Ie $R^d$ = Aryl (when present)
$R^3$ = 2-OMe, 3-OMe, $OCF_3$
q = 1, 2, 3 or 4

Synthesis of Intermediate XXII

To a stirred solution NaH (21 mmol) in DMF (10 ml) at 0° C. was added aryl acetonitrile XX (4.2 mmol) in DMF slowly and stirred for 15 minutes at the same temperature. Dibromoalkane (4.2 mmol, n=2, 3, 4, 5) in DMF (5 ml) followed by sodium iodide was added to reaction mixture and was heated to 120° C. for 4 h. After completion of reaction, mixture was diluted with water and extracted with EtOAc. The organic layer was washed with water, dried over $Na_2SO_4$, and evaporated under reduced pressure. The residue was purified by column chromatography (silica gel, 60-120 mesh; EA-Hexane, 1:9) to afford product XXII in 75-89% yield.

Synthesis of Intermediate XXIII

In a sealed tube a stirred solution of Nitrile XXII (3 mmol) in HCl (aqueous, 6 ml) was heated for 24 h at 100° C. After completion of the reaction the reaction mixture was poured into ice water and extracted with ethyl acetate (20 ml). The organic layer was washed with brine, dried over $Na_2SO_4$, and evaporated under reduced pressure. The residue was purified by column chromatography (silica gel, 60-120 mesh; EA-Hexane, 1:9) to afford product XXIII as a white solid in 50-65% yield.

Synthesis of Intermediate XXIV

Diphenylphosphoryl azide (0.85 ml, 0.00386 moles, 1.1 eq) was added to a solution of the acid XXIII (0.00346 moles, 1 eq) and triethylamine (1 ml, 0.00776 moles, 2.2 eq) in Toluene (12 ml) and the mixture was stirred at 90° C. for 2 h. The mixture was cooled, diluted with ethyl acetate (15 ml) and washed with sodium carbonate (2×20 ml). The combined aqueous fractions were washed with brine (40 ml), dried ($Na_2SO_4$) and the solvent was evaporated under reduced pressure. The residue was suspended in hydrochloric acid (5M, 2 ml) and the mixture was heated under reflux for 2 h. The mixture was cooled, the solvent was evaporated under reduced pressure and the residue was dried azetropically by evaporating toluene under reduced pressure to give the crude compound as a white solid. The solid was taken in ethyl acetate (20 ml), cooled and saturated solution of $NaHCO_3$ was added to achieve pH-7. The organic phase was dried ($Na_2SO_4$), concentrated to leave the compound XXIV as pale yellow liquid.

Synthesis of Intermediate XXV

A mixture of dibromide XVI (0.150 g, 0.000389 moles, 1.1 eq) and amine XXIV (0.000354 moles, 1 eq) and N,N-diisopropylethyl amine (0.15 ml) under nitrogen atmosphere was heated at 125° C. for 20 h. The reaction was allowed to cool to room temperature. The reaction mixture was extracted with water (10 ml), ethyl acetate (20 ml) and the organic phase was dried (Na$_2$SO$_4$), and concentrated under pressure. The crude product was purified by column chromatography (silica gel, 60-120 mess, 20% ethyl acetate in hexane) to leave the product XXV as a pale yellow liquid (yield 45-55%).

Synthesis of Intermediate XXVI

To a mixture of compound N-tosylpiperazine derivative XXV (0.000398 moles, 1 eq) and 4-hydroxybenzoic acid (0.164 g, 0.00119 moles, 3 eq) was added hydrogen bromide solution (33 wt % in acetic acid, 1.8 ml) at room temperature. The reaction mixture was stirred under nitrogen atmosphere for 2 days at room temperature. Water (10 ml) was slowly added to the reaction mixture and the reaction mixture was continuously stirred for 2 h. A white precipitate was formed which was removed by filtration. The filter cake was washed with water (2×10 ml). The combined acidic aqueous washes were washed with toluene (20 ml). The aqueous phase was then cooled to 0° C. and basified with KOH pellets portion wise until pH>10, and extracted with toluene (20 ml) and ethyl acetate (2×20 ml). The combined organic phases were washed with brine, dried (Na$_2$SO$_4$), and concentrated under pressure to give the product XXVI as a pale yellow liquid which is used for the next step (Yield 90%).

Synthesis of Compounds of Formula Ie

To a stirred solution of acid VIII (0.000315 moles, 1 eq) in DMF (5 ml), were added EDCI (0.066 g, 0.000346 moles, 1.1 eq), HOBt (0.047 g, 0.000346 moles, 1.1 eq) and DIPEA (0.13 ml, 0.00078 moles, 2.5 eq) at 0° C. and stirred for 15 minutes. A solution of amine XXVI (0.000315 moles, 1 eq) was then added at 0° C. and then the resulting mixture was allowed to stir at room temperature overnight. After completion of the reaction, water (20 mL) was added and extracted with ethyl acetate (2×30 mL). The combined organic layer was dried over anhydrous Na$_2$SO$_4$ and concentrated under reduced pressure. The crude product was purified by column chromatography (silica gel, 60-120 mess, 70% ethyl acetate in hexane) to give XXVIII in 40-45% yield.

The above procedure was used to produce the following compounds of Formula Ie using the appropriate aryl acetonitrile XX, dibromoalkane XXI, and acid VIII intermediates.

N-(4-(4-(1-phenylcyclopropyl)piperazine-1-carbonyl)phenyl)quinoline-8-sulfonamide (Compound 330)

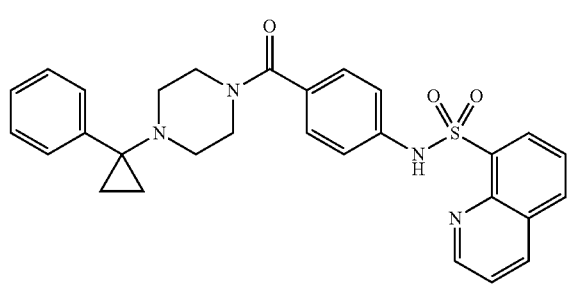 [SMILES: O=C(c1ccc(NS(=O)(=O)c2cccc3cccnc23)cc1)N1CCN(C2(c3ccccc3)CC2)CC1]

$^1$H NMR (400 MHz, CDCl$_3$) δ: 1.6 (m, 4H), 2.5 (m, 4H), 3.2 (m, 2H), 3.6 (m, 2H), 7.0 (m, 3H), 7.2 (m, 6H), 7.6 (m, 2H), 8.0 (m, 1H), 8.3 (m, 2H), 8.5 (s, 1H), 9.1 (m, 1H); HPLC Purity: 97.71%; Mass (M+1): 513.30.

N-(4-(4-(1-(4-fluorophenyl)cyclopropyl)piperazine-1-carbonyl)phenyl)quinoline-8-sulfonamide (Compound 399)

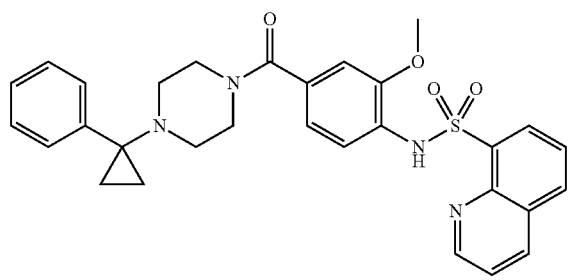 [SMILES: COc1cc(C(=O)N2CCN(C3(c4ccccc4)CC3)CC2)ccc1NS(=O)(=O)c1cccc2cccnc12]

$^1$H NMR (400 MHz, CDCl$_3$) δ: 0.9-1.0 (m, 5H), 2.2-2.7 (m, 4H), 3.15-3.7 (m, 4H), 6.9-7.3 (m, 7H), 7.58-7.61 (m, 2H), 8.0 (d, 1H), 8.2-8.4 (m, 2H), 8.5 (s, 1H), 9.0 (s, 1H); HPLC Purity: 99.60%; Mass (M+1): 531.45.

N-(2-methoxy-4-(4-(1-phenylcyclopropyl)piperazine-1-carbonyl)phenyl)quinoline-8-sulfonamide (Compound 352)

¹H NMR (400 MHz, CDCl₃) δ: 0.9-1.0 (m, 4H), 2.5 (s, 3H), 3.2-3.7 (m, 8H), 6.5 (m, 2H), 7.2 (m, 6H), 7.7 (m, 3H), 8.0-8.4 (m, 3H), 9.0 (m, 1H); HPLC Purity: 92.0%; Mass (M+1): 543.43.

N-(4-(4-(1-phenylcyclopropyl)piperazine-1-carbonyl)-2-(trifluoromethoxy)phenyl)quinoline-8-sulfonamide (Compound 353)

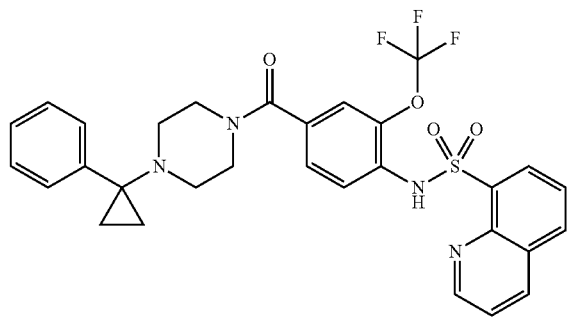 [SMILES: O=C(c1ccc(NS(=O)(=O)c2cccc3cccnc23)c(OC(F)(F)F)c1)N1CCN(C2(c3ccccc3)CC2)CC1]

¹H NMR (400 MHz, CDCl₃) δ: 0.9-1.0 (m, 4H), 2.5 (m, 4H), 3.2-3.7 (m, 5H), 6.8-7.1 (m, 4H), 7.5 (m, 3H), 7.7 (m, 3H), 8.0-8.4 (m, 3H), 9.0 (m, 2H); HPLC Purity: 96.83%; Mass (M+1): 597.34.

N-(3-methoxy-4-(4-(1-phenylcyclopropyl)piperazine-1-carbonyl)phenyl)quinoline-8-sulfonamide (Compound 393)

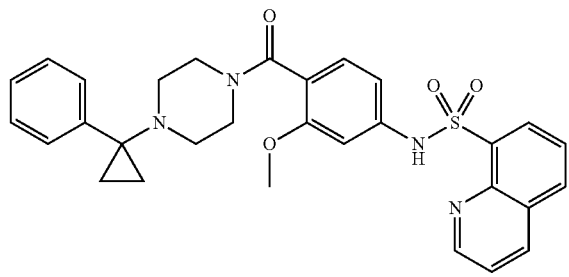 [SMILES: COc1cc(NS(=O)(=O)c2cccc3cccnc23)ccc1C(=O)N1CCN(C2(c3ccccc3)CC2)CC1]

¹H NMR (400 MHz, CDCl₃) δ: 0.89 (m, 2H), 0.90 (m, 1H), 0.95 (m, 2H), 2.2-2.6 (m, 4H), 2.8-3.0 (m, 2H), 3.4 (s, 3H), 3.45-3.6 (m, 2H), 6.3 (m, 1H), 6.7-6.9 (m, 2H), 7.0-7.2 (m, 4H), 7.55-7.6 (m, 2H), 8.0 (d, 1H), 8.2-8.4 (d, 2H), 8.5 (s, 1H), 9.0 (m, 1H); HPLC Purity: 99.86%; Mass (M+1): 543.4.

N-(4-(4-(1-(4-fluorophenyl)cyclopropyl)piperazine-1-carbonyl)-2-methoxyphenyl)quinoline-8-sulfonamide (Compound 400)

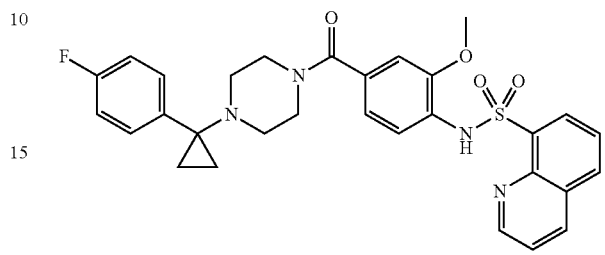

¹H NMR (400 MHz, CDCl₃) δ: 0.8 (m, 2H), 0.85 (m, 1H), 1.0 (m, 2H), 2.2-2.7 (m, 4H), 3.4 (s, 3H), 3.15-3.7 (m, 4H), 6.6-6.7 (m, 2H), 6.9-7.0 (m, 2H), 7.15-7.2 (m, 4H), 7.55-7.6 (m, 3H), 8.0 (d, 1H), 8.2 (d, 1H), 8.4 (d, 1H), 8.5 (s, 1H), 9.0 (s, 1H); HPLC Purity: 99.93%; Mass (M+1): 561.50.

N-(4-(4-(1-(4-fluorophenyl)cyclopropyl)piperazine-1-carbonyl)-3-methoxyphenyl)quinoline-8-sulfonamide (Compound 401)

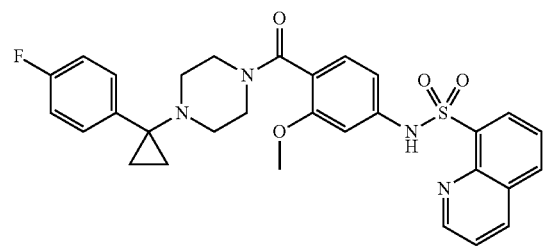 [SMILES: COc1cc(NS(=O)(=O)c2cccc3cccnc23)ccc1C(=O)N1CCN(C2(c3ccc(F)cc3)CC2)CC1]

¹H NMR (400 MHz, CDCl₃) δ: 0.89-1.0 (m, 4H), 2.2-2.7 (m, 4H), 3.0-3.6 (m, 4H), 3.58 (s, 3H), 6.3 (d, 1H), 6.8-7.2 (m, 6H), 7.55-7.6 (m, 2H), 8.0 (d, 1H), 8.2 (d, 1H), 8.38 (d, 1H), 8.5 (s, 1H), 9.0 (s, 1H); HPLC Purity: 99.68%; Mass (M+1): 561.45.

N-(4-(4-(1-(4-fluorophenyl)cyclopropyl)piperazine-1-carbonyl)-2-(trifluoromethoxy)phenyl)quinoline-8-sulfonamide (Compound 402)

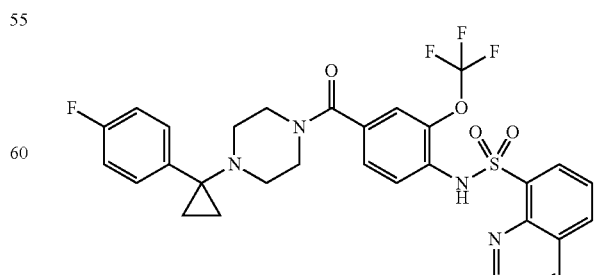

¹H NMR (400 MHz, CDCl₃) δ: 0.79 (m, 2H), 0.8 (m, 2H), 2.2-2.7 (m, 4H), 3.0-3.6 (m, 4H), 6.95-7.25 (m, 5H), 7.55-7.6 (m, 2H), 8.0 (d, 1H), 7.9-7.95 (d, 1H), 8.0-8.1 (d, 1H), 8.38-8.4 (d, 2H), 9.1 (m, 1H); HPLC Purity: 99.75%; Mass (M+1): 615.45.

N-(4-(4-(1-phenylcyclobutyl)piperazine-1-carbonyl)phenyl)quinoline-8-sulfonamide (Compound 408)

¹H NMR (400 MHz, CDCl₃) δ: 1.5-2.4 (m, 8H), 1.9-2.4 (m, 4H), 3.0-3.8 (m, 4H), 7.0-7.18 (m, 4H), 7.19-7.3 (m, 4H), 7.5-7.6 (m, 2), 8.0 (d, 1H), 8.2-8.4 (m, 2H), 8.45 (m, 1H), 9.1 (m, 1H); HPLC Purity: 97.95%; Mass (M+1): 541.55.

N-(4-(4-(1-phenylcyclohexyl)piperazine-1-carbonyl)phenyl)quinoline-8-sulfonamide (Compound 407)

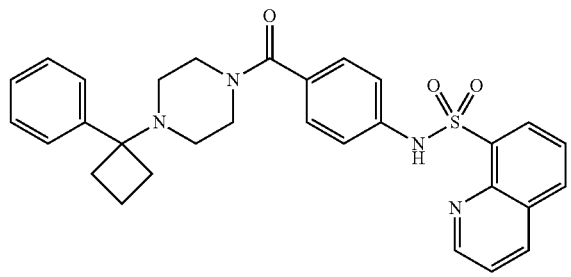 [SMILES: O=C(c1ccc(NS(=O)(=O)c2cccc3cccnc23)cc1)N1CCN(C2(c3ccccc3)CCC2)CC1]

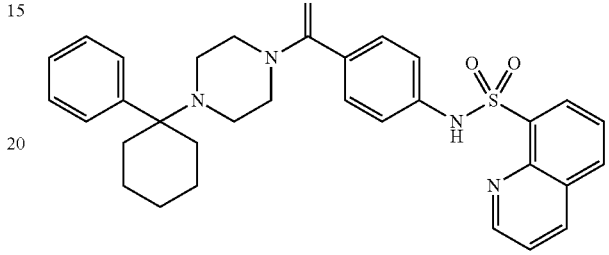

¹H NMR (400 MHz, DMSO-d₆) δ: 0.92 (m, 1H), 1.22 (m, 2H), 1.8-2.1 (m, 2H), 2.2-2.4 (m, 4H), 2.85-3.2 (m, 4H), 3.4-3.6 (m, 4H), 7.0-7.2 (m, 4H), 7.22-7.4 (m, 5H), 7.6-7.8 (d, 2H), 8.25 (d, 1H), 8.4-8.5 (m, 2H), 9.1 (m, 1H), 10.4 (s, 1H); HPLC Purity: 99.15%; Mass (M+1):527.55.

N-(4-(4-(1-phenylcyclopentyl)piperazine-1-carbonyl)phenyl)quinoline-8-sulfonamide (Compound 406)

¹H NMR (400 MHz, DMSO-d₆) δ: 1.15-1.45 (m, 4H), 1.5-1.7 (m, 2H), 2.85-2.2 (m, 8H), 3.0-3.5 (m, 4H), 7.0-7.2 (m, 4H), 7.2-7.4 (m, 5H), 7.6-7.8 (m, 2H), 8.2-8.23 (d, 1H), 8.4-8.5 (m, 2H), 9.1 (m, 1H), 10.4 (s, 1H); HPLC Purity: 96.17%; Mass (M+1): 555.40.

Example 4

Preparation of Compounds of Formula If

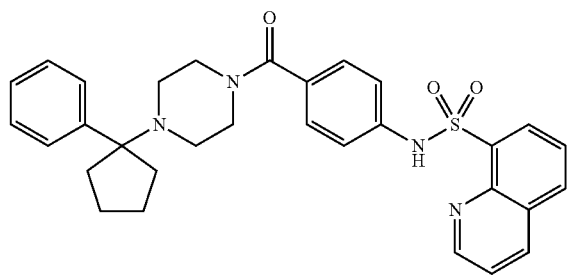 [SMILES: O=C(c1ccc(NS(=O)(=O)c2cccc3cccnc23)cc1)N1CCN(C2(c3ccccc3)CCCC2)CC1]

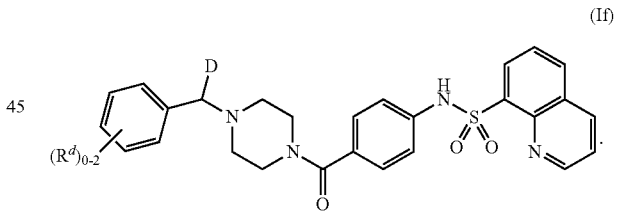

Scheme 4:

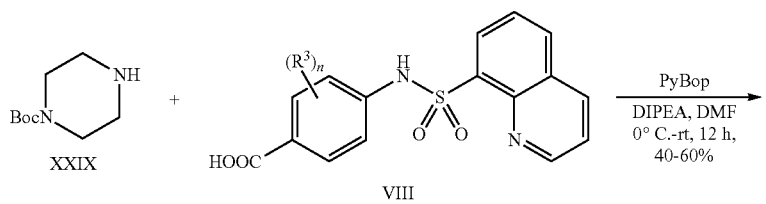

-continued

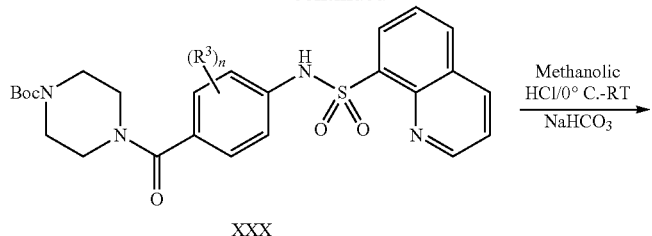

XXX

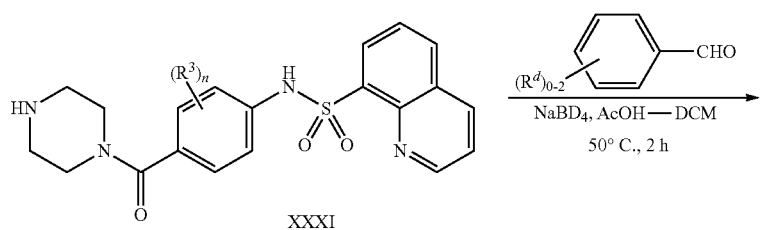

XXXI

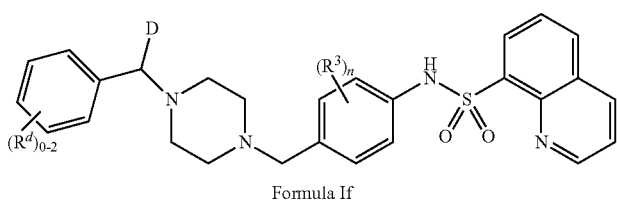

Formula If

Synthesis of Intermediate XXX

To a solution of acid VIII (6.09 mmol) in DMF, PyBoP (Benzotriazole-1-yl-oxy-tris-(dimethylamino)-phosphonium hexafluorophosphate) (4.75 gm, 9.14 mmol) was added at 0° C. and allowed to stir for 5 minutes. Then Boc protected piperizine XXIX (6.09 mmol) was added to the reaction mixture at the same temperature under $N_2$ atmosphere and stirred overnight at room temperature. After completion of reaction, mixture was diluted with water and extracted with EtOAc. The organic layer was washed with water, dried over $Na_2SO_4$, and evaporated under reduced pressure. The residue was purified by column chromatography (silica gel, 60-120 mesh; MeOH-DCM, 1:9) to afford product XXVIII in 66% yield.

Synthesis of Intermediate XXXI

To a solution of MeOH.HCl (10 ml) Boc protected amine XXX (4.03 mmol) was added and the resulting mixture was stirred for 1 hr. After completion of reaction, solvent was removed under reduced pressure, washed with water followed by addition of $NaHCO_3$ and extracted with DCM. The organic layer was dried over $Na_2SO_4$ and evaporated under reduced pressure to afford product XXXI in 94.30% yield.

Synthesis of Compounds of Formula If

To a solution of amine XXXI (0.25 mmoles) and appropriate aldehyde (0.27 mmol) in DCM, acetic acid (0.2 mL) was added at room temperature and the resulting mixture was allowed to stir for 30 min. Then $NaBD_4$ (0.25 mmol) was added to reaction mixture and the resulting mixture was allowed to stir at 50° C. for 2 hr. After completion of reaction, the crude mixture was diluted with DCM washed with water, dried over $Na_2SO_4$ and concentrated under reduced pressure. The residue was purified by column chromatography (silica gel, 60-120 mesh; MeOH-DCM, 2:8) to afford product XXXII in 45-55% yield.

The above procedure was used to produce the following compounds of Formula If using the appropriate aldehyde in the final step.

N-(4-(4-(4-fluorobenzyl)piperazine-1-carbonyl)phenyl)quinoline-8-sulfonamide-(D) (Compound 448)

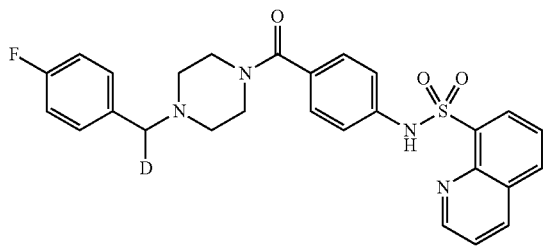 [SMILES: [2H]C(c1ccc(F)cc1)N1CCN(C(=O)c2ccc(NS(=O)(=O)c3cccc4cccnc34)cc2)CC1]

¹H NMR (400 MHz, DMSOd₆) δ: 2.2-2.4 (m, 4H), 3.1-3.6 (m, 4H), 3.7 (m, 1H), 7.2 (m, 6), 7.3 (m, 2H), 7.7 (m, 2H), 8.3 (m, 3H), 9.0 (m, 1H) 10.2 (bs, 1H); HPLC Purity: 97.28%; Mass (M+1): 506.25

N-(4-(4-(3,5-difluorobenzyl)piperazine-1-carbonyl)phenyl)quinoline-8-sulfonamide-(D) (Compound 450)

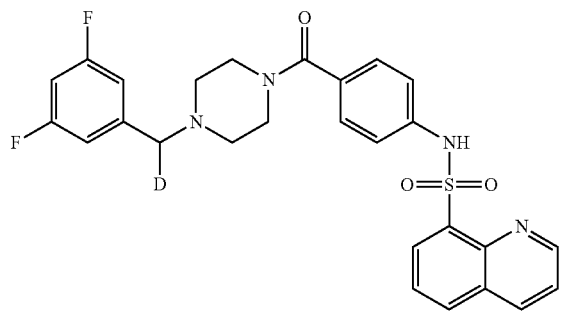 [SMILES: [2H]C(c1cc(F)cc(F)c1)N1CCN(C(=O)c2ccc(NS(=O)(=O)c3cccc4cccnc34)cc2)CC1]

¹H NMR (400 MHz, DMSOd₆) δ: 2.2-2.4 (m, 4H), 3.1-3.6 (m, 4H), 3.7 (m, 1H), 7.2 (m, 7), 7.8 (m, 2H), 8.3 (m, 3H), 9.0 (m, 1H) 10.2 (bs, 1H); HPLC Purity: 99.50%; Mass (M+1): 524.35

Example 5

Preparation of Compound of Formula Ig

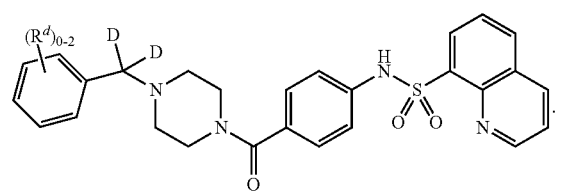

Scheme 5:

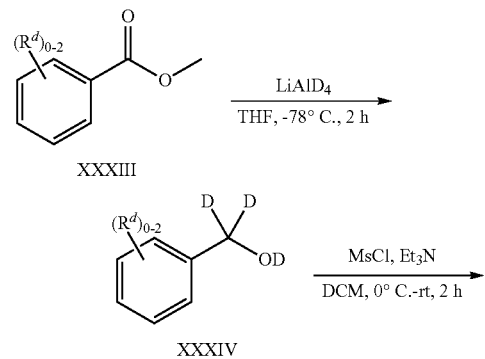

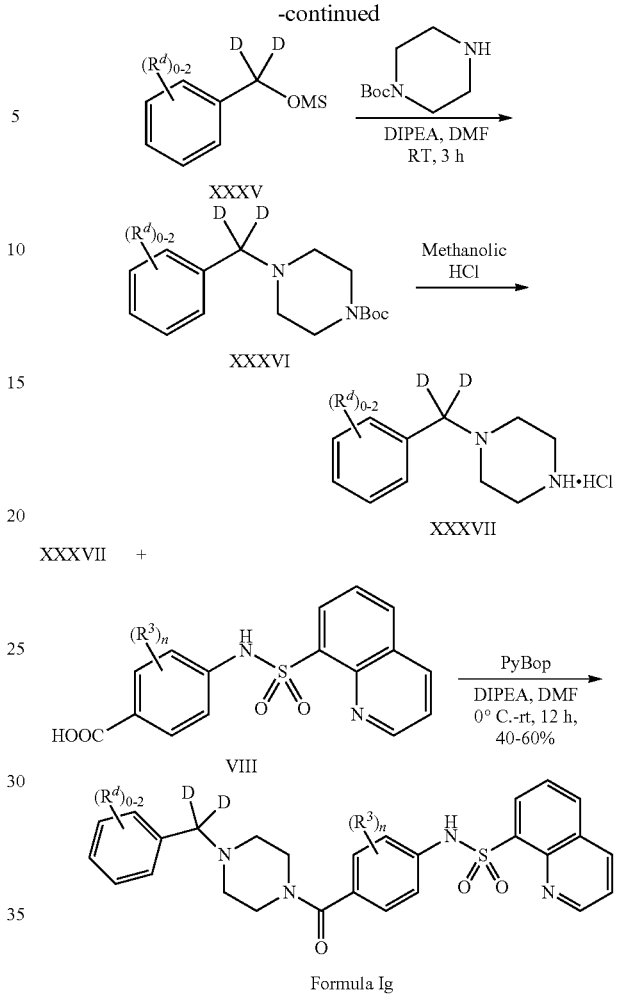

Synthesis of Intermediate XXXIV

To a stirred solution of optionally substituted ethyl benzoate XXXIII (0.38 g, 0.00204 moles) in dry THF (5 ml) was added LiAlD₄ at −78° C. The reaction mixture was stirred further for 2 h at −78° C. and quenched with saturated solution of ammonium chloride. The crude mixture was diluted with ethyl acetate, washed with water, dried over Na₂SO₄ and concentrated under reduced pressure. The residue was purified by column chromatography (silica gel, 60-120 mesh; EA-Hexane, 2:8) to afford product XXXIV in 60% yield.

Synthesis of Intermediate XXXV

To a stirred solution of compound XXXIV (0.00204 moles) in dry DCM (10 ml) was added Et₃N (0.75 ml, 0.0051 moles) at 0° C. and stirred for 2 h. Mesyl chloride (0.16 ml, 0.00204 moles) was added to the reaction mixture and the mixture was stirred further for 2 h at room temperature. The crude mixture was diluted with DCM and washed with water. The organic layer dried over Na₂SO₄ and concentrated under reduced pressure. The residue was purified by column chromatography (silica gel, 60-120 mesh; EA-Hexane, 2:8) to afford product XXXV in 75% yield.

Synthesis of Intermediate XXXVI

To a stirred solution of compound XXXV (0.0013 moles) in dry DMF (10 ml) was added DIPEA (0.7 ml, 0.0039 moles) at room temperature and stirred for 2 h. Boc-piperazine (0.24 gm, 0.0013 moles) was added to the reaction mixture and the mixture was stirred further for 3 h at room temperature. After completion of the reaction, the mixture was quenched with water and diluted with ethyl acetate. The organic layer dried over $Na_2SO_4$ and concentrated under reduced pressure. The residue was purified by column chromatography (silica gel, 60-120 mesh; EA-Hexane, 3:7) to afford product XXXVI in 70% yield.

Synthesis of Intermediate XXXVII

To a solution of MeOH.HCl (10 ml) Boc protected amine XXXVI (4.03 mmol) was added and the resulting mixture was stirred for 1 h. After completion of reaction, solvent was removed under reduced pressure, washed with water followed by addition of $NaHCO_3$ and extracted with DCM. The organic layer was dried over $Na_2SO_4$ and evaporated under reduced pressure to afford product XXXVII in 92% yield.

Synthesis of Compounds of Formula Ig

To a solution of unsubstituted acid VIII (6.09 mmol) in DMF, PyBoP (Benzotriazole-1-yl-oxy-tris-(dimethylamino)-phosphonium hexafluorophosphate) (4.75 gm, 9.14 mmol) was added at 0° C. and allowed to stir for 5 minutes. Then Boc protected piperizine XXXVII (6.09 mmol) was added to the reaction mixture at the same temperature under $N_2$ atmosphere and stirred overnight at room temperature. After completion of reaction, mixture was diluted with water and extracted with EtOAc. The organic layer was washed with water, dried over $Na_2SO_4$, and evaporated under reduced pressure. The residue was purified by column chromatography (silica gel, 60-120 mesh; MeOH-DCM, 2:8) to afford product.

The following compound was produced by the above-described method using ethyl-3,5-difluorobenzoate as starting material.

N-(4-(4-(3,5-difluorobenzyl)piperazine-1-carbonyl)phenyl)quinoline-8-sulfonamide-(D2) (Compound 449)

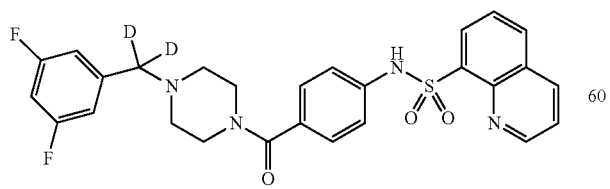

$^1$H NMR (400 MHz, $CDCl_3$) δ: 2.2-2.6 (m, 4H), 2.4-2.49 (m, 2H), 3.2-3.8 (m, 4H), 6.7-7.0 (m, 3H), 7.0-7.2 (m, 4H), 7.6 (m, 2H), 8.1 (d, 1H), 8.2-8.6 (m, 3H), 9.0 (m, 1H), 10.46 (bs, 1H); HPLC Purity: 98.11%; Mass (M+1): 525.15.

Example 6

Preparation of Compounds of Formula Ih

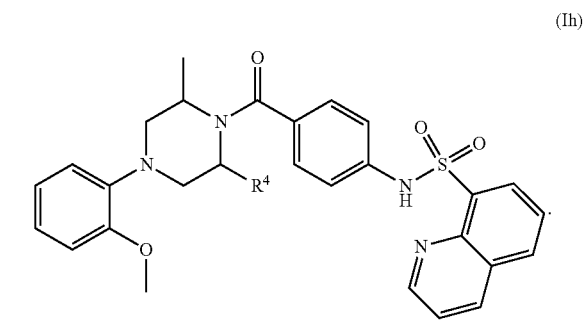

(Ih)

Scheme 6

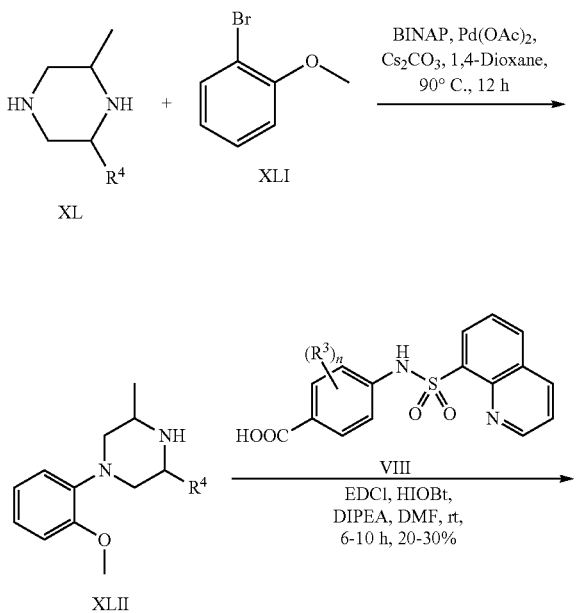

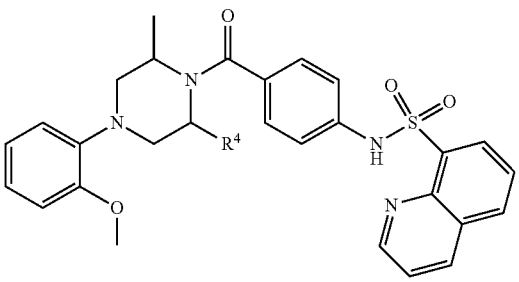

Formula Ih

Synthesis of Intermediate XLII

Nitrogen was purged through a stirred solution of arylbromide (XLI, 2.15 mmol) in 1,4-dioxane (20 ml) at room temperature for 30 minutes. BINAP (0.134 gm, 0.215 mmol), palladium acetate (0.0096 g, 0.043 mmol) and cesium carbonate (1.40 gm, 4.3 mmol) were added to the reaction mixture and the nitrogen purging was continued for another 20 minutes and finally diamine (XL, 2.15 mmol) was added and stirred at 100° C. overnight under nitrogen atmosphere. After completion of the reaction (monitored by TLC), the reaction mixture was concentrated under vacuum. The residue was dissolved in water, extracted with ethyl acetate (3×50 ml). Combined organic extracts were washed with brine (20 ml), dried over anhydrous sodium sulfate, filtered and concentrated under reduced pressure. The crude product was then purified by column chromatography (60-120 silica gel) using 20% ethyl acetate-hexane to afford compound XLII (40-60%).

Synthesis of Compounds of Formula Ih

To a stirred solution of the carboxylic acid (VIII, 0.61 mmol) in DMF at 0° C. under nitrogen atmosphere, EDCI (0.129 gm, 0.671 mmol), HOBt (0.91 gm, 0.671 mmol) and DIPEA (0.31 ml, 1.83 mmol) were added and the resultant solution was stirred at room temperature for 30 min. Amine (XLII 0.61 mmol) was then added at 0° C. and stirred overnight at room temperature. After completion of the reaction (monitored by TLC), the reaction mixture was poured into 1.0 M HCl and extracted with EtOAc. The organic layer was washed with saturated NaHCO$_3$ solution, dried over NaSO$_4$ and filtered. The solvent was removed by rotary evaporation and the product was isolated by chromatography on silica gel (60-120 silica gel, 2% MeOH-DCM) or preparative HPLC to yield product (40-60%) as an off-white solid.

The following compounds were produced by the above-described method using the appropriate amine XL.

N-(4-(4-(2-methoxyphenyl)-2-methylpiperazine-1-carbonyl)phenyl)quinoline-8-sulfonamide (Compound 223)

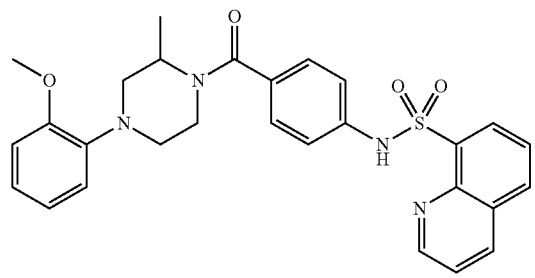 [SMILES: COc1ccccc1N1CCN(C(=O)c2ccc(NS(=O)(=O)c3cccc4cccnc34)cc2)C(C)C1]

$^1$H NMR (400 MHz, DMSOd$_6$) δ: 1.2 (d, 3H), 2.5-2.55 (m, 2H), 2.6-2.69 (m, 1H), 3.0-3.2 (m, 4H), 3.8 (s, 3H), 6.8-7.0 (d, 4H), 7.1-7.2 (m, 4H), 7.6-7.8 (m, 2H), 8.2-8.6 (m, 3H), 9.0 (m, 1H), 10.46 (bs, 1H); HPLC Purity: 99.04%; Mass (M+1): 517.40.

N-(4-((2R,6S)-4-(2-methoxyphenyl)-2,6-dimethylpiperazine-1-carbonyl)phenyl)quinoline-8-sulfonamide (Compound 222)

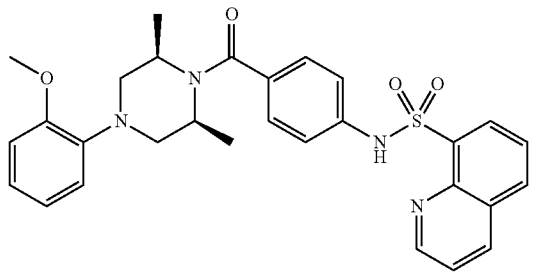 [SMILES: COc1ccccc1N1C[C@@H](C)N(C(=O)c2ccc(NS(=O)(=O)c3cccc4cccnc34)cc2)[C@@H](C)C1]

$^1$H NMR (400 MHz, DMSOd$_6$) δ: 1.2-1.4 (s, 6H), 2.4-2.49 (m, 2H), 2.6-2.69 (m, 2H), 3.0-3.2 (m, 2H), 3.8 (s, 3H), 4.2 (bs, 1H), 6.8-7.0 (d, 4H), 7.1-7.2 (m, 4H), 7.6-7.8 (m, 2H), 8.2-8.6 (m, 3H), 9.0 (m, 1H), 10.46 (bs, 1H); HPLC Purity: 99.74%; Mass (M+1):531.40.

Example 7

Preparation of Compounds of Formula Ii

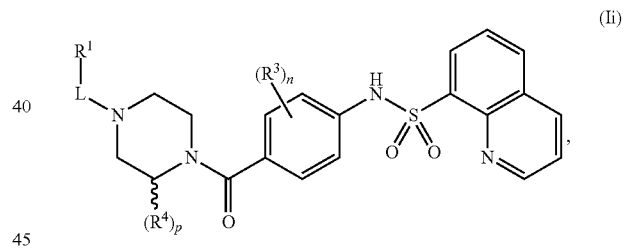

wherein R$^1$ is cycloalkyl, heterocyclyl, aryl, or heteroaryl; R$^3$ is chloro, fluoro, CF$_3$ or OCF$_3$; and R$^4$ is alkyl or phenyl.

Scheme 7

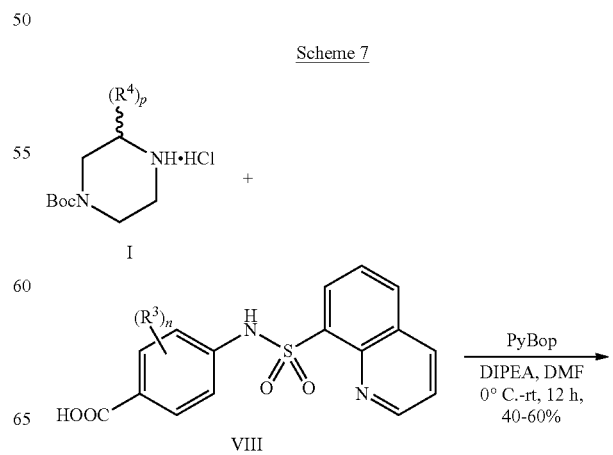

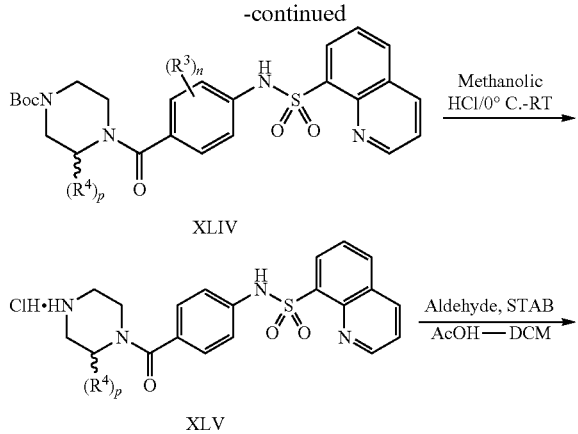

XLIV

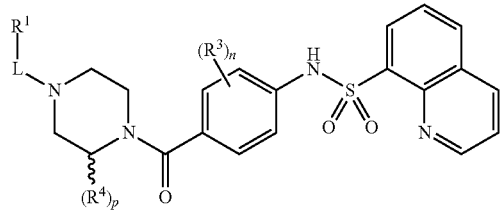

XLV

STAB = Sodium tri-acetoxy borohydride

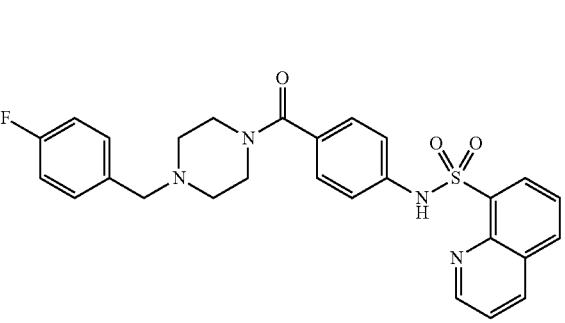 [SMILES: O=C(c1ccc(NS(=O)(=O)c2cccc3cccnc23)cc1)N1CCN(Cc2ccc(F)cc2)CC1]

Formula Ii $R^4$ = alkyl, phenyl
$R^3$ = Cl, F, CF$_3$, OCF$_3$
$R^1$ = Cycloalkyl, Heterocyclyl, Aryl, Heteroaryl
L = —(CR$^c$R$^c$)$_m$—
p = 0 or 1

Synthesis of Intermediate XLIV

To a solution of acid VIII (6.09 mmol) in DMF, PyBoP (Benzotriazole-1-yl-oxy-tris-(dimethylamino)-phosphonium hexafluorophosphate) (4.75 gm, 9.14 mmol) was added at 0° C. and allowed to stir for 5 minutes. Then Boc protected piperazine/substituted piperizine I (1.13 gm, 6.09 mmol) was added to the reaction mixture at the same temperature under N$_2$ atmosphere and stirred overnight at room temperature. After completion of reaction, mixture was diluted with water and extracted with EtOAc. The organic layer was washed with water, dried over Na$_2$SO$_4$, and evaporated under reduced pressure. The residue was purified by column chromatography (silica gel, 60-120 mesh; MeOH-DCM, 2:8) to afford product XLIV in 66% yield.

Synthesis of Intermediate XLV

To a solution of MeOH.HCl, Boc protected amine XLIV (4.03 mmol) was added and the resulting mixture was stirred for 1 hr. After completion of reaction, solvent was removed under reduced pressure, washed with water followed by addition of NaHCO$_3$ and extracted with DCM. The organic layer was dried over Na$_2$SO$_4$ and evaporated under reduced pressure to afford product XLV (94.30% yield).

Synthesis of Compounds of Formula Ii

To a solution of amine XLV (0.25 mmol) and appropriate aldehyde (0.27 mmol) in DCM, acetic acid (0.2 mL) was added at room temperature and the resulting mixture was allowed to stir for 30 minutes. Then sodium triacetoxyborohydride (STAB) (0.26 gm, 1.26 mmol) was added to reaction mixture and the resulting mixture was allowed to stir at 50° C. for 1 h. After completion of reaction, the crude mixture was diluted with DCM washed with water, dried over Na$_2$SO$_4$ and concentrated under reduced pressure. The residue was purified by column chromatography (silica gel, 60-120 mesh; MeOH-DCM, 2:8) to afford product in 32-45% yield.

The following compounds were produced by the above-described method using the appropriate N-Boc protected piperazine I and acid VIII.

N-(4-(4-(4-fluorobenzyl)piperazine-1-carbonyl)phenyl)quinoline-8-sulfonamide (Compound 341)

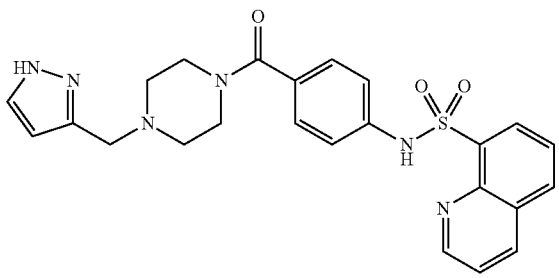 [SMILES: O=C(c1ccc(NS(=O)(=O)c2cccc3cccnc23)cc1)N1CCN(Cc2cc[nH]n2)CC1]

$^1$H NMR (400 MHz, CDCl$_3$) δ: 2.2-2.6 (m, 4H), 2.8 (s, 2H), 3.2-3.5 (m, 2H), 3.6-3.8 (m, 2H), 6.9-7.3 (m, 9H), 7.6 (m, 2H), 8.0 (m, 1H), 8.3 (m, 2H), 9.0 (m, 1H); HPLC Purity: 98.15%; Mass (M+1): 503.76.

N-(4-(4-((1H-pyrazol-3-yl)methyl)piperazine-1-carbonyl)phenyl)quinoline-8-sulfonamide (Compound 384)

$^1$H NMR (400 MHz, DMSO-d$_6$) δ: 2.2-2.4 (m, 2H), 2.65 (s, 2H), 3.2-3.6 (m, 6H), 6.1 (s, 1H), 7.0-7.2 (m, 4H), 7.4 (s, 1H), 7.6-7.8 (m, 3H), 8.3 (d, 1H), 8.4 (d, 1H), 8.5 (d, 1H), 9.0 (m, 1H), 10.4 (s, 1H), 12.6 (s, 1H); HPLC Purity: 96.98%; Mass (M+1): 477.30.

N-(4-(4-(3,5-difluorobenzyl)piperazine-1-carbonyl) phenyl)quinoline-8-sulfonamide (Compound 394)

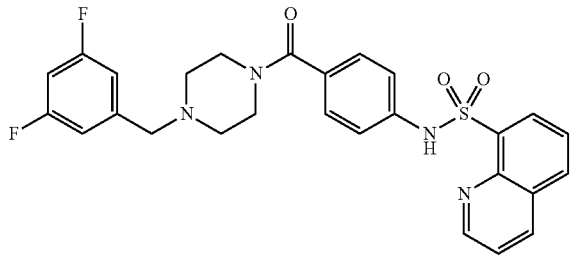 [SMILES: O=C(c1ccc(NS(=O)(=O)c2cccc3cccnc23)cc1)N1CCN(Cc2cc(F)cc(F)c2)CC1]

$^1$H NMR (400 MHz, CDCl$_3$) δ: 2.2-2.6 (m, 4H), 2.4-2.49 (m, 2H), 3.2-3.8 (m, 4H), 6.7-7.0 (m, 3H), 7.0-7.2 (m, 4H), 7.6 (m, 2H), 8.1 (d, 1H), 8.2-8.6 (m, 3H), 9.0 (m, 1H), 10.46 (bs, 1H); HPLC Purity: 98.11%; Mass (M+1): 525.15.

N-(4-(4-((1H-pyrazol-4-yl)methyl)piperazine-1-carbonyl)phenyl)quinoline-8-sulfonamide (Compound 385)

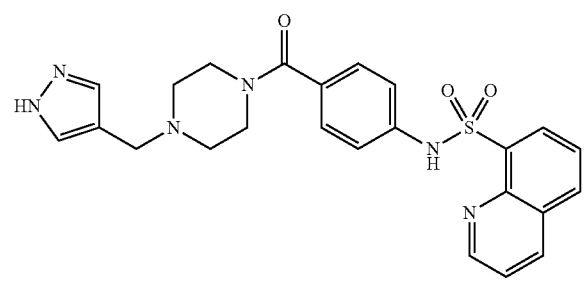 [SMILES: O=C(c1ccc(NS(=O)(=O)c2cccc3cccnc23)cc1)N1CCN(Cc2cn[nH]c2)CC1]

$^1$H NMR (400 MHz, DMSO-d$_6$) δ: 2.2-2.4 (m, 2H), 2.6 (s, 2H), 3.2-3.6 (m, 6H), 6.1 (s, 1H), 7.0-7.2 (m, 4H), 7.4 (s, 1H), 7.6 (s, 1H), 7.7 (m, 2H), 8.3 (d, 1H), 8.4 (d, 1H), 8.5 (d, 1H), 9.0 (m, 1H), 10.4 (s, 1H), 12.7 (s, 1H); HPLC Purity: 99.42%; Mass (M+1): 477.30.

N-(4-(4-(1H-imidazol-4-yl)methyl)piperazine-1-carbonyl)phenyl)quinoline-8-sulfonamide (Compound 386)

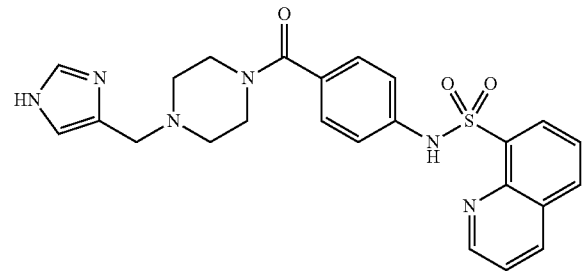 [SMILES: O=C(c1ccc(NS(=O)(=O)c2cccc3cccnc23)cc1)N1CCN(Cc2c[nH]cn2)CC1]

$^1$H NMR (400 MHz, DMSO-d$_6$) δ: 2.2-2.4 (m, 4H), 3.2-3.4 (s, 2H), 3.4-3.6 (m, 3H), 6.1 (s, 1H), 6.9 (s, 1H), 7.0-7.2 (m, 4H), 7.5 (m, 2H), 7.6-7.8 (m, 2H), 8.3 (d, 3H), 8.4 (d, 1H), 8.5 (d, 1H), 9.0 (m, 1H), 10.45 (s, 1H), 12.9 (s, 1H); HPLC Purity: 99.31%; Mass (M+1): 477.40.

N-(3-fluoro-4-(4-(4-fluorobenzyl)piperazine-1-carbonyl)phenyl)quinoline-8-sulfonamide (Compound 420)

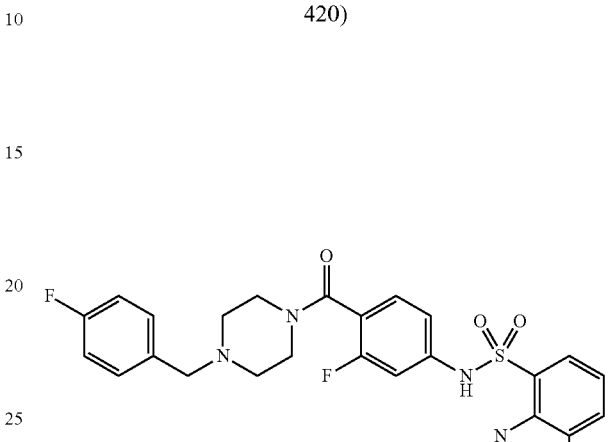

$^1$H NMR (400 MHz, DMSO-d$_6$) δ: 2.2-2.4 (m, 4H), 3.0-3.2 (m, 2H), 3.4 (s, 2H), 3.5-3.6 (m, 2H), 6.9-7.4 (m, 7H), 7.5-7.7 (m, 2H), 8.2-8.4 (m, 3H), 9.1-9.2 (m, 1H), 10.6 (s, 1H); HPLC Purity: 98.69%; Mass (M+1): 523.3.

N-(4-(4-(3,5-difluorobenzyl)piperazine-1-carbonyl)-3-fluorophenyl)quinoline-8-sulfonamide (Compound 421)

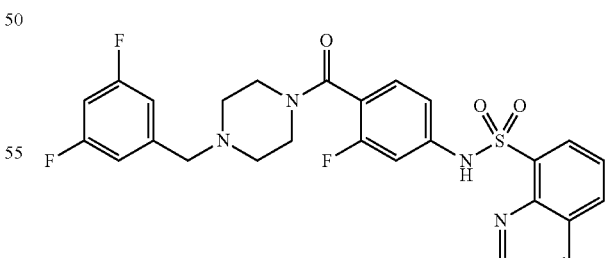

$^1$H NMR (400 MHz, DMSO-d$_6$) δ: 2.2-2.4 (m, 4H), 3.0-3.2 (m, 2H), 3.4 (s, 2H), 3.5-3.6 (m, 2H), 6.9-7.4 (m, 6H), 7.5-7.7

(m, 2H), 8.2-8.4 (m, 3H), 9.1-9.2 (m, 1H), 10.6 (s, 1H); HPLC Purity: 95.95%; Mass (M+1): 541.3.

N-(4-(4-(4-chloro-3-fluorobenzyl)piperazine-1-carbonyl)-3-fluorophenyl)quinoline-8-sulfonamide (Compound 422)

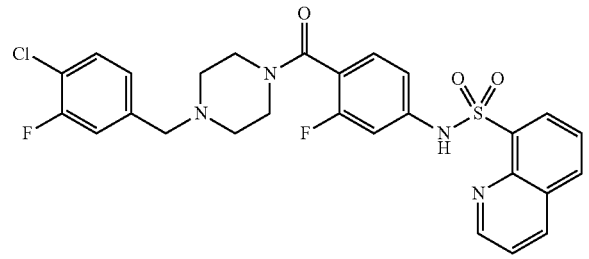

$^1$H NMR (400 MHz, DMSO-$d_6$) δ: 2.2-2.4 (m, 4H), 3.0-3.2 (m, 2H), 3.4 (s, 2H), 3.5-3.6 (m, 2H), 6.9-7.4 (m, 6H), 7.5-7.7 (m, 2H), 8.2-8.4 (m, 3H), 9.1-9.2 (m, 1H), 10.6 (s, 1H); HPLC Purity: 92.56%; Mass (M+1): 557.6.

N-(3-fluoro-4-(4-(3,4,5-trifluorobenzyl)piperazine-1-carbonyl)phenyl)quinoline-8-sulfonamide (Compound 423)

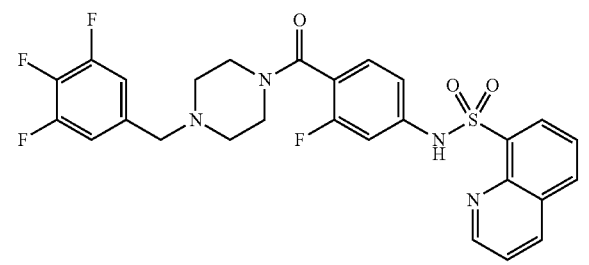 [SMILES: O=C(c1ccc(NS(=O)(=O)c2cccc3cccnc23)cc1F)N1CCN(Cc2cc(F)c(F)c(F)c2)CC1]

$^1$H NMR (400 MHz, DMSO-$d_6$) δ: 2.2-2.4 (m, 4H), 3.0-3.2 (m, 2H), 3.4 (s, 2H), 3.5-3.6 (m, 2H), 6.9-7.1 (m, 2H), 7.2-7.4 (m, 3H), 7.5-7.7 (m, 2H), 8.2-8.25 (d, 1H), 8.4-8.6 (m, 2H), 9.1-9.2 (m, 1H), 10.78 (s, 1H); HPLC Purity: 98.93%; Mass (M+1): 559.5.

N-(4-(4-(cyclopropylmethyl)piperazine-1-carbonyl)-3-fluorophenyl)quinoline-8-sulfonamide (Compound 424)

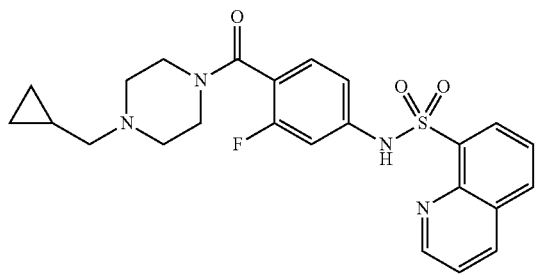 [SMILES: O=C(c1ccc(NS(=O)(=O)c2cccc3cccnc23)cc1F)N1CCN(CC2CC2)CC1]

$^1$H NMR (400 MHz, DMSO-$d_6$) δ: 0.1-0.2 (m, 2H), 0.35-0.45 (m, 2H), 0.8-0.9 (m, 1H), 2.0-2.4 (m, 6H), 3.0-3.2 (m, 2H), 3.4-3.6 (m, 2H), 6.9-7.2 (m, 3H), 7.59-7.7 (m, 2H), 8.2-8.25 (d, 1H), 8.4-8.6 (m, 2H), 9.1-9.2 (m, 1H), 10.78 (s, 1H); HPLC Purity: 98.95%; Mass (M+1): 469.3.

N-(3-fluoro-4-(4-((tetrahydrofuran-3-yl)methyl)piperazine-1-carbonyl)phenyl)quinoline-8-sulfonamide (Compound 425)

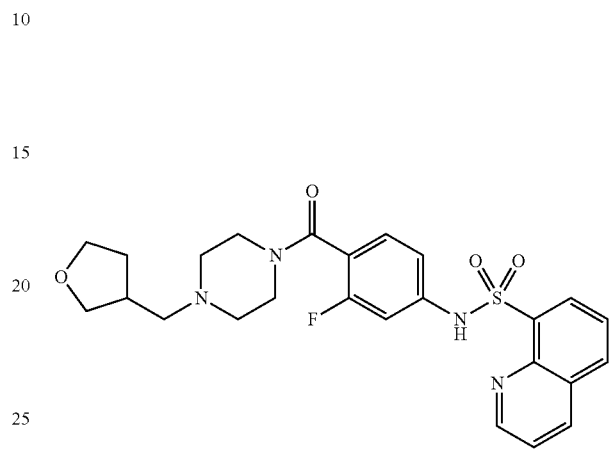

$^1$H NMR (400 MHz, DMSO-$d_6$) δ: 1.4-1.5 (m, 1H), 1.8-2.0 (m, 1H), 2.0-2.4 (m, 7H), 3.0-3.2 (m, 2H), 3.4-3.6 (m, 7H), 6.9-7.2 (m, 3H), 7.59-7.7 (m, 2H), 8.2-8.25 (d, 1H), 8.4-8.6 (m, 2H), 9.1-9.2 (m, 1H), 10.78 (s, 1H); HPLC Purity: 99.36%; Mass (M+1): 499.3.

N-(3-chloro-4-(4-(3,5-difluorobenzyl)piperazine-1-carbonyl)phenyl)quinoline-8-sulfonamide (Compound 426)

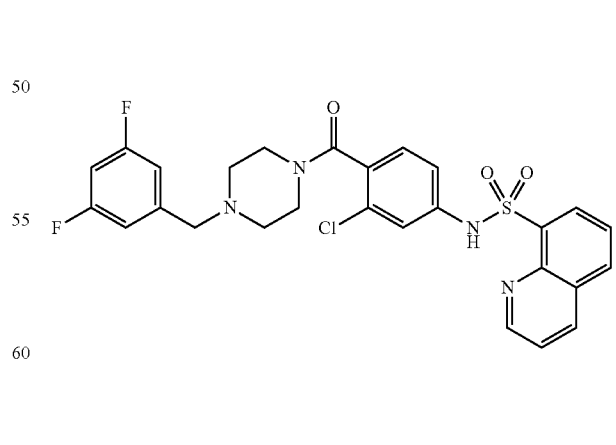

$^1$H NMR (400 MHz, DMSO-$d_6$) δ: 2.2-2.4 (m, 2H), 3.0 (s, 2H), 3.4-3.6 (m, 4H), 7.0-7.2 (m, 6H), 7.59-7.7 (m, 2H), 8.2-8.25 (d, 1H), 8.4-8.6 (m, 3H), 9.1-9.2 (m, 1H), 10.6 (s, 1H); HPLC Purity: 99.12%; Mass (M+1): 557.45.

N-(3-chloro-4-(4-(cyclopropylmethyl)piperazine-1-carbonyl)phenyl)quinoline-8-sulfonamide (Compound 427)

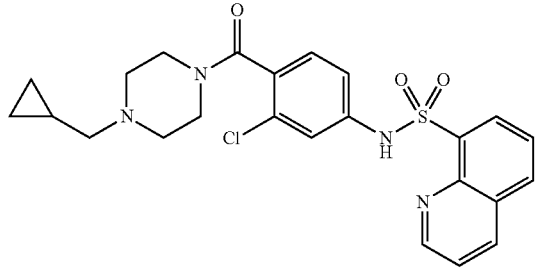

¹H NMR (400 MHz, DMSO-d₆) δ: 0.1-0.2 (m, 2H), 0.3-0.4 (m, 2H), 0.8-0.85 (m, 1H), 2.2-2.4 (m, 6H), 3.0 (s, 2H), 3.5-3.6 (m, 2H), 7.0-7.2 (m, 3H), 7.59-7.7 (m, 2H), 8.2-8.25 (d, 1H), 8.4-8.6 (m, 2H), 9.1-9.2 (m, 1H), 10.6 (s, 1H); HPLC Purity: 99.57%; Mass (M+1): 485.5.

N-(3-chloro-4-(4-(cyclopentylmethyl)piperazine-1-carbonyl)phenyl)quinoline-8-sulfonamide (Compound 428)

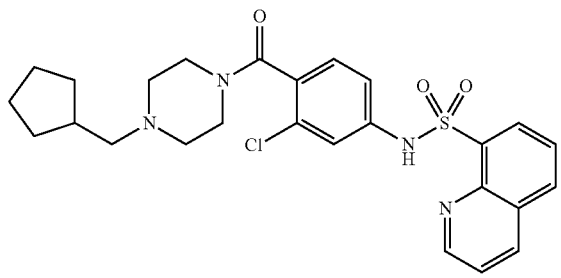

¹H NMR (400 MHz, DMSO-d₆) δ: 1.0-1.2 (m, 2H), 1.4-1.6 (m, 6H), 2.2-2.4 (m, 7H), 3.0 (s, 2H), 3.5-3.6 (m, 2H), 7.0-7.2 (m, 3H), 7.59-7.7 (m, 2H), 8.2-8.6 (m, 2H), 9.1-9.2 (m, 1H), 10.6 (s, 1H); HPLC Purity: 99.40%; Mass (M+1): 513.45.

N-(3-chloro-4-(4-((tetrahydrofuran-3-yl)methyl)piperazine-1-carbonyl)phenyl)quinoline-8-sulfonamide (Compound 429)

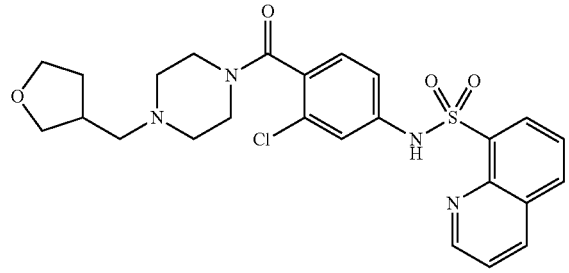 [SMILES: O=C(c1ccc(NS(=O)(=O)c2cccc3cccnc23)cc1F)N1CCN(CC2CCOC2)CC1]

¹H NMR (400 MHz, DMSO-d₆) δ: 1.2-1.5 (m, 1H), 1.8-2.0 (m, 1H), 2.0-2.4 (m, 8H), 3.0 (m, 2H), 3.5-3.8 (m, 5H), 7.0-7.2 (m, 3H), 7.59-7.7 (m, 2H), 8.2-8.6 (m, 3H), 9.1-9.2 (m, 1H), 10.6 (s, 1H); HPLC Purity: 95.96%; Mass (M+1): 515.45.

N-(3-chloro-4-(4-(4-fluorobenzyl)piperazine-1-carbonyl)phenyl)quinoline-8-sulfonamide (Compound 431)

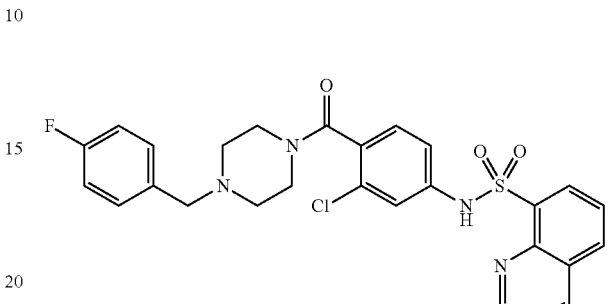

¹H NMR (400 MHz, DMSO-d₆) δ: 2.2-2.4 (m, 4H), 2.9-3.2 (s, 2H), 3.4-3.7 (m, 4H), 7.0-7.2 (m, 5H), 7.3-7.4 (m, 2H), 7.6-7.8 (m, 2H), 8.0-8.6 (m, 3H), 9.1-9.2 (m, 1H), 10.5 (s, 1H); HPLC Purity: 98.11%; Mass (M+1): 539.50.

N-(3-chloro-4-(4-(4-chloro-3-fluorobenzyl)piperazine-1-carbonyl)phenyl)quinoline-8-sulfonamide (Compound 432)

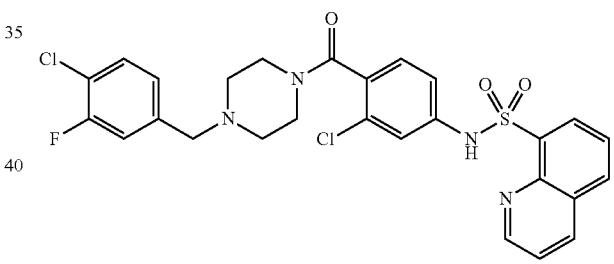

¹H NMR (400 MHz, DMSO-d₆) δ: 2.2-2.4 (m, 4H), 2.9-3.2 (s, 2H), 3.4-3.7 (m, 4H), 7.0-7.2 (m, 5H), 7.3-7.4 (m, 1H), 7.6-7.8 (m, 2H), 8.0-8.6 (m, 3H), 9.1-9.2 (m, 1H), 10.6 (s, 1H); HPLC Purity: 97.27%; Mass (M+1): 573.45.

N-(3-chloro-4-(4-(2,4,5-trifluorobenzyl)piperazine-1-carbonyl)phenyl)quinoline-8-sulfonamide (Compound 433)

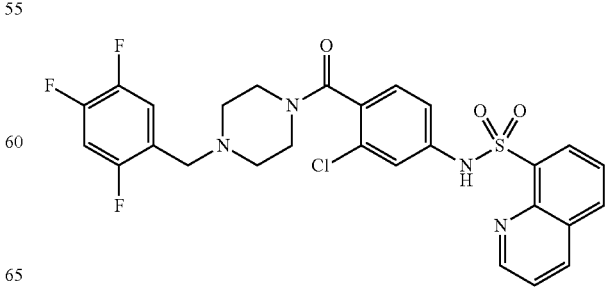

¹H NMR (400 MHz, DMSO-d₆) δ: 2.2-2.4 (m, 4H), 2.9-3.2 (s, 2H), 3.4-3.7 (m, 4H), 7.0-7.2 (m, 3H), 7.3-7.4 (m, 2H), 7.6-7.8 (m, 2H), 8.0-8.6 (m, 3H), 9.1-9.2 (m, 1H), 10.6 (s, 1H); HPLC Purity: 99.17%; Mass (M+1): 575.45.

N-(3-chloro-4-(4-(3,4,5-trifluorobenzyl)piperazine-1-carbonyl)phenyl)quinoline-8-sulfonamide (Compound 434)

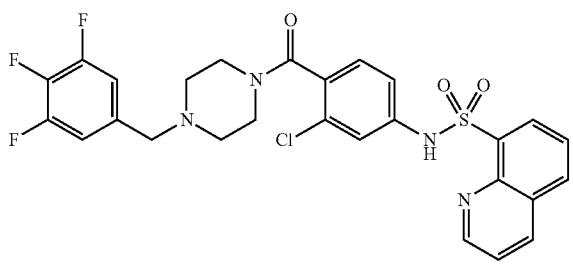 [SMILES: O=C(c1ccc(NS(=O)(=O)c2cccc3cccnc23)cc1Cl)N1CCN(Cc2cc(F)c(F)c(F)c2)CC1]

¹H NMR (400 MHz, DMSO-d₆) δ: 2.2-2.4 (m, 4H), 2.9-3.2 (s, 2H), 3.4-3.7 (m, 4H), 7.0-7.2 (m, 5H), 7.6-7.8 (m, 2H), 8.0-8.6 (m, 3H), 9.1-9.2 (m, 1H), 10.6 (s, 1H); HPLC Purity: 99.55%; Mass (M+1): 575.50.

N-(3-fluoro-4-(4-((tetrahydro-2H-pyran-2-yl)methyl)piperazine-1-carbonyl)phenyl)quinoline-8-sulfonamide (Compound 435)

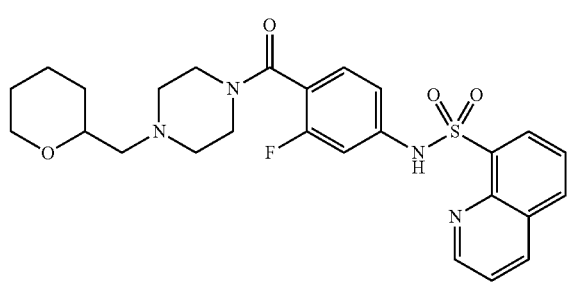 [SMILES: O=C(c1ccc(NS(=O)(=O)c2cccc3cccnc23)cc1F)N1CCN(CC2CCCCO2)CC1]

¹H NMR (400 MHz, DMSO-d₆) δ: 1.0-1.2 (m, 1H), 1.3-1.56 (m, 5H), 1.6-1.7 (m, 1H), 2.2-2.4 (m, 6H), 2.9-3.4 (m, 3H), 3.7-3.8 (m, 1H), 7.0-7.2 (m, 3H), 7.6-7.8 (m, 2H), 8.0-8.6 (m, 3H), 9.1-9.2 (m, 1H), 10.6 (s, 1H); HPLC Purity: 95.44%; Mass (M+1): 513.3.

N-(3-fluoro-4-(4-((tetrahydro-2H-pyran-4-yl)methyl)piperazine-1-carbonyl)phenyl)quinoline-8-sulfonamide (Compound 436)

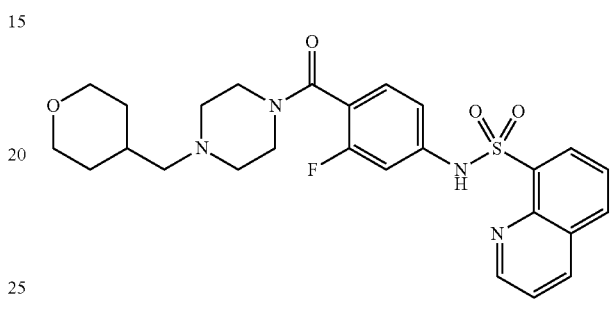

¹H NMR (400 MHz, DMSO-d₆) δ: 1.0-1.2 (m, 3H), 1.56-1.6 (m, 3H), 2.2-2.6 (m, 5H), 2.99-3.4 (m, 5H), 3.6-3.8 (m, 3H), 7.0-7.2 (m, 3H), 7.6-7.8 (m, 2H), 8.0-8.6 (m, 3H), 9.1-9.2 (m, 1H), 10.4 (s, 1H); HPLC Purity: 93.35%; Mass (M+1): 513.3.

N-(3-fluoro-4-(4-((tetrahydrofuran-2-yl)methyl)piperazine-1-carbonyl)phenyl)quinoline-8-sulfonamide (Compound 437)

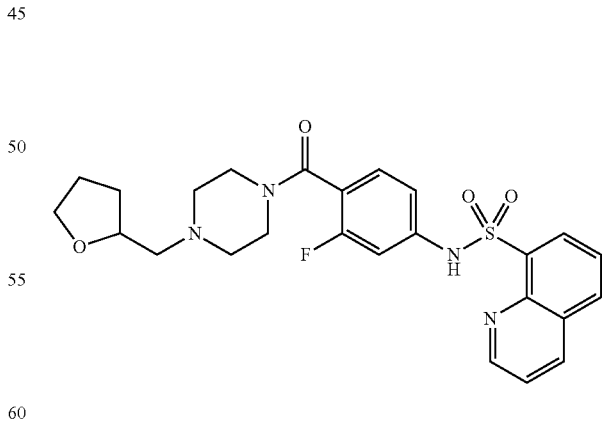

¹H NMR (400 MHz, DMSO-d₆) δ: 1.4-1.45 (m, 1H), 1.7-2.0 (m, 3H), 2.2-2.6 (m, 6H), 2.99-3.2 (m, 2H), 3.4-4.0 (m,

5H), 7.0-7.2 (m, 3H), 7.6-7.8 (m, 2H), 8.0-8.6 (m, 3H), 9.1-9.2 (m, 1H), 10.4 (s, 1H); HPLC Purity: 97.02%; Mass (M+1): 499.3.

N-(3-chloro-4-(4-((tetrahydro-2H-pyran-2-yl)methyl)piperazine-1-carbonyl)phenyl)quinoline-8-sulfonamide (Compound 439)

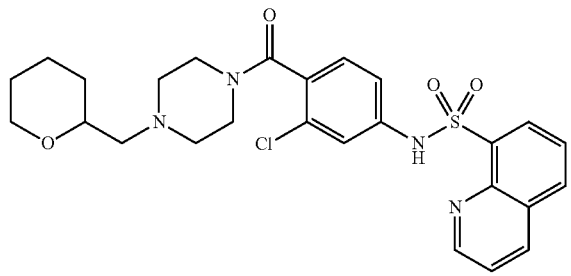 [SMILES: O=C(c1ccc(NS(=O)(=O)c2cccc3cccnc23)cc1Cl)N1CCN(CC2CCCCO2)CC1]

$^1$H NMR (400 MHz, DMSO-d$_6$) δ: 1.0-1.8 (m, 6H), 2.1-2.7 (m, 6H), 3.0-3.8 (m, 7H), 7.0-7.2 (m, 3H), 7.6-7.8 (m, 2H), 8.2-8.6 (m, 3H), 9.1-9.2 (m, 1H) 10.6 (s, 1H); HPLC Purity: 95.14%; Mass (M+1): 529.4.

N-(3-chloro-4-(4-((tetrahydro-2H-pyran-4-yl)methyl)piperazine-1-carbonyl)phenyl)quinoline-8-sulfonamide (Compound 440)

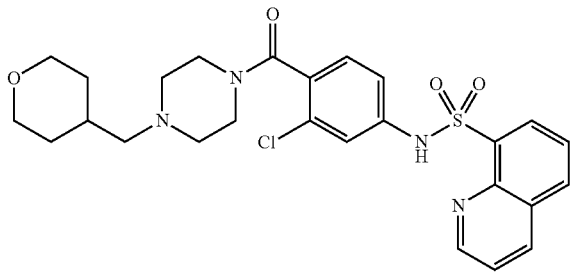 [SMILES: O=C(c1ccc(NS(=O)(=O)c2cccc3cccnc23)cc1Cl)N1CCN(CC2CCOCC2)CC1]

$^1$H NMR (400 MHz, DMSO-d$_6$) δ: 1.0-1.8 (m, 4H), 2.1-2.5 (m, 7H), 2.7-3.85 (m, 8H), 7.0-7.2 (m, 3H), 7.6-7.8 (m, 2H), 8.2-8.6 (m, 3H), 9.1-9.2 (m, 1H) 10.6 (bs, 1H); HPLC Purity: 96.39%; Mass (M+1): 529.4.

N-(3-chloro-4-(4-((tetrahydrofuran-2-yl)methyl)piperazine-1-carbonyl)phenyl)quinoline-8-sulfonamide (Compound 441)

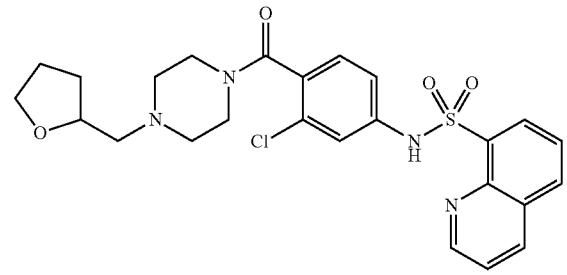 [SMILES: O=C(c1ccc(NS(=O)(=O)c2cccc3cccnc23)cc1Cl)N1CCN(CC2CCCO2)CC1]

$^1$H NMR (400 MHz, DMSO-d$_6$) δ: 1.6-2.0 (m, 4H), 2.1-3.0 (m, 7H), 3.4-4.0 (m, 6H), 7.0-7.2 (m, 3H), 7.6-7.8 (m, 2H), 8.2-8.6 (m, 3H), 9.1-9.2 (m, 1H) 10.6 (bs, 1H); HPLC Purity: 97.11%; Mass (M+1): 515.3.

N-(4-(4-((5-fluoropyridin-3-yl)methyl)piperazine-1-carbonyl)-2-(trifluoromethoxy)phenyl)quinoline-8-sulfonamide (Compound 390)

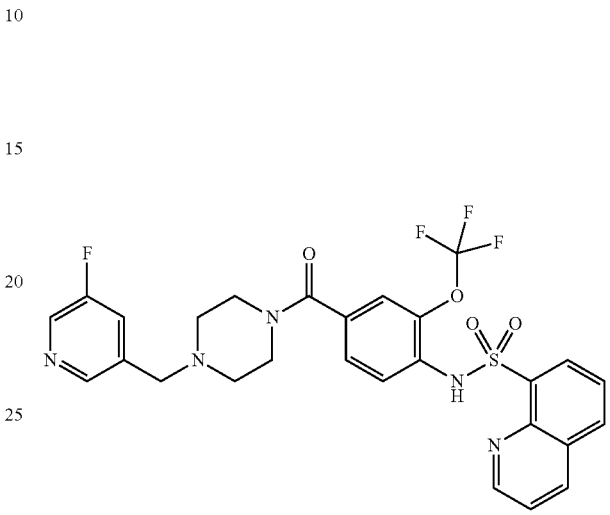

$^1$H NMR (400 MHz, DMSO-d$_6$) δ: 2.3-2.4 (m, 4H), 2.8 (s, 2H), 3.4-3.6 (m, 4H), 7.2-7.4 (m, 2H), 7.5-7.8 (m, 4H), 8.2-8.6 (m, 5H), 9.1 (m, 1H), 10.0 (bs, 1H); HPLC Purity: 97.9%; Mass (M+1): 590.0.

N-(4-(4-(cyclopropylmethyl)piperazine-1-carbonyl)-2-(trifluoromethoxy)phenyl)quinoline-8-sulfonamide (Compound 301)

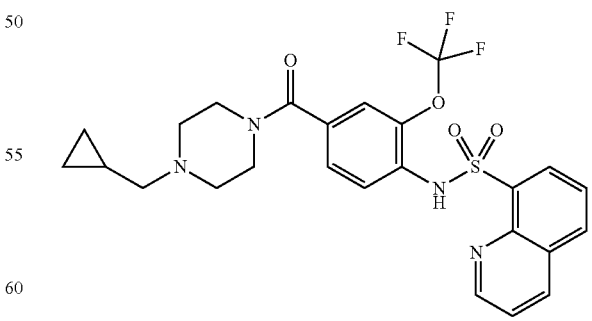

$^1$H NMR (400 MHz, DMSO-d$_6$) δ: 0.1 (m, 2H), 0.4 (m, 2H), 0.8 (m, 1H), 2.2 (d, 2H), (2.4-2.6 (m, 4H), 3.2-3.6 (m,

3H), 7.3 (d, 2H), 7.5 (d, 1H), 7.8 (m, 2H), 8.3 (m, 2H), 8.6 (m, 1H), 9.1 (m, 1H), 10 (bs, 1H); HPLC Purity: 98.12%; Mass (M+1): 535.0.

N-(4-(4-((tetrahydrofuran-3-yl)methyl)piperazine-1-carbonyl)-2-(trifluoromethoxy)phenyl)quinoline-8-sulfonamide (Compound 302)

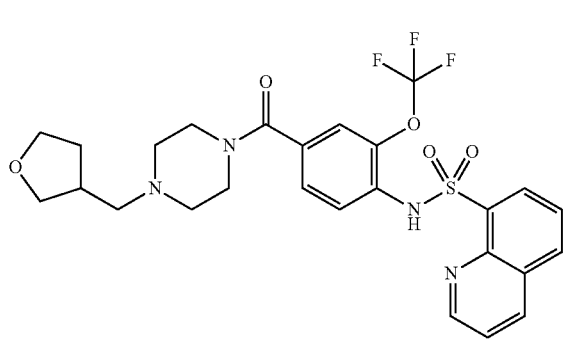 [SMILES: O=C(c1ccc(NS(=O)(=O)c2cccc3cccnc23)c(OC(F)(F)F)c1)N1CCN(CC2CCOC2)CC1]

$^1$H NMR (400 MHz, DMSO-d$_6$) δ: 0.6 (m, 2H), 0.9 (m, 2H), 0.8 (m, 1H), 2.5 (m, 6H), 3.0 (m, 2H), 3.6 (m, 1H), 3.7 (m, 4H), 7.2 (m, 2H), 7.5 (d, 1H), 7.8 (m, 2H), 8.3 (m, 2H), 8.6 (m, 1H), 9.1 (m, 1H), 10 (bs, 1H); HPLC Purity: 97.93%; Mass (M+1): 565.0.

N-(4-(4-phenethylpiperazine-1-carbonyl)-2-(trifluoromethoxy)phenyl)quinoline-8-sulfonamide (Compound 303)

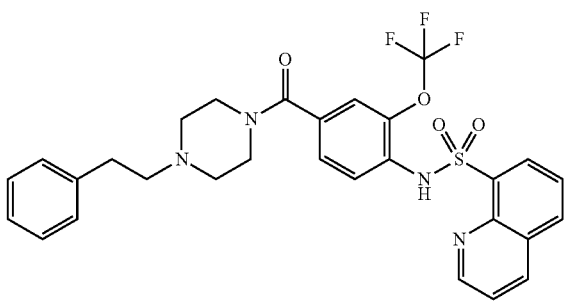 [SMILES: O=C(c1ccc(NS(=O)(=O)c2cccc3cccnc23)c(OC(F)(F)F)c1)N1CCN(CCc2ccccc2)CC1]

$^1$H NMR (400 MHz, DMSO-d$_6$) δ: 2.4-2.6 (m, 4H), 2.7 (m, 4H), 3.2 (m, 2H), 3.7 (m, 2H), 7.1-7.4 (m, 7H), 7.6 (s, 1H), 7.8 (m, 2H), 8.3 (m, 2H), 8.6 (m, 1H), 9.1 (m, 1H), 10.0 (bs, 1H); HPLC Purity: 99.67%; Mass (M+1): 585.

N-(4-(4-(2-(3-fluoropyridin-4-yl)ethyl)piperazine-1-carbonyl)-2-(trifluoromethoxy)phenyl)quinoline-8-sulfonamide (Compound 304)

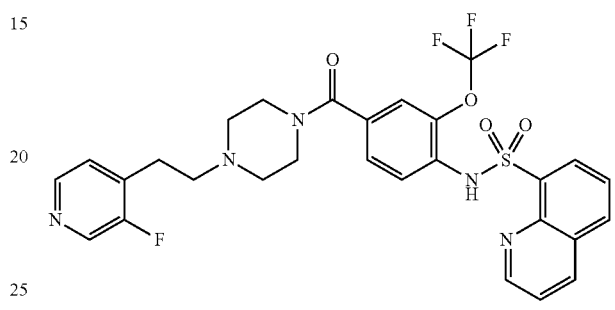

$^1$H NMR (400 MHz, DMSO-d$_6$) δ: 2.4 (m, 4H), 3.0 (m, 2H), 4.6 (m, 4H), 3.7 (m, 2H), 7.3 (m, 2H), 7.5 (m, 2H), 7.8 (m, 2H), 8.3 (m, 2H), 8.6 (m, 2H), 9.1 (m, 1H), 10.0 (bs, 1H); HPLC Purity: 97.7%; Mass (M+1): 590.

N-(4-(4-(2-(4-methoxypyridin-3-yl)ethyl)piperazine-1-carbonyl)-2-(trifluoromethoxy)phenyl)quinoline-8-sulfonamide (Compound 305)

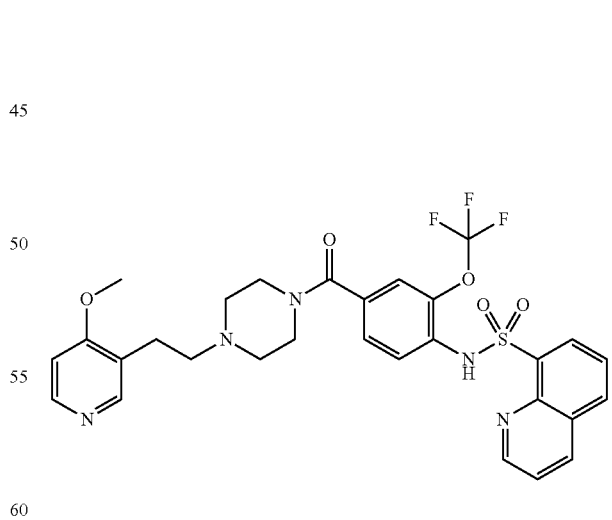

$^1$H NMR (400 MHz, DMSO-d$_6$) δ: 2.4 (m, 4H), 3.4 (m, 6H), 3.8 (s, 3H), 7.0 (m, 1H), 7.3 (m, 2H), 7.5 (m, 1H), 7.7 (m,

2H), 8.3 (m, 4H), 8.6 (m, 1H), 9.1 (m, 1H), 10.0 (bs, 1H); HPLC Purity: 98.7%; Mass (M+1): 602.

N-(4-(4-(2,3-dichlorophenethyl)piperazine-1-carbonyl)-2-(trifluoromethoxy)phenyl)quinoline-8-sulfonamide (Compound 306)

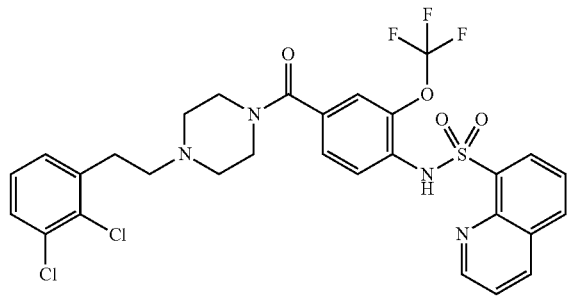 [SMILES: O=C(c1ccc(NS(=O)(=O)c2cccc3cccnc23)c(OC(F)(F)F)c1)N1CCN(CCc2cccc(Cl)c2Cl)CC1]

$^1$H NMR (400 MHz, DMSO-d$_6$) δ: 2.4 (m, 4H), 3.4 (m, 2H), 3.8 (m, 4H), 7.2-7.4 (m, 6H), 7.8 (m, 2H), 8.3 (m, 2H), 8.6 (m, 1H), 9.1 (m, 1H), 10.0 (bs, 1H); HPLC Purity: 99%; Mass (M+1): 639.

N-(4-(4-((3-chloropyridin-4-yl)methyl)piperazine-1-carbonyl)-2-(trifluoromethoxy)phenyl)quinoline-8-sulfonamide (Compound 307)

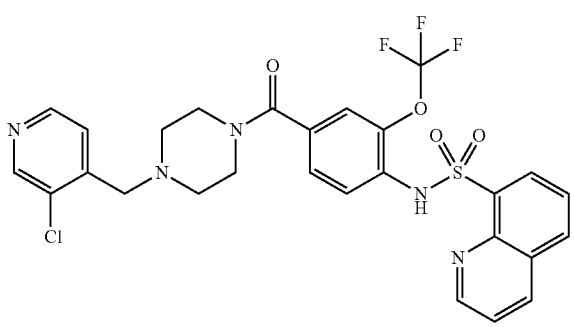 [SMILES: O=C(c1ccc(NS(=O)(=O)c2cccc3cccnc23)c(OC(F)(F)F)c1)N1CCN(Cc2ccncc2Cl)CC1]

$^1$H NMR (400 MHz, DMSO-d$_6$) δ: 2.4 (m, 4H), 3.2 (s, 2H), 3.6 (m, 4H), 7.3 (m, 2H), 7.6 (m, 2H), 7.8 (m, 2H), 8.3 (m, 2H), 8.6 (m, 2H), 9.1 (m, 1H), 10.0 (bs, 1H); HPLC Purity: 99.24%; Mass (M+1): 606.

N-(4-(4-(2-fluoro-6-methoxybenzyl)piperazine-1-carbonyl)-2-(trifluoromethoxy)phenyl)quinoline-8-sulfonamide (Compound 308)

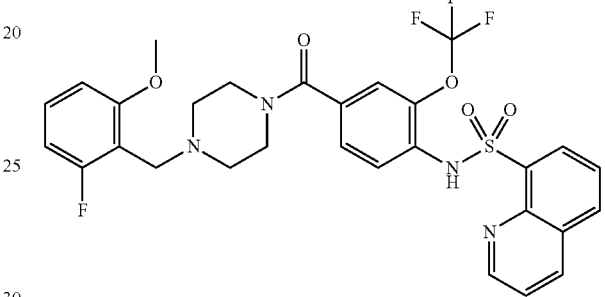

$^1$H NMR (400 MHz, DMSO-d$_6$) δ: 2.4 (m, 4H), 3.6 (s, 3H), 3.7 (s, 2H), 3.8 (m, 4H), 6.8 (m, 2H), 7.2 (m, 3H), 7.5 (m, 1H), 7.8 (m, 2H), 8.3 (m, 2H), 8.6 (m, 1H), 9.1 (m, 1H), 10.0 (bs, 1H); HPLC Purity: 96.97%; Mass (M+1): 619.

N-(2-(trifluoromethoxy)-4-(4-((3-(trifluoromethyl)pyridin-2-yl)methyl)piperazine-1-carbonyl)phenyl)quinoline-8-sulfonamide (Compound 309)

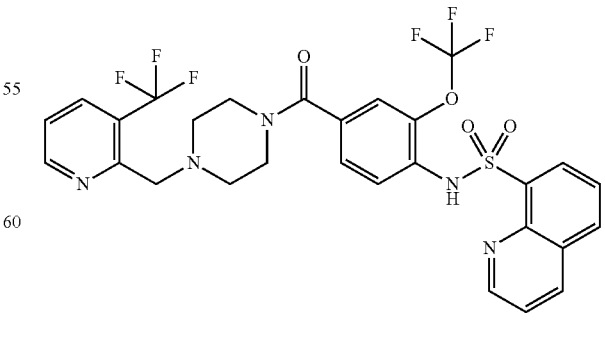

$^1$H NMR (400 MHz, DMSO-d$_6$) δ: 2.4 (m, 4H), 3.2 (s, 2H), 3.6-3.8 (m, 4H), 7.2 (m, 2H), 7.5 (m, 2H), 7.8 (m, 2H), 8.3 (m,

2H), 8.6 (m, 1H), 8.8 (m, 1H), 9.1 (m, 1H), 10.0 (bs, 1H); HPLC Purity: 98.32%; Mass (M+1): 640.

N-(4-(4-(4-methoxybenzyl)piperazine-1-carbonyl)-2-(trifluoromethoxy)phenyl)quinoline-8-sulfonamide (Compound 310)

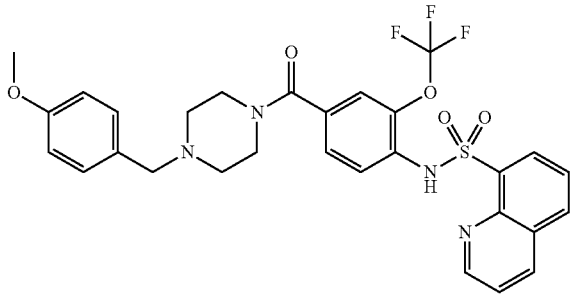

$^1$H NMR (400 MHz, DMSO-d$_6$) δ: 2.4 (m, 4H), 3.2 (s, 2H), 3.6-3.8 (m, 4H), 7.2 (m, 2H), 7.5 (m, 2H), 7.8 (m, 2H), 8.3 (m, 2H), 8.6 (m, 1H), 8.8 (m, 1H), 9.1 (m, 1H), 10.0 (bs, 1H); HPLC Purity: 97.32%; Mass (M+1): 640.

N-(4-(4-(pyridin-4-ylmethyl)piperazine-1-carbonyl)-2-(trifluoromethyl)phenyl)quinoline-8-sulfonamide (Compound 328)

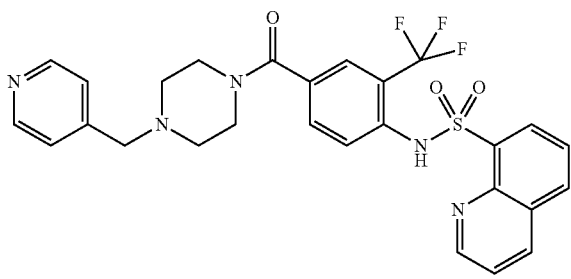 [SMILES: O=C(c1ccc(NS(=O)(=O)c2cccc3cccnc23)c(C(F)(F)F)c1)N1CCN(Cc2ccncc2)CC1]

$^1$H NMR (400 MHz, CDCl$_3$) δ: 2.2-2.8 (m, 4H), 2.9 (s, 2H), 3.2-3.7 (m, 4H), 7.2 (m, 1H), 7.6 (m, 4H), 7.9 (m, 1H), 8.1 (m, 1H), 8.3 (m, 2H), 8.6 (m, 3H), 9.1 (m, 1H); HPLC Purity: 99.67%; Mass (M+1): 556.2.

N-(4-(4-((tetrahydrofuran-2-yl)methyl)piperazine-1-carbonyl)-2-(trifluoromethyl)phenyl)quinoline-8-sulfonamide (Compound 329)

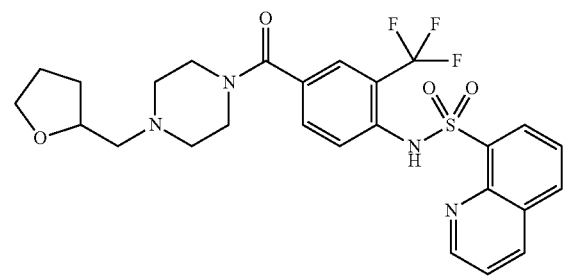 [SMILES: O=C(c1ccc(NS(=O)(=O)c2cccc3cccnc23)c(C(F)(F)F)c1)N1CCN(CC2CCCO2)CC1]

$^1$H NMR (400 MHz, CDCl$_3$) δ: 1.5 (m, 1H), 1.8-2.0 (m, 3H), 2.3-2.6 (m, 6H), 3.6 (s, 2H), 3.8 (m, 4H), 4.0 (m, 1H), 7.4 (m, 1H), 7.6 (m, 3H), 7.8 (m, 1H), 8.0 (m, 1H), 8.3 (m, 1H), 8.5 (m, 1H), 9.1 (m, 1H); HPLC Purity: 98.77%; Mass (M+1): 549.2.

N-(2-(trifluoromethoxy)-4-(4-(4-(trifluoromethyl)benzyl)piperazine-1-carbonyl)phenyl)quinoline-8-sulfonamide (Compound 334)

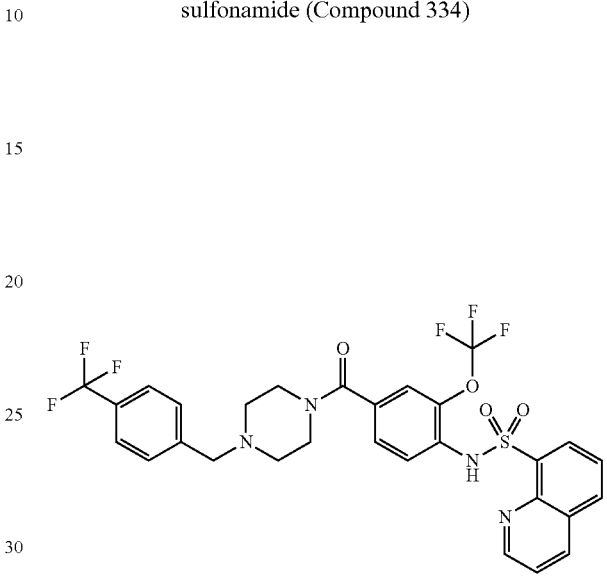

$^1$H NMR (400 MHz, DMSOd$_6$) δ: 2.2-2.5 (m, 4H), 2.8 (s, 2H), 3.2-3.6 (m, 2H), 3.8 (m, 2H), 7.2 (m, 2H), 7.5 (m, 3H), 7.8 (m, 4H), 8.3 (m, 2H), 8.6 (m, 1H), 9.0 (m, 1H), 10.0 (bs, 1H); HPLC Purity: 99.88%; Mass (M+1): 639.25.

N-(4-(4-(2-fluorobenzyl)piperazine-1-carbonyl)-2-(trifluoromethoxy)phenyl)quinoline-8-sulfonamide (Compound 335)

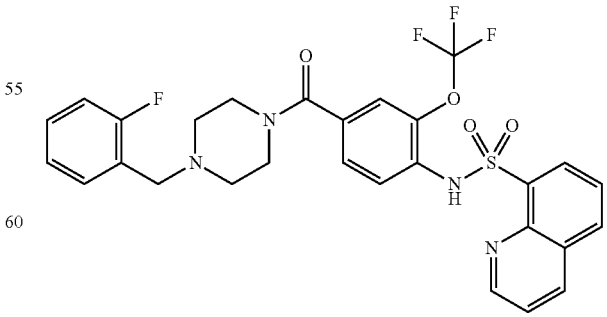 [SMILES: O=C(c1ccc(NS(=O)(=O)c2cccc3cccnc23)c(OC(F)(F)F)c1)N1CCN(Cc2ccc(F)cc2)CC1]

$^1$H NMR (400 MHz, DMSOd$_6$) δ: 2.2-2.5 (m, 4H), 2.8 (s, 2H), 3.2-3.6 (m, 2H), 3.8 (m, 2H), 7.2 (m, 6H), 7.5 (m, 1H), 7.8 (m, 2H), 8.3 (m, 2H), 8.6 (m, 1H), 9.0 (m, 1H), 10.0 (bs, 1H); HPLC Purity: 99.63%; Mass (M+1): 589.35.

N-(4-(4-(cyclopentylmethyl)piperazine-1-carbonyl)-2-(trifluoromethoxy)phenyl)quinoline-8-sulfonamide (Compound 336)

7.7 (m, 2H), 8.3 (m, 2H), 8.6 (m, 1H), 9.0 (m, 1H), 10.0 (bs, 1H); HPLC Purity: 97.29%; Mass (M+1): 589.40.

N-(4-(4-(4-chlorobenzyl)piperazine-1-carbonyl)-2-(trifluoromethoxy)phenyl)quinoline-8-sulfonamide (Compound 338)

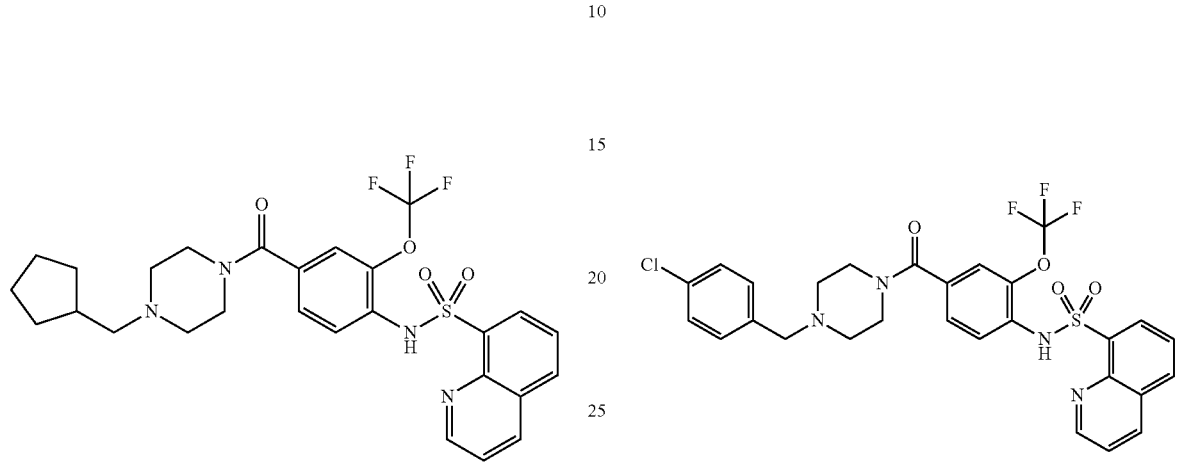

¹H NMR (400 MHz, DMSOd₆) δ: 1.0 (m, 2H), 1.5 (m, 4H), 1.6 (m, 2H), 2.0 (m, 1H), 2.3 (s, 2H), 2.2-2.5 (m, 4H), 3.2-3.6 (m, 4H), 7.2 (m, 2H), 7.5 (m, 1H), 7.7 (m, 2H), 8.3 (m, 2H), 8.6 (m, 1H), 9.0 (m, 1H), 10.0 (bs, 1H); HPLC Purity: 99.92%; Mass (M+1): 563.40.

¹H NMR (400 MHz, DMSOd₆) δ: 2.2-2.5 (m, 4H), 3.1 (s, 2H), 3.2-3.6 (m, 4H), 7.3 (m, 5.0), 7.5 (m, 1H), 7.7 (m, 2H), 8.3 (m, 2H), 8.6 (m, 1H), 9.0 (m, 1H), 10.0 (bs, 1H); HPLC Purity: 99.95%; Mass (M+1): 605.35.

N-(4-(4-(4-fluorobenzyl)piperazine-1-carbonyl)-2-(trifluoromethoxy)phenyl)quinoline-8-sulfonamide (Compound 337)

N-(4-(4-(4-chloro-2-fluorobenzyl)piperazine-1-carbonyl)-2-(trifluoromethoxy)phenyl)quinoline-8-sulfonamide (Compound 339)

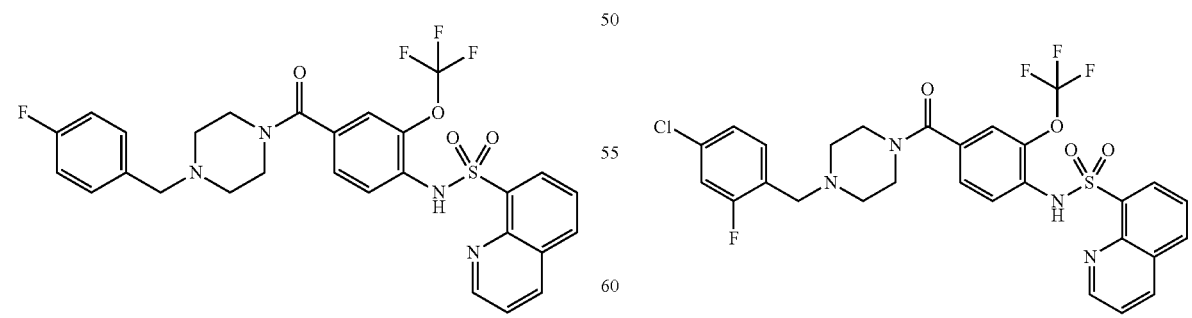

¹H NMR (400 MHz, DMSOd₆) δ: 2.2-2.5 (m, 4H), 3.1 (s, 2H), 3.2-3.6 (m, 4H), 7.0 (m, 2H), 7.1 (m, 3.0), 7.5 (m, 1H),

¹H NMR (400 MHz, DMSOd₆) δ: 2.2-2.5 (m, 4H), 3.1 (s, 2H), 3.2-3.6 (m, 4H), 7.3 (m, 5.0), 7.5 (m, 1H), 7.7 (m, 2H), 8.3 (m, 2H), 8.6 (m, 1H), 9.0 (m, 1H), 10.0 (bs, 1H); HPLC Purity: 99.20%; Mass (M+1): 623.25.

N-(2-(trifluoromethoxy)-4-(4-(4-(trifluoromethyl)pyridin-3-yl)methyl)piperazine-1-carbonyl)phenyl)quinoline-8-sulfonamide (Compound 366)

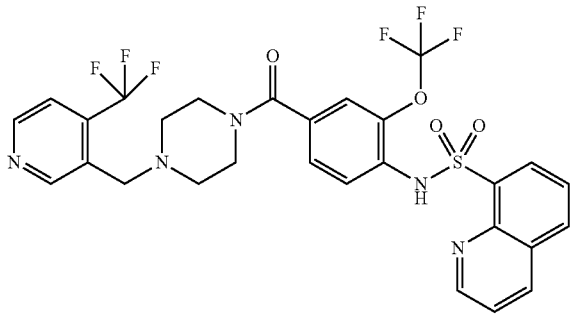 [SMILES: O=C(c1ccc(NS(=O)(=O)c2cccc3cccnc23)c(OC(F)(F)F)c1)N1CCN(Cc2cnccc2C(F)(F)F)CC1]

$^1$H NMR (400 MHz, DMSO-d$_6$) δ: 2.2 (s, 4H), 3.2-3.6 (m, 4H), 3.9 (m, 2H), 7.2 (m, 2H), 7.5 (m, 1H), 7.8 (m, 3H), 8.3 (m, 2H), 8.6-9.1 (m, 4H), 10.0 (s, 1H); HPLC Purity: 99.76%; Mass (M+1): 640.40.

N-(4-(4-((5-chloropyridin-3-yl)methyl)piperazine-1-carbonyl)-2-(trifluoromethoxy)phenyl)quinoline-8-sulfonamide (Compound 367)

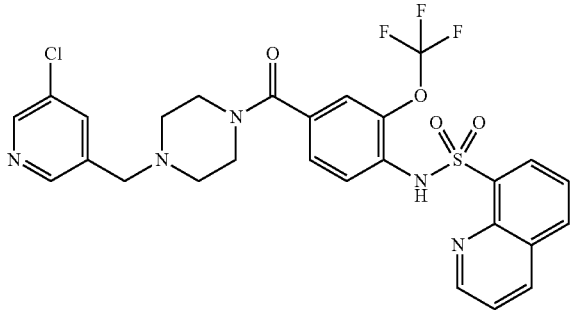 [SMILES: O=C(c1ccc(NS(=O)(=O)c2cccc3cccnc23)c(OC(F)(F)F)c1)N1CCN(Cc2cncc(Cl)c2)CC1]

$^1$H NMR (400 MHz, DMSO-d$_6$) δ: 2.2-2.6 (m, 4H), 2.8 (s, 2H), 3.2-3.6 (m, 4H), 7.0-7.8 (m, 6H), 8.3-8.6 (m, 5H), 9.0 (m, 1H), 10.0 (s, 1H); HPLC Purity: 99.85%; Mass (M+1): 606.30.

N-(4-(4-((2-methoxypyridin-3-yl)methyl)piperazine-1-carbonyl)-2-(trifluoromethoxy)phenyl)quinoline-8-sulfonamide (Compound 368)

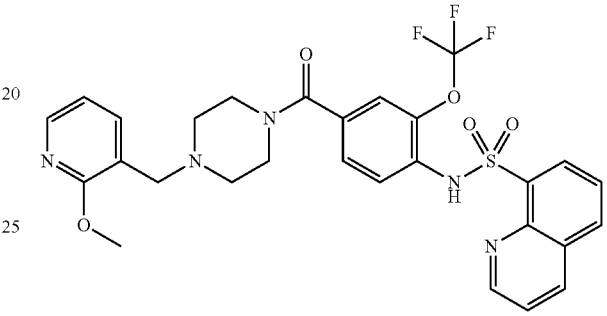

$^1$H NMR (400 MHz, DMSO-d$_6$) δ: 2.2-2.6 (m, 4H), 2.8 (s, 2H), 3.2-3.6 (m, 4H), 7.0-7.8 (m, 7H), 8.3-8.6 (m, 4H), 9.0 (m, 1H), 10.0 (s, 1H); HPLC Purity: 99.38%; Mass (M+1): 602.40.

N-(4-(4-(2,4-difluorobenzyl)piperazine-1-carbonyl)-2-(trifluoromethoxy)phenyl)quinoline-8-sulfonamide (Compound 369)

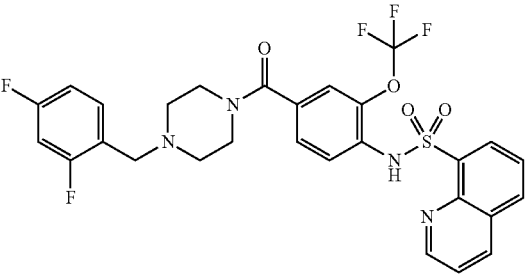 [SMILES: O=C(c1ccc(NS(=O)(=O)c2cccc3cccnc23)c(OC(F)(F)F)c1)N1CCN(Cc2ccc(F)cc2F)CC1]

$^1$H NMR (400 MHz, DMSO-d$_6$) δ: 2.2-2.4 (m, 4H), 3.5 (s, 2H), 3.2-3.4 (m, 4H), 7.0 (m, 1H), 7.2-7.3 (m, 3H), 7.4-7.6

(m, 2H), 7.8 (m, 2H), 8.3-8.6 (m, 3H), 9.0 (m, 1H), 10.0 (s, 1H); HPLC Purity: 99.17%; Mass (M+1): 607.30.

N-(4-(4-((3-methoxypyridin-2-yl)methyl)piperazine-1-carbonyl)-2-(trifluoromethoxy)phenyl)quinoline-8-sulfonamide (Compound 373)

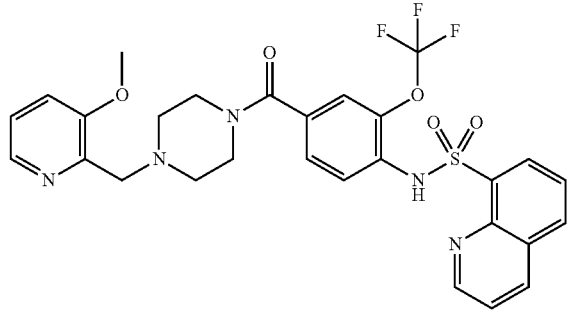 [SMILES: COc1cccnc1CN1CCN(C(=O)c2ccc(NS(=O)(=O)c3cccc4cccnc34)c(OC(F)(F)F)c2)CC1]

$^1$H NMR (400 MHz, DMSO-d$_6$) δ: 2.3-2.5 (m, 4H), 3.1-3.45 (s, 2H), 3.5-3.6 (m, 4H), 7.2-7.6 (m, 5H), 7.7 (m, 2H), 8.1 (m, 1H), 8.3 (m, 2H), 8.6 (d, 1H), 9.0 (m, 1H), 9.90 (s, 1H); HPLC Purity: 97.46%; Mass (M+1): 402.30.

N-(4-(4-(2,4-dichlorobenzyl)piperazine-1-carbonyl)-2-(trifluoromethoxy)phenyl)quinoline-8-sulfonamide (Compound 374)

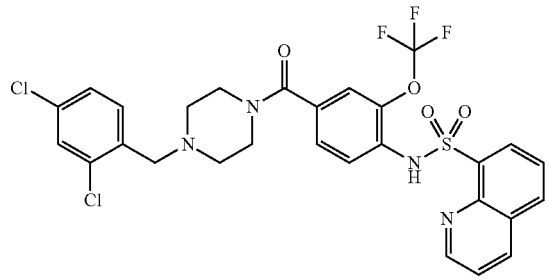

$^1$H NMR (400 MHz, DMSO-d$_6$) δ: 2.3-2.5 (m, 4H), 3.1-3.40 (m, 4H), 3.5-3.6 (s, 2H), 7.2-7.8 (m, 7H), 8.3 (m, 2H), 8.6 (d, 1H), 9.0 (m, 1H), 9.90 (bs, 1H); HPLC Purity: 99.16%; Mass (M+1): 640.40.

N-(4-(4-(2,3-difluorobenzyl)piperazine-1-carbonyl)-2-(trifluoromethoxy)phenyl)quinoline-8-sulfonamide (Compound 375)

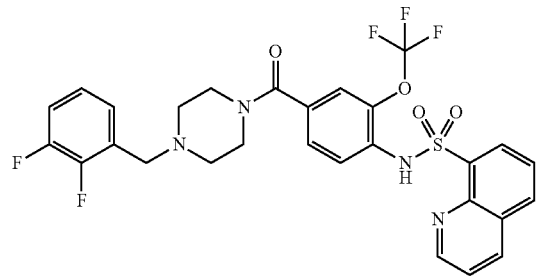 [SMILES: O=C(c1ccc(NS(=O)(=O)c2cccc3cccnc23)c(OC(F)(F)F)c1)N1CCN(Cc2cccc(F)c2F)CC1]

$^1$H NMR (400 MHz, DMSO-d$_6$) δ: 2.2-2.5 (m, 2H), 2.8 (s, 2H), 3.1-3.8 (m, 6H), 7.2-7.4 (m, 5H), 7.58 (m, 1H), 7.75 (m, 2H), 8.3 (m, 2H), 8.6 (d, 1H), 9.0 (m, 1H), 9.90 (bs, 1H); HPLC Purity: 98.91%; Mass (M+1): 607.30.

N-(4-(4-(3-chloro-4-fluorobenzyl)piperazine-1-carbonyl)-2-(trifluoromethoxy)phenyl)quinoline-8-sulfonamide (Compound 376)

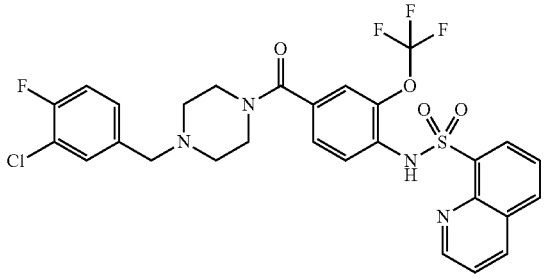 [SMILES: O=C(c1ccc(NS(=O)(=O)c2cccc3cccnc23)c(OC(F)(F)F)c1)N1CCN(Cc2ccc(F)c(Cl)c2)CC1]

$^1$H NMR (400 MHz, DMSO-d$_6$) δ: 2.2-2.5 (m, 4H), 2.69 (s, 2H), 3.2-3.8 (m, 4H), 7.2-7.2 (m, 4H), 7.58 (m, 2H), 7.75 (m,

2H), 8.3 (m, 2H), 8.6 (m, 1H), 9.0 (m, 1H), 9.90 (bs, 1H); HPLC Purity: 95.94%; Mass (M+1): 623.25.

N-(4-(4-(3-fluorobenzyl)piperazine-1-carbonyl)-2-(trifluoromethoxy)phenyl)quinoline-8-sulfonamide (Compound 377)

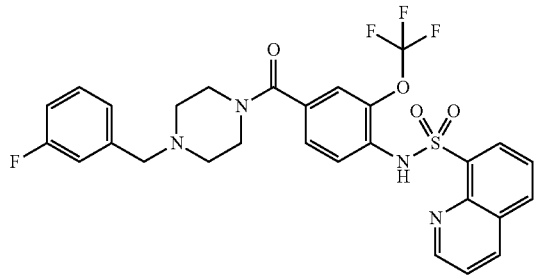 [SMILES: O=C(c1ccc(NS(=O)(=O)c2cccc3cccnc23)c(OC(F)(F)F)c1)N1CCN(Cc2cccc(F)c2)CC1]

$^1$H NMR (400 MHz, DMSO-d$_6$) δ: 2.2-2.5 (m, 4H), 2.7 (s, 2H), 3.2-3.8 (m, 4H), 7.2-7.4 (m, 6H), 7.58 (m, 1H), 7.75 (m, 2H), 8.3 (m, 2H), 8.6 (m, 1H), 9.0 (m, 1H), 9.90 (bs, 1H); HPLC Purity: 98.81%; Mass (M+1): 589.35.

N-(4-(4-(3,4-difluorobenzyl)piperazine-1-carbonyl)-2-(trifluoromethoxy)phenyl)quinoline-8-sulfonamide (Compound 378)

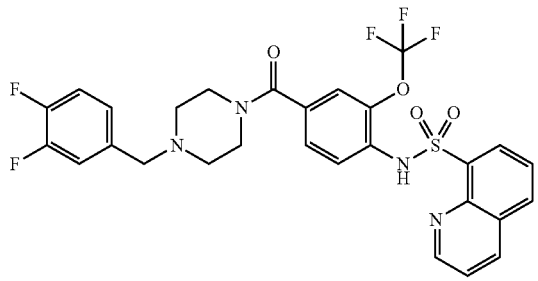 [SMILES: O=C(c1ccc(NS(=O)(=O)c2cccc3cccnc23)c(OC(F)(F)F)c1)N1CCN(Cc2ccc(F)c(F)c2)CC1]

$^1$H NMR (400 MHz, DMSO-d$_6$) δ: 2.2-2.5 (m, 4H), 2.8 (s, 2H), 3.2-3.8 (m, 4H), 7.18-7.2 (m, 2H), 7.2-7.4 (m, 3H), 7.58 (m, 1H), 7.75 (m, 2H), 8.3 (m, 2H), 8.6 (m, 1H), 9.0 (m, 1H), 10.0 (bs, 1H); HPLC Purity: 99.27%; Mass (M+1): 607.35.

N-(4-(4-(3-chlorobenzyl)piperazine-1-carbonyl)-2-(trifluoromethoxy)phenyl)quinoline-8-sulfonamide (Compound 379)

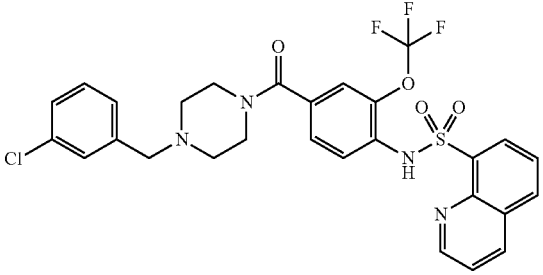 [SMILES: O=C(c1ccc(NS(=O)(=O)c2cccc3cccnc23)c(OC(F)(F)F)c1)N1CCN(Cc2cccc(Cl)c2)CC1]

$^1$H NMR (400 MHz, DMSO-d$_6$) δ: 2.2-2.5 (m, 4H), 3.2-3.8 (m, 6H), 7.18-7.4 (m, 6H), 7.58 (m, 1H), 7.75 (m, 2H), 8.3 (m, 2H), 8.6 (m, 1H), 9.0 (m, 1H), 10.0 (bs, 1H); HPLC Purity: 97.70%; Mass (M+1): 607.25

N-(4-(4-((1H-imidazol-2-yl)methyl)piperazine-1-carbonyl)-2-(trifluoromethoxy)phenyl)quinoline-8-sulfonamide (Compound 380)

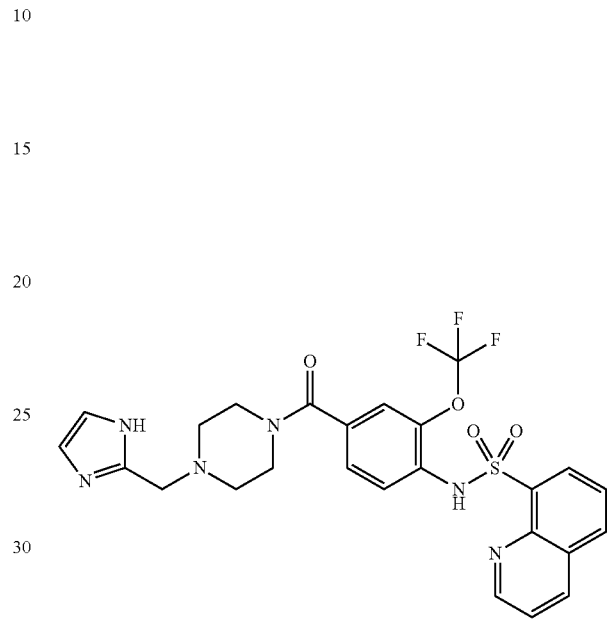

$^1$H NMR (400 MHz, DMSO-d$_6$) δ: 2.2-2.4 (m, 4H), 2.67 (s, 2H), 3.2-3.6 (m, 4H), 6.9 (s, 1H), 7.2-7.58 (m, 2H), 7.75 (m, 4H), 8.3 (m, 2H), 8.6 (d, 1H), 9.0 (m, 1H); HPLC Purity: 98.55%; Mass (M+1): 561.10.

N-(4-(4-((1H-imidazol-4-yl)methyl)piperazine-1-carbonyl)-2-(trifluoromethoxy)phenyl)quinoline-8-sulfonamide (Compound 381)

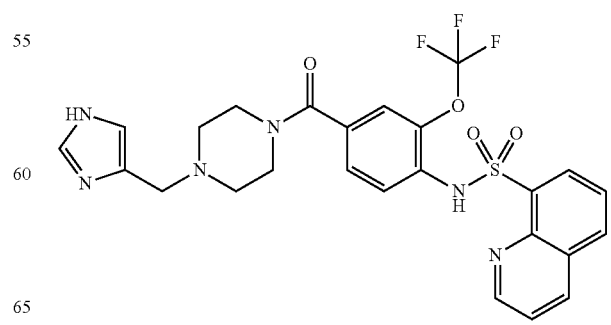

¹H NMR (400 MHz, DMSO-d₆) δ: 2.2-2.4 (m, 2H), 2.8 (s, 2H), 3.2-3.6 (m, 6H), 6.9 (s, 1H), 7.2-7.58 (m, 2H), 7.75 (m, 4H), 8.3 (m, 3H), 9.0 (m, 1H); HPLC Purity: 99.39%; Mass (M+1): 561.10.

N-(4-(4-((1H-pyrazol-5-yl)methyl)piperazine-1-carbonyl)-2-(trifluoromethoxy)phenyl)quinoline-8-sulfonamide (Compound 382)

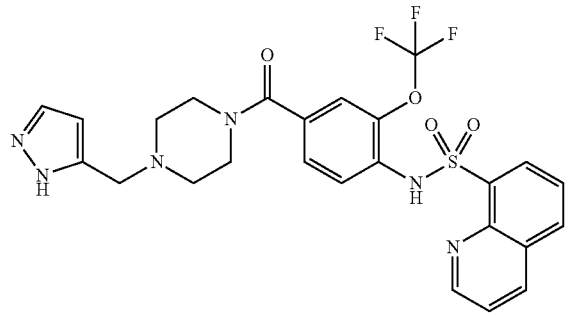 [SMILES: O=C(c1ccc(NS(=O)(=O)c2cccc3cccnc23)c(OC(F)(F)F)c1)N1CCN(Cc2ccn[nH]2)CC1]

¹H NMR (400 MHz, DMSO-d₆) δ: 2.2-2.4 (m, 2H), 2.6 (s, 2H), 3.2-3.6 (m, 6H), 6.1 (s, 1H), 7.2-7.75 (m, 6H), 8.3 (m, 3H), 8.6 (m, 1H), 9.0 (m, 1H); HPLC Purity: 96.98%; Mass (M+1): 561.10.

N-(4-(4-((1H-pyrazol-5-yl)methyl)piperazine-1-carbonyl)-2-(trifluoromethoxy)phenyl)quinoline-8-sulfonamide (Compound 389)

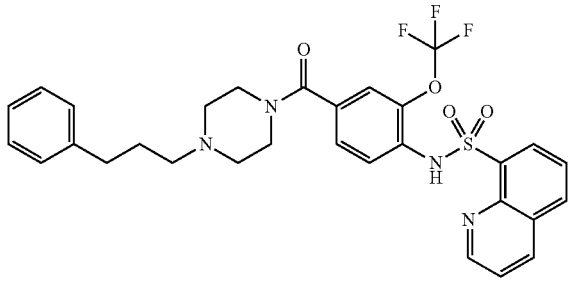 [SMILES: O=C(c1ccc(NS(=O)(=O)c2cccc3cccnc23)c(OC(F)(F)F)c1)N1CCN(CCCc2ccccc2)CC1]

¹H NMR (400 MHz, DMSO-d₆) δ: 1.7 (m, 2H), 2.3 (m, 6H), 2.5 (m, 2H), 3.2-3.8 (m, 2H), 7.1-7.3 (m, 7H), 7.55 (d, 1H), 7.78 (m, 2H), 8.38 (m, 2H), 8.6 (d, 1H), 9.0 (m, 1H), 9.9 (bs, 1H); HPLC Purity: 89.93%; Mass (M+1): 599.35.

N-(4-(4-((5-fluoropyridin-2-yl)methyl)piperazine-1-carbonyl)-2-(trifluoromethoxy)phenyl)quinoline-8-sulfonamide (Compound 390)

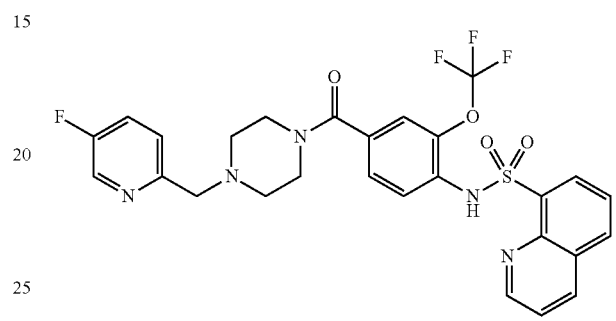

¹H NMR (400 MHz, DMSO-d₆) δ: 2.2-2.6 (m, 2H), 2.8 (s, 2H), 3.2-3.8 (m, 6H), 7.2-7.3 (m, 2H), 7.55 (m, 2H), 7.78 (m, 3H), 8.38 (m, 2H), 8.6 (d, 2H), 9.0 (m, 1H), 9.9 (bs, 1H); HPLC Purity: 96.54%; Mass (M+1): 590.35.

N-(4-(4-(3,5-dichlorobenzyl)piperazine-1-carbonyl)-2-(trifluoromethoxy)phenyl)quinoline-8-sulfonamide (Compound 391)

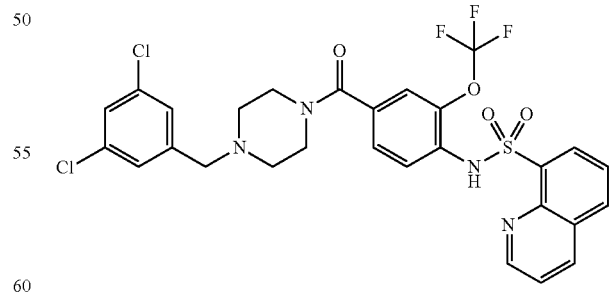

¹H NMR (400 MHz, DMSO-d₆) δ: 2.2-2.6 (m, 2H), 2.8 (s, 2H), 3.2-3.8 (m, 6H), 7.2-7.3 (m, 4H), 7.55 (m, 2H), 7.78 (m,

2H), 8.38 (m, 2H), 8.6 (d, 1H), 9.0 (m, 1H); HPLC Purity: 96.54%; Mass (M+1): 639.15.

N-(4-(4-(2,6-dimethoxybenzyl)piperazine-1-carbonyl)-2-(trifluoromethoxy)phenyl)quinoline-8-sulfonamide (Compound 392)

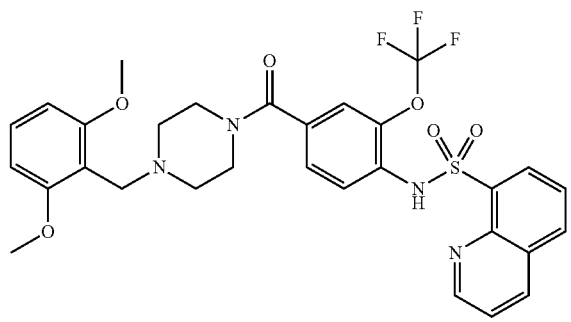 [SMILES: COc1cccc(OC)c1CN1CCN(C(=O)c2ccc(NS(=O)(=O)c3cccc4cccnc34)c(OC(F)(F)F)c2)CC1]

¹H NMR (400 MHz, DMSO-d₆) δ: 2.2-2.6 (m, 2H), 2.8 (s, 2H), 3.0-3.5 (m, 6H), 3.8 (s, 6H) 6.67 (m, 2H), 7.2-7.3 (m, 3H), 7.55 (m, 1H), 7.78 (m, 2H), 8.38 (m, 2H), 8.6 (d, 1H), 9.0 (m, 1H); HPLC Purity: 99.67%; Mass (M+1): 631.20.

(R)—N-(4-(4-(cyclopropylmethyl)-2-methylpiperazine-1-carbonyl)phenyl)quinoline-8-sulfonamide (Compound 113)

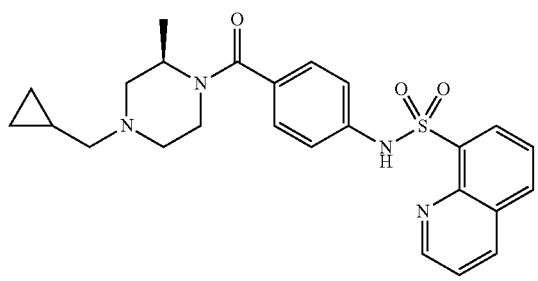 [SMILES: C[C@@H]1CN(CC2CC2)CCN1C(=O)c1ccc(NS(=O)(=O)c2cccc3cccnc23)cc1]

¹H NMR (400 MHz, DMSO-d₆) δ: 0.12 (m, 2H), 0.4 (m, 2H), 0.9 (m, 1H), 2.0 (s, 2H), 2.1-2.2 (d, 2H), 2.6-3.2 (m, 2H), 4.0 (bs, 1H), 7.0-7.2 (m, 4H), 7.6-7.69 (m, 2H), 8.2-8.6 (m, 3H), 9.0 (m, 1H), 10.46 (bs, 1H); HPLC Purity: 99.84%; Mass (M+1): 465.05.

(R)—N-(4-(4-(cyclopentylmethyl)-2-methylpiperazine-1-carbonyl)phenyl)quinoline-8-sulfonamide (Compound 114)

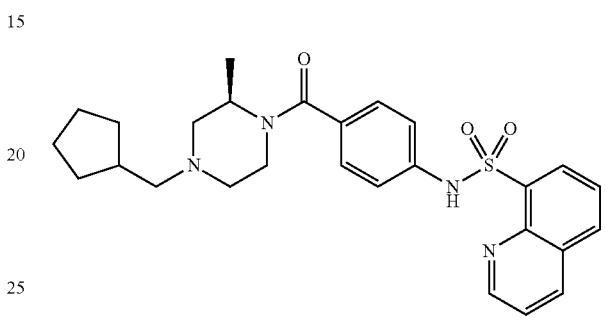

¹H NMR (400 MHz, DMSO-d₆) δ: 1.2 (m, 5H), 1.4-1.5 (m, 4H), 1.59-1.6 (m, 2H), 1.9 (s, 2H), 2.4 (d, 3H), 2.6-2.8 (m, 2H), 4.0 (bs, 1H), 7.0-7.2 (m, 4H), 7.6-7.69 (m, 2H), 8.2-8.6 (m, 3H), 9.0 (m, 1H), 10.46 (bs, 1H); HPLC Purity: 99.94%; Mass (M+1): 493.10.

N-(4-((2R)-2-methyl-4-((tetrahydrofuran-3-yl)methyl)piperazine-1-carbonyl)phenyl)quinoline-8-sulfonamide (Compound 115)

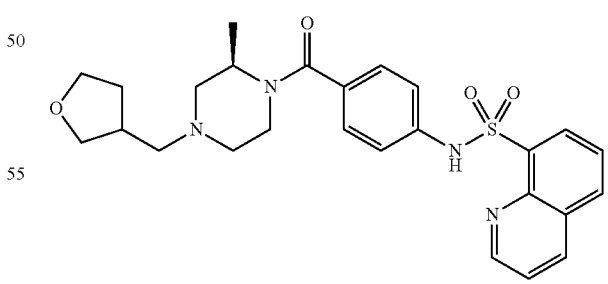

¹H NMR (400 MHz, DMSO-d₆) δ: 1.19 (m, 4H), 1.45-1.5 (m, 1H), 1.7-2.0 (m, 3H), 2.0-2.2 (m, 2H), 2.35-2.4 (m, 1H), 2.6-2.8 (m, 2H), 3.0 (bs, 1H), 3.59-3.7 (m, 4H), 7.0-7.15 (m,

4H), 7.6-7.69 (m, 2H), 8.2-8.6 (m, 3H), 9.0 (m, 1H), 10.46 (bs, 1H); HPLC Purity: 98.25%; Mass (M+1): 495.10.

(R)—N-(4-(2-methyl-4-(2,3,4-trifluorobenzyl)piperazine-1-carbonyl)phenyl)quinoline-8-sulfonamide (Compound 118)

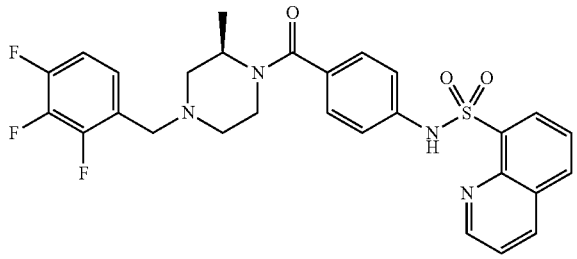 [SMILES: C[C@@H]1CN(Cc2ccc(F)c(F)c2F)CCN1C(=O)c1ccc(NS(=O)(=O)c2cccc3cccnc23)cc1]

$^1$H NMR (400 MHz, DMSO-d$_6$) δ: 1.16 (s, 3H), 1.9-2.1 (m, 2H), 2.5-2.7 (m, 2H), 3.0-3.13 (m, 1H), 3.5 (s, 2H), 4.1 (m, 2H), 7.1-7.4 (m, 6H), 7.7-7.8 (m, 2H), 8.3-8.6 (m, 3H), 9.0 (s, 1H), 10.6-10.7 (bs, 1H); HPLC Purity: 99.83%; Mass (M+1): 555.35.

(R)—N-(4-(4-(3,5-difluorobenzyl)-2-methylpiperazine-1-carbonyl)phenyl)quinoline-8-sulfonamide (Compound 119)

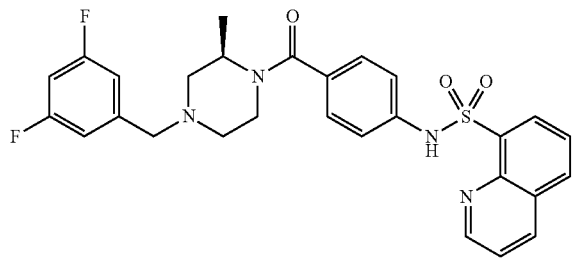 [SMILES: C[C@@H]1CN(Cc2cc(F)cc(F)c2)CCN1C(=O)c1ccc(NS(=O)(=O)c2cccc3cccnc23)cc1]

$^1$H NMR (400 MHz, DMSO-d$_6$) δ: 1.2 (d, 3H), 1.21 (q, 1H), 1.9-2.1 (m, 2H), 2.5-2.8 (m, 3H), 3.0-3.2 (s, 2H), 3.4-3.6 (m, 2H), 4.0 (bs, 1H), 7.1-7.4 (m, 7H), 7.6-7.8 (m, 2H), 8.3-8.6 (m, 3H), 9.0 (s, 1H), 10.6-10.7 (bs, 1H); HPLC Purity: 99.64%; Mass (M+1): 537.35.

(R)—N-(4-(4-(2,3-dimethoxybenzyl)-2-methylpiperazine-1-carbonyl)phenyl)quinoline-8-sulfonamide (Compound 130)

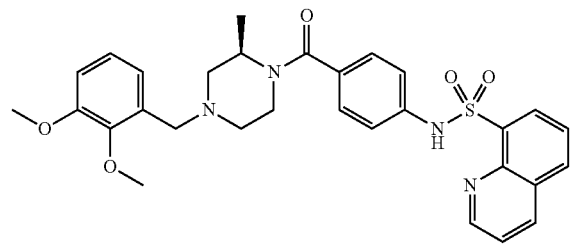 [SMILES: COc1cccc(CN2CCN(C(=O)c3ccc(NS(=O)(=O)c4cccc5cccnc45)cc3)[C@H](C)C2)c1OC]

$^1$H NMR (400 MHz, DMSO-d$_6$) δ: 1.18-1.95 (d, 3H), 2.0 (m, 1H), 1.8-2.1 (m, 2H), 2.45-2.8 (s, 2H), 2.99-3.2 (m, 1H), 3.25-3.5 (m, 4H), 3.7 (s, 3H), 3.8 (s, 3H), 6.82-7.19 (m, 7H), 7.6-7.8 (m, 2H), 8.2-8.23 (d, 1H), 8.4-8.5 (m, 2H), 9.1 (m, 1H), 10.4 (s, 1H); HPLC Purity: 98.21%; Mass (M+1): 561.40.

(R)—N-(4-(4-(4-fluorobenzyl)-2-methylpiperazine-1-carbonyl)phenyl)quinoline-8-sulfonamide (Compound 131)

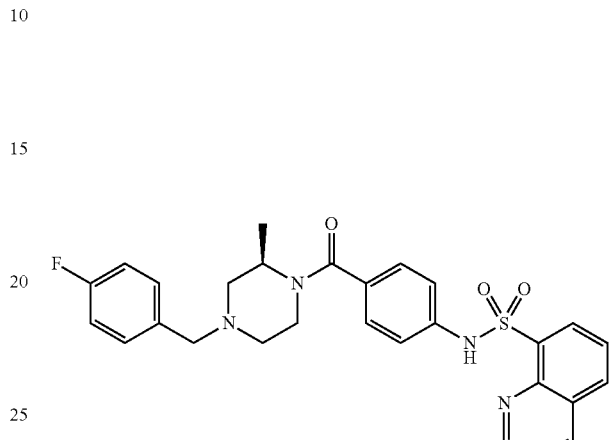

$^1$H NMR (400 MHz, DMSO-d$_6$) δ: 1.18-1.95 (d, 3H), 2.0 (m, 1H), 2.1 (s, 2H), 2.45-2.8 (m, 1H), 3.0-3.2 (m, 1H), 3.8-4.0 (m, 4H), 7.0-7.2 (m, 6H), 7.22-7.4 (m, 2H), 7.6-7.8 (d, 2H), 8.25 (d, 1H), 8.4-8.5 (m, 2H), 9.1 (m, 1H), 10.4 (s, 1H); HPLC Purity: 99.51%; Mass (M+1): 519.35.

(R)—N-(4-(2-methyl-4-(2,4,5-trifluorobenzyl)piperazine-1-carbonyl)phenyl)quinoline-8-sulfonamide (Compound 120)

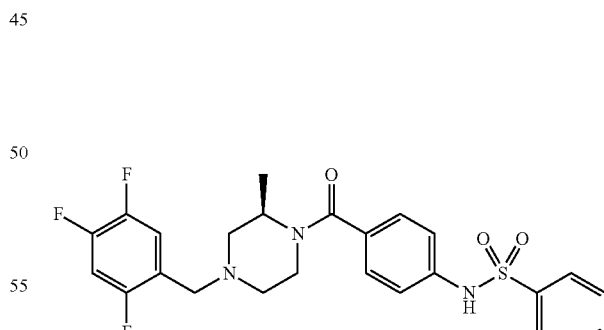

$^1$H NMR (400 MHz, DMSO-d$_6$) δ: 1.2 (d, 3H), 1.9-2.15 (m, 2H), 2.6-2.8 (m, 2H), 3.0-3.2 (m, 2H), 3.4 (s, 2H), 4.0 (bs,

1H), 7.4-7.5 (m, 2H), 7.6-7.8 (m, 2H), 8.3-8.6 (m, 3H), 9.0 (s, 1H), 10.4 (bs, 1H); HPLC Purity: 99.97%; Mass (M+1): 555.25.

(R)—N-(4-(4-(4-chloro-3-fluorobenzyl)-2-methylpiperazine-1-carbonyl)phenyl)quinoline-8-sulfonamide (Compound 125)

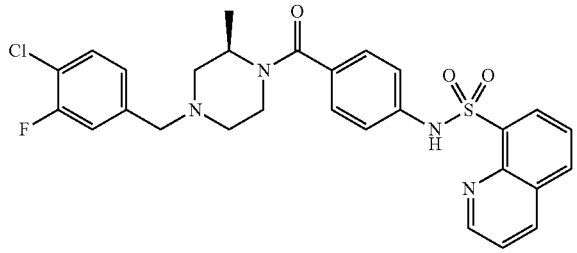 [SMILES: C[C@@H]1CN(Cc2ccc(Cl)c(F)c2)CCN1C(=O)c1ccc(NS(=O)(=O)c2cccc3cccnc23)cc1]

¹H NMR (400 MHz, DMSO-d$_6$) δ: 1.2 (d, 3H), 1.23 (m, 1H), 1.5 (m, 1H), 1.6-1.7 (m, 2H), 1.89-2.0 (s, 2H), 2.7-3.2 (m, 4H), 3.8-4.85 (m, 6H), 7.0-7.2 (m, 4H), 7.5-7.6 (m, 2H), 7.69-7.8 (m, 2H), 8.0 (d, 1H), 8.2-8.4 (m, 2H), 9.1 (m, 1H), 10.4 (s, 1H); HPLC Purity: 99.96%; Mass (M+1): 553.25.

(R)—N-(4-(2-methyl-4-(2,3,6-trifluorobenzyl)piperazine-1-carbonyl)phenyl)quinoline-8-sulfonamide (Compound 132)

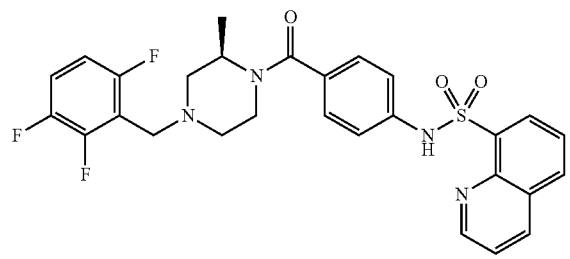

¹H NMR (400 MHz, DMSO-d$_6$) δ: 1.12 (d, 3H), 1.2 (m, 1H), 1.8-2.1 (m, 2H), 2.45-2.8 (s, 2H), 2.85-3.2 (m, 1H), 3.8-4.0 (m, 3H), 7.0-7.2 (m, 5H), 7.22-7.4 (m, 1H), 7.6-7.8 (d, 2H), 8.25 (d, 1H), 8.4-8.5 (m, 2H), 9.1 (m, 1H), 10.4 (s, 1H); HPLC Purity: 99.18%; Mass (M+1): 555.25.

(S)—N-(4-(2-ethyl-4-(4-fluorobenzyl)piperazine-1-carbonyl)phenyl)quinoline-8-sulfonamide (Compound 134)

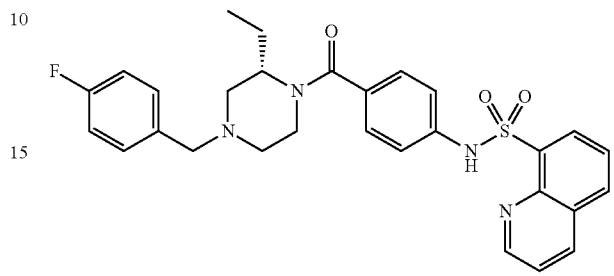

¹H NMR (400 MHz, DMSO-d$_6$) δ: 0.8 (d, 2H), 1.59-2.0 (m, 2H), 2.3-2.5 (s, 2H), 3.2-3.6 (m, 4H), 7.0-7.4 (m, 8H), 7.56-7.8 (m, 2H), 8.0 (d, 1H), 8.2-8.5 (m, 2H), 9.1 (m, 1H) 10.4 (s, 1H); HPLC Purity: 99.88%; Mass (M+1): 533.1.

(S)—N-(4-(4-(3,5-difluorobenzyl)-2-ethylpiperazine-1-carbonyl)phenyl)quinoline-8-sulfonamide (Compound 136)

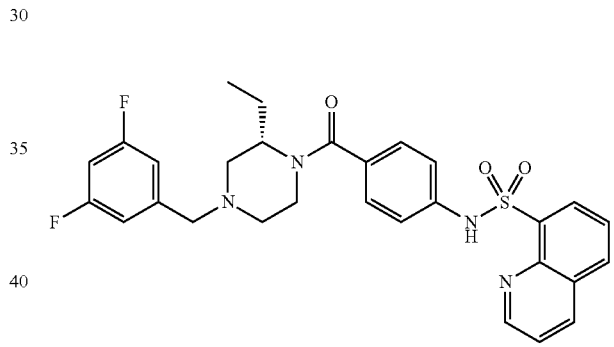

¹H NMR (400 MHz, DMSO-d$_6$) δ: 1.1-1.21 (d, 6H), 1.82-2.1 (m, 2H), 2.6 (m, 1H), 2.8-3.2 (s, 2H), 3.8-4.0 (m, 3H), 7.0-7.2 (m, 7H), 7.6-7.8 (d, 2H), 8.25 (d, 1H), 8.4-8.5 (m, 2H), 9.1 (m, 1H), 10.4 (s, 1H); HPLC Purity: 99.95%; Mass (M+1): 551.3.

(S)—N-(4-(2-methyl-4-(2,3,5-trifluorobenzyl)piperazine-1-carbonyl)phenyl)quinoline-8-sulfonamide (Compound 137)

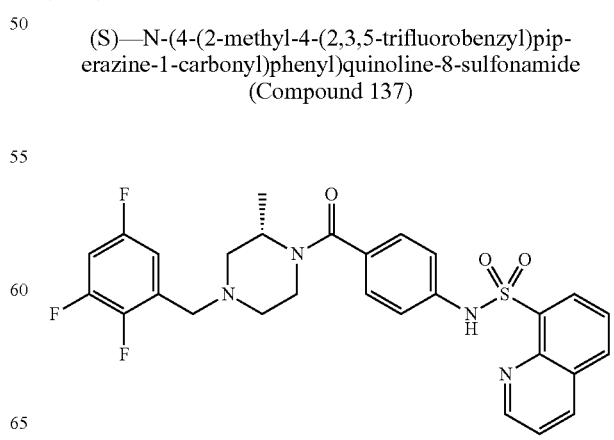

¹H NMR (400 MHz, DMSO-d₆) δ: 1.21 (d, 3H), 1.23 (m, 1H), 1.82-2.1 (m, 2H), 2.5-2.8 (s, 2H), 3.0-3.2 (m, 2H), 3.4-3.6 (m, 2H), 7.0-7.2 (m, 5H), 7.4-7.45 (m, 1H), 7.6-7.8 (m, 2H), 8.25 (d, 1H), 8.4-8.5 (m, 2H), 9.1 (m, 1H), 10.4 (s, 1H); HPLC Purity: 99.60%; Mass (M+1): 555.3.

(S)—N-(4-(4-(4-chloro-3-fluorobenzyl)-2-methylpiperazine-1-carbonyl)phenyl)quinoline-8-sulfonamide (Compound 138)

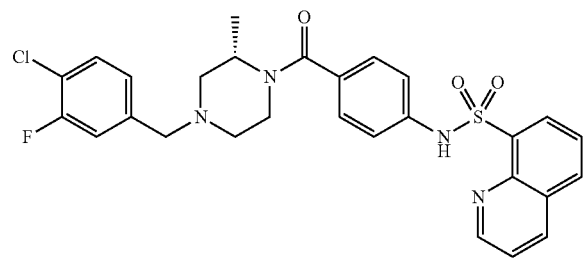 [SMILES: C[C@H]1CN(Cc2ccc(Cl)c(F)c2)CCN1C(=O)c1ccc(NS(=O)(=O)c2cccc3cccnc23)cc1]

¹H NMR (400 MHz, DMSO-d₆) δ: 1.96 (d, 3H), 1.23 (m, 1H), 1.82-2.1 (m, 2H), 2.5-2.8 (s, 2H), 3.0-3.2 (m, 2H), 3.4-3.6 (m, 2H), 7.0-7.2 (m, 5H), 7.3 (d, 1H), 7.4-7.45 (m, 1H), 7.6-7.8 (m, 2H), 8.25 (d, 1H), 8.4-8.5 (m, 2H), 9.1 (m, 1H), 10.4 (s, 1H); HPLC Purity: 99.98%; Mass (M+1): 553.3.

N-(4-((2S)-2-methyl-4-((tetrahydrofuran-3-yl)methyl)piperazine-1-carbonyl)phenyl)quinoline-8-sulfonamide (Compound 139)

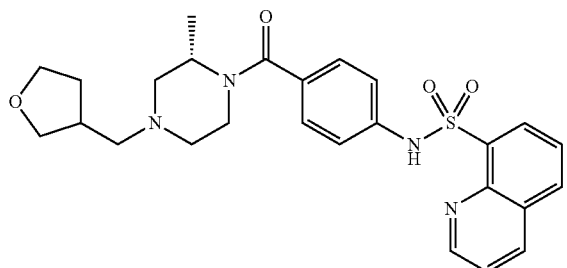

¹H NMR (400 MHz, DMSO-d₆) δ: 1.96 (d, 3H), 1.23 (m, 1H), 1.5 (m, 1H), 1.8-2.0 (m, 3H), 2.15-2.44 (s, 2H), 2.8-3.1 (m, 4H), 3.6-3.8 (m, 4H), 7.0-7.2 (m, 4H), 7.6-7.8 (m, 2H), 8.25-8.6 (m, 3H), 9.1 (m, 1H), 10.4 (s, 1H); HPLC Purity: 92.25%; Mass (M+1): 495.35.

(S)—N-(4-(4-(cyclopentylmethyl)-2-methylpiperazine-1-carbonyl)phenyl)quinoline-8-sulfonamide (Compound 140)

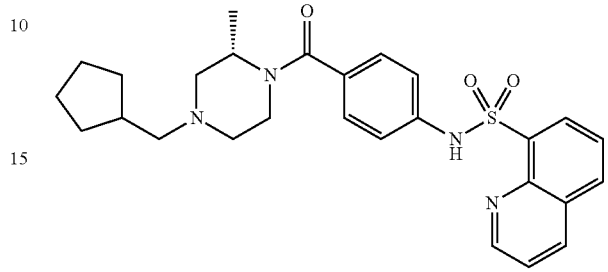

¹H NMR (400 MHz, DMSO-d₆) δ: 1.2 (d, 3H), 1.23 (m, 3H), 1.45-1.6 (m, 4H), 1.61-1.8 (m, 3H), 1.86-2.2 (m, 5H), 2.6-3.2 (s, 2H), 7.0-7.2 (m, 4H), 7.6-7.8 (m, 2H), 8.25-8.6 (m, 3H), 9.1 (m, 1H), 10.4 (s, 1H); HPLC Purity: 96.35%; Mass (M+Na): 515.15.

(S)—N-(4-(2-methyl-4-(2,3,6-trifluorobenzyl)piperazine-1-carbonyl)phenyl)quinoline-8-sulfonamide (Compound 141)

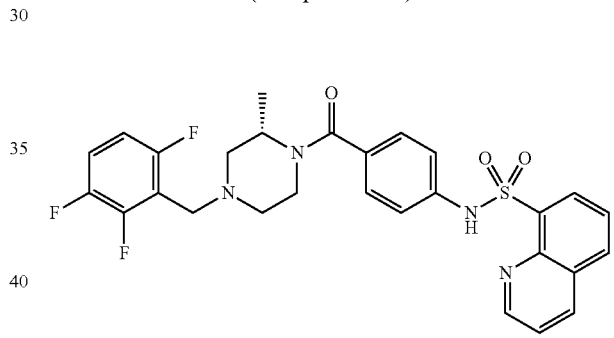

¹H NMR (400 MHz, DMSO-d₆) δ: 1.15 (d, 3H), 1.23 (m, 1H), 1.86-2.2 (m, 2H), 2.6-3.2 (s, 3H), 7.0-7.2 (m, 5H), 7.4-7.8 (m, 3H), 8.25-8.6 (m, 3H), 9.1 (m, 1H), 10.4 (s, 1H); HPLC Purity: 99.77%; Mass (M+1): 555.05.

(S)—N-(4-(4-(3,5-difluorobenzyl)-2-methylpiperazine-1-carbonyl)phenyl)quinoline-8-sulfonamide (Compound 142)

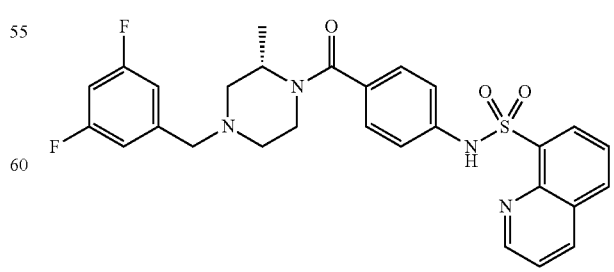

¹H NMR (400 MHz, DMSO-d₆) δ: 1.2 (d, 3H), 1.86-2.2 (m, 2H), 2.6-3.2 (m, 1H), 3.0-3.2 (s, 2H), 3.3-4.0 (m, 4H), 7.0-7.2 (m, 6H), 7.6-7.8 (m, 2H), 8.25-8.6 (m, 3H), 9.1 (m, 1H), 10.4 (s, 1H); HPLC Purity: 99.80%; Mass (M+1): 537.30.

(S)—N-(4-(4-(2-fluorobenzyl)-2-methylpiperazine-1-carbonyl)phenyl)quinoline-8-sulfonamide (Compound 143)

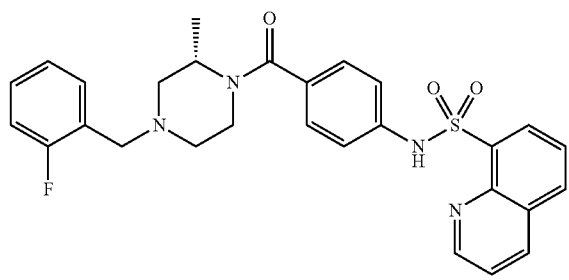 [SMILES: C[C@H]1CN(Cc2ccccc2F)CCN1C(=O)c1ccc(NS(=O)(=O)c2cccc3cccnc23)cc1]

¹H NMR (400 MHz, DMSO-d₆) δ: 1.2 (d, 3H), 1.23 (m, 1H), 1.86-2.2 (m, 2H), 2.6-3.2 (s, 2H), 3.0-3.2 (m, 2H), 3.3-3.6 (m, 2H), 7.0-7.2 (m, 6H), 7.3-7.4 (m, 2H), 7.6-7.8 (m, 2H), 8.23 (d, 1H), 8.3-8.6 (m, 2H), 9.1 (m, 1H), 10.4 (s, 1H); HPLC Purity: 98.56%; Mass (M+1): 519.10.

(S)—N-(4-(4-(cyclopropylmethyl)-2-methylpiperazine-1-carbonyl)phenyl)quinoline-8-sulfonamide (Compound 144)

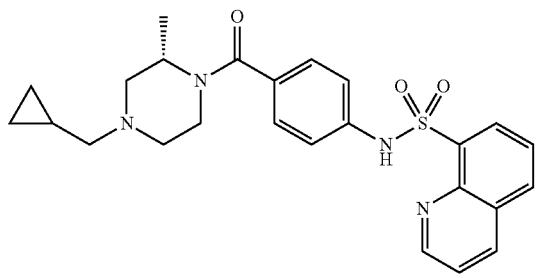 [SMILES: C[C@H]1CN(CC2CC2)CCN1C(=O)c1ccc(NS(=O)(=O)c2cccc3cccnc23)cc1]

¹H NMR (400 MHz, DMSO-d₆) δ: 0.12-0.2 (d, 2H), 0.2-0.24 (m, 2H), 0.8-0.86 (m, 1H), 1.1 (d, 3H), 1.23 (m, 1H), 1.8-2.2 (m, 4H), 2.7-3.2 (s, 2H), 3.6-4.0 (m, 2H), 7.0-7.2 (m, 4H), 7.6-7.8 (m, 2H), 8.23 (d, 1H), 8.3-8.6 (m, 2H), 9.1 (m, 1H), 10.4 (s, 1H); HPLC Purity: 96.91%; Mass (M+1): 465.35.

(S)—N-(4-(2-methyl-4-(2,4,5-trifluorobenzyl)piperazine-1-carbonyl)phenyl)quinoline-8-sulfonamide (Compound 145)

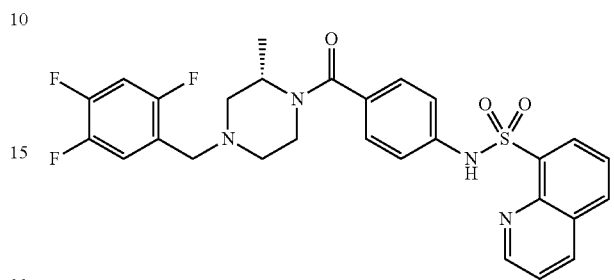

¹H NMR (400 MHz, DMSO-d₆) δ: 1.1 (d, 3H), 1.23 (m, 1H), 1.8-2.2 (s, 2H), 2.7-3.2 (m, 4H), 3.4-3.6 (m, 2H), 7.0-7.2 (m, 4H), 7.4-7.6 (m, 1H), 7.6-7.8 (m, 2H), 8.23 (d, 1H), 8.3-8.6 (m, 2H), 9.1 (m, 1H), 10.4 (s, 1H); HPLC Purity: 99.12%; Mass (M+1): 465.35.

(S)—N-(4-(4-(2,3-dimethoxybenzyl)-2-methylpiperazine-1-carbonyl)phenyl)quinoline-8-sulfonamide (Compound 146)

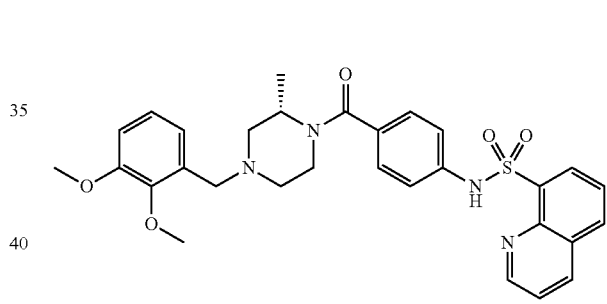

¹H NMR (400 MHz, DMSO-d₆) δ: 1.1 (d, 3H), 1.23 (m, 1H), 1.8-2.2 (s, 2H), 2.6-3.2 (m, 3H), 3.3-3.5 (m, 3H), 3.7 (s, 3H), 3.8 (s, 3H), 7.0-7.2 (m, 7H), 7.6-7.8 (m, 2H), 8.23 (d, 1H), 8.3-8.6 (m, 2H), 9.1 (m, 1H), 10.4 (s, 1H); HPLC Purity: 97.84%; Mass (M+1): 561.40.

N-(4-((2R)-2-methyl-4-((tetrahydrofuran-2-yl)methyl)piperazine-1-carbonyl)phenyl)quinoline-8-sulfonamide (Compound 147)

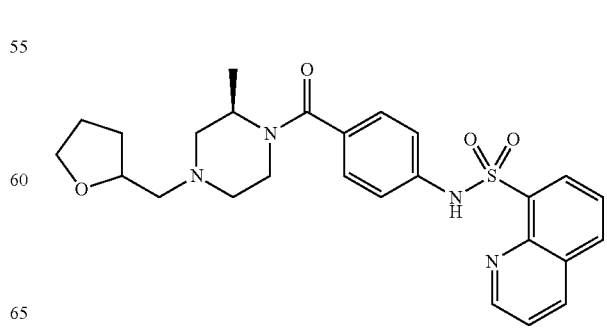

¹H NMR (400 MHz, DMSO-d₆) δ: 1.1 (d, 3H), 1.5 (m, 1H), 1.76-2.2 (m, 5H), 2.3-2.4 (s, 2H), 2.8-3.2 (m, 4H), 3.6-4.0 (m, 4H), 7.0-7.2 (m, 4H), 7.6-7.8 (m, 2H), 8.23 (d, 1H), 8.3-8.6 (m, 2H), 9.1 (m, 1H), 10.4 (s, 1H); HPLC Purity: 97.78%; Mass (M+1): 495.40.

N-(4-(4-(2-methoxybenzyl)-2-methylpiperazine-1-carbonyl)phenyl)quinoline-8-sulfonamide (Compound 224)

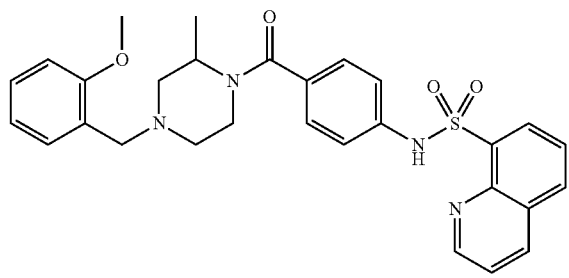 [SMILES: COc1ccccc1CN1CCN(C(=O)c2ccc(NS(=O)(=O)c3cccc4cccnc34)cc2)C(C)C1]

¹H NMR (400 MHz, DMSO-d₆) δ: 1.1 (d, 3H), 2.5 (m, 1H), 3.0-3.4 (m, 4H), 3.7 (s, 3H), 3.8-4.0 (s, 2H), 6.8-7.2 (m, 8H), 7.6-7.8 (m, 2H), 8.23 (d, 1H), 8.3-8.6 (m, 2H), 9.1 (m, 1H), 10.4 (s, 1H); HPLC Purity: 99.69%; Mass (M+1): 517.35

N-(4-(4-(2-methoxybenzyl)-2-methylpiperazine-1-carbonyl)phenyl)quinoline-8-sulfonamide (Compound 148)

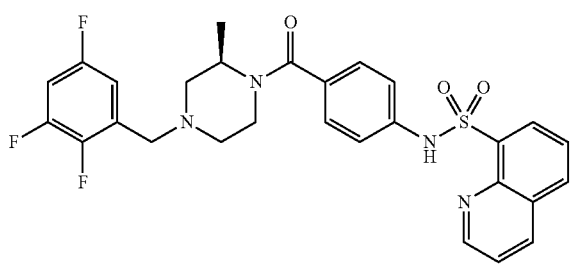 [SMILES: C[C@@H]1CN(Cc2cc(F)cc(F)c2F)CCN1C(=O)c1ccc(NS(=O)(=O)c2cccc3cccnc23)cc1]

¹H NMR (400 MHz, DMSO-d₆) δ: 1.1 (d, 3H), 1.8-2.2 (s, 2H), 2.6-3.2 (m, 3H), 3.8-4.0 (m, 4H), 7.0-7.2 (m, 5H), 7.36-

7.4 (m, 1H), 7.6-7.8 (m, 2H), 8.23 (d, 1H), 8.3-8.6 (m, 2H), 9.1 (m, 1H), 10.4 (s, 1H); HPLC Purity: 99.69%; Mass (M+1): 555.0.

(R)—N-(4-(2-methyl-4-(3,4,5-trifluorobenzyl)piperazine-1-carbonyl)phenyl)quinoline-8-sulfonamide (Compound 149)

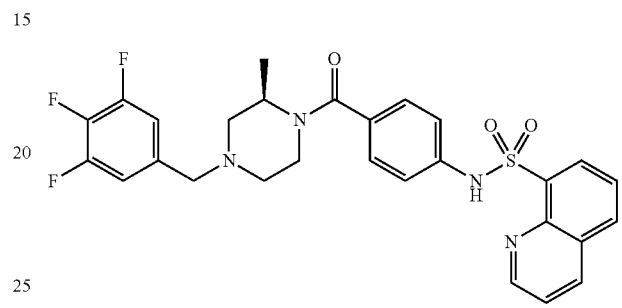

¹H NMR (400 MHz, DMSO-d₆) δ: 1.2 (d, 3H), 1.8-2.2 (m, 2H), 2.6-2.8 (s, 2H), 3.0-3.2 (m, 1H), 3.6-3.86 (m, 4H), 7.0-7.3 (m, 6H), 7.6-7.8 (m, 2H), 8.23 (d, 1H), 8.3-8.6 (m, 2H), 9.1 (m, 1H), 10.4 (s, 1H); HPLC Purity: 99.97%; Mass (M+1): 554.95.

(R)—N-(4-(4-(2-fluorobenzyl)-2-methylpiperazine-1-carbonyl)phenyl)quinoline-8-sulfonamide (Compound 150)

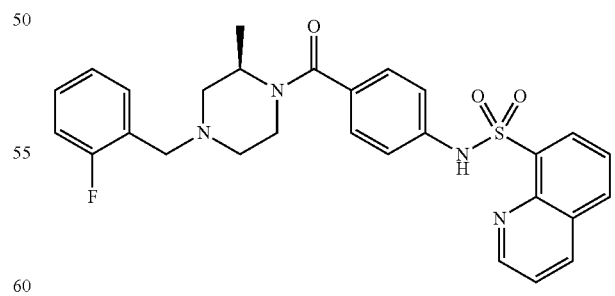

¹H NMR (400 MHz, DMSO-d₆) δ: 1.2 (d, 3H), 1.8-2.2 (m, 2H), 2.6-2.85 (s, 2H), 3.0-3.2 (m, 1H), 3.8-4.0 (m, 4H), 7.0-

7.5 (m, 8H), 7.7-7.8 (m, 2H), 8.23 (d, 1H), 8.3-8.6 (m, 2H), 9.1 (m, 1H), 10.4 (s, 1H); HPLC Purity: 99.67%; Mass (M+1): 519.05.

(R)—N-(4-(4-(cyclohexylmethyl)-2-methylpiperazine-1-carbonyl)phenyl)quinoline-8-sulfonamide (Compound 151)

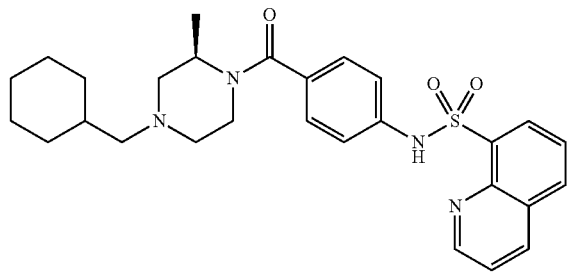 [SMILES: C[C@@H]1CN(CC2CCCCC2)CCN1C(=O)c1ccc(NS(=O)(=O)c2cccc3cccnc23)cc1]

$^1$H NMR (400 MHz, CDCl$_3$) δ: 0.8-0.9 (d, 3H), 1.0-1.4 (m, 8H), 1.5-1.6 (m, 2H), 1.61-1.8 (m, 9H), 2.0-2.1 (4H), 2.6-2.85 (s, 2H), 3.0-3.2 (m, 1H), 4.0-4.1 (m, 1H), 7.0-7.4 (m, 4H), 7.6-7.7 (m, 2H), 8.0 (d, 1H), 8.3-8.6 (m, 2H), 9.1 (m, 1H), 10.4 (s, 1H); HPLC Purity: 99.85%; Mass (M+1): 507.40.

(S)—N-(4-(4-(4-fluorobenzyl)-2-methylpiperazine-1-carbonyl)phenyl)quinoline-8-sulfonamide (Compound 152)

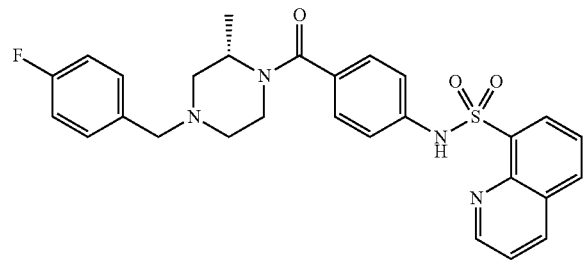

$^1$H NMR (400 MHz, DMSO-d$_6$) δ: 1.2 (d, 3H), 1.21-1.3 (m, 1H), 1.8-2.1 (m, 2H), 2.6-2.85 (s, 2H), 3.0-3.2 (m, 1H), 3.4-3.5 (m, 3H), 7.0-7.4 (m, 8H), 7.6-7.7 (m, 2H), 8.0 (d, 1H), 8.3-8.6 (m, 2H), 9.1 (m, 1H), 10.4 (s, 1H); HPLC Purity: 97.31%; Mass (M+1): 519.35.

(S)—N-(4-(4-(cyclohexylmethyl)-2-methylpiperazine-1-carbonyl)phenyl)quinoline-8-sulfonamide (Compound 153)

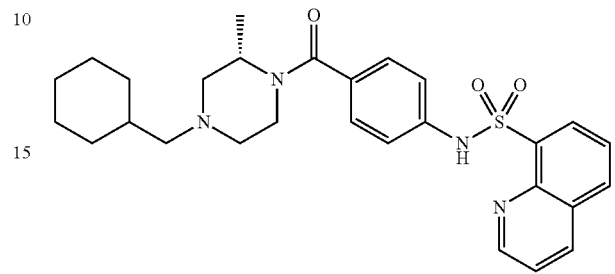

$^1$H NMR (400 MHz, DMSO-d$_6$) δ: 0.8-0.9 (m, 2H), 1.21-1.3 (m, 6H), 1.4-1.42 (m, 1H), 1.6-1.8 (m, 6H), 1.96-2.12 (m, 3H), 2.5-2.6 (s, 2H), 3.6-3.8 (m, 2H), 7.0-7.2 (m, 4H), 7.6-7.7 (m, 2H), 8.0 (d, 1H), 8.3-8.6 (m, 2H), 9.1 (m, 1H), 10.4 (s, 1H); HPLC Purity: 99.20%; Mass (M+1): 507.15.

(S)—N-(4-(2-methyl-4-(2,3,4-trifluorobenzyl)piperazine-1-carbonyl)phenyl)quinoline-8-sulfonamide (Compound 154)

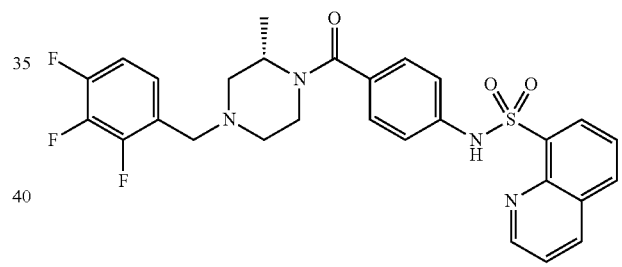

$^1$H NMR (400 MHz, DMSO-d$_6$) δ: 1.21-1.3 (d, 3H), 1.8-2.1 (m, 2H), 2.5-2.8 (s, 2H), 3.0-3.4 (m, 1H), 3.8-4.0 (m, 4H), 7.0-7.2 (m, 6H), 7.6-7.7 (m, 2H), 8.0 (d, 1H), 8.3-8.6 (m, 2H), 9.1 (m, 1H), 10.4 (s, 1H); HPLC Purity: 99.99%; Mass (M+1): 555.35.

(S)—N-(4-(2-methyl-4-(3,4,5-trifluorobenzyl)piperazine-1-carbonyl)phenyl)quinoline-8-sulfonamide (Compound 155)

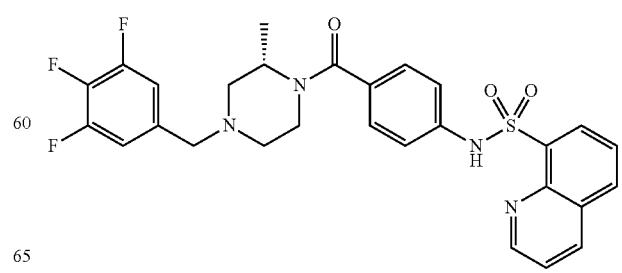

¹H NMR (400 MHz, DMSO-d₆) δ: 1.21-1.3 (d, 3H), 1.8-2.1 (m, 3H), 2.6-2.8 (s, 2H), 3.0-3.4 (m, 1H), 3.4-3.5 (m, 2H), 3.8-4.0 (m, 1H), 7.0-7.2 (m, 6H), 7.6-7.7 (m, 2H), 8.0 (d, 1H), 8.3-8.6 (m, 2H), 9.1 (m, 1H), 10.4 (s, 1H); HPLC Purity: 99.65%; Mass (M+1): 575.05.

N-(4-((2S)-2-methyl-4-((tetrahydro-2H-pyran-2-yl)methyl)piperazine-1-carbonyl)phenyl)quinoline-8-sulfonamide (Compound 156)

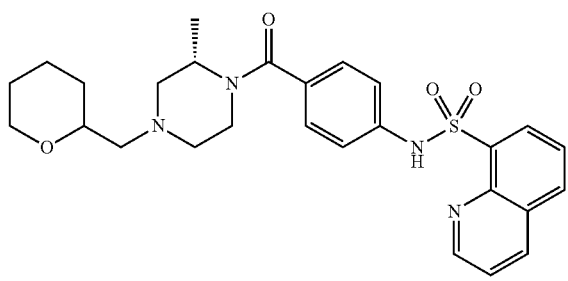 [SMILES: C[C@H]1CN(CC2CCCCO2)CCN1C(=O)c1ccc(NS(=O)(=O)c2cccc3cccnc23)cc1]

¹H NMR (400 MHz, DMSO-d₆) δ: 1.21 (d, 3H), 1.23-1.3 (m, 1H), 1.31-1.4 (m, 3H), 1.59-1.6 (m, 2H), 1.8-2.1 (m, 4H), 2.1-2.2 (s, 2H), 2.6-2.8 (m, 2H), 3.0-3.4 (m, 3H), 3.8-4.0 (m, 1H), 7.0-7.2 (m, 4H), 7.6-7.7 (m, 2H), 8.0 (d, 1H), 8.3-8.6 (m, 2H), 9.1 (m, 1H), 10.4 (s, 1H); HPLC Purity: 94.56%; Mass (M+1): 509.05.

N-(4-((2R)-2-methyl-4-((tetrahydro-2H-pyran-2-yl)methyl)piperazine-1-carbonyl)phenyl)quinoline-8-sulfonamide (Compound 163)

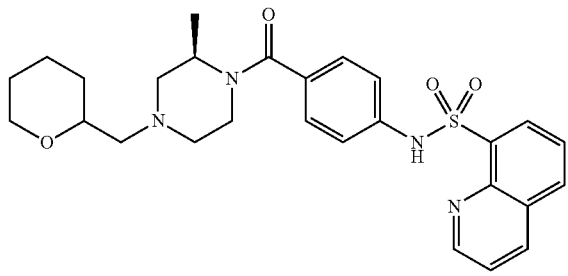 [SMILES: C[C@@H]1CN(CC2CCCCO2)CCN1C(=O)c1ccc(NS(=O)(=O)c2cccc3cccnc23)cc1]

¹H NMR (400 MHz, DMSO-d₆) δ: 1.0-1.4 (m, 7H), 1.56-1.6 (m, 2H), 1.6-1.65 (m, 2H), 2.0-2.4 (s, 2H), 2.6-3.4 (m, 5H), 3.8-3.9 (m, 3H), 7.0-7.4 (m, 4H), 7.6-7.7 (m, 2H), 8.0 (d, 1H), 8.3-8.6 (m, 2H), 9.1 (m, 1H), 10.4 (s, 1H); HPLC Purity: 97.32%; Mass (M+1): 509.15.

(S)—N-(4-(2-methyl-4-(2,4,6-trifluorobenzyl)piperazine-1-carbonyl)phenyl)quinoline-8-sulfonamide (Compound 164)

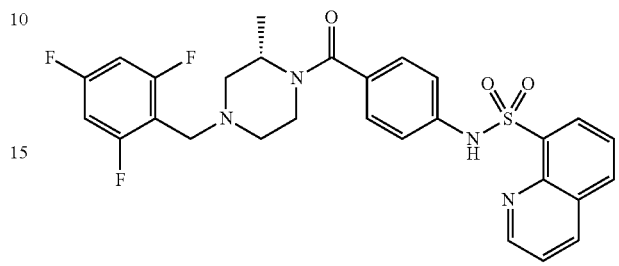

¹H NMR (400 MHz, DMSO-d₆) δ: 1.2 (d, 3H), 1.8-2.1 (m, 2H), 2.6-2.7 (s, 2H), 2.9-3.2 (m, 1H), 3.6-4.0 (m, 4H), 7.0-7.2 (m, 6H), 7.6-7.7 (m, 2H), 8.0 (d, 1H), 8.3-8.6 (m, 2H), 9.1 (m, 1H), 10.6 (s, 1H); HPLC Purity: 96.52%; Mass (M+1): 544.7.

(S)—N-(3-chloro-4-(4-(4-fluorobenzyl)-2-methylpiperazine-1-carbonyl)phenyl)quinoline-8-sulfonamide (Compound 184)

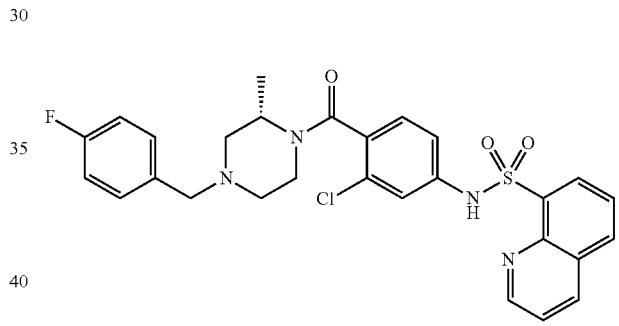

¹H NMR (400 MHz, CDCl₃) δ: 1.0 (d, 3H), 2.0 (m, 1H), 2.8-3.2 (m, 4H), 3.5-3.6 (m, 2H), 4.2 (m, 1H), 7.0-7.4 (m, 6H), 7.6-7.8 (m, 2H), 8.0 (d, 1H), 8.3-8.6 (m, 2H), 9.1 (m, 1H); HPLC Purity: 99.81%; Mass (M+1): 553.2.

(S)—N-(3-chloro-4-(4-(4-chloro-3-fluorobenzyl)-2-methylpiperazine-1-carbonyl)phenyl)quinoline-8-sulfonamide (Compound 185)

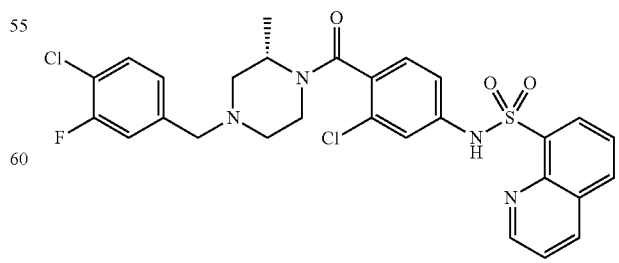

¹H NMR (400 MHz, CDCl₃) δ: 1.0 (d, 3H), 1.99 (m, 1H), 1.8-2.2 (m, 2H), 2.6-3.6 (m, 4H), 4.2 (m, 1H), 4.6 (s, 1H), 7.0-7.6 (m, 6H), 7.61-7.8 (m, 2H), 8.0 (d, 1H), 8.3-8.6 (m, 2H), 9.1 (m, 1H), 10.6 (s, 1H); HPLC Purity: 99.85%; Mass (M+1): 587.1.

(S)—N-(3-chloro-4-(4-(cyclopentylmethyl)-2-methylpiperazine-1-carbonyl)phenyl)quinoline-8-sulfonamide (Compound 186)

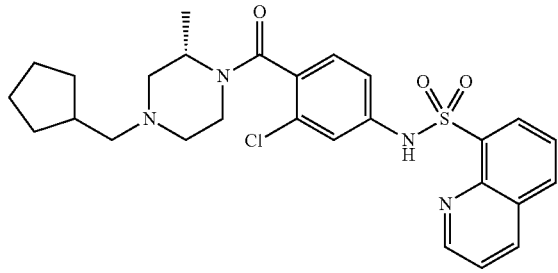 [SMILES: C[C@H]1CN(CC2CCCC2)CCN1C(=O)c1ccc(NS(=O)(=O)c2cccc3cccnc23)cc1Cl]

¹H NMR (400 MHz, DMSO-d$_6$) δ: 0.8 (m, 1H), 1.2-1.4 (m, 7H), 1.5-1.6 (m, 6H), 1.8-2.0 (m, 3H), 2.0-2.2 (m, 2H), 4.2 (m, 1H), 4.6 (m, 1H), 7.0-7.2 (m, 3H), 7.61-7.8 (m, 2H), 8.0 (d, 1H), 8.3-8.6 (m, 2H), 9.1 (m, 1H), 10.6 (s, 1H); HPLC Purity: 99.85%; Mass (M+1): 527.6.

N-(3-chloro-4-((2S)-2-methyl-4-((tetrahydrofuran-3-yl)methyl)piperazine-1-carbonyl)phenyl)quinoline-8-sulfonamide (Compound 187)

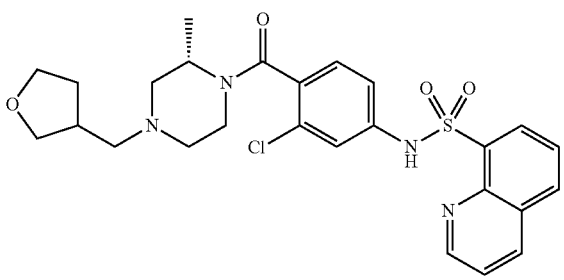 [SMILES: C[C@H]1CN(CC2CCOC2)CCN1C(=O)c1ccc(NS(=O)(=O)c2cccc3cccnc23)cc1Cl]

¹H NMR (400 MHz, DMSO-d$_6$) δ: 0.8 (m, 1H), 1.0-1.4 (m, 4H), 1.5-1.6 (m, 1H), 1.8-2.0 (m, 2H), 2.0-2.4 (m, 3H), 2.8-3.0 (m, 2H), 3.3-3.4 (m, 1H), 3.6-3.7 (m, 3H), 4.2 (m, 1H), 4.6 (m, 1H), 7.0-7.2 (m, 3H), 7.61-7.8 (m, 2H), 8.0 (d, 1H), 8.3-8.6 (m, 2H), 9.1 (m, 1H), 10.6 (s, 1H); HPLC Purity: 94.53%; Mass (M+1): 529.55.

(S)—N-(3-chloro-4-(2-methyl-4-(2,4,6-trifluorobenzyl)piperazine-1-carbonyl)phenyl)quinoline-8-sulfonamide (Compound 188)

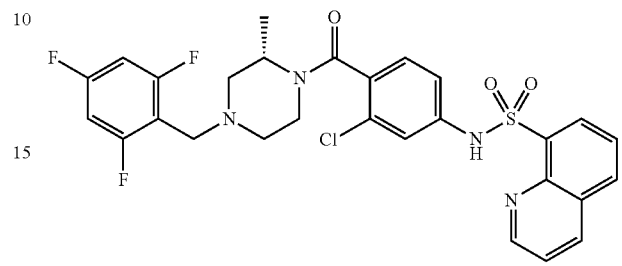

¹H NMR (400 MHz, DMSO-d$_6$) δ: 0.8 (m, 1H), 1.0-1.3 (m, 4H), 1.8-2.0 (m, 2H), 2.6-2.8 (m, 1H), 3.4 (s, 2H), 4.0-4.1 (m, 1H), 4.55-4.6 (m, 1H), 7.0-7.2 (m, 5H), 7.61-7.8 (m, 2H), 8.0 (d, 1H), 8.3-8.6 (m, 2H), 9.1 (m, 1H), 10.6 (s, 1H); HPLC Purity: 99.17%; Mass (M+1): 589.55.

N-(4-((2R)-2-methyl-4-(1-(2,3,4-trifluorophenyl)ethyl)piperazine-1-carbonyl)phenyl)quinoline-8-sulfonamide (Compound 189)

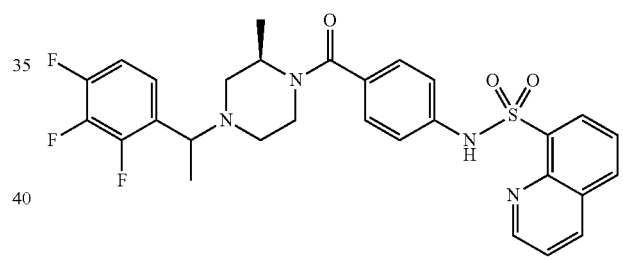

¹H NMR (400 MHz, DMSO-d$_6$) δ: 1.3 (d, 6H), 1.8-2.0 (m, 2H), 2.6-3.0 (m, 4H), 3.6-3.8 (m, 2H), 7.0-7.4 (m, 6H), 7.61-7.8 (m, 2H), 8.0 (d, 1H), 8.3-8.6 (m, 2H), 9.1 (m, 1H), 10.6 (s, 1H); HPLC Purity: 97.92%; Mass (M+1): 569.3.

N-(4-((2R)-2-methyl-4-(1-(2,3,6-trifluorophenyl)ethyl)piperazine-1-carbonyl)phenyl)quinoline-8-sulfonamide (Compound 190)

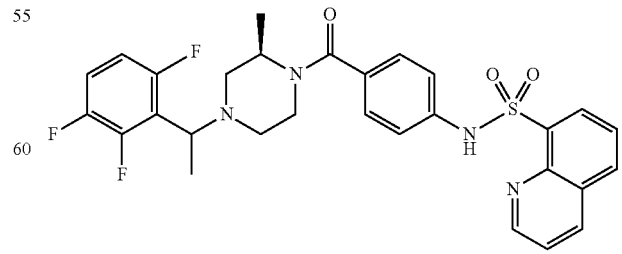

¹H NMR (400 MHz, DMSO-d$_6$) δ: 1.3 (d, 3H), 1.4 (m, 2H), 1.8-2.0 (m, 2H), 2.6-2.6 (m, 2H), 3.0-3.4 (s, 2H), 4.0 (m, 1H), 7.0-7.2 (m, 5H), 7.3-7.4 (m, 1H), 7.61-7.8 (m, 3H), 8.0 (d, 1H), 8.3-8.6 (m, 2H), 9.1 (m, 1H), 10.6 (s, 1H); HPLC Purity: 99.36%; Mass (M+1): 569.3.

N-(4-((2R)-4-(1-(2-chloro-4-fluorophenyl)ethyl)-2-methylpiperazine-1-carbonyl)phenyl)quinoline-8-sulfonamide (Compound 191)

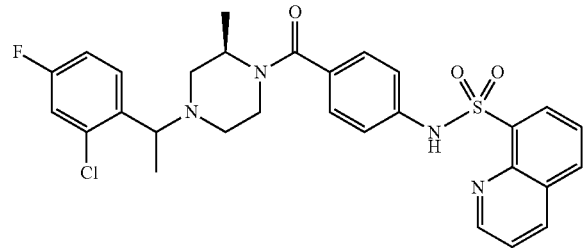 [SMILES: CC(c1ccc(F)cc1Cl)N1CCN(C(=O)c2ccc(NS(=O)(=O)c3cccc4cccnc34)cc2)[C@H](C)C1]

¹H NMR (400 MHz, DMSO-d₆) δ: 1.3 (d, 6H), 1.8-2.0 (m, 3H), 2.2-2.4 (m, 1H), 2.8-3.2 (m, 3H), 3.6-4.8 (m, 1H), 7.0-7.6 (m, 6H), 7.61-7.8 (m, 3H), 8.0 (d, 1H), 8.3-8.6 (m, 2H), 9.1 (m, 1H), 10.6 (s, 1H); HPLC Purity: 94.03%; Mass (M+1): 567.5.

N-(4-((2S)-2-methyl-4-(1-(2,3,6-trifluorophenyl)ethyl)piperazine-1-carbonyl)phenyl)quinoline-8-sulfonamide (Compound 192)

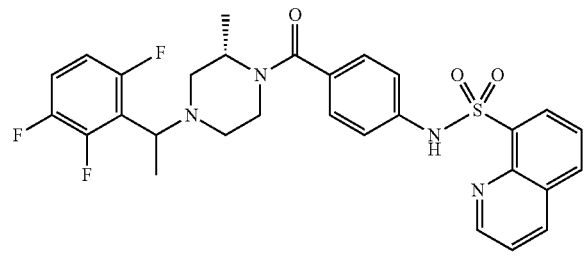 [SMILES: CC(c1c(F)ccc(F)c1F)N1CCN(C(=O)c2ccc(NS(=O)(=O)c3cccc4cccnc34)cc2)[C@@H](C)C1]

¹H NMR (400 MHz, DMSO-d₆) δ: 1.3 (d, 6H), 1.4-1.6 (m, 3H), 1.8-2.2 (m, 2H), 2.8-3.2 (m, 4H), 3.6-4.8 (m, 2H), 7.0-7.5 (m, 6H), 7.61-7.8 (m, 2H), 8.0 (d, 1H), 8.3-8.6 (m, 2H), 9.1 (m, 1H), 10.4 (s, 1H); HPLC Purity: 98.39%; Mass (M+1): 569.55.

(S)—N-(4-(4-(cyclobutylmethyl)-2-methylpiperazine-1-carbonyl)phenyl)quinoline-8-sulfonamide (Compound 207)

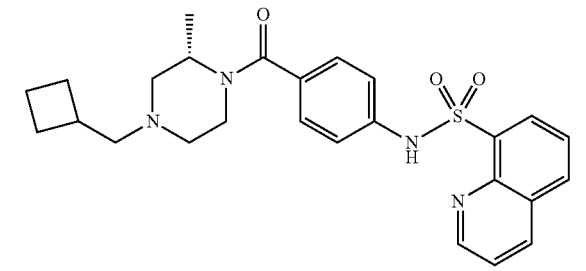 [SMILES: C[C@H]1CN(CC2CCC2)CCN1C(=O)c1ccc(NS(=O)(=O)c2cccc3cccnc23)cc1]

¹H NMR (400 MHz, DMSO-d₆) δ: 1.2 (d, 3H), 1.5-1.6 (m, 2H), 1.8-1.85 (m, 3H), 2.0-2.1 (m, 3H), 2.2-2.4 (m, 4H), 2.6-2.99 (m, 4H), 7.0-7.2 (m, 4H), 7.6-7.8 (m, 2H), 8.0-8.6 (m, 3H), 9.1-9.2 (m, 1H), 10.5 (s, 1H); HPLC Purity: 99.03%; Mass (M+1): 479.3.

N-(4-((2S)-2-methyl-4-((tetrahydrofuran-2-yl)methyl)piperazine-1-carbonyl)phenyl)quinoline-8-sulfonamide (Compound 225)

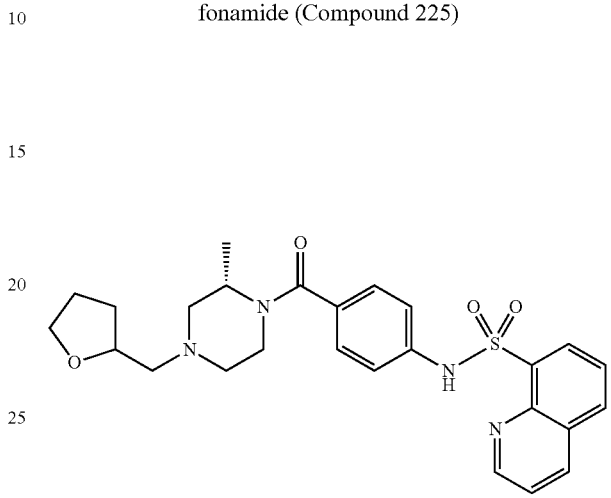

¹H NMR (400 MHz, DMSO-d₆) δ: 1.0-1.6 (m, 6H), 1.8-2.4 (m, 6H), 2.6-3.0 (m, 3H), 3.4-3.8 (m, 4H), 7.0-7.2 (m, 4H), 7.5-7.8 (m, 2H), 8.0-8.4 (m, 3H), 9.1-9.2 (m, 1H), 10.4 (s, 1H); HPLC Purity: 99.37%; Mass (M+1): 495.10

N-(4-((2S)-2R-methyl-4-((tetrahydrofuran-2-yl)methyl)piperazine-1-carbonyl)phenyl)quinoline-8-sulfonamide (Compound 211)

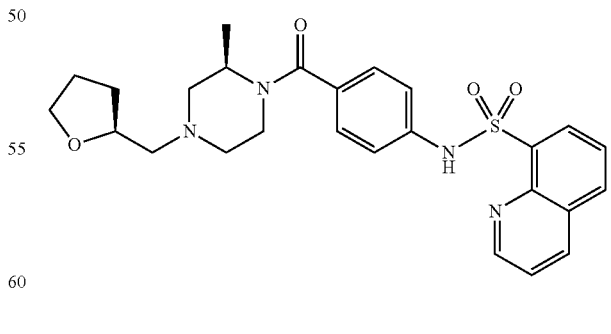

¹H NMR (400 MHz, DMSO-d₆) δ: 1.0 (d, 3H), 1.2-1.8 (m, 6H), 2.0-2.4 (m, 3H), 2.6-3.0 (m, 3H), 3.4-4.0 (m, 4H), 7.0-

7.2 (m, 4H), 7.5-7.8 (m, 2H), 8.0-8.4 (m, 3H), 9.1-9.2 (m, 1H), 10.4 (s, 1H); HPLC Purity: 96.80%; Mass (M+1): 495.20.

N-(4-((R)-2-methyl-4-(((R)-tetrahydrofuran-2-yl)methyl)piperazine-1-carbonyl)phenyl)quinoline-8-sulfonamide (Compound 212)

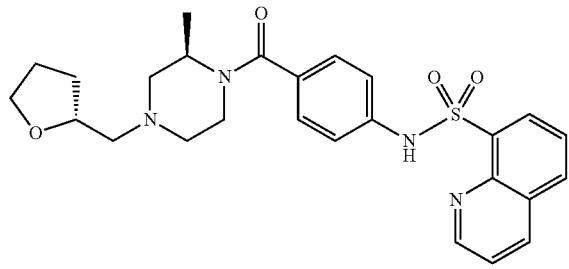 [SMILES: C[C@@H]1CN(C[C@H]2CCCO2)CCN1C(=O)c1ccc(NS(=O)(=O)c2cccc3cccnc23)cc1]

$^1$H NMR (400 MHz, DMSO-$d_6$) δ: 1.0 (d, 3H), 1.2-1.8 (m, 6H), 2.0-2.4 (m, 3H), 2.6-3.0 (m, 3H), 3.4-4.0 (m, 4H), 7.0-7.2 (m, 4H), 7.5-7.8 (m, 2H), 8.0-8.4 (m, 3H), 9.1-9.2 (m, 1H), 10.4 (s, 1H); HPLC Purity: 99.80%; Mass (M+1): 495.20.

(R)— and (S)—N-(4-(4-((tetrahydrofuran-3-yl)methyl)piperazine-1-carbonyl)phenyl)quinoline-8-sulfonamide (Compound 444 and 445)

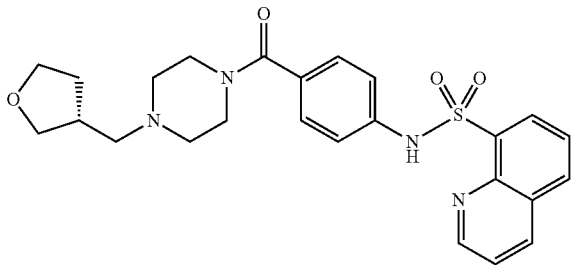

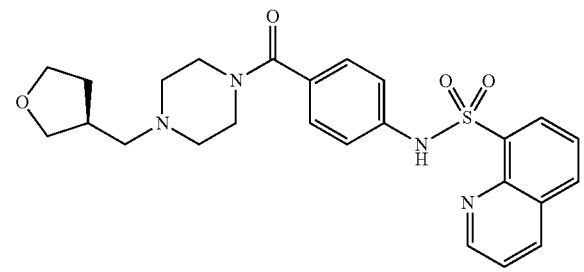

$^1$H-NMR (400 MHz, DMSO-$d_6$) δ: 1.5 (m, 1H), 1.9 (m, 1H), 2.2-2.4 (m, 7H), 3.3 (m, 5H), 3.56-3.8 (m, 3H), 7.0-7.2 (m, 4H), 7.6-7.8 (m, 2H), 8.3 (d, 1H), 8.4 (d, 1H), 8.5 (d, 1H), 9.1-9.2 (m, 1H), 10.4 (s, 1H); HPLC Purity: 99%; R$_T$ 31.15 min and 36.57 min; Mass (M+1): 481.20.

Example 8

Preparation of Compounds of Formula Ij

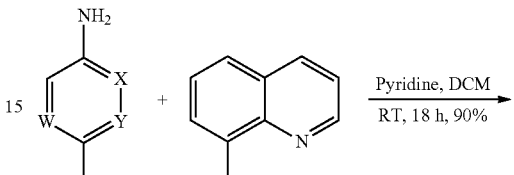

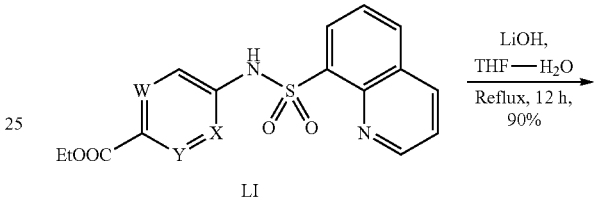

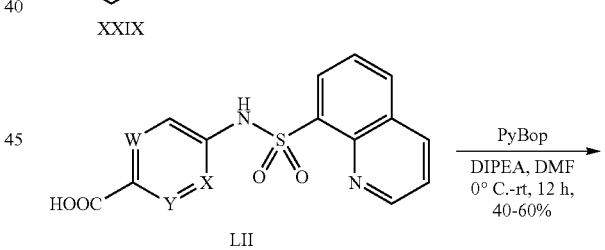

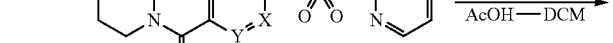

STAB = Sodium tri-acetoxy borohydride

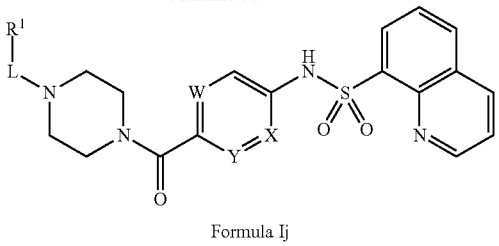

Formula Ij

W, Y, Z = N or CH
L = ——(CR$^c$R$^c$)$_m$——
R$^1$ = carbocyclyl, aryl, heterocyclyl, heteroaryl

Synthesis of Intermediate LI

To a solution of appropriate amine L (9.6 mmol) in a mixture (1:1) of DCM and pyridine, sulfonyl chloride XLIX (12.1 mmol) was added at room temperature under N$_2$ atmosphere. The resulting mixture was allowed to stir for 16 h. After completion of reaction, the crude mixture was diluted with DCM, washed with water followed by 1N HCl. The organic layer was then dried over Na$_2$SO$_4$ and concentrated under reduced pressure to afford product LI in 78% yield.

Synthesis of Intermediate LII

To a solution of sulfonamide LI (9.5 mmol) in THF and water (1:1), LiOH (4.7 mmol) was added and the resulting mixture was allowed to stir at 80° C. overnight. After completion of reaction, the crude mixture was washed with EtOAc. The aqueous layer was acidified with citric acid and filtered. Thus obtained solid was washed with Et$_2$O and azeotroped by toluene, under reduced pressure to afford acid LII (75% yield) which was taken forward for the next step without further purification.

Synthesis of Intermediate LIII

To a solution of acid LII (6.09 mmol) in DMF, PyBoP (Benzotriazole-1-yl-oxy-tris-(dimethylamino)-phosphonium hexafluorophosphate) (4.75 gm, 9.14 mmol) was added at 0° C. and allowed to stir for 5 minutes. Then Boc protected piperazine/substituted piperizine XXIX (1.13 gm, 6.09 mmol) was added to the reaction mixture at the same temperature under N$_2$ atmosphere and stirred overnight at room temperature. After completion of reaction, mixture was diluted with water and extracted with EtOAc. The organic layer was washed with water, dried over Na$_2$SO$_4$, and evaporated under reduced pressure. The residue was purified by column chromatography (silica gel, 60-120 mesh; MeOH-DCM, 1:9) to afford product LIII in 56% yield.

Synthesis of Intermediate LIV

To a solution of MeOH.HCl, Boc protected amine LIII (4.03 mmol) was added and the resulting mixture was stirred for 1 h. After completion of reaction, solvent was removed under reduced pressure, washed with water followed by addition of NaHCO$_3$ and extracted with DCM. The organic layer was dried over Na$_2$SO$_4$ and evaporated under reduced pressure to afford product LIV (84% yield).

Synthesis of Compounds of Formula Ij

To a solution of amine LIV (0.25 mmoles) and appropriate aldehyde (0.27 mmol) in DCM, acetic acid (0.2 mL) was added at room temperature and the resulting mixture was allowed to stir for 30 minutes. Then STAB (0.26 gm, 1.26 mmol) was added to reaction mixture and the resulting mixture was allowed to stir at 50° C. for 2 hr. After completion of reaction, the crude mixture was diluted with DCM washed with water, dried over Na$_2$SO$_4$ and concentrated under reduced pressure. The residue was purified by column chromatography (silica gel, 60-120 mesh; MeOH-DCM, 2:8) to afford product in 22-45% yield.

The following compounds were prepared according to the above methods using the appropriate amine L and the appropriate aldehyde.

N-(5-(4-(cyclopropylmethyl)piperazine-1-carbonyl)pyridin-2-yl)quinoline-8-sulfonamide (XIV-1) (Compound 411)

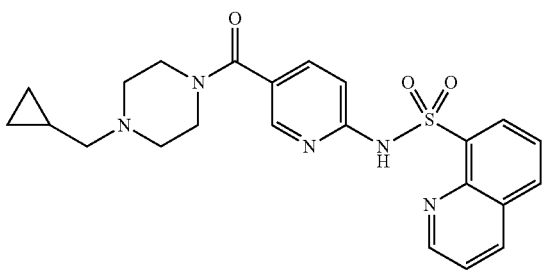 [SMILES: O=C(c1ccc(NS(=O)(=O)c2cccc3cccnc23)nc1)N1CCN(CC2CC2)CC1]

$^1$H NMR (400 MHz, DMSO-d$_6$) δ: 0.1-0.15 (m, 2H), 0.4-0.6 (m, 2H), 08-0.85 (m, 1H), 2.2-2.3 (m, 2H), 2.4-2.8 (m, 4H), 3.6-3.8 (m, 4H), 3.99-4.0 (m, 2H), 7.5-7.7 (m, 4H), 8.3-8.5 (m, 4H), 9.1 (m, 1H); HPLC Purity: 99.67%; Mass (M+1): 452.5.

N-(5-(4-(4-fluorobenzyl)piperazine-1-carbonyl)pyridin-2-yl)quinoline-8-sulfonamide (Compound 412)

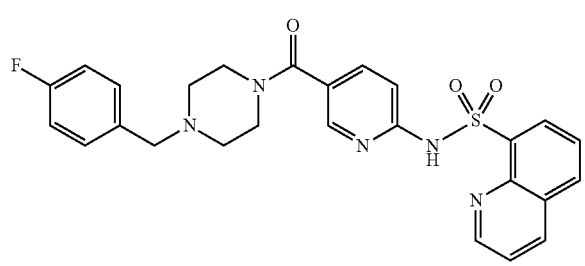 [SMILES: O=C(c1ccc(NS(=O)(=O)c2cccc3cccnc23)nc1)N1CCN(Cc2ccc(F)cc2)CC1]

¹H NMR (400 MHz, DMSO-d₆) δ: 2.3 (s, 2H), 2.35-2.4 (m, 4H), 3.4-3.6 (m, 4H), 7.0-7.4 (m, 4H), 7.6-7.8 (m, 3H), 8.0 (m, 1H), 8.3-8.5 (m, 3H), 8.9-9.0 (m, 1H); HPLC Purity: 99.86%; Mass (M+1): 506.4.

N-(5-(4-(3,5-difluorobenzyl)piperazine-1-carbonyl)pyridin-2-yl)quinoline-8-sulfonamide (Compound 413)

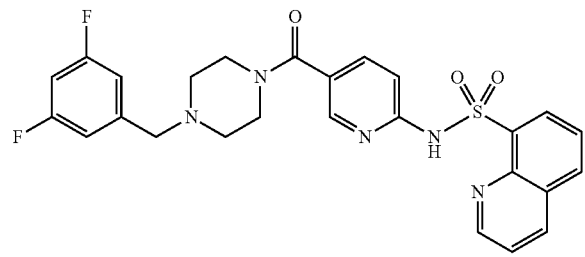 [SMILES: O=C(c1ccc(NS(=O)(=O)c2cccc3cccnc23)nc1)N1CCN(Cc2cc(F)cc(F)c2)CC1]

¹H NMR (400 MHz, CDCl₃) δ: 2.35-2.7 (m, 4H), 3.4-3.59 (m, 4H), 3.6-3.8 (s, 2H), 6.6-7.0 (m, 3H), 7.5-7.7 (m, 4H), 8.3-8.5 (m, 4H), 8.9-9.0 (m, 1H); HPLC Purity: 93.78%; Mass (M+1): 524.5.

N-(6-(4-(3,5-difluorobenzyl)piperazine-1-carbonyl)pyridin-3-yl)quinoline-8-sulfonamide (Compound 414)

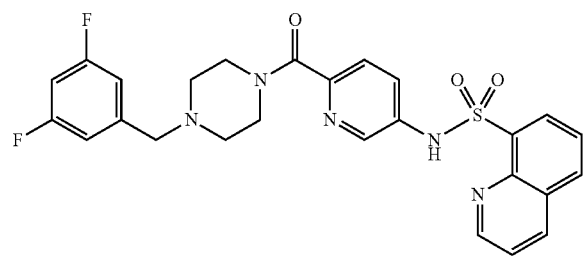 [SMILES: O=C(c1ccc(NS(=O)(=O)c2cccc3cccnc23)cn1)N1CCN(Cc2cc(F)cc(F)c2)CC1]

¹H NMR (400 MHz, CDCl₃) δ: 2.35-2.7 (m, 4H), 3.4-3.59 (m, 4H), 3.6-3.8 (s, 2H), 6.6-7.0 (m, 4H), 7.4-7.8 (m, 3H), 8.0-8.4 (m, 4H), 8.9-9.0 (m, 1H); HPLC Purity: 96.0%; Mass (M+1): 524.3.

N-(6-(4-(cyclopropylmethyl)piperazine-1-carbonyl)pyridin-3-yl)quinoline-8-sulfonamide (Compound 415)

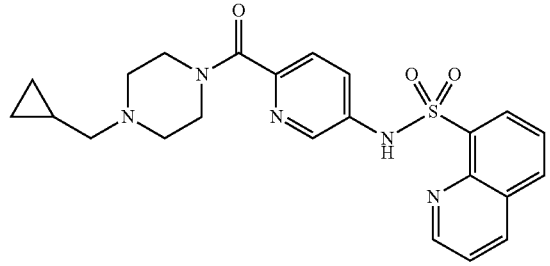 [SMILES: O=C(c1ccc(NS(=O)(=O)c2cccc3cccnc23)cn1)N1CCN(CC2CC2)CC1]

¹H NMR (400 MHz, CDCl₃) δ: 0.9-1.0 (m, 2H), 1.2-1.4 (m, 4H), 1.6-1.8 (m, 3H), 3.4-3.59 (m, 1H), 3.9-4.3 (m, 5H), 7.2-7.75 (m, 9H), 8.2-8.4 (m, 1H); HPLC Purity: 99.35%; Mass (M+1): 452.3.

N-(6-(4-(4-fluorobenzyl)piperazine-1-carbonyl)pyridin-3-yl)quinoline-8-sulfonamide (Compound 416)

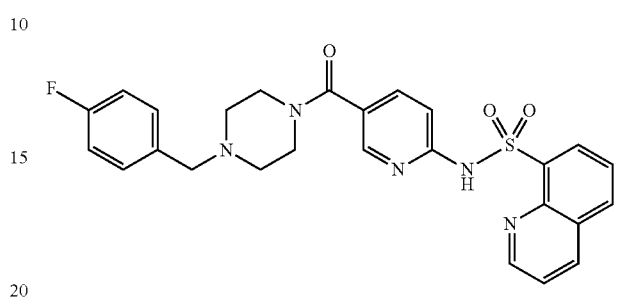

¹H NMR (400 MHz, CDCl₃) δ: 2.2-2.7 (m, 4H), 3.2-3.8 (m, 8H), 7.0-7.5 (m, 4H), 7.56-7.8 (m, 3H), 8.2-8.4 (m, 4H), 8.6-8.8 (m, 1H), 9.1-9.2 (m, 1H); HPLC Purity: 99.85%; Mass (M+1): 506.3.

N-(5-(4-(cyclopropylmethyl)piperazine-1-carbonyl)pyrazin-2-yl)quinoline-8-sulfonamide (Compound 451)

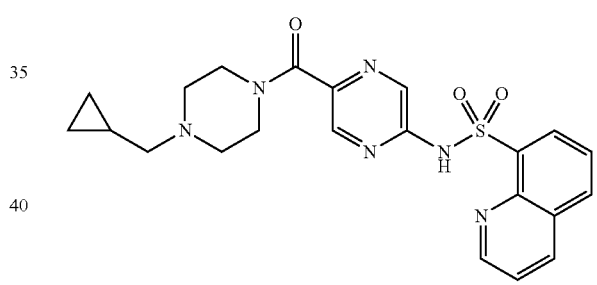

¹H NMR (400 MHz, DMSO-d₆) δ: 0.2 (m, 2H), 0.6 (m, 2H), 0.8-1.0 (m, 1H), 1.2 (s, 2H), 2.5-2.8 (m, 4H), 3.1-3.8 (m, 4H), 7.6-7.8 (m, 2H), 8.2 (m, 1H), 8.2-8.6 (m, 4H), 9.0 (m, 1H); HPLC Purity: 94.0%; Mass (M+1): 453.25.

N-(5-(4-(cyclopropylmethyl)piperazine-1-carbonyl)pyrazin-2-yl)quinoline-8-sulfonamide (Compound 345)

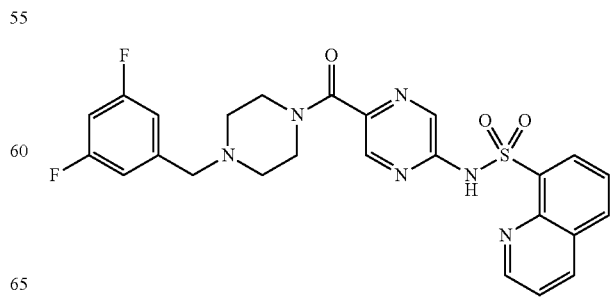

¹H NMR (400 MHz, DMSO-d₆) δ: 2.5-2.8 (m, 4H), 3.1-3.8 (m, 6H), 7.0-7.2 (m, 4H), 7.6-7.8 (m, 2H), 8.2-8.6 (m, 4H), 9.0 (m, 1H); HPLC Purity: 97.74%; Mass (M+1): 525.20.

N-(5-(4-(4-fluorobenzyl)piperazine-1-carbonyl)pyrazin-2-yl)quinoline-8-sulfonamide (Compound 452)

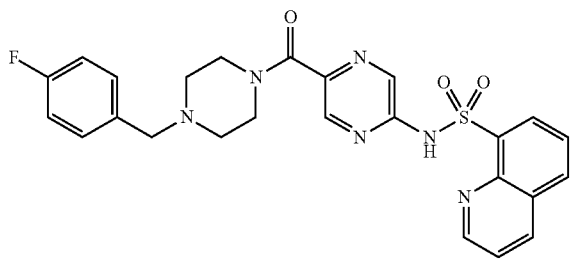 [SMILES: O=C(c1cnc(NS(=O)(=O)c2cccc3cccnc23)cn1)N1CCN(Cc2ccc(F)cc2)CC1]

¹H NMR (400 MHz, CDCl₃) δ: 2.5-2.8 (m, 6H), 3.1-3.6 (m, 4H), 3.5-3.8 (s, 2H), 7.0-7.2 (m, 3H), 7.6-7.8 (m, 3H), 8.2-8.6 (m, 4H), 8.8-8.85 (m, 1H), 9.0 (m, 1H); HPLC Purity: 92.85%; Mass (M+1): 507.30.

Example 9

Preparation of Compounds of Formula Ik

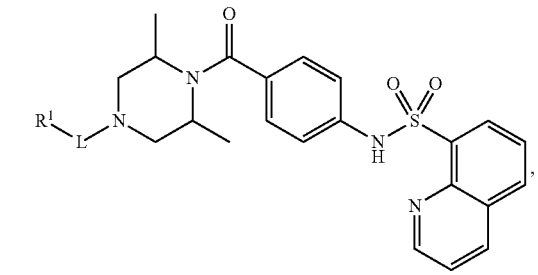

(Ik)

wherein L is —(CR^cR^c)_m—; and R¹ is alkyl, carbocyclyl or aryl.

Scheme 9:

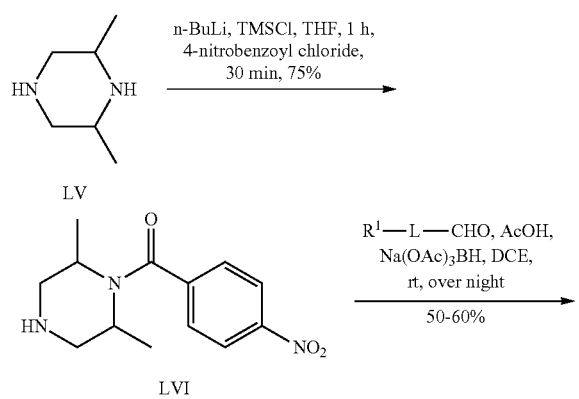

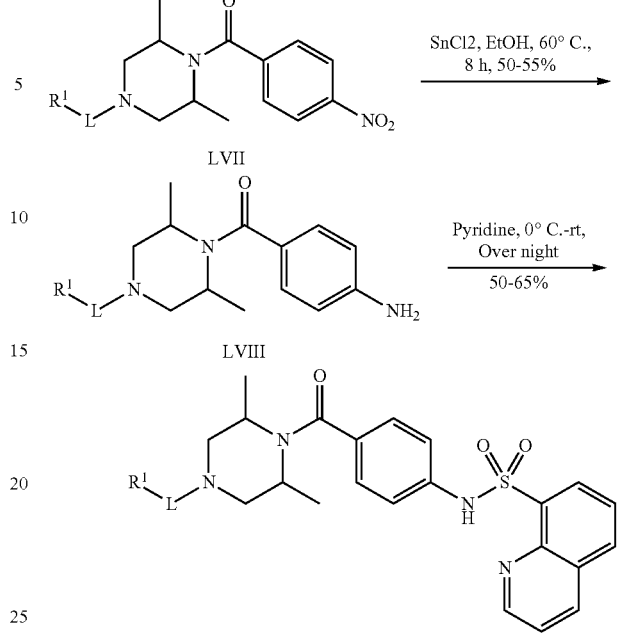

Formula Ik

R¹ = aryl, alkyl
L = ——(CR^cR^c)_m——

Synthesis of N¹-(4-nitrobenzoyl)-2,6-dimethylpiperazine (LVI)

To a stirred solution of 2,6-di-methylpiperazine (LV, 5.0 g, 43.8 mmol) in dry THF (50 mL), maintained at room temperature under an argon atmosphere, was added a solution of 2.5 M n-BuLi in THF (38.54 mL, 96.36 mmol). After the mixture was stirred for 30 min at room temperature, trimethylsilyl chloride (5.5 mL, 43.8 mmol) was added and the reaction mixture stirred for 1 h before the addition of 4-nitrobenzoyl chloride (7.8 gm, 42.05 mmol). After 10 min, the reaction mixture was quenched with MeOH and the solvents were evaporated in vacuo. The residue was purified by silica gel column chromatography to provide product LVI (10.37 gm, 90% yield):

N⁴-alkylation of N¹-(4-nitrobenzoyl)-2,6-dimethylpiperazine (LVII)

To a solution of amine LVI (0.5 gm, 1.9 mmol) and appropriate aldehyde (2.28 mmol) in dichloroethane, acetic acid (0.2 mL) was added at room temperature and the resulting mixture was allowed to stir for 30 minutes. Then sodium triacetoxyborohydride (1.2 gm, 5.7 mmol) was added to the reaction mixture and the resulting mixture was allowed to stir at room temperature over night. After completion of reaction, the crude mixture was concentrated, diluted with DCM washed with water, dried over Na₂SO₄, concentrated under reduced pressure and purified by column chromatography (silica gel, 60-120 mesh) to afford product LVII in 50-60% yield.

Reduction of N⁴-alkyl-N¹-(4-nitrobenzoyl)-2,6-dimethylpiperazine (LVIII)

To a solution of nitro compound (LVII, 1.10 mmol) in 15 ml of ethanol and ethyl acetate (1:1), SnCl₂ (0.418 gm, 2.2 mmol) was added and the mixture was stirred at 60° C. for overnight. The mixture was quenched by the addition of 10 ml of saturated solution of NaHCO₃ and extracted with ethyl acetate (2×25 mL). The combined organic layers were washed with brine solution, dried over anhydrous Na₂SO₄ and concentrated under reduced pressure to afford amine product LVIII in 50-55% yield.

Synthesis of Compounds of Formula Ik

To a solution of amine (LVIII, 0.55 mmol) in a 5 mL mixture (1:1) of DCM and pyridine, 8-quinoline sulfonyl chloride (0.14 gm, 0.61 mmol) was added at room temperature under N₂ atmosphere. The resulting mixture was allowed to stir for overnight. After completion of reaction, the crude mixture was diluted with DCM, washed with water followed by 1N HCl. The organic layer was then dried over Na₂SO₄, concentrated under reduced pressure to afford product in 50-65% yields.

The following compounds were produced by the above-described method using the appropriate aldehyde.

N-(5-(4-(4-fluorobenzyl)piperazine-1-carbonyl)pyrazin-2-yl)quinoline-8-sulfonamide (Compound 195)

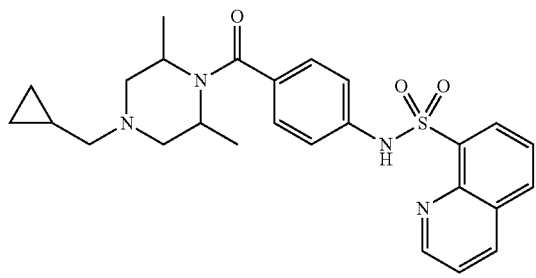 [SMILES: CC1CN(CC2CC2)CC(C)N1C(=O)c1ccc(NS(=O)(=O)c2cccc3cccnc23)cc1]

¹H NMR (400 MHz, DMSO-d₆) δ: 0.1-0.15 (m, 2H), 0.3-0.4 (m, 2H), 0.8-0.9 (m, 1H), 1.1-1.4 (d, 6H), 1.99-2.3 (m, 4H), 2.4-3.0 (m, 2H), 3.8-4.2 (d, 2H), 7.0-7.2 (m, 4H), 7.61-7.8 (m, 2H), 8.0 (d, 1H), 8.3-8.6 (m, 2H), 9.1 (m, 1H), 10.4 (s, 1H); HPLC Purity: 99.46%; Mass (M+1): 479.50.

N-(4-(2,6-dimethyl-4-((tetrahydrofuran-3-yl)methyl)piperazine-1-carbonyl)phenyl)quinoline-8-sulfonamide (Compound 204)

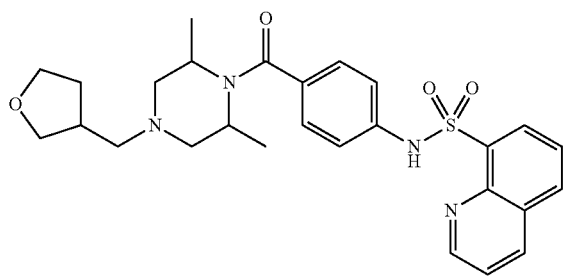 [SMILES: CC1CN(CC2CCOC2)CC(C)N1C(=O)c1ccc(NS(=O)(=O)c2cccc3cccnc23)cc1]

¹H NMR (400 MHz, DMSO-d₆) δ: 1.0-1.3 (d, 6H), 1.4-1.6 (m, 2H), 1.9-2.67 (m, 8H), 3.6-3.8 (m, 3H), 3.99-4.0 (m, 2H), 7.0-7.27 (m, 4H), 7.6-7.8 (m, 2H), 8.3-8.6 (m, 3H), 9.1 (m, 1H), 10.4 (s, 1H); HPLC Purity: 96.92%; Mass (M+1): 509.5.

N-(4-(4-(cyclohexylmethyl)-2,6-dimethylpiperazine-1-carbonyl)phenyl)quinoline-8-sulfonamide (Compound 198)

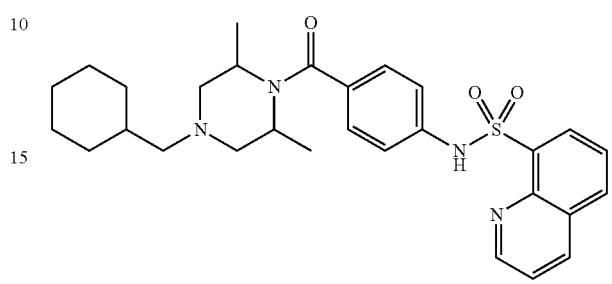

¹H NMR (400 MHz, DMSO-d₆) δ: 0.9-1.0 (m, 2H), 1.1-1.4 (m, 11H), 1.45-1.5 (m, 2H), 1.55-1.75 (m, 5H), 1.8-2.1 (m, 4H), 2.2-2.7 (m, 2H), 3.99-4.0 (m, 3H), 7.0-7.2 (m, 4H), 7.55-7.8 (m, 2H), 8.3-8.6 (m, 3H), 9.1 (m, 1H), 10.4 (s, 1H); HPLC Purity: 99.53%; Mass (M+1): 521.60.

N-(4-(4-(4-fluorobenzyl)-2,6-dimethylpiperazine-1-carbonyl)phenyl)quinoline-8-sulfonamide (Compound 196)

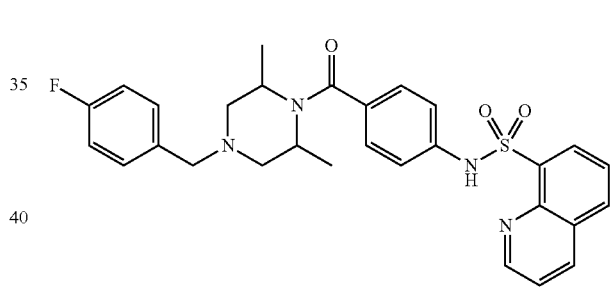

¹H NMR (400 MHz, CDCl₃) δ: 0.1-0.15 (m, 2H), 1.0-1.4 (d, 6H), 1.99-2.3 (m, 2H), 2.4-2.8 (m, 2H), 3.3-3.6 (s, 2H), 4.19-4.2 (m, 1H), 6.9-7.2 (m, 6H), 7.23-7.4 (m, 2H), 7.55-7.7 (m, 2H), 8.3-8.6 (m, 3H), 9.1 (m, 1H); HPLC Purity: 99.02%; Mass (M+1): 533.55.

N-(4-(4-(3,5-difluorobenzyl)-2,6-dimethylpiperazine-1-carbonyl)phenyl)quinoline-8-sulfonamide (Compound 194)

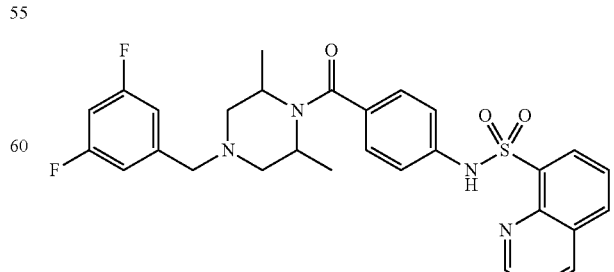

¹H NMR (400 MHz, DMSO-d₆) δ: 1.2 (d, 6H), 1.3 (m, 2H), 2.0-2.4 (m, 2H), 2.4-2.6 (s, 2H), 3.2-3.6 (s, 2H), 7.0-7.5 (m, 7H), 7.61-7.8 (m, 2H), 8.0 (d, 1H), 8.3-8.6 (m, 2H), 9.1 (m, 1H), 10.4 (s, 1H); HPLC Purity: 98.34%; Mass (M+1): 551.55.

N-(4-(4-(4-chloro-3-fluorobenzyl)-2,6-dimethylpiperazine-1-carbonyl)phenyl)quinoline-8-sulfonamide (Compound 197)

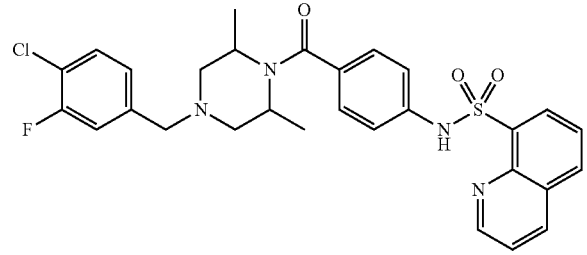 [SMILES: CC1CN(Cc2ccc(Cl)c(F)c2)CC(C)N1C(=O)c1ccc(NS(=O)(=O)c2cccc3cccnc23)cc1]

¹H NMR (400 MHz, DMSO-d₆) δ: 1.0-1.4 (d, 6H), 2.0-2.2 (m, 2H), 2.4-2.6 (m, 2H), 3.5 (s, 2H), 3.9-4.0 (m, 2H), 7.23-7.4 (m, 6H), 7.55-7.8 (m, 3H), 8.3-8.6 (m, 3H), 9.1 (m, 1H), 10.4 (s, 1H); HPLC Purity: 95.27%; Mass (M+1): 567.50.

N-(4-(2,6-dimethyl-4-(2,3,6-trifluorobenzyl)piperazine-1-carbonyl)phenyl)quinoline-8-sulfonamide (Compound 199)

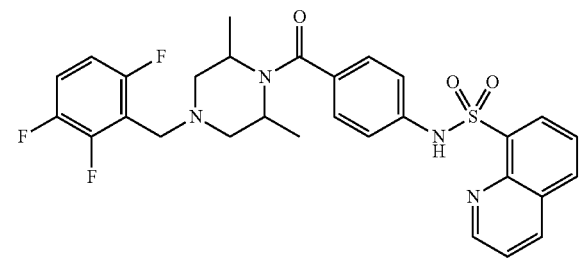 [SMILES: CC1CN(Cc2c(F)ccc(F)c2F)CC(C)N1C(=O)c1ccc(NS(=O)(=O)c2cccc3cccnc23)cc1]

¹H NMR (400 MHz, DMSO-d₆) δ: 1.0-1.2 (d, 6H), 1.1-1.4 (m, 2H), 2.0-2.2 (m, 2H), 2.4-2.6 (m, 2H), 3.6 (s, 2H), 7.0-7.2 (m, 4H), 7.55-7.8 (m, 3H), 8.3-8.6 (m, 3H), 9.1 (m, 1H), 10.4 (s, 1H); HPLC Purity: 99.82%; Mass (M+1): 569.55.

N-(4-(2,6-dimethyl-4-(2,3,5-trifluorobenzyl)piperazine-1-carbonyl)phenyl)quinoline-8-sulfonamide (Compound 200)

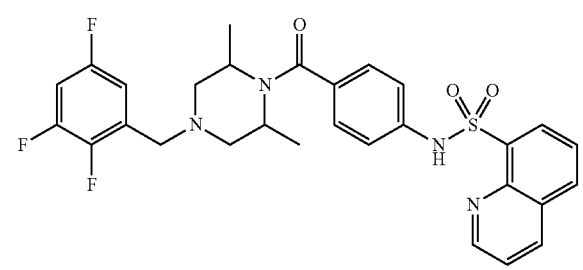 [SMILES: CC1CN(Cc2cc(F)cc(F)c2F)CC(C)N1C(=O)c1ccc(NS(=O)(=O)c2cccc3cccnc23)cc1]

¹H NMR (400 MHz, DMSO-d₆) δ: 1.0-1.2 (d, 6H), 1.25-1.4 (m, 4H), 2.0-2.2 (m, 2H), 2.4-2.6 (m, 2H), 3.6 (s, 2H), 7.0-7.2 (m, 4H), 7.4-7.5 (m, 1H), 7.6-7.8 (m, 2H), 8.3-8.6 (m, 3H), 9.1 (m, 1H), 10.4 (s, 1H); HPLC Purity: 99.92%; Mass (M+1): 569.55.

N-(4-(2,6-dimethyl-4-(3,4,5-trifluorobenzyl)piperazine-1-carbonyl)phenyl)quinoline-8-sulfonamide (Compound 201)

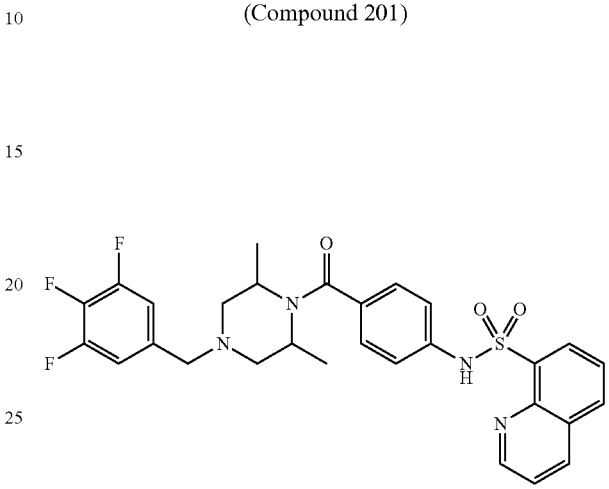

¹H NMR (400 MHz, DMSO-d₆) δ: 1.0-1.2 (d, 6H), 1.3-1.4 (m, 2H), 2.0-2.2 (m, 2H), 2.4-2.6 (m, 1H), 3.6 (s, 2H), 3.99-4.0 (m, 1H), 7.0-7.4 (m, 6H), 7.6-7.8 (m, 2H), 8.3-8.6 (m, 3H), 9.1 (m, 1H), 10.4 (s, 1H); HPLC Purity: 96.13%; Mass (M+1): 569.5.

N-(4-(2,6-dimethyl-4-(2,4,6-trifluorobenzyl)piperazine-1-carbonyl)phenyl)quinoline-8-sulfonamide (Compound 202)

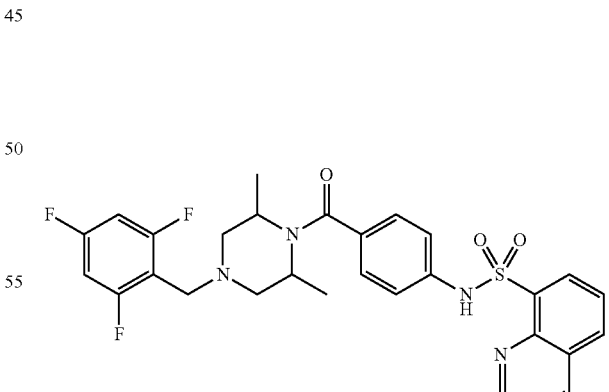

¹H NMR (400 MHz, DMSO-d₆) δ: 1.0-1.2 (d, 6H), 1.3-1.4 (m, 1H), 2.0-2.2 (m, 3H), 3.6 (s, 2H), 3.99-4.0 (m, 2H), 7.0-7.27 (m, 6H), 7.6-7.8 (m, 2H), 8.3-8.6 (m, 3H), 9.1 (m, 1H), 10.4 (s, 1H); HPLC Purity: 96.21%; Mass (M+1): 569.6.

N-(4-(2,6-dimethyl-4-(2,4,5-trifluorobenzyl)piperazine-1-carbonyl)phenyl)quinoline-8-sulfonamide (Compound 203)

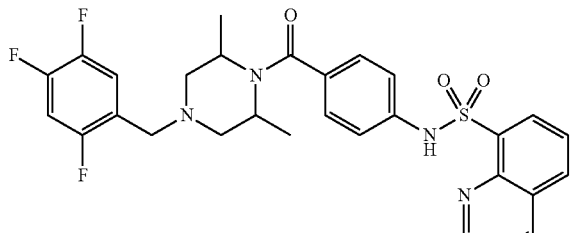

$^1$H NMR (400 MHz, DMSO-d$_6$) δ: 1.0-1.4 (d, 6H), 2.0-2.2 (m, 2H), 2.5-2.7 (m, 2H), 3.6 (s, 2H), 3.99-4.0 (m, 2H), 7.0-7.27 (m, 6H), 7.4-7.8 (m, 4H), 8.3-8.6 (m, 3H), 9.1 (m, 1H), 10.4 (s, 1H); HPLC Purity: 98.34%; Mass (M+1): 569.5.

Example 10

Preparation of Compounds of Formula II

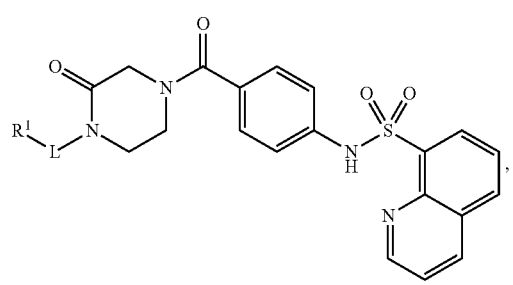

(II)

wherein R$^1$ is alkyl or aryl; and L is —(CR$^c$R$^c$)$_m$—.

Scheme 10:

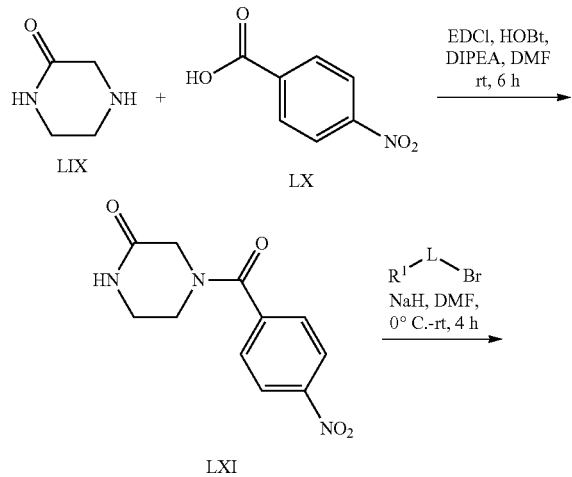

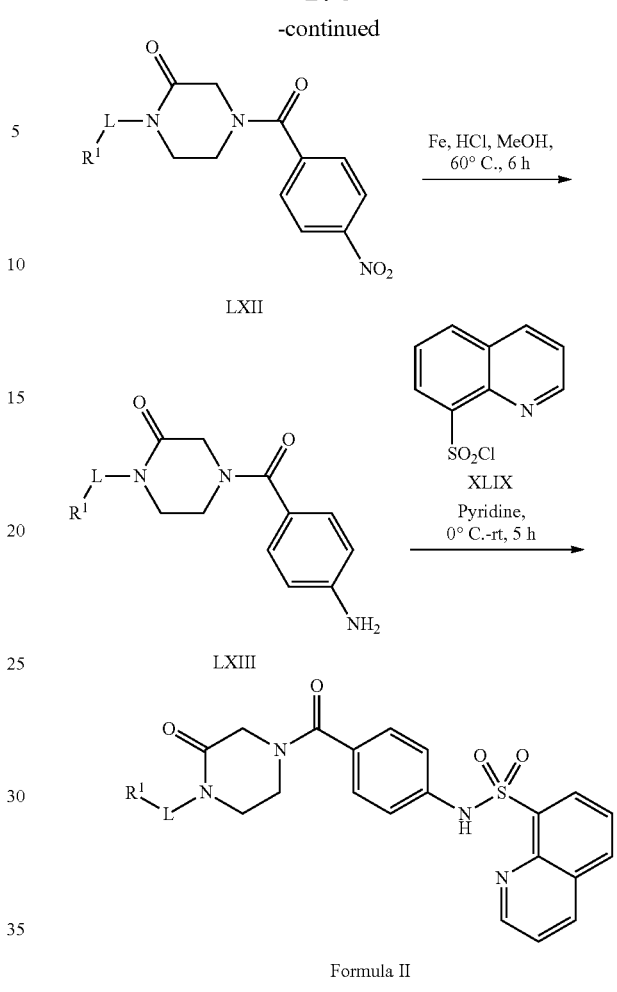

Formula II

R$^1$ = Alkyl, Aryl
L = —(CR$^c$R$^c$)$_m$—

Synthesis of 4-(4-nitrobenzoyl)piperazin-2-one (LXI)

EDCI (0.394 gm, 2.05 mmol) and HOBT (0.276 gm, 2.05 mmol) were added to a stirred solution of the 4-nitrobenzoic acid (LX, 0.253 gm, 2.05 mmol) in anhydrous DMF. The temperature of the mixture was reduced to 0° C., at which time DIPEA (1.14 ml, 6.15 mmol) was added under nitrogen atmosphere and the resultant solution (or suspension) was stirred at room temperature for 30 min. 2-piperazinone (LIX, 2.05 mmol) was then added at 0° C. The reaction mixture was then brought to room temperature and stirred for 6 h. After completion of the reaction, the reaction mixture was diluted with water and extracted with ethyl acetate (3×25 ml). The organic layer was washed with water (3×10 ml), dried over anhydrous sodium sulfate, filtered and concentrated over the rotary evaporator to get the crude product. The crude product was purified by column chromatography (60-120 silica gel, ethyl acetate:hexane, 4:6) to afford pure product LXI (0.3 gm, 60%) as an off-white solid.

Synthesis of Intermediate LXII

A solution of 4-(4-nitrobenzoyl)piperazin-2-one (LXI) (0.1 gm, 0.4 mmol) in anhydrous DMF was cooled to 0° C.

and added sodium hydride (0.02 gm, 0.48 mmol) under nitrogen atmosphere. The mixture was then stirred at room temperature for 30 min. Then the mixture was added appropriate alkyl bromide ($R^1$-L-Br) (0.4 mmol) at 0° C. and stirred at room temperature for 24 h. After completion of reaction, the reaction mixture was quenched by the addition of water (10 mL), diluted with diethyl ether (100 mL), washed with water (2×25 mL), brine (25 mL), dried over anhydrous sodium sulfate and concentrated in vacuo. The crude product was purified by column chromatography (Silica gel, 60:120; ethyl acetate:hexane, 3:7) to afford product LXII in 65-72% yield.

Synthesis of Intermediate LXIII

To a solution of compound LXII (0.77 mmol) in 15 mL of methanol, iron powder (0.215 gm, 3.85 mmol) and concentrated hydrochloric acid (0.2 mL) were added. The mixture was then heated to 60° C. and stirred for 6 h. After completion of reaction, evaporated the solvent, the residue was added 10 mL of saturated sodium bicarbonate solution and extracted with ethyl acetate (3×25 mL). The combined organic layers were washed with water (10 mL), brine (10 mL), dried over anhydrous sodium sulfate and concentrated under reduced pressure to afford amine LXIII in 60-70% yield.

Synthesis of Compounds of Formula II

To a stirred solution of amine LXIII (0.26 mmol) in 5 mL of 1:1 mixture of pyridine and dichloromethane at 0° C. was added 8-quinoline sulfonylchloride (XLIX; 0.066 gm, 0.29 mmol). The mixture was allowed to stir for 6 h at room temperature. After completion of reaction, the mixture was concentrated under reduced pressure, residue dissolved in dichloromethane (50 mL), washed with dilute HCl (10 mL), water (10 mL), brine (10 mL) and concentrated. The crude product was purified by column chromatography (Silica gel, 60-120; 2% MeOH-DCM) to afford pure product as an off-white solid in 55-60% yields.

The following compounds were prepared according to the above methods using the appropriate alkyl bromide.

N-(4-(4-(cyclopropylmethyl)-3-oxopiperazine-1-carbonyl)phenyl)quinoline-8-sulfonamide (Compound 215)

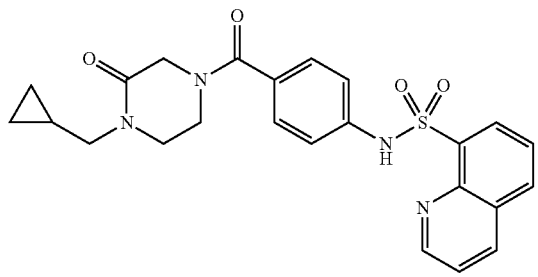 [SMILES: O=C1CN(C(=O)c2ccc(NS(=O)(=O)c3cccc4cccnc34)cc2)CCN1CC1CC1]

$^1$H NMR (400 MHz, DMSO-$d_6$) δ: 0.2-0.4 (m, 2H), 0.45-0.8 (m, 2H), 1.0 (m, 1H), 2.6-2.8 (s, 2H), 3.2-3.4 (m, 2H), 3.5-4.0 (m, 4H), 7.2-7.4 (m, 4H), 7.4-7.6 (m, 2H), 8.0-8.4 (m, 3H), 8.79-8.8 (m, 1H), 10.5 (s, 1H); HPLC Purity: 94.48%; Mass (M+1): 465.2.

N-(4-(4-(3,5-difluorobenzyl)-3-oxopiperazine-1-carbonyl)phenyl)quinoline-8-sulfonamide (Compound 216)

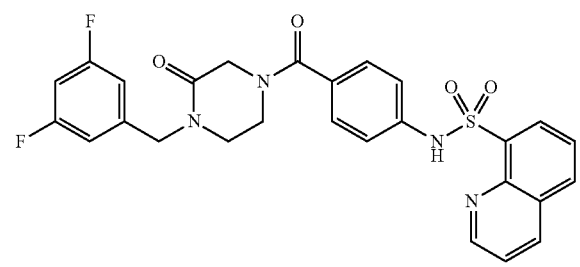 [SMILES: O=C1CN(C(=O)c2ccc(NS(=O)(=O)c3cccc4cccnc34)cc2)CCN1Cc1cc(F)cc(F)c1]

$^1$H NMR (400 MHz, DMSO-$d_6$) δ: 3.2-4.0 (m, 6H), 4.5 (s, 2H), 7.0-7.4 (m, 7H), 7.4-7.6 (m, 2H), 8.0-8.4 (m, 3H), 8.79-8.8 (m, 1H), 10.5 (s, 1H); HPLC Purity: 97.06%; Mass (M+1): 537.45.

Example 11

Preparation of a Compound of Formula Im

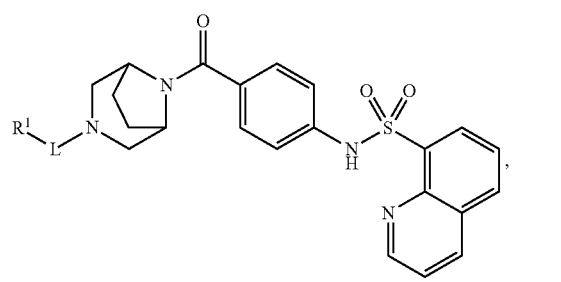

wherein $R^1$ is aryl or carbocyclyl; and L is —$(CR^cR^c)_m$—.

Scheme 11

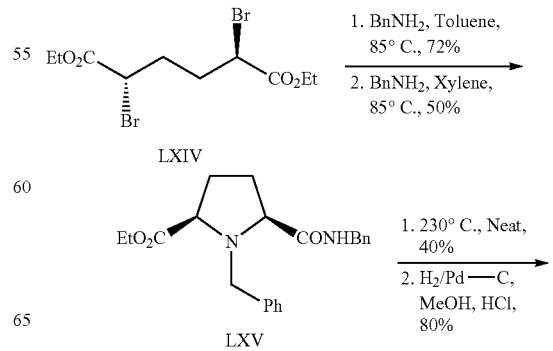

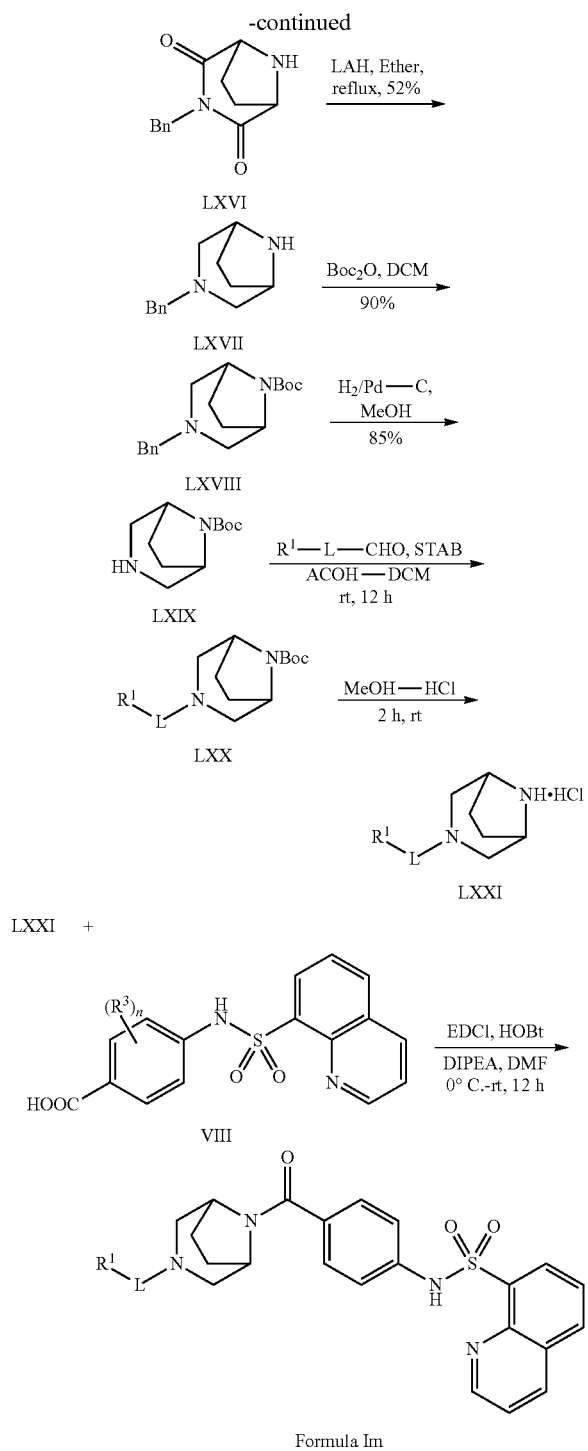

and the formed solid was filtered. The filtrate was concentrated under reduced pressure to leave the product as pale yellow liquid. The residue was purified by column chromatography (silica gel, 60-120 mesh; EA-Hexane, 2:8) to afford Diethyl pyrrolidine-2,5-carboxylate in 72% yield.

To a stirred solution of Diethyl pyrrolidine-2,5-carboxylate (0.000327 mol, 100 mg) in xylene (5 mL) was added benzylamine (0.000327 mol, 0.035 mL) under nitrogen atmosphere and heated under reflux for 18 h. After completion of the reaction (checked by TLC), the reaction mixture was cooled and concentrated under reduced pressure to leave the product as yellow liquid. The residue was purified by column chromatography (silica gel, 60-120 mesh; EA-Hexane, 4:6) to afford the product LXV in 50% yield.

Synthesis of
3-benzyl-3,8-diazabicyclo[3.2.1]octane-2,4-dione
(LXVI)

Ethyl 1-benzyl-5-(benzylcarbamoyl)pyrrolidine-2-carboxylate (LXV, 0.00122 mol, 450 mg) was heated under stirring at 210-220° C. for 3 h under atmospheric pressure and the formed ethyl alcohol was collected. After completion of the reaction (checked by TLC), the reaction mixture was cooled at room temperature and the residue was purified by column chromatography (silica gel, 60-120 mesh; EA-Hexane, 2:8) to afford the 3,8-dibenzyl-3,8-diazabicyclo[3.2.1]octane-2,4-dione in 40-45% yield.

To a stirred solution of 3,8-dibenzyl-3,8-diazabicyclo[3.2.1]octane-2,4-dione (0.00025 mol, 80 mg) in MeOH (2 mL) containing few drops of HCl was hydrogenated with 10% Pd—C (8 mg) for 4 h at room temperature. After completion of the reaction (checked by TLC), the reaction mixture was filtered through celite and the filtrate was concentrated under reduced pressure. The crude residue was purified by column chromatography (silica gel, 60-120 mesh; EA-Hexane, 6:4) to afford the 3-benzyl-3,8-diazabicyclo[3.2.1]octane-2,4-dione (LXVI) in 80% yield.

Synthesis of 3-benzyl-3,8-diazabicyclo[3.2.1]octane
(LXVII)

A solution of 3-benzyl-3,8-diazabicyclo[3.2.1]octane-2,4-dione LXVI (0.00108 mol, 250 mg) in dry ether (2 mL) was added to a stirred suspension of LiAlH$_4$ (122 mg, 0.00315 mol) in dry ether (8 mL) at 0° C. under nitrogen atmosphere. The reaction bath was allowed to return at room temperature and stirring was continued for 30 h. After completion of the reaction (checked by TLC), the reaction mixture was quenched with chilled water and then stirred for 1 h. The reaction mixture was diluted with ether (20 mL) and the organic layer was washed with water, dried over Na$_2$SO$_4$, concentrated under reduced pressure. The crude residue was purified by column chromatography (silica gel, 60-120 mesh; EA-Hexane, 1:1) to afford the product LXVII in 52% yield.

Synthesis of tert-butyl 3-benzyl-3,8-diazabicyclo
[3.2.1]octane-8-carboxylate (LXVIII)

To a stirred solution of compound LXVII (0.00108 mol, 220 mg) in DCM (10 mL) was added Boc$_2$O (0.00108 mol, 237 mg) and the reaction mixture was stirred for 16 h at room temperature. The progress of the reaction was monitored by TLC. The reaction mixture was diluted with DCM (30 mL) and washed with water. The organic layer was dried over Synthesis of (2R,5S)-ethyl 1-benzyl-5-(benzylcarbamoyl)pyrrolidine-2-carboxylate (LXV)

To a stirred solution of Diethyl meso-2,5-dibromoadipate (LXIV, 0.00069 mol, 250 mg) in toluene (5 mL) was added benzylamine (0.0021 mol, 0.234 mL) and the reaction mixture was heated at 85° C. for 16 h. After completion of the reaction (checked by TLC), the reaction mixture was cooled Na$_2$SO$_4$ and concentrated under reduced pressure to give the crude product LXVII which was used for the next step without further purification.

Synthesis of tert-butyl
3,8-diazabicyclo[3.2.1]octane-8-carboxylate (LXIX)

To a stirred solution of compound LXVIII (0.00028 mol, 85 mg) in MeOH (5 mL) was hydrogenated with 10% Pd—C (15 mg) for 4 h at room temperature. After completion of the reaction (checked by TLC), the reaction mixture was filtered through celite and the filtrate was concentrated under reduced pressure. The crude residue was purified by column chromatography (silica gel, 60-120 mesh; MeOH-DCM, 1:9) to afford Compound LXIX in 85% yield.

Synthesis of Intermediate LXX

To a solution of amine LXIX (0.00023 mol) and appropriate aldehyde (0.00023 mol) in DCM (5 mL), acetic acid (0.1 mL) was added at room temperature and the resulting mixture was allowed to stir for 30 min. Then STAB (0.100 gm, 0.00047 mol) was added to reaction mixture and the resulting mixture was allowed to stir at room temperature for 16 h. After completion of reaction, the crude mixture was diluted with DCM washed with water, dried over Na$_2$SO$_4$ and concentrated under reduced pressure. The residue was purified by column chromatography (silica gel, 60-120 mesh; EtOAc-Hexane, 2:8) to afford product LXX in 70-75% yield.

Synthesis of Intermediate LXXI

To a solution of MeOH.HCl (5 mL), Boc protected amine LX (1.03 mmol) was added and the resulting mixture was stirred for 1 hr. After completion of reaction, solvent was removed under reduced pressure, washed with water followed by addition of NaHCO$_3$ and extracted with DCM. The organic layer was dried over Na$_2$SO$_4$ and evaporated under reduced pressure to afford product LXXI as free base (94.30% yield).

Synthesis of Compounds of Formula Im

To a stirred solution of acid VIII (0.00021 mol, 1 eq) in DMF (5 mL), EDCI (0.048 g, 0.00024 mol, 1.1 eq), HOBt (0.038 g, 0.00024 mol, 1.1 eq) and DIPEA (0.15 mL, 0.00078 mol, 2.5 eq) were added at 0° C. and stirred for 15 minutes. A solution of amine LXXI (0.00021 mol, 1 eq) was then added at 0° C. and then the resulting mixture was allowed to stir at room temperature for overnight. After completion of the reaction, water (20 mL) was added and extracted with ethyl acetate (2×30 mL). The combined organic layer was dried over anhydrous Na$_2$SO$_4$ and concentrated under reduced pressure. The crude product was purified by column chromatography (silica gel, 60-120 mess, 70% ethyl acetate in hexane) to give compound in 49-55% yield.

The above-described method was used to prepare the following compounds using the appropriate aldehyde (R$^1$-L-CHO) and the appropriate acid VIII.

(2R,5S)-ethyl 1-benzyl-5-(benzylcarbamoyl)pyrrolidine-2-carboxylate (Compound 213)

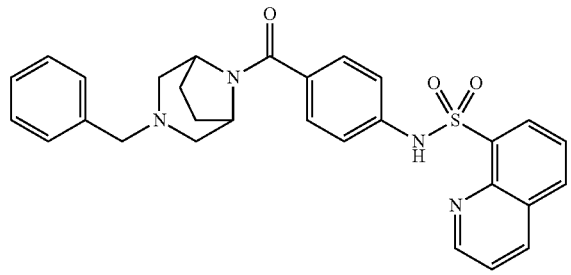 [SMILES: O=C(c1ccc(NS(=O)(=O)c2cccc3cccnc23)cc1)N1C2CCC1CN(Cc1ccccc1)C2]

$^1$H NMR (400 MHz, CDCl$_3$) δ: 1.6-1.9 (m, 4H), 2.2-2.4 (m, 2H), 2.6-2.8 (m, 2H), 3.5-3.6 (m, 2H), 3.9 (s, 1H), 4.6 (s, 1H), 7.0 (d, 1H), 7.2-7.3 (m, 6H), 7.5-7.6 (m, 2H), 8.0 (d, 1H), 8.2-8.5 (m, 3H), 9.1 (d, 1H); HPLC Purity: 91.41%; Mass (M+1): 513.33.

N-(4-(3-(4-fluorobenzyl)-3,8-diazabicyclo[3.2.1]
octane-8-carbonyl)phenyl)quinoline-8-sulfonamide
(Compound 226)

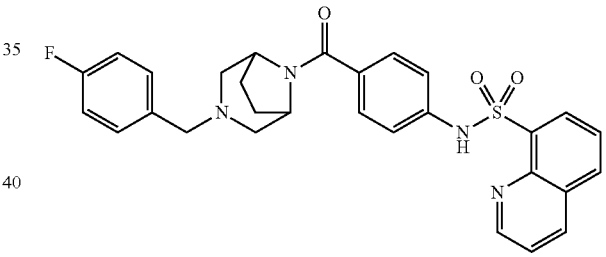

$^1$H NMR (400 MHz, CDCl$_3$) δ: 1.6-1.9 (m, 4H), 2.2-2.4 (m, 2H), 2.6-2.8 (m, 2H), 3.5-3.6 (m, 2H), 3.9 (s, 1H), 4.7 (s, 1H), 6.9-7.1 (m, 4H), 7.2-7.3 (m, 3H), 7.5-7.6 (m, 2H), 8.0 (d, 1H), 8.2-8.5 (m, 3H), 9.1 (d, 1H); HPLC Purity: 96.11%; Mass (M+1): 531.25.

N-(4-(3-(3,5-difluorobenzyl)-3,8-diazabicyclo[3.2.1]
octane-8-carbonyl)phenyl)quinoline-8-sulfonamide
(Compound 227)

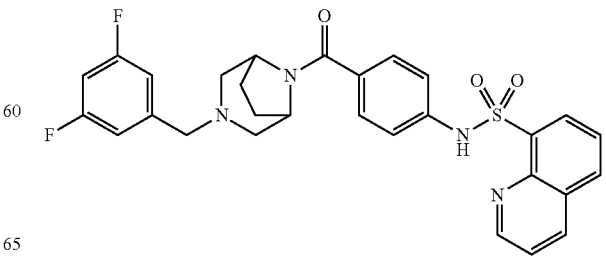

$^1$H NMR (400 MHz, CDCl$_3$) δ: 1.6-1.9 (m, 4H), 2.2-2.4 (m, 2H), 2.6-2.8 (m, 2H), 3.5-3.6 (m, 2H), 3.9 (s, 1H), 4.7 (s, 1H), 6.6 (m, 1H), 6.8 (d, 2H), 6.9-7.1 (m, 2H), 7.2-7.3 (m, 1H), 7.5-7.6 (m, 2H), 8.0 (d, 1H), 8.2-8.5 (m, 3H), 9.1 (d, 1H); HPLC Purity: 94.31%; Mass (M+1): 549.23.

N-(4-(3-(cyclopropylmethyl)-3,8-diazabicyclo[3.2.1]octane-8-carbonyl)phenyl)quinoline-8-sulfonamide (Compound 228)

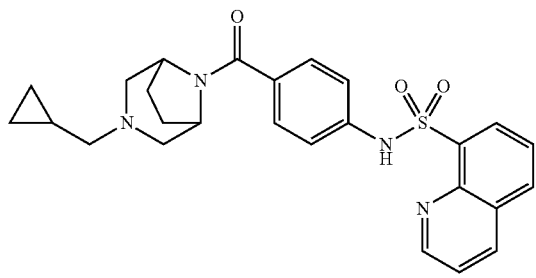 [SMILES: O=C(c1ccc(NS(=O)(=O)c2cccc3cccnc23)cc1)N1C2CCC1CN(CC1CC1)C2]

$^1$H NMR (400 MHz, CDCl$_3$) δ: 0.2-0.3 (m, 2H), 0.4-0.5 (m, 2H), 0.8-0.9 (m, 1H), 1.6-1.9 (m, 4H), 2.1-2.4 (m, 4H), 2.6-2.8 (m, 2H), 3.9 (s, 1H), 4.7 (s, 1H), 7.0-7.1 (m, 2H), 7.2-7.3 (m, 1H), 7.6-7.7 (m, 1H), 8.0 (d, 1H), 8.2-8.6 (m, 3H), 9.1 (d, 1H); HPLC Purity: 99.28%; Mass (M+1): 477.41.

Example 12

Preparation of Compounds of Formula In

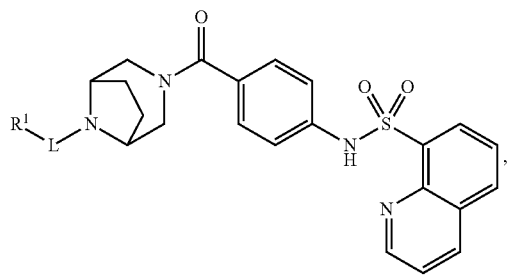

wherein R$^1$ is aryl or carbocyclyl; and L is —(CR$^c$R$^c$)$_m$—.

Scheme 12

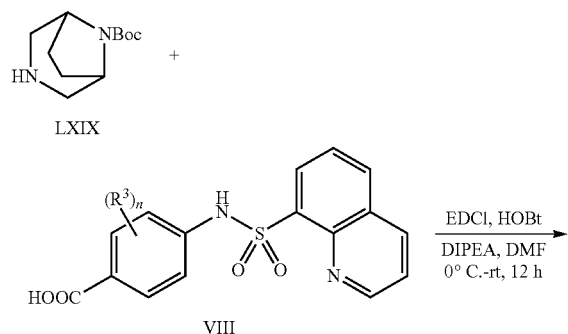

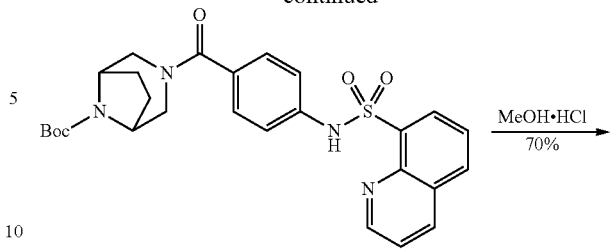

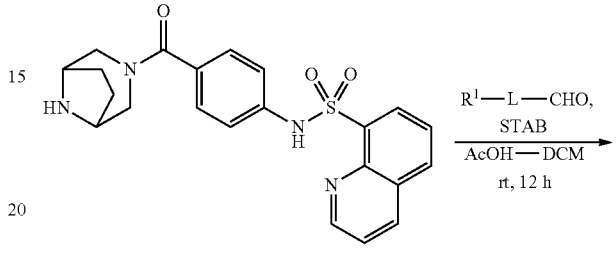

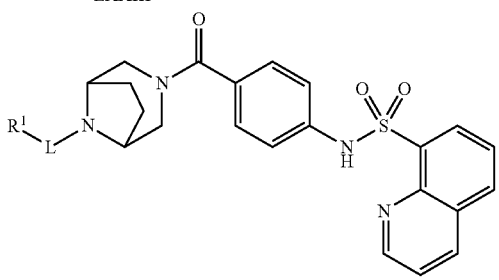

Formula In

R = aryl, carbocyclyl
L = —(CR$^c$R$^c$)$_m$—

Synthesis of tert-butyl 3-(4-(quinoline-8-sulfonamido)benzoyl)-3,8-diazabicyclo[3.2.1]octane-8-carboxylate (LXXII)

To a stirred solution of acid VIII (0.001179 mol, 1 eq) in DMF (5 mL), EDCI (0.248 g, 0.00129 mol, 1.1 eq), HOBt (0.198 g, 0.00129 mol, 1.1 eq) and DIPEA (0.30 g, 0.00235 mol, 2 eq) were added at 0° C. and stirred for 15 minutes. A solution of amine LXIX from Example 11 (0.00117 mol, 1 eq) was then added at 0° C. and then the resulting mixture was allowed to stir at room temperature for overnight. After completion of the reaction, water (20 mL) was added and extracted with ethyl acetate (2×30 mL). The combined organic layer was dried over anhydrous Na$_2$SO$_4$ and concentrated under reduced pressure. The crude product was purified by column chromatography (silica gel, 60-120 mess, 70% ethyl acetate in hexane) to give LXXII in 57% yield.

Synthesis of N-(4-(3,8-diazabicyclo[3.2.1]octane-3-carbonyl)phenyl)quinoline-8-sulfonamide (LXXIII)

To a solution of MeOH.HCl (5 mL), Boc protected amine LXXII (1 mmol) was added and the resulting mixture was stirred for 2 hr. After completion of reaction, solvent was removed under reduced pressure, washed with water followed by addition of NaHCO$_3$ and extracted with DCM. The organic layer was dried over Na$_2$SO$_4$ and evaporated under reduced pressure to afford product LXXIII as free base (92% yield).

Synthesis of Compounds of Formula In

To a solution of amine LXXIII (0.118 mmol) and appropriate aldehyde (0.118 mmol) in DCM (5 mL), acetic acid (0.1 mL) was added at room temperature and the resulting mixture was allowed to stir for 30 min. Then STAB (0.050 gm, 0.236 mol) was added to reaction mixture and the resulting mixture was allowed to stir at room temperature for 16 h. After completion of reaction, the crude mixture was diluted with DCM washed with water, dried over $Na_2SO_4$ and concentrated under reduced pressure. The residue was purified by column chromatography (silica gel, 60-120 mesh; EtOAc-Hexane, 2:1) to afford product in 25-45% yield.

The following compounds were made by the above-described method using the appropriate aldehyde ($R^1$-L-CHO) and the appropriate acid VIII.

N-(4-(3-(4-fluorobenzyl)-3,8-diazabicyclo[3.2.1]octane-8-carbonyl)phenyl)quinoline-8-sulfonamide (Compound 220)

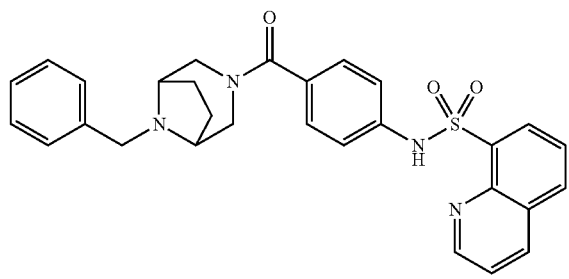 [SMILES: O=C(c1ccc(NS(=O)(=O)c2cccc3cccnc23)cc1)N1CC2CCC(C1)N2Cc1ccccc1]

$^1$H NMR (400 MHz, CDCl$_3$) δ: 1.7 (br s, 1H), 1.9 (br s, 2H), 3.0 (br s, 2H), 3.2 (br s, 2H), 3.5 (s, 2H), 3.8 (d, 1H), 4.3 (d, 1H), 7.0-7.2 (m, 4H), 7.3-7.4 (m, 4H), 7.6-7.7 (m, 2H), 8.0 (d, 1H), 8.2-8.5 (m, 3H), 9.1 (d, 1H); HPLC Purity: 99.85%; Mass (M+1): 512.62.

N-(4-(8-(4-fluorobenzyl)-3,8-diazabicyclo[3.2.1]octane-3-carbonyl)phenyl)quinoline-8-sulfonamide (Compound 219)

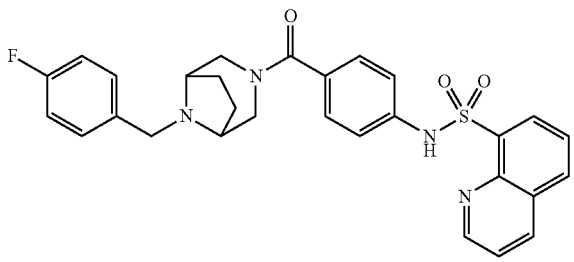 [SMILES: O=C(c1ccc(NS(=O)(=O)c2cccc3cccnc23)cc1)N1CC2CCC(C1)N2Cc1ccc(F)cc1]

$^1$H NMR (400 MHz, CDCl$_3$) δ: 1.7 (br s, 1H), 1.9 (br s, 2H), 3.0 (br s, 2H), 3.2 (br s, 2H), 3.5 (s, 2H), 3.8 (d, 1H), 4.3 (d, 1H), 6.9-7.2 (m, 5H), 7.2-7.3 (m, 2H), 7.6-7.7 (m, 2H), 8.0 (d, 1H), 8.2-8.5 (m, 3H), 9.1 (d, 1H); HPLC Purity: 99.07%; Mass (M+1): 530.62.

N-(4-(8-(3,5-difluorobenzyl)-3,8-diazabicyclo[3.2.1]octane-3-carbonyl)phenyl)quinoline-8-sulfonamide (Compound 218)

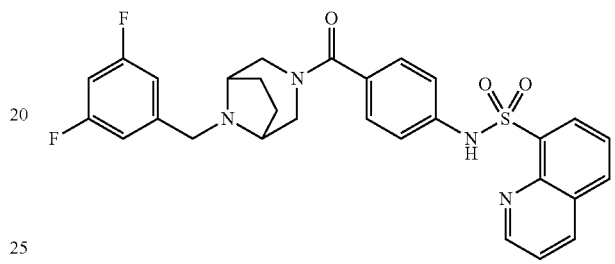

$^1$H NMR (400 MHz, CDCl$_3$) δ: 1.7 (br s, 1H), 1.9 (br s, 2H), 3.0 (br s, 2H), 3.2 (br s, 2H), 3.5 (s, 2H), 3.8 (d, 1H), 4.3 (d, 1H), 6.7 (t, 1H), 6.8-6.9 (m, 2H), 7.0-7.2 (m, 3H), 7.5-7.6 (m, 2H), 8.0 (d, 1H), 8.2-8.5 (m, 3H), 9.1 (d, 1H); HPLC Purity: 94.61%; Mass (M+1): 548.60.

N-(4-(8-(cyclopropylmethyl)-3,8-diazabicyclo[3.2.1]octane-3-carbonyl)phenyl)quinoline-8-sulfonamide (Compound 221)

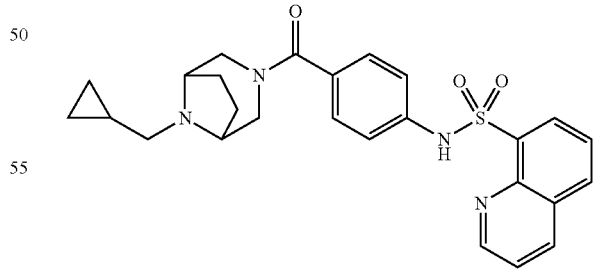

$^1$H NMR (400 MHz, CDCl$_3$) δ: 0.2-0.3 (m, 2H), 0.4-0.5 (m, 2H), 0.8-0.9 (m, 1H), 1.6-1.9 (m, 4H), 2.1-2.3 (m, 2H), 3.0 (d, 1H), 3.2-3.5 (m, 4H), 4.4 (d, 1H), 7.0-7.2 (m, 3H), 7.5-7.6 (m, 2H), 8.0 (d, 1H), 8.2-8.6 (m, 3H), 9.1 (d, 1H); HPLC Purity: 99.37%; Mass (M+1): 477.59.

Example 13

Preparation of Compounds of Formula Io

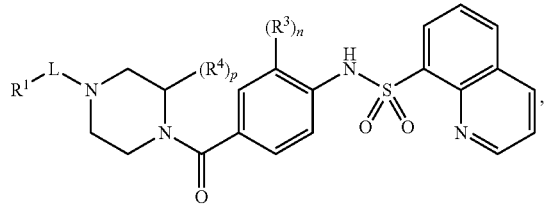

wherein $R^1$ is aryl, carbocyclyl, heterocyclyl or heteroaryl; $R^3$ is $OCF_3$ or $OCH_3$; $R^4$ is alkyl; L is —C(O)— or —($CR^cR^c$)—C(O)—; n is 0 or 1; and p is 0 or 1.

Scheme 13:

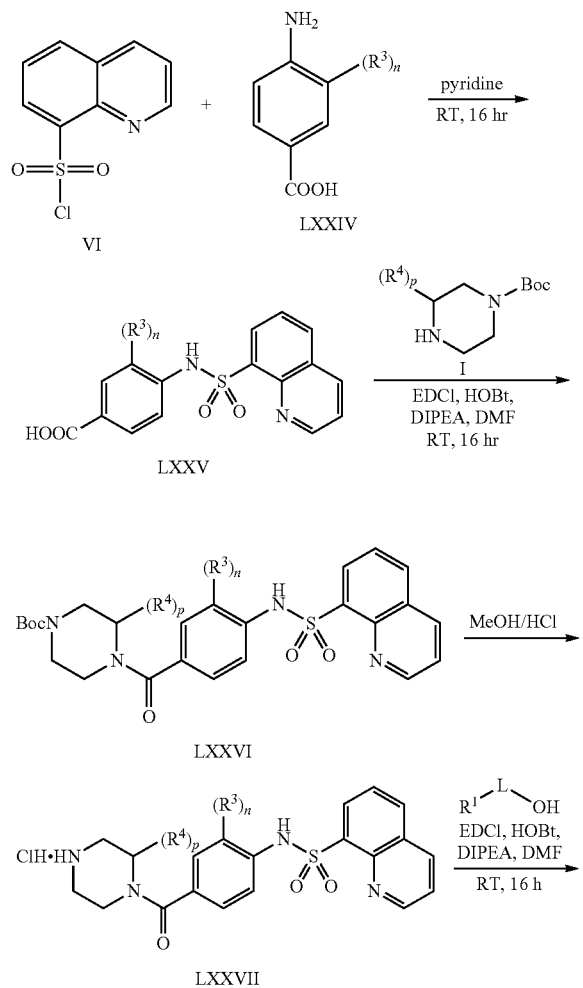

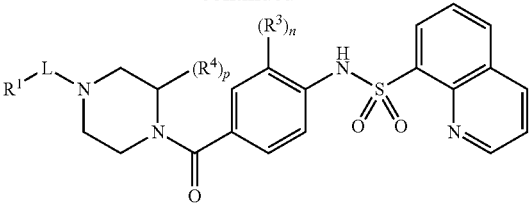

Formula Io

Synthesis of Intermediate LXXV

To a stirred solution of substituted amine LXXIV (30.3 mmol) under nitrogen atmosphere was added pyridine (50 ml) at 0° C. and stirred for 10 min. Quinoline-8-sulfonyl chloride VI (8.94 gm, 39.4 mmol) was then added to the reaction mixture at the same temperature. The resulting mixture was stirred for 16 h at room temperature. After completion of the reaction, the solvent was removed under reduced pressure. The traces of pyridine were removed by co-distillation with toluene. Diethylether was added to the resulting residue, and the solid product was filtered out and air-dried. The resulting crude product (74%) was taken to the next step without further purification.

Synthesis of Intermediate LXXVI

To a stirred solution of acid LXXV (0.000315 moles) in DMF (5 ml), were added EDCI (0.066 g, 0.000346 moles), HOBt (0.047 g, 0.000346 moles) and DIPEA (0.13 ml, 0.00078 moles) at 0° C. and stirred for 15 minutes. A solution of amine I (0.000315 moles) was then added at 0° C. and then the resulting mixture was allowed to stir at room temperature overnight. After completion of the reaction, water (20 mL) was added and extracted with ethyl acetate (2×30 ml). The combined organic layer was dried over anhydrous $Na_2SO_4$ and concentrated under reduced pressure. The crude product was purified by column chromatography (silica gel, 60-120 mess, 70% ethyl acetate in hexane) to give LXXVI in 65-70% yield.

Synthesis of Intermediate LXXVII

To a solution of MeOH.HCl (10 ml), Boc protected amine LXXVI (4.03 mmol) was added and the resulting mixture was stirred for 2 hr. After completion of reaction, solvent was removed under reduced pressure, washed with water followed by addition of $NaHCO_3$ and extracted with DCM. The organic layer was dried over $Na_2SO_4$ and evaporated under reduced pressure to afford product LXXVII in 92% yield.

General Procedure for Syntheses of Compounds of Formula Io

To a stirred solution of aryl/heteroaryl acid (0.000315 moles) in DMF (5 ml), were added EDCI (0.066 g, 0.000346 moles), HOBt (0.047 g, 0.000346 moles) and DIPEA (0.13 ml, 0.00078 moles) at 0° C. and stirred for 15 minutes. A solution of amine LXXVII (0.000315 moles) was then added at 0° C. and then the resulting mixture was allowed to stir at room temperature overnight. After completion of the reaction, water (20 mL) was added and extracted with ethyl acetate (2×30 ml). The combined organic layer was dried over anhydrous $Na_2SO_4$ and concentrated under reduced pressure.

The crude product was purified by column chromatography (silica gel, 60-120 mess, MeOH-DCM, 2:8) to give a compound of Formula Io in 35-50% yield.

The following compounds of Formula Io were made by the above-described method using the appropriate acid (R¹—C(O)OH) and the appropriate Boc-protected amine I.

N-(4-(4-(1,2,3-thiadiazole-5-carbonyl)piperazine-1-carbonyl)phenyl)quinoline-8-sulfonamide (VI-1) Compound 313

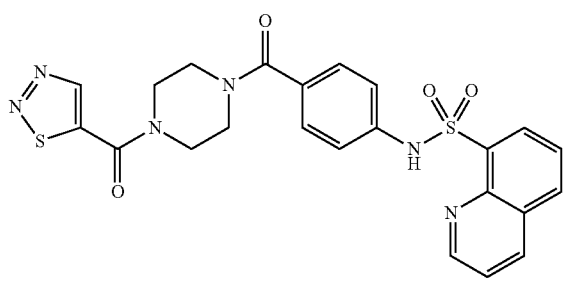

¹H NMR (400 MHz, CDCl₃) δ: 3.2-3.5 (m, 8H), 7.2 (m, 4H), 7.6 (m, 2H), 8.3 (m, 2H), 8.8 (m, 2H), 9.1 (m, 1H), 10.0 (bs, 1H); HPLC Purity: 99.55%; Mass (M+1): 509.2.

N-(4-(4-(3-fluoroisonicotinoyl)piperazine-1-carbonyl)phenyl)quinoline-8-sulfonamide (Compound 317)

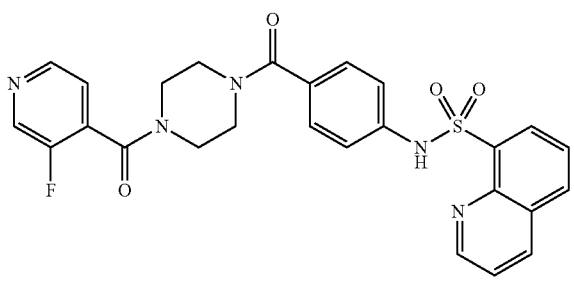 [SMILES: O=C(c1ccc(NS(=O)(=O)c2cccc3cccnc23)cc1)N1CCN(C(=O)c2ccncc2F)CC1]

¹H NMR (400 MHz, CDCl₃) δ: 3.2-3.8 (m, 8H), 7.0 (m, 4H), 7.3 (m, 1H), 7.6 (m, 2H), 8.1 (m, 1H), 8.3 (m, 2H), 8.6 (m, 3H), 9.1 (m, 1H); HPLC Purity: 98.06%; Mass (M+1): 520.30.

N-(4-(4-(3,5-difluorobenzoyl)piperazine-1-carbonyl)phenyl)quinoline-8-sulfonamide (Compound 342)

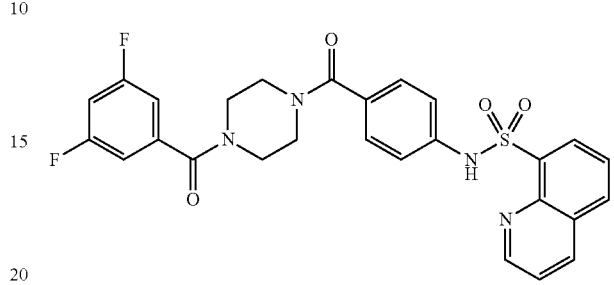

¹H NMR (400 MHz, CDCl₃) δ: 3.0-3.8 (m, 8H), 6.9-7.3 (m, 6H), 7.6 (m, 2H), 7.7-7.9 (m, 2H), 8.0 (m, 1H), 8.3 (m, 1H), 8.6 (m, 1H), 9.0 (m, 1H); HPLC Purity: 99.30%; Mass (M+1): 537.4.

N-(4-(4-(5-methylpyrazine-2-carbonyl)piperazine-1-carbonyl)phenyl)quinoline-8-sulfonamide (Compound 346)

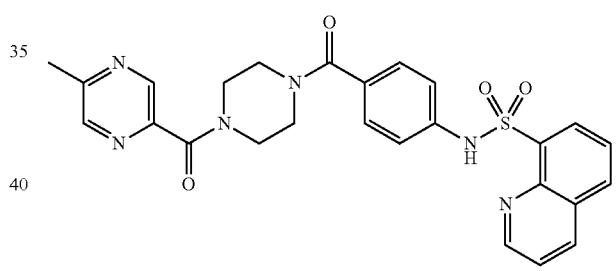

¹H NMR (400 MHz, CDCl₃) δ: 2.6 (s, 3H), 3.2-3.9 (m, 8H), 7.0-7.2 (m, 4H), 7.6 (m, 2H), 8.0 (m, 1H), 8.3 (m, 3H), 8.6 (s, 1H), 8.9 (m, 1H), 9.0 (m, 1H); HPLC Purity: 99.74%; Mass (M+1): 517.2.

N-(4-(4-(oxazole-4-carbonyl)piperazine-1-carbonyl)phenyl)quinoline-8-sulfonamide (Compound 347)

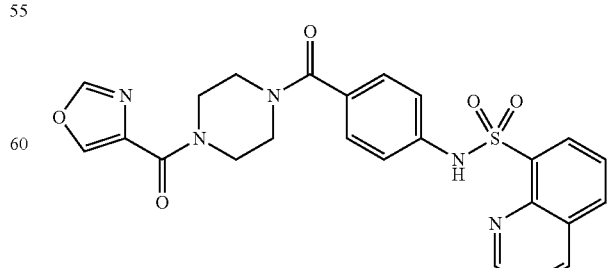

¹H NMR (400 MHz, CDCl₃) δ: 3.2-3.9 (m, 8H), 7.0-7.2 (m, 4H), 7.6 (m, 2H), 8.3-8.5 (m, 4H), 9.0 (m, 1H), 10.5 (s, 1H); HPLC Purity: 95.63%; Mass (M+1): 492.15.

N-(4-(4-(thiazole-5-carbonyl)piperazine-1-carbonyl)phenyl)quinoline-8-sulfonamide (Compound 348)

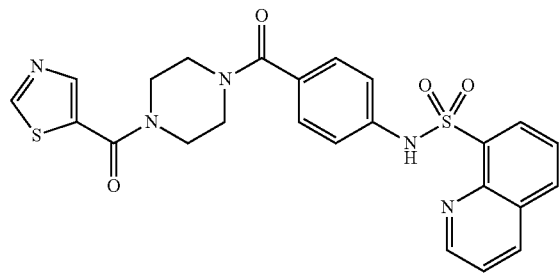

¹H NMR (400 MHz, CDCl₃) δ: 3.2-3.9 (m, 8H), 7.0-7.2 (m, 4H), 7.6 (m, 2H), 8.0 (m, 2H), 8.3 (m, 2H), 8.6 (s, 1H), 9.0 (m, 1H), 10.5 (s, 1H); HPLC Purity: 97.14%; Mass (M+1): 508.2.

N-(4-(4-(1H-imidazole-4-carbonyl)piperazine-1-carbonyl)phenyl)quinoline-8-sulfonamide (Compound 349)

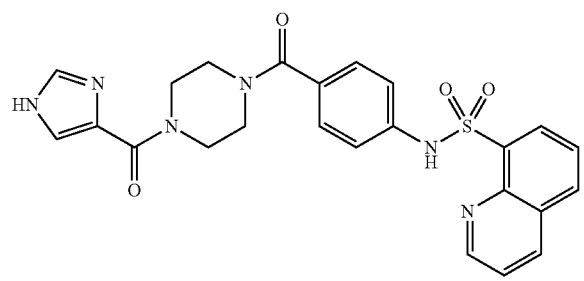 [SMILES: O=C(c1ccc(NS(=O)(=O)c2cccc3cccnc23)cc1)N1CCN(C(=O)c2c[nH]cn2)CC1]

¹H NMR (400 MHz, CDCl₃) δ: 3.2-3.9 (m, 8H), 7.0-7.2 (m, 4H), 7.6 (m, 4H), 8.0 (m, 1H), 8.3 (m, 2H), 8.6 (s, 1H), 9.0 (m, 1H); HPLC Purity: 99.40%; Mass (M+1): 491.2.

N-(4-(4-(1H-imidazole-2-carbonyl)piperazine-1-carbonyl)phenyl)quinoline-8-sulfonamide (Compound 354)

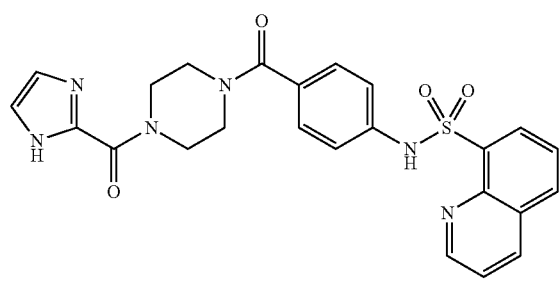 [SMILES: O=C(c1ccc(NS(=O)(=O)c2cccc3cccnc23)cc1)N1CCN(C(=O)c2ncc[nH]2)CC1]

¹H NMR (400 MHz, CDCl₃) δ: 3.2-3.7 (m, 6H), 4.3-4.8 (m, 2H), 7.0-7.1 (m, 5H), 7.6 (m, 2H), 8.0 (m, 1H), 8.2-8.4 (m, 2H), 8.6 (m, 1H), 9.0 (m, 2H) 10.3 (s, 1H); HPLC Purity: 99.22%; Mass (M+1): 491.2.

N-(4-(4-(isoxazole-5-carbonyl)piperazine-1-carbonyl)phenyl)quinoline-8-sulfonamide (Compound 365)

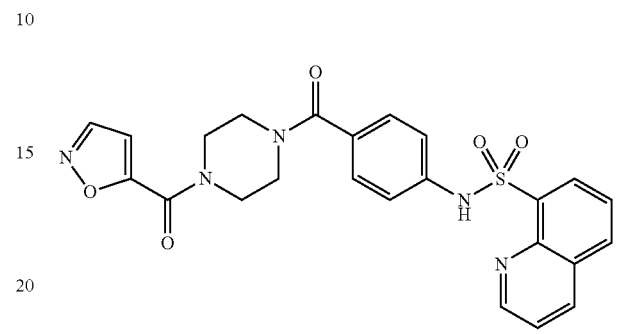

¹H NMR (400 MHz, CDCl₃) δ: 3.2-3.8 (m, 8H), 6.8-7.3 (m, 5H), 7.6 (m, 2H), 8.0 (m, 1H), 8.3-8.4 (m, 3H), 9.0 (m, 1H), 10.4 (m, 1H); HPLC Purity: 99.30%; Mass (M+1): 492.2.

N-(4-(4-(1H-pyrazole-3-carbonyl)piperazine-1-carbonyl)phenyl)quinoline-8-sulfonamide (Compound 350)

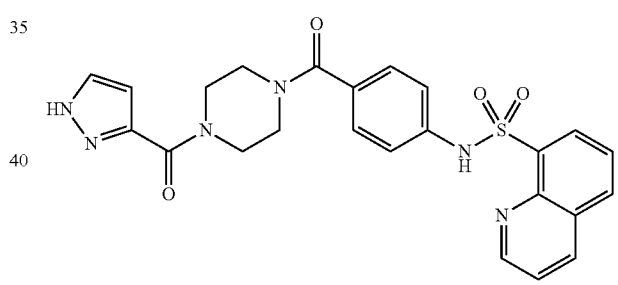

¹H NMR (400 MHz, CDCl₃) δ: 3.2-3.9 (m, 8H), 7.0-7.2 (m, 4H), 7.6 (m, 3H), 8.0 (m, 1H), 8.3 (m, 2H), 8.6 (s, 1H), 9.0 (m, 1H); HPLC Purity: 99.97%; Mass (M+1): 491.2.

N-(4-(4-(thiazole-2-carbonyl)piperazine-1-carbonyl)phenyl)quinoline-8-sulfonamide (Compound 371)

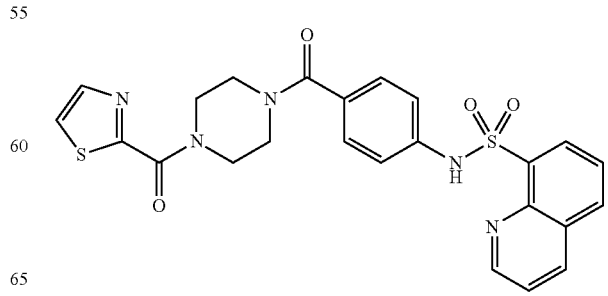

¹H NMR (400 MHz, CDCl₃) δ: 3.4-3.8 (m, 8H), 7.1-7.2 (m, 4H), 7.6 (m, 2H), 8.1-8.4 (m, 4H), 8.6 (m, 1H), 8.9 (m, 1H), 9.0 (m, 1H); HPLC Purity: 97.89%; Mass (M+1): 508.30.

N-(4-(4-(tetrahydro-2H-pyran-4-carbonyl)piperazine-1-carbonyl)phenyl)quinoline-8-sulfonamide (Compound 417)

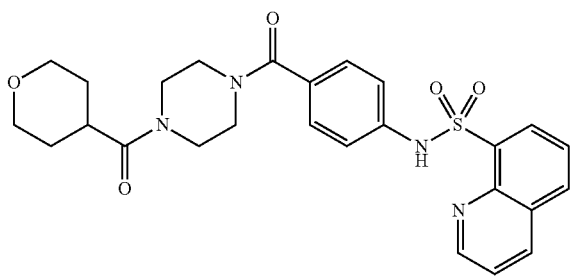 [SMILES: O=C(c1ccc(NS(=O)(=O)c2cccc3cccnc23)cc1)N1CCN(C(=O)C2CCOCC2)CC1]

¹H NMR (400 MHz, DMSOd₆) δ: 1.2-1.6 (m, 8H), 2.8-3.0 (m, 2H), 3.4-3.7 (m, 4H), 3.75-3.8 (m, 2H), 7.0-7.2 (m, 4H), 7.56-7.8 (m, 2H), 8.2-8.4 (m, 3H), 9.0-9.2 (m, 1H), 10.45 (s, 1H); HPLC Purity: 96.68%; Mass (M+Na): 531.2.

N-(4-(4-(tetrahydrofuran-3-carbonyl)piperazine-1-carbonyl)phenyl)quinoline-8-sulfonamide (Compound 418)

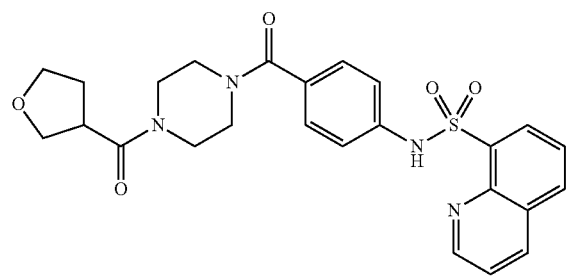 [SMILES: O=C(c1ccc(NS(=O)(=O)c2cccc3cccnc23)cc1)N1CCN(C(=O)C2CCOC2)CC1]

¹H NMR (400 MHz, CDCl₃) δ: 1.95-2.2 (m, 2H), 3.2-3.6 (m, 8H), 3.65-3.8 (m, 5H), 7.0-7.5 (m, 4H), 7.56-7.8 (m, 2H), 8.2-8.4 (m, 3H), 9.1-9.2 (m, 1H), 10.5 (m, 1H); HPLC Purity: 99.65%; Mass (M+1): 495.2.

N-(4-(4-(2-cyclobutylacetyl)piperazine-1-carbonyl)phenyl)quinoline-8-sulfonamide (Compound 419)

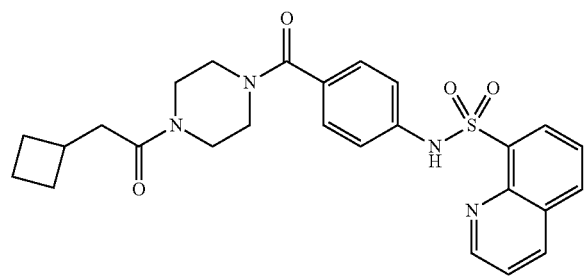 [SMILES: O=C(CC1CCC1)N1CCN(C(=O)c2ccc(NS(=O)(=O)c3cccc4cccnc34)cc2)CC1]

¹H NMR (400 MHz, CDCl₃) δ: 1.6-2.1 (m, 6H), 2.2-2.8 (m, 7H), 3.2-3.8 (m, 4H), 7.0-7.3 (m, 4H), 7.5-7.7 (m, 2H), 8.2-8.4 (m, 3H), 9.1-9.2 (m, 1H); HPLC Purity: 95.52%; Mass (M+1): 465.2.

N-(4-(4-(tetrahydro-2H-pyran-2-carbonyl)piperazine-1-carbonyl)phenyl)quinoline-8-sulfonamide (Compound 430)

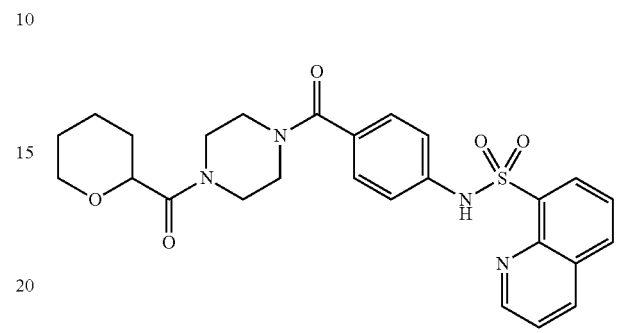

¹H NMR (400 MHz, CDCl₃) δ: 1.2-1.6 (m, 5H), 1.6-1.8 (m, 1H), 3.0-3.2 (m, 3H), 3.4-3.6 (m, 6H), 3.8-4.2 (m, 2H), 7.0-7.4 (m, 4H), 7.6-7.8 (m, 2H), 8.0-8.6 (m, 3H), 9.1-9.2 (m, 1H), 10.5 (s, 1H); HPLC Purity: 97.96%; Mass (M+1): 509.2.

N-(4-(4-(tetrahydrofuran-2-carbonyl)piperazine-1-carbonyl)phenyl)quinoline-8-sulfonamide (Compound 443)

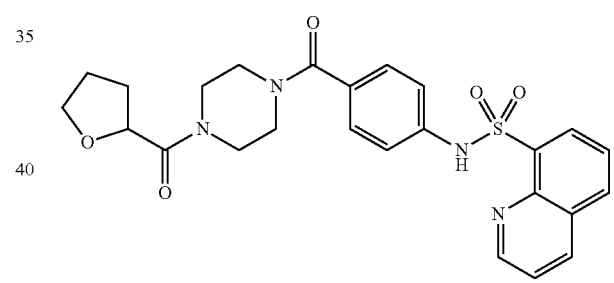

¹H NMR (400 MHz, DMSOd₆) δ: 1.2-1.4 (m, 3H), 1.6-2.1 (m, 4H), 2.9-3.3 (m, 6H), 3.4-3.6 (m, 2H), 7.0-7.25 (m, 4H), 7.6-7.8 (m, 2H), 8.2-8.6 (m, 3H), 9.1-9.2 (m, 1H) 10.5 (bs, 1H); HPLC Purity: 97.44%; Mass (M+1): 484.25.

(R)—N-(4-(4-(2-cyclobutylacetyl)-2-methylpiperazine-1-carbonyl)phenyl)quinoline-8-sulfonamide (Compound 206)

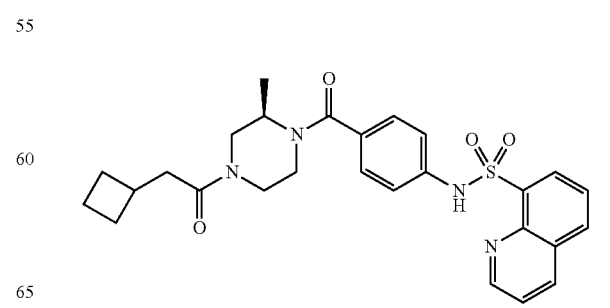

¹H NMR (400 MHz, CDCl₃) δ: 1.2 (d, 3H), 1.6-2.1 (m, 8H), 2.2-2.8 (m, 5H), 4.0-4.1 (m, 3H), 7.0-7.2 (m, 4H), 7.5-7.7 (m, 2H), 8.2-8.4 (m, 3H), 9.1-9.2 (m, 1H), 10.4 (s, 1H); HPLC Purity: 96.13%; Mass (M+1): 479.15.

N-(4-(4-(2,3-difluorobenzoyl)piperazine-1-carbonyl)-2-methoxyphenyl)quinoline-8-sulfonamide (Compound 318)

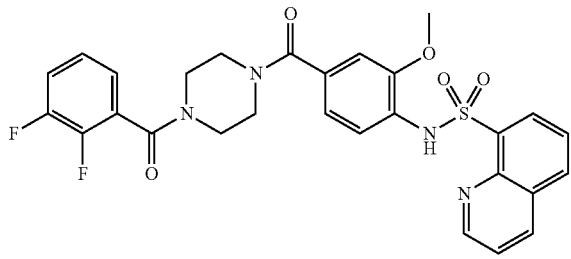 [SMILES: COc1cc(C(=O)N2CCN(C(=O)c3cccc(F)c3F)CC2)ccc1NS(=O)(=O)c1cccc2cccnc12]

¹H NMR (400 MHz, CDCl₃) δ: 3.3 (s, 3H), 3.2-3.8 (m, 8H), 6.8 (m, 2H), 7.2 (m, 2H), 7.6 (m, 3H), 8.0 (m, 1H), 8.2-8.4 (m, 2H), 9.1 (m, 1H); HPLC Purity: 96.96%; Mass (M+1): 567.30.

N-(4-(4-(3,4-difluorobenzoyl)piperazine-1-carbonyl)-2-methoxyphenyl)quinoline-8-sulfonamide (Compound 319)

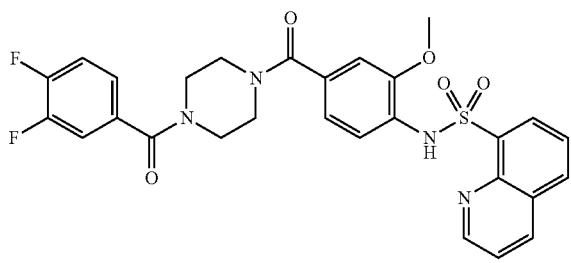 [SMILES: COc1cc(C(=O)N2CCN(C(=O)c3ccc(F)c(F)c3)CC2)ccc1NS(=O)(=O)c1cccc2cccnc12]

¹H NMR (400 MHz, CDCl₃) δ: 3.4 (s, 3H), 3.5-3.8 (m, 8H), 6.8 (m, 2H), 7.2 (m, 2H), 7.6 (m, 3H), 8.0 (m, 1H), 8.2-8.4 (m, 2H), 8.8 (m, 1H), 9.1 (m, 1H); HPLC Purity: 95.87%; Mass (M+1): 567.30.

N-(4-(4-(2-fluoro-3-methoxybenzoyl)piperazine-1-carbonyl)-2-methoxyphenyl)quinoline-8-sulfonamide (Compound 320)

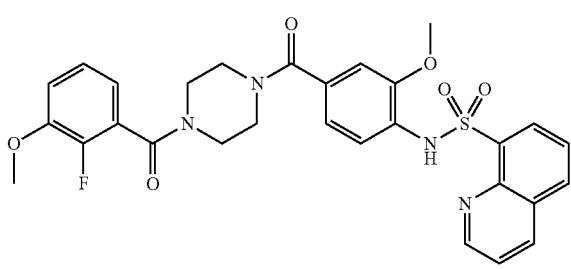

¹H NMR (400 MHz, CDCl₃) δ: 3.2 (s, 3H), 3.4 (s, 3H), 3.6-3.8 (m, 8H), 6.8-7.0 (m, 5H), 7.6 (m, 3H), 8.0 (m, 1H), 8.2-8.4 (m, 2H), 8.8 (m, 1H), 9.1 (m, 1H); HPLC Purity: 95.65%; Mass (M+1): 579.40.

N-(4-(4-(1,2,3-thiadiazole-4-carbonyl)piperazine-1-carbonyl)-2-methoxyphenyl)quinoline-8-sulfonamide (Compound 321)

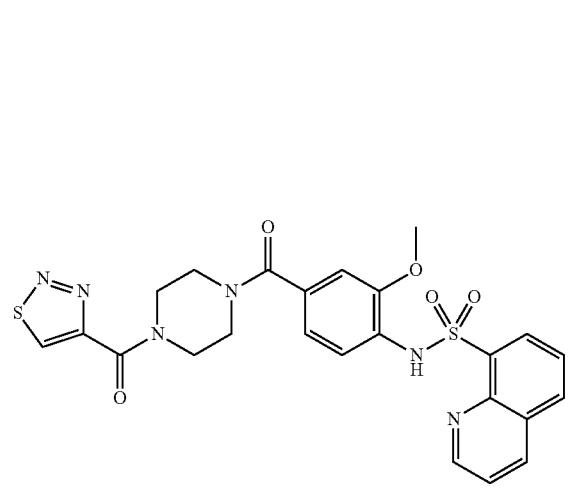 [SMILES: COc1cc(C(=O)N2CCN(C(=O)c3csnn3)CC2)ccc1NS(=O)(=O)c1cccc2cccnc12]

¹H NMR (400 MHz, CDCl₃) δ: 3.4 (s, 3H), 3.6-3.8 (m, 8H), 6.8 (m, 2H), 7.6 (m, 3H), 8.0 (m, 1H), 8.2 (m, 1H), 8.4 (m, 1H), 8.9 (s, 1H), 9.1 (m, 1H), 9.2 (m, 1H); HPLC Purity: 98.30%; Mass (M+1): 539.25.

N-(2-methoxy-4-(4-(thiazole-4-carbonyl)piperazine-1-carbonyl)phenyl)quinoline-8-sulfonamide (Compound 322)

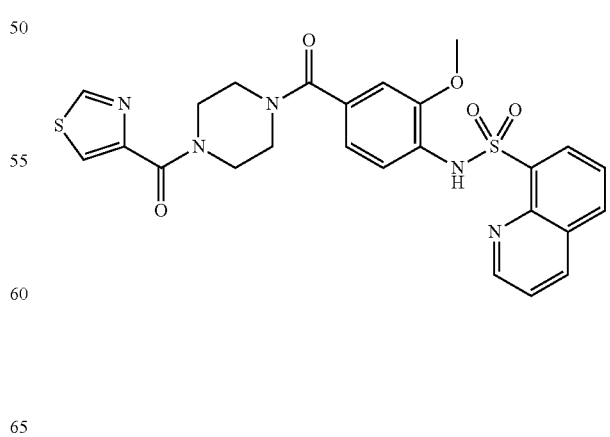

¹H NMR (400 MHz, CDCl₃) δ: 3.4 (s, 3H), 3.6-3.8 (m, 8H), 6.8 (m, 2H), 7.6 (m, 4H), 8.0 (m, 2H), 8.2 (m, 1H), 8.4

(m, 1H), 8.7 (m, 1H), 8.9 (s, 1H), 9.1 (m, 1H); HPLC Purity: 96.49%; Mass (M+1): 538.10.

N-(4-(4-nicotinoylpiperazine-1-carbonyl)-2-(trifluoromethoxy)phenyl)quinoline-8-sulfonamide (Compound 323)

$^1$H NMR (400 MHz, CDCl$_3$) δ: 3.4-3.8 (m, 8H), 7.2 (m, 2H), 7.5 (m, 2H), 8.0 (m, 3H), 8.4 (m, 2H), 8.8 (m, 1H), 9.1 (m, 1H); HPLC Purity: 99.30%; Mass (M+1): 592.15.

N-(4-(4-(5-methylpyrazine-2-carbonyl)piperazine-1-carbonyl)-2-trifluoromethoxy)phenyl)quinoline-8-sulfonamide (Compound 325)

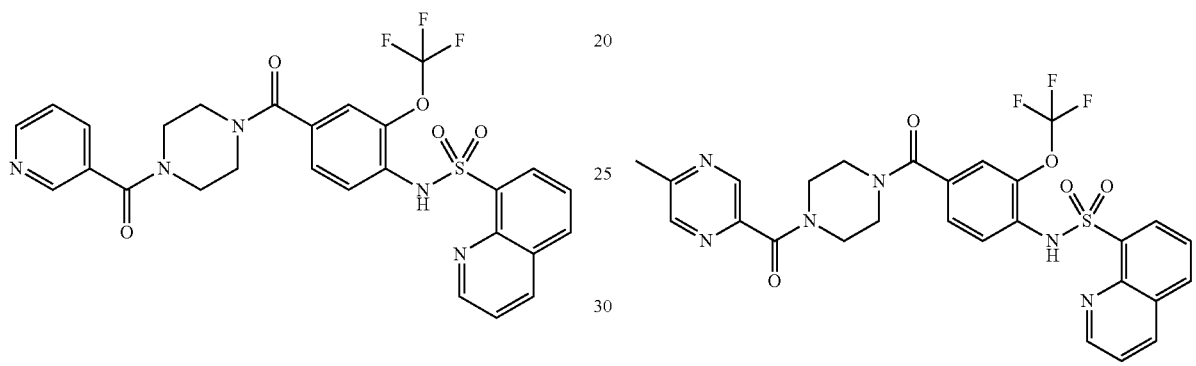

$^1$H NMR (400 MHz, CDCl$_3$) δ: 3.4-3.8 (m, 8H), 7.2 (m, 2H), 7.4 (m, 1H), 7.6 (m, 2H), 7.8 (m, 1H), 8.0 (m, 1H), 8.1 (m, 1H), 8.2 (m, 1H), 8.4 (m, 2H), 8.6 (m, 1H), 9.1 (m, 1H); HPLC Purity: 99.38%; Mass (M+1): 586.27.

N-(4-(4-(thiazole-4-carbonyl)piperazine-1-carbonyl)-2-(trifluoromethoxy)phenyl)quinoline-8-sulfonamide (Compound 324)

$^1$H NMR (400 MHz, CDCl$_3$) δ: 2.6 (s, 3H), 3.5-3.8 (m, 3H), 7.2 (m, 2H), 7.6 (m, 2H), 8.0 (m, 2H), 8.4 (m, 3H), 8.9 (m, 1H), 9.1 (m, 1H); HPLC Purity: 97.67%; Mass (M+1): 601.30.

N-(4-(4-(3,5-difluorobenzoyl)piperazine-1-carbonyl)-2-(trifluoromethoxy)phenyl)quinoline-8-sulfonamide (Compound 326)

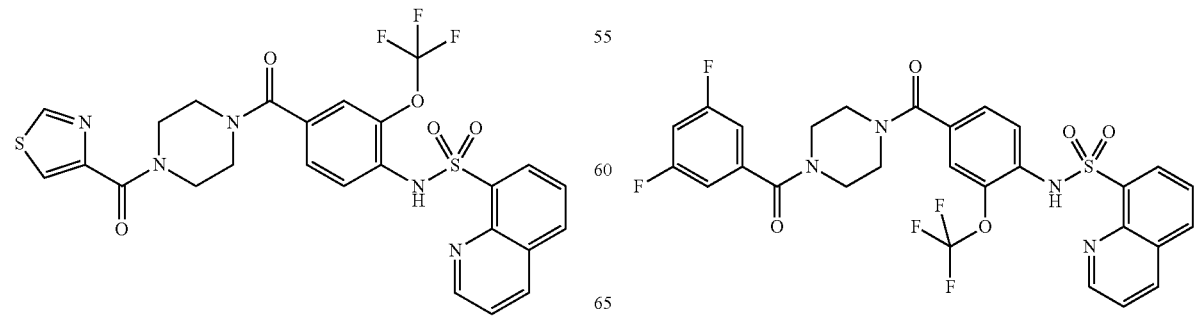

¹H NMR (400 MHz, CDCl₃) δ: 3.3-3.8 (m, 8H), 6.9 (m, 3H), 7.2 (m, 2H), 7.6 (m, 2H), 8.0 (m, 2H), 8.4 (m, 2H), 9.1 (m, 1H); HPLC Purity: 99.48%; Mass (M+1): 621.25

N-(4-(4-(3,5-dimethylbenzoyl)piperazine-1-carbonyl)-2-(trifluoromethoxy)phenyl)quinoline-8-sulfonamide (Compound 327)

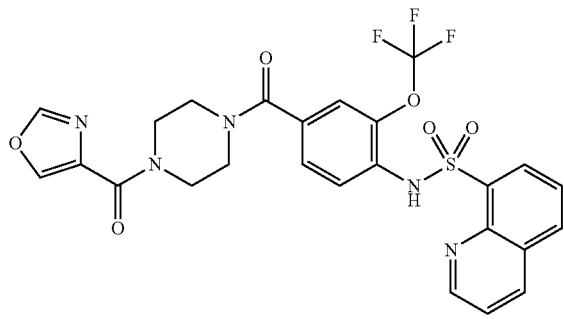 [SMILES: O=C(c1ccc(NS(=O)(=O)c2cccc3cccnc23)c(OC(F)(F)F)c1)N1CCN(C(=O)c2cocn2)CC1]

¹H NMR (400 MHz, CDCl₃) δ: 3.5-4.2 (m, 8H), 7.2 (m, 3H), 7.6 (m, 2H), 7.9 (m, 1H), 8.1 (m, 1H), 8.3 (m, 1H), 8.4 (m, 1H), 9.1 (m, 2H); HPLC Purity: 96.80%; Mass (M+1): 576.25.

Example 14

Preparation of Compounds of Formula Ip

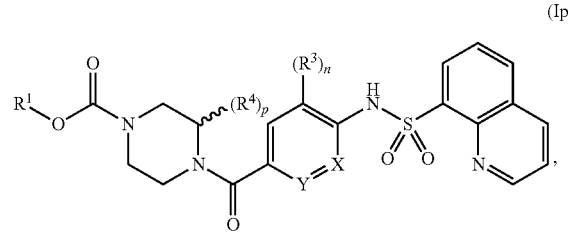

wherein R¹ is alkyl, cycloalkyl, aryl, or heteroaryl; R³ is OCH₃, or OCF₃; R⁴ is alkyl; X and Y are independently selected from CH and N; p is 0 or 1; and n is 0 or 1.

Scheme 14

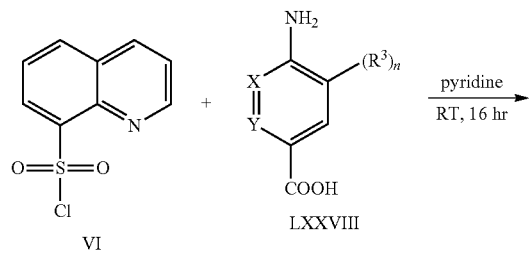

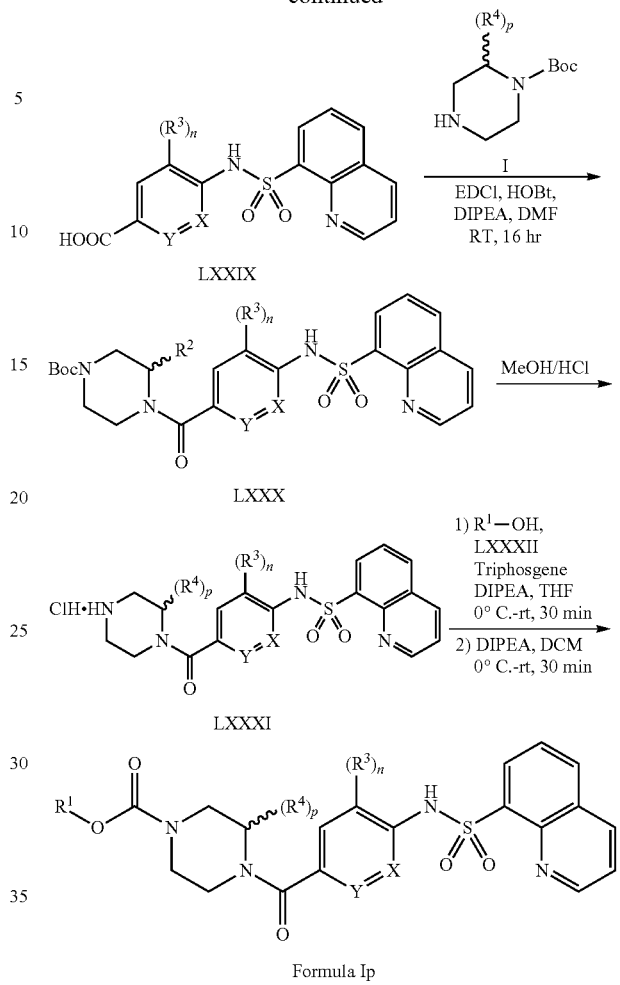

Synthesis of Intermediate LXXIX

To a stirred solution of appropriately substituted amine LXXVIII (30.3 mmol) under nitrogen atmosphere was added pyridine (50 ml) at 0° C. and stirred for 10 min. Quinoline-8-sulfonyl chloride VI (8.94 gm, 39.4 mmol) was then added to the reaction mixture at the same temperature. The resulting mixture was stirred for 16 h at room temperature. After completion of the reaction, the solvent was removed under reduced pressure. The traces of pyridine were removed by co-distillation with toluene. Diethyl ether was added to the resulting residue, and the solid product was filtered out and air-dried. The resulting crude product LXXIX (74%) was taken to the next step without further purification.

Synthesis of Intermediate LXXX

To a stirred solution of acid LXXIX (0.000315 moles) in DMF (5 ml), were added EDCI (0.066 g, 0.000346 moles), HOBt (0.047 g, 0.000346 moles) and DIPEA (0.13 ml, 0.00078 moles) at 0° C. and stirred for 15 minutes. A solution of amine I (0.000315 moles) was then added at 0° C. and the resulting mixture was allowed to stir at room temperature overnight. After completion of the reaction, water (20 mL) was added and extracted with ethyl acetate (2×30 ml). The combined organic layer was dried over anhydrous Na₂SO₄ and concentrated under reduced pressure. The crude product was purified by column chromatography (silica gel, 60-120 mess, 70% ethyl acetate in hexane) to give LXXX in 45-55% yield.

Synthesis of Intermediate LXXXI

To a solution of MeOH.HCl (12 ml), Boc protected amine LXXX (4.03 mmol) was added and the resulting mixture was stirred for 2 h. After completion of reaction, solvent was removed under reduced pressure, washed with water followed by addition of NaHCO$_3$ and extracted with DCM. The organic layer was dried over Na$_2$SO$_4$ and evaporated under reduced pressure to afford product LXXXI in 94% yield.

General Procedure for Syntheses of Compounds of Formula Ip.

To a stirred solution of Triphosgene (1.7 g, 57 mmol) in dry THF (15 ml) was added alcohol LXXXII (39 mmol) at 0° C. under nitrogen atmosphere and reaction mixture was stirred further for 15 minutes at room temperature. DIPEA (2.5 ml, 0.014 moles) was added slowly to the reaction mixture and stirred for further 30 minutes. The reaction mixture was filtered and filtrate was concentrated under reduced pressure to leave the crude chloroformate which was used for the next step.

To a stirred solution of amine IX (24.3 mmol) in dry DCM (10 ml) was added DIPEA (0.1 ml, 0.007 moles) at 0° C. under nitrogen atmosphere. The crude chloroformate (29.2 mmol) was added to the reaction mixture and stirred further for 30 minutes at room temperature. After completion of the reaction, water (10 mL) was added and extracted with DCM (2×30 ml). The combined organic layer was dried over anhydrous Na$_2$SO$_4$ and concentrated under reduced pressure. The crude product was purified by column chromatography (silica gel, 60-120 mess, MeOH-DCM, 1:9) to give a compound of Formula Ip in 50-60% yield.

The following compounds of Formula Ip were made by the above-described method using the appropriate acid LXXVIII, the appropriate alcohol LXXXII and the appropriate Boc-protected amine I.

Pyridin-2-yl 4-(3-methoxy-4-(quinoline-8-sulfonamido)benzoyl)piperazine-1-carboxylate (XI-3) (Compound 315)

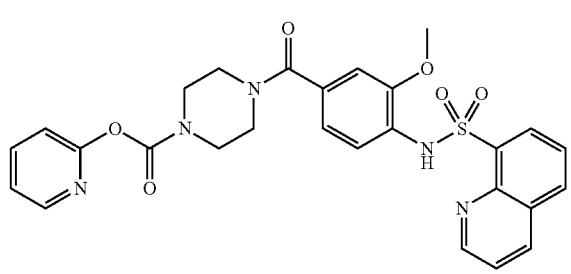 [SMILES: COc1cc(C(=O)N2CCN(C(=O)Oc3ccccn3)CC2)ccc1NS(=O)(=O)c1cccc2cccnc12]

$^1$H NMR (400 MHz, CDCl$_3$) δ: 3.4-3.7 (m, 8H), 6.9 (m, 2H), 7.2 (m, 2H), 7.6 (m, 3H), 7.9 (m, 1H), 8.1 (m, 1H), 8.3 (m, 1H), 8.5 (m, 1H), 9.1 (m, 1H); HPLC Purity: 97.17%; Mass (M+1): 548.20.

(S)-Tetrahydrofuran-3-yl-4-(4-(quinoline-8-sulfonamido)-3-(trifluoromethoxy)benzoyl)piperazine-1-carboxylate (Compound 343)

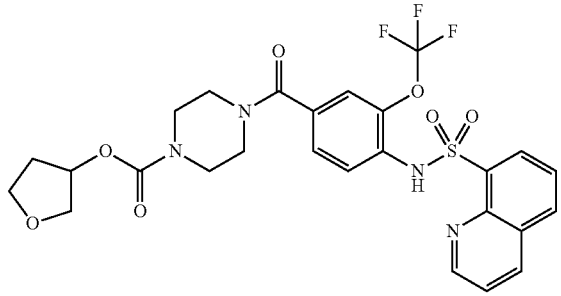 [SMILES: O=C(OC1CCOC1)N1CCN(C(=O)c2ccc(NS(=O)(=O)c3cccc4cccnc34)c(OC(F)(F)F)c2)CC1]

$^1$H NMR (400 MHz, DMSO-d$_6$) δ: 2.2 (m, 2H), 3.2-3.7 (m, 4H), 3.9 (m, 2H), 5.1 (m, 1H), 7.2 (m, 2H), 7.6 (m, 2H), 7.8 (m, 1H), 8.1 (m, 1H), 8.4 (m, 2H), 9.1 (m, 1H), 10.0 (bs, 1H); HPLC Purity: 98.45%; Mass (M+1): 595.3.

2-cyclopentylethyl-4-(4-(quinoline-8-sulfonamido)-3-(trifluoromethoxy)benzoyl)piperazine-1-carboxylate (Compound 312)

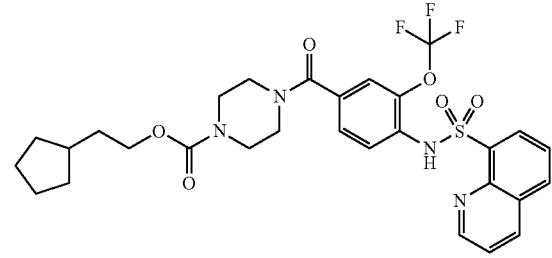 [SMILES: O=C(OCCC1CCCC1)N1CCN(C(=O)c2ccc(NS(=O)(=O)c3cccc4cccnc34)c(OC(F)(F)F)c2)CC1]

201

¹H NMR (400 MHz, CDCl₃) δ: 1.2 (m, 6H), 1.7 (m, 6H), 3.2-3.5 (m, 8H), 4.6 (m, 1H), 7.2 (m, 2H), 7.6 (m, 2H), 8.1 (m, 2H), 8.4 (m, 2H), 9.1 (m, 1H), 10.0 (bs, 1H); HPLC Purity: 99.18%; Mass (M+1): 621.4.

tetrahydro-2H-pyran-4-yl-4-(4-(quinoline-8-sulfonamido)-3-(trifluoromethoxy)benzoyl)piperazine-1-carboxylate (Compound 314)

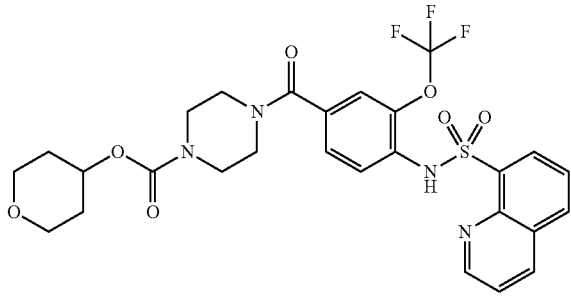 [SMILES: O=C(OC1CCOCC1)N1CCN(C(=O)c2ccc(NS(=O)(=O)c3cccc4cccnc34)c(OC(F)(F)F)c2)CC1]

¹H NMR (400 MHz, CDCl₃) δ: 1.6 (m, 3H), 2.1 (m, 1H), 3.3-3.6 (m, 10H), 3.9 (m, 2H), 4.8 (m, 1H), 7.2 (m, 2H), 7.6 (m, 2H), 7.9 (m, 1H), 8.1 (m, 1H), 8.4 (m, 2H), 9.1 (m, 1H); HPLC Purity: 99.45%; Mass (M+1): 609.4.

(tetrahydrofuran-2-yl)methyl-4-(4-(quinoline-8-sulfonamido)-3-(trifluoromethoxy)benzoyl)piperazine-1-carboxylate (Compound 316)

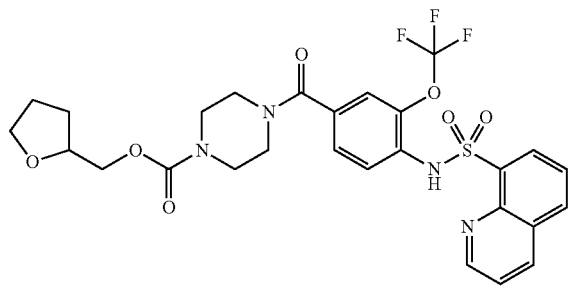 [SMILES: O=C(OCC1CCCO1)N1CCN(C(=O)c2ccc(NS(=O)(=O)c3cccc4cccnc34)c(OC(F)(F)F)c2)CC1]

¹H NMR (400 MHz, CDCl₃) δ: 1.6 (m, 1H), 1.9-2.0 (m, 3H), 3.4-3.7 (m, 8H), 3.8 (m, 2H), 4.2 (m, 3H), 6.9 (m, 2H),

202

7.2 (m, 2H), 7.6 (m, 3H), 7.9 (m, 1H), 8.1 (m, 1H), 8.3 (m, 1H), 8.5 (m, 1H), 9.1 (m, 1H); HPLC Purity: 96%; Mass (M+1): 609.30.

(R)-tetrahydrofuran-3-yl-4-(4-(quinoline-8-sulfonamido)-3-(trifluoromethoxy)benzoyl)piperazine-1-carboxylate (Compound 311)

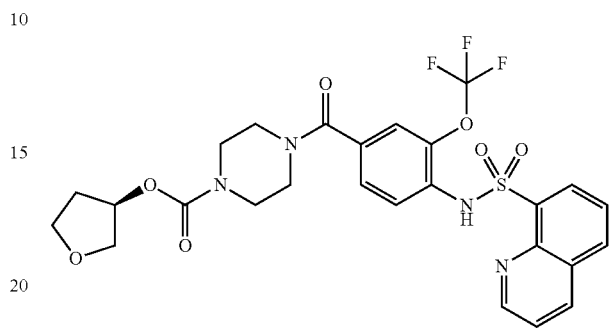

¹H NMR (400 MHz, DMSOd₆) δ: 2.2 (m, 2H), 3.2-3.7 (m, 8H), 4.0 (m, 4H), 5.2 (m, 1H), 7.2 (m, 2), 7.8 (m, 2H), 8.0 (m, 2H), 8.4 (m, 2H), 9.0 (m, 1H); HPLC Purity: 99.63%; Mass (M+1): 595.35.

Pyridin-2-yl-4-(4-(quinoline-8-sulfonamido)-3-(trifluoromethoxy)benzoyl)piperazine-1-carboxylate (Compound 344)

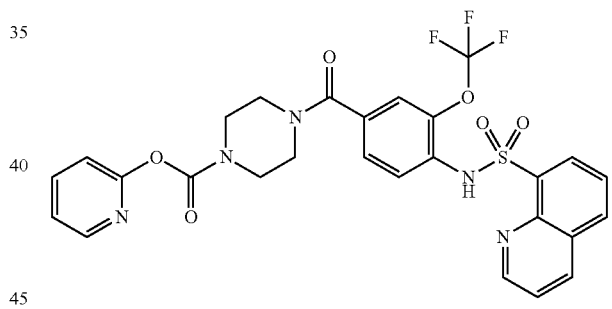

¹H NMR (400 MHz, CDCl₃) δ: 3.0-3.8 (m, 8H), 7.0 (m, 6H), 7.6 (m, 2H), 7.7-7.9 (m, 2H), 8.0 (m, 1H), 8.4 (m, 3H), 9.0 (m, 1H); HPLC Purity: 94.84%; Mass (M+1): 601.0.

(S)-Ethyl 3-methyl-4-(4-(quinoline-8-sulfonamido)benzoyl)piperazine-1-carboxylate (Compound 107)

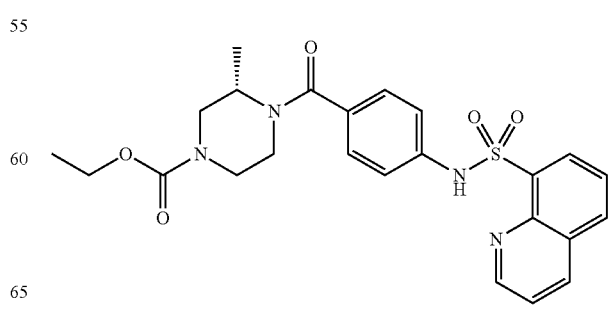

¹H NMR (400 MHz, CDCl₃) δ: 1.2 (t, 3H), 1.6 (q, 2H), 3.0-3.4 (m, 3H), 3.8-4.2 (m, 4H), 5.0 (m, 1H), 7.0-7.3 (m, 4H), 7.6 (m, 2H), 8.0 (m, 1H), 8.2-8.4 (m, 2H), 8.6 (s, 1H), 9.0 (m, 1H); HPLC Purity: 99.05%; Mass (M+1): 483.2.

(S)-isopropyl 3-methyl-4-(4-(quinoline-8-sulfonamido)benzoyl)piperazine-1-carboxylate (Compound 108)

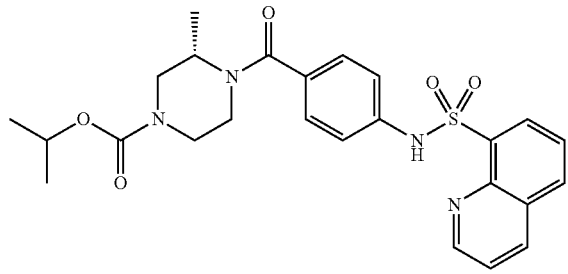 [SMILES: CC(C)OC(=O)N1CCN(C(=O)c2ccc(NS(=O)(=O)c3cccc4cccnc34)cc2)[C@@H](C)C1]

¹H NMR (400 MHz, CDCl₃) δ: 1.2 (d, 6H), 1.4 (m, 1H), 2.8-3.2 (m, 2H), 3.8-4.2 (m, 4H), 5.0 (m, 1H), 7.0-7.2 (m, 4H), 7.6 (m, 2H), 8.0 (m, 1H), 8.2-8.4 (m, 2H), 8.6 (s, 1H), 9.0 (m, 1H); HPLC Purity: 99.77%; Mass (M+1): 497.3.

(R)-Ethyl 3-methyl-4-(4-(quinoline-8-sulfonamido)benzoyl)piperazine-1-carboxylate (Compound 109)

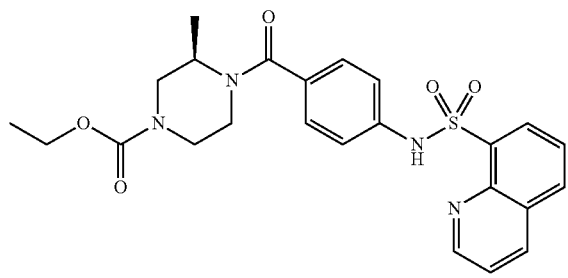 [SMILES: CCOC(=O)N1CCN(C(=O)c2ccc(NS(=O)(=O)c3cccc4cccnc34)cc2)[C@H](C)C1]

¹H NMR (400 MHz, CDCl₃) δ: 1.2 (t, 2H), 1.4 (q, 2H), 2.2 (d, 3H), 3.4-3.8 (m, 7H), 7.0-7.2 (m, 4H), 7.6 (m, 2H), 8.1 (m, 1H), 8.2-8.4 (m, 2H), 8.6 (m, 1H), 9.0 (m, 1H); HPLC Purity: 99.23%; Mass (M+1): 483.20.

(R)-Isopropyl 3-methyl-4-(4-(quinoline-8-sulfonamido)benzoyl)piperazine-1-carboxylate (Compound 110)

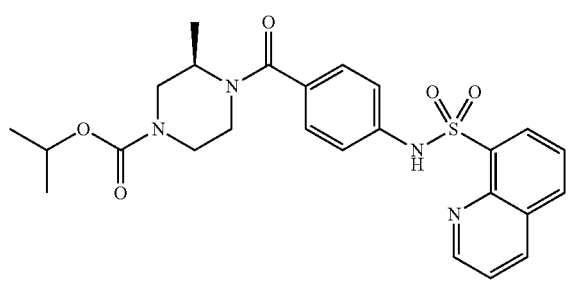 [SMILES: CC(C)OC(=O)N1CCN(C(=O)c2ccc(NS(=O)(=O)c3cccc4cccnc34)cc2)[C@H](C)C1]

¹H NMR (400 MHz, DMSO-d₆) δ: 1.2 (d, 9H), 1.25 (m, 1H), 2.8-3.2 (m, 4H), 3.8-4.2 (m, 2H), 4.9 (m, 1H), 7.0-7.2 (m, 4H), 7.55-7.6 (m, 2H), 8.0 (d, 1H), 8.38 (d, 2H), 8.5 (s, 1H), 9.0 (m, 1H); HPLC Purity: 99.23%; Mass (M+1): 497.40.

(S)-Cyclopropylmethyl 3-methyl-4-(4-(quinoline-8-sulfonamido)benzoyl)piperazine-1-carboxylate (Compound 111)

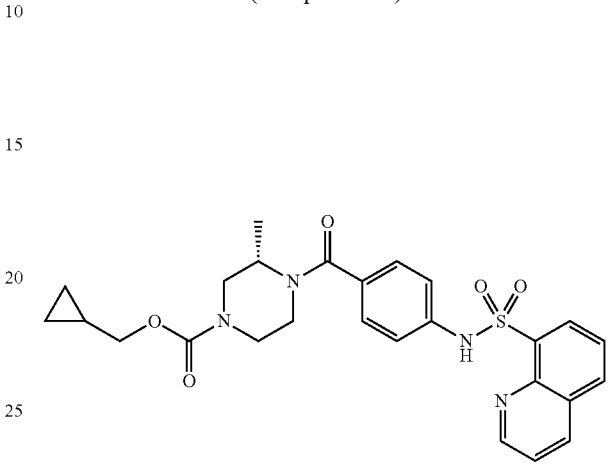

¹H NMR (400 MHz, CDCl₃) δ: 0.1 (m, 1H), 0.2 (m, 2H), 0.5 (m, 2H), 1.2 (s, 3H), 2.6-3.2 (m, 4H), 2.8-3.0 (m, 3H), 3.8-4.2 (m, 6H), 7.0-7.2 (m, 4H), 7.55-7.6 (m, 2H), 8.0 (d, 1H), 8.2-8.4 (d, 2H), 8.5 (s, 1H), 9.0 (m, 1H); HPLC Purity: 99.02%; Mass (M+1): 509.3.

(R)-Cyclopropylmethyl 3-methyl-4-(4-(quinoline-8-sulfonamido)benzoyl)piperazine-1-carboxylate (Compound 112)

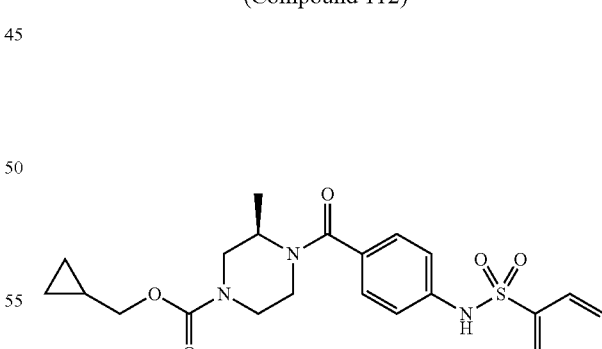

¹H NMR (400 MHz, CDCl₃) δ: 0.3 (m, 2H), 0.5 (m, 2H), 1.2 (d, 3H), 1.3 (m, 1H), 2.8-3.2 (m, 4H), 3.8-4.2 (m, 5H), 7.0-7.2 (m, 4H), 7.55-7.6 (m, 1H), 8.0 (d, 1H), 8.2-8.4 (d, 2H), 8.57 (s, 1H), 9.0 (m, 1H); HPLC Purity: 92.31%; Mass (M+1): 509.3.

(R)-2-Cyclohexylethyl 3-methyl-4-(4-(quinoline-8-sulfonamido)benzoyl)piperazine-1-carboxylate (Compound 121)

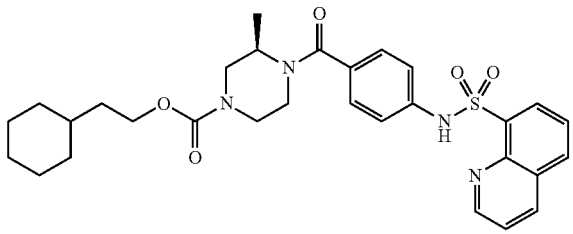 [SMILES: C[C@@H]1CN(C(=O)OCCC2CCCCC2)CCN1C(=O)c1ccc(NS(=O)(=O)c2cccc3cccnc23)cc1]

$^1$H NMR (400 MHz, CDCl$_3$) δ: 0.85 (m, 2H), 1.15-1.2 (m, 10H), 1.4-1.56 (m, 2H), 1.59-1.67 (m, 1H), 1.8 (d, 3H), 2.7-3.2 (m, 4H), 3.8-4.2 (m, 2H), 7.19-7.3 (m, 4H), 7.5-7.6 (m, 2), 8.0 (d, 1H), 8.2-8.4 (m, 2H), 9.1 (m, 1H); HPLC Purity: 97.73%; Mass (M+1): 565.25.

(R)-2-Cyclopentylethyl-3-methyl-4-(4-(quinoline-8-sulfonamido)benzoyl)piperazine-1-carboxylate (Compound 122)

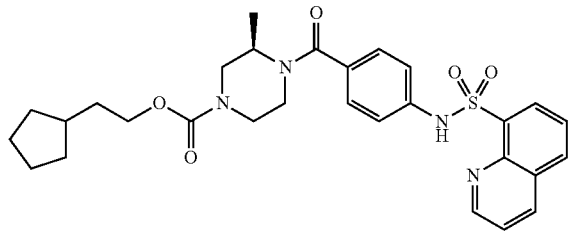 [SMILES: C[C@@H]1CN(C(=O)OCCC2CCCC2)CCN1C(=O)c1ccc(NS(=O)(=O)c2cccc3cccnc23)cc1]

$^1$H NMR (400 MHz, CDCl$_3$) δ: 1.2-1.4 (m, 10H), 1.4-1.56 (m, 5H), 2.0 (m, 1H), 2.7-3.2 (m, 3H), 3.8-4.2 (m, 2H), 7.0-7.2 (m, 4H), 7.5-7.6 (m, 2), 8.0 (d, 1H), 8.2-8.4 (m, 2H), 9.1 (m, 1H); HPLC Purity: 99.96%; Mass (M+1): 551.23.

(R)-Cyclohexyl 3-methyl-4-(4-(quinoline-8-sulfonamido)benzoyl)piperazine-1-carboxylate (Compound 123)

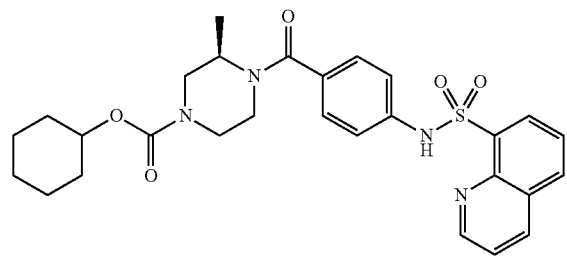 [SMILES: C[C@@H]1CN(C(=O)OC2CCCCC2)CCN1C(=O)c1ccc(NS(=O)(=O)c2cccc3cccnc23)cc1]

$^1$H NMR (400 MHz, CDCl$_3$) δ: 1.2 (d, 3H), 1.23-1.4 (m, 8H), 1.5 (m, 1H), 1.6 (m, 2H), 1.89 (m, 2H), 2.7-3.2 (m, 3H), 3.8-4.2 (m, 3H), 7.0-7.2 (m, 4H), 7.5-7.6 (m, 2), 8.0 (d, 1H), 8.2-8.4 (m, 2H), 9.1 (m, 1H); HPLC Purity: 99.72%; Mass (M+1): 537.50.

(R)-Tetrahydro-2H-pyran-4-yl-3-methyl-4-(4-(quinoline-8-sulfonamido)benzoyl)piperazine-1-carboxylate (Compound 124)

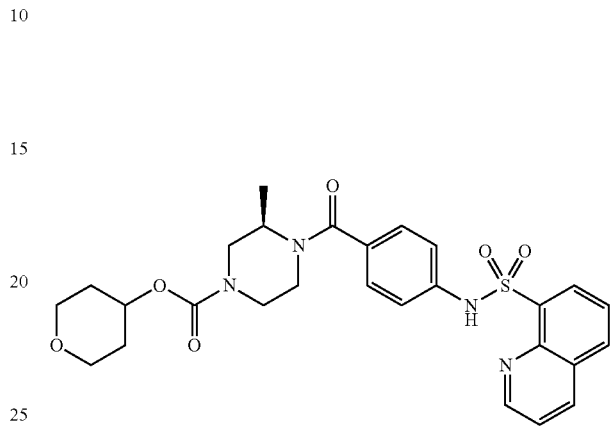

$^1$H NMR (400 MHz, CDCl$_3$) δ: 1.2 (d, 3H), 1.23 (m, 1H), 1.5 (m, 1H), 1.6-1.7 (m, 2H), 1.89-2.0 (m, 2H), 2.7-3.2 (m, 4H), 3.8-4.85 (m, 6H), 7.0-7.2 (m, 4H), 7.5-7.6 (m, 2H), 8.0 (d, 1H), 8.2-8.4 (m, 2H), 9.1 (m, 1H); HPLC Purity: 98.83%; Mass (M+1): 539.30.

(R)—((R)-tetrahydrofuran-3-yl)-3-methyl-4-(4-(quinoline-8-sulfonamido)benzoyl)piperazine-1-carboxylate (Compound 126)

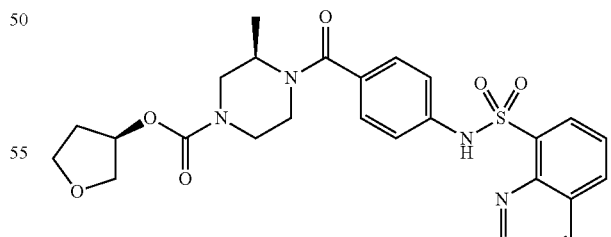

$^1$H NMR (400 MHz, DMSO-d$_6$) δ: 1.0 (d, 3H), 1.23 (m, 1H), 1.8-2.2 (m, 2H), 2.7-3.2 (m, 3H), 3.6-4.0 (m, 6H), 5.17

(m, 1H), 7.0-7.2 (m, 3H), 7.6-7.8 (m, 2H), 8.0 (d, 1H), 8.2-8.4 (m, 2H), 9.1 (m, 1H), 10.45 (s, 1H); HPLC Purity: 99.52%; Mass (M+1): 525.45.

(R)—((R)-tetrahydro-2H-pyran-3-yl)-3-methyl-4-(4-(quinoline-8-sulfonamido)benzoyl)piperazine-1-carboxylate (Compound 127)(R)

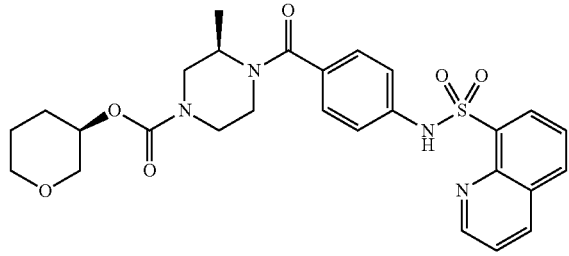 [SMILES: C[C@@H]1CN(C(=O)O[C@@H]2CCCOC2)CCN1C(=O)c1ccc(NS(=O)(=O)c2cccc3cccnc23)cc1]

¹H NMR (400 MHz, DMSO-d₆) δ: 1.0 (d, 3H), 1.23 (m, 1H), 1.75-1.78 (m, 3H), 2.85-2.9 (m, 3H), 3.41-3.79 (m, 6H), 3.89-3.9 (m, 1H), 4.44 (m, 1H), 7.0-7.2 (m, 4H), 7.6-7.8 (m, 2H), 8.23 (d, 1H), 8.4 (d, 1H), 8.5 (d, 1H), 9.1 (m, 1H), 10.45 (s, 1H); HPLC Purity: 99.67%; Mass (M+1): 539.1.

(3R)-(Tetrahydrofuran-2-yl)methyl3-methyl-4-(4-(quinoline-8-sulfonamido)benzoyl)piperazine-1-carboxylate (Compound 128)

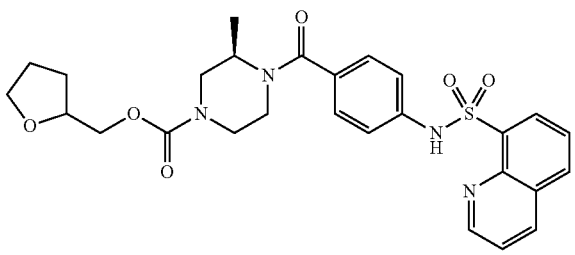 [SMILES: C[C@@H]1CN(C(=O)OCC2CCCO2)CCN1C(=O)c1ccc(NS(=O)(=O)c2cccc3cccnc23)cc1]

¹H NMR (400 MHz, DMSO-d₆) δ: 1.0 (d, 3H), 1.53 (m, 1H), 1.57-2.0 (m, 3H), 2.8-3.1 (m, 3H), 3.6-4.1 (m, 9H), 7.0-7.2 (m, 4H), 7.6-7.8 (m, 2H), 8.23 (d, 1H), 8.4-8.5 (m, 2H), 9.1 (m, 1H), 10.45 (s, 1H); HPLC Purity: 99.80%; Mass (M+1): 539.1.

(R)-Cyclopentyl3-methyl-4-(4-(quinoline-8-sulfonamido)benzoyl)piperazine-1-carboxylate (Compound 129)

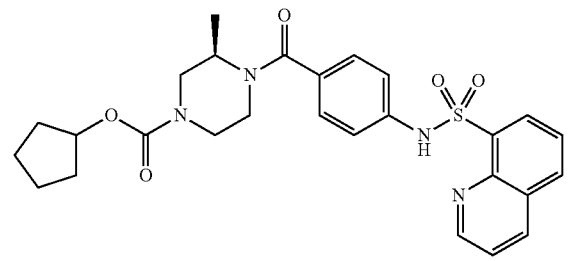 [SMILES: C[C@@H]1CN(C(=O)OC2CCCC2)CCN1C(=O)c1ccc(NS(=O)(=O)c2cccc3cccnc23)cc1]

¹H NMR (400 MHz, DMSO-d₆) δ: 1.0 (d, 3H), 1.38 (m, 1H), 1.39-1.8 (m, 8H), 2.6-3.0 (m, 3H), 3.5-3.8 (m, 3H), 4.95 (m, 1H), 7.0-7.2 (m, 4H), 7.6-7.8 (m, 2H), 8.23 (d, 1H), 8.4-8.5 (m, 2H), 9.1 (m, 1H); HPLC Purity: 99.68%; Mass (M+1): 523.50.

(R)—((S)-tetrahydrofuran-3-yl)-3-methyl-4-(4-(quinoline-8-sulfonamido)benzoyl)piperazine-1-carboxylate (Compound 129)(S)

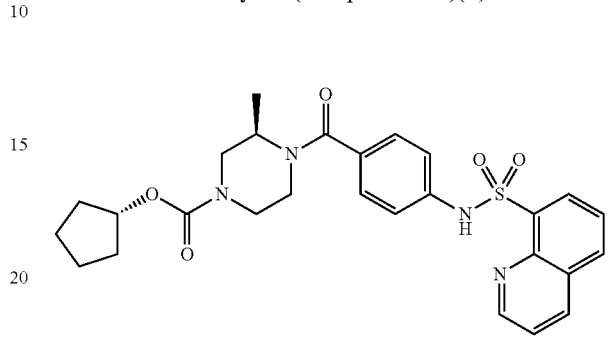

¹H NMR (400 MHz, DMSO-d₆) δ: 1.0 (d, 3H), 1.8 (m, 1H), 2.0-2.2 (m, 1H), 2.8-3.3 (m, 3H), 4.0-4.2 (m, 8H), 7.0-7.2 (m, 4H), 7.6-7.7 (m, 2H), 8.0 (d, 1H), 8.3-8.6 (m, 2H), 9.1 (m, 1H), 10.4 (s, 1H); HPLC Purity: 96.16%; Mass (M+1): 525.45.

Ethyl 4-(5-(quinoline-8-sulfonamido)picolinoyl)piperazine-1-carboxylate (Compound 447)

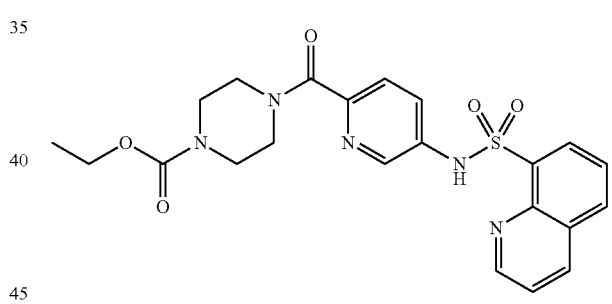

¹H NMR (400 MHz, CDCl₃) δ: 1.2 (t, 3H), 3.2-3.6 (m, 8H), 4.0-4.2 (q, 2H), 7.4-7.8 (m, 4H), 8.0-8.6 (m, 4H), 9.1-9.2 (m, 1H); HPLC Purity: 97.7%; Mass (M+1): 470.2.

Ethyl 4-(6-(quinoline-8-sulfonamido)nicotinoyl)piperazine-1-carboxylate (Compound 446)

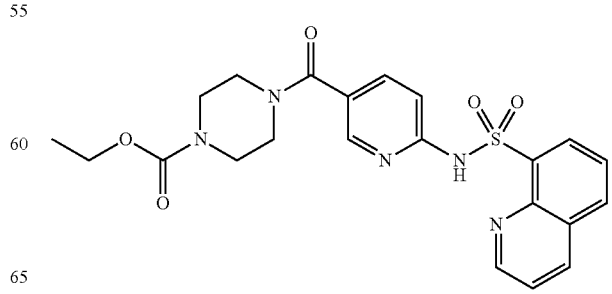

$^1$H NMR (400 MHz, DMSO-d$_6$) δ: 1.0-1.2 (t, 3H), 2.2-2.4 (m, 2H), 3.2-3.35 (q, 2H), 3.4-3.6 (m, 4H), 3.99-4.0 (m, 2H), 7.5-7.7 (m, 4H), 8.3-8.5 (m, 4H), 9.1 (m, 1H); HPLC Purity: 99.89%; Mass (M+1): 470.4.

Example 15

Preparation of Compound 104 (Racemic)

Scheme 15:

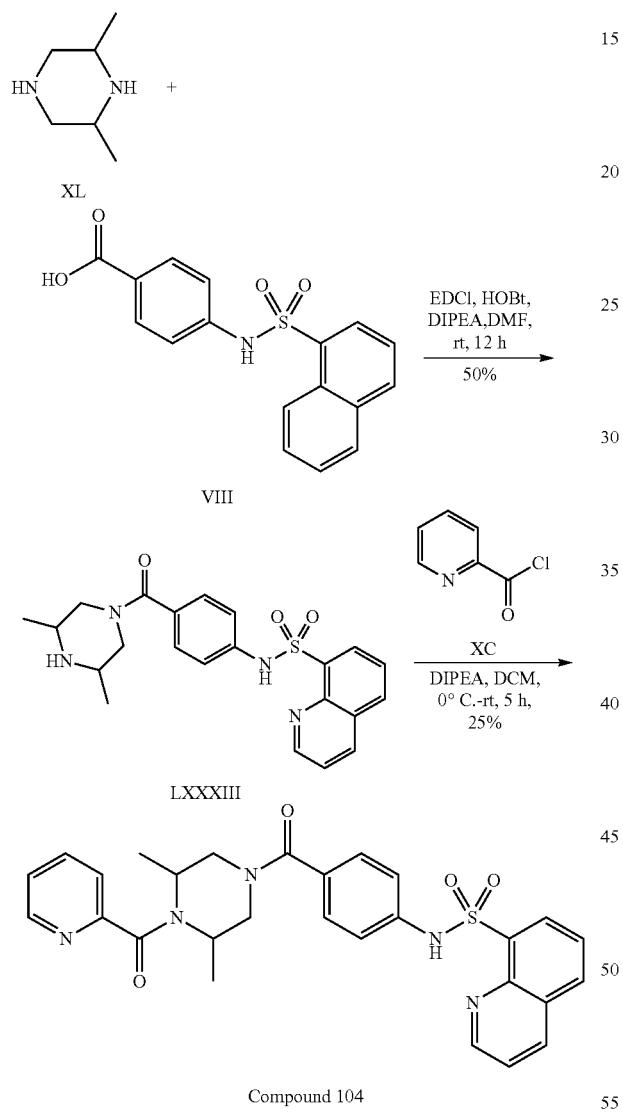

Synthesis of Intermediate LXXXIII

The product LXXXIII was prepared by following similar method used for the preparation of intermediate LXXVI (Scheme 13) using carboxylic acid VIII (0.226 gm, 0.69 mmol) and cis-2,6-dimethylpiperazine XL (0.079 gm, 0.69 mmol). Crude product was purified by column chromatography (60-120 silica gel, 2% MeOH-DCM) to get 0.146 gm of pure product LXXXIII in 50% yields.

Synthesis of N-(4-(3,5-dimethylpiperazine-1-carbonyl)phenyl)quinoline-8-sulfonamide (Compound 104) (Racemic)

To a solution of amine LXXXIII (0.125 gm, 0.29 mmol) and ethyldiisopropylamine in dichloromethane was added picolyl chloride (XC, 0.045 gm, 0.32 mmol) at 0° C. The reaction mixture was allowed to warm to room temperature and stirred for 5 h. After completion of reaction, the mixture was diluted with dichloromethane, washed with water (2×10 ml), brine (10 ml), dried over anhydrous Na$_2$SO$_4$ and concentrated. The crude material was then purified by column chromatography (60-120 silica gel, 2% MeOH-DCM) to get 0.039 gm of pure Compound 104 (racemic) in 25% yield.

$^1$H NMR (400 MHz, CDCl$_3$) δ: 1.2 (s, 6H), 3.0 (m, 1H), 3.6 (m, 2H), 4.3 (m, 2H), 7.0 (m, 4H), 7.4-7.6 (m, 4H), 8.0 (m, 1H), 8.2 (m, 1H), 8.4 (m, 3H), 9.0 (m, 1H); HPLC Purity: 98.75%; Mass (M+1): 530.3.

Example 16

Preparation of Compound 116 (Racemic)

Scheme 16:

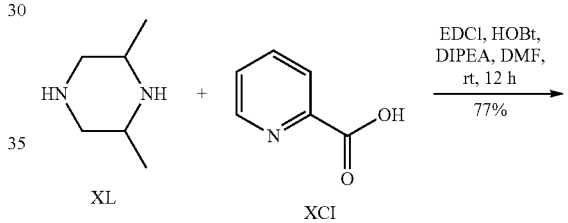

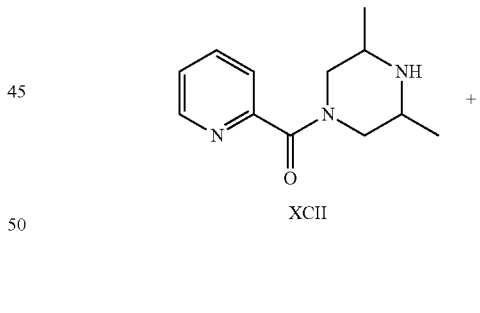

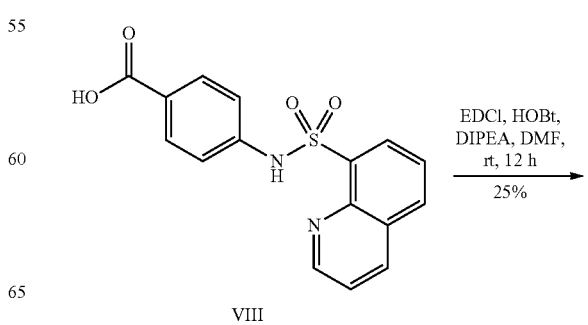

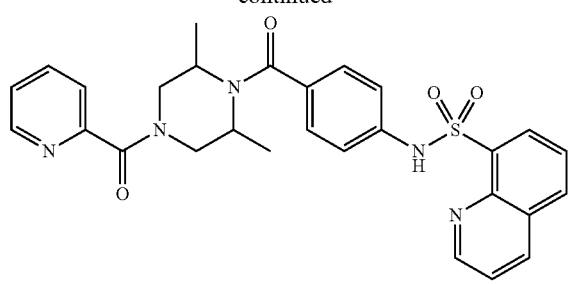

Compound 116

Synthesis of Intermediate XCII

The product XCII was prepared by following similar method used for the preparation of intermediate LXXVI (Scheme 13) using picolinic acid XCI (0.092 gm, 0.75 mmol) and cis-2,6-dimethylpiperazine XL (0.086 gm, 0.75 mmol). The crude material was purified by column chromatography (60-120 silica gel, 2% MeOH-DCM) to get 0.126 gm of pure product XCII in 77% yield.

Synthesis of Compound 116 (Racemic)

Compound 116 was prepared by following similar method used for the preparation of a compound of Formula Io (Scheme 13) using carboxylic acid VIII (0.164 gm, 0.50 mmol) and amine XCII (0.110 gm, 0.50 mmol). Crude product was purified by column chromatography (60-120 silica gel, 2% MeOH-DCM) to get 0.066 gm of pure Compound 116 (racemic) in 25% yields.

$^1$H NMR (400 MHz, CDCl$_3$) δ: 2.8-3.0 (s, 6H), 3.35-3.4 (m, 2H), 4.0 (m, 2H), 4.5-4.66 (m, 1H), 7.0-7.2 (m, 4H), 7.3-7.8 (m, 6H), 8.0-8.1 (m, 1H), 8.2-8.6 (m, 4H), 9.0 (m, 1H); HPLC Purity: 93.09%; Mass (M+1): 530.45.

Example 17

Preparation of a Compound of Formula Iq

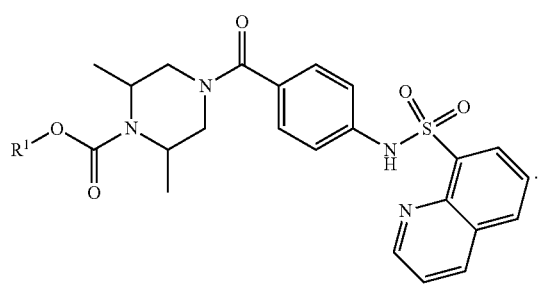

(Iq)

Scheme 17:

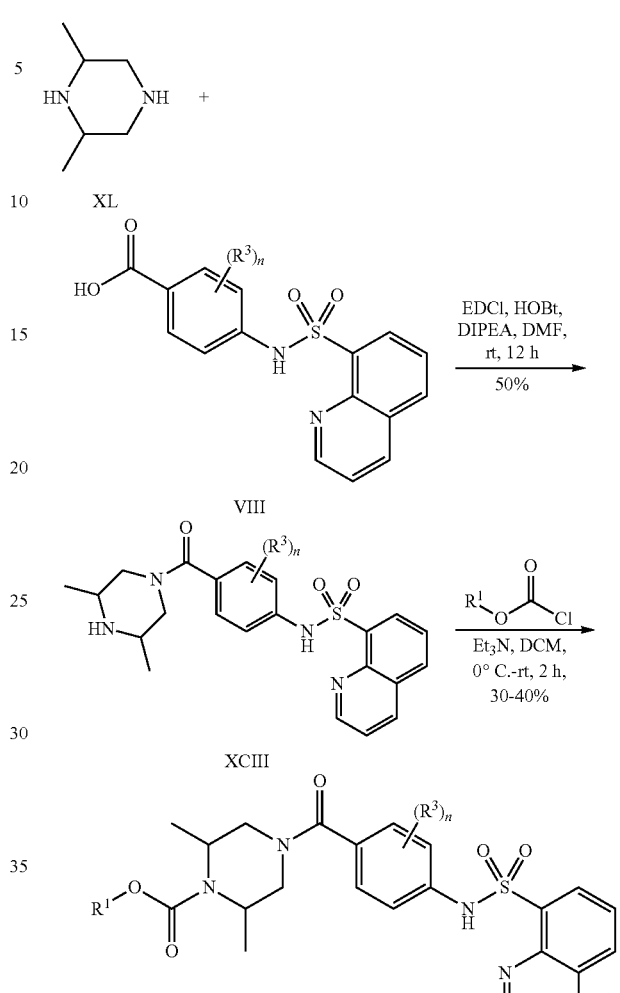

Synthesis of Intermediate XCII

EDCI (0.09 gm, 0.46 mmol) and HOBt (0.062 gm, 0.46 mmol) were added to a stirred solution of the carboxylic acid (VIII, 0.151 gm, 0.46 mmol) in anhydrous DMF. The temperature of the mixture was reduced to 0° C., at which time DIPEA (0.24 mL, 1.38 mmol) was added under nitrogen atmosphere and the resultant solution (or suspension) was stirred at room temperature for 30 min. Amine XL (VI, 0.46 mmol) was then added at 0° C. The reaction mixture was then brought to room temperature and stirred for 12 h. After completion of the reaction, the reaction mixture was diluted with water and extracted with ethyl acetate (2×25 ml). The organic layer was washed with water (2×10 ml), dried over anhydrous sodium sulfate, filtered and concentrated under vacuum to get the crude product. The obtained crude product was purified by column chromatography (60-120 silica gel, 2% MeOH-DCM) to get pure product XCIII as an off-white solid in 40-50% yields.

Synthesis of Compounds of Formula Iq

To a solution of amine XI (0.102 gm, 0.24 mmol) and triethyl amine (0.66 mmol) in 5 mL of dichloromethane, appropriate chloroformate (0.26 mmol) was added at 0° C. and allowed to stir at room temperature for 1-2 h. After completion of reaction, the mixture was diluted with dichloromethane (25 mL), washed with water (2×10 mL), brine (10 mL), dried over anhydrous Na₂SO₄ and concentrated. The crude product was purified by column chromatography (60-120 silica gel, 2% MeOH-DCM) to afford a Compound of Formula Iq as an off-white solid in 30-40% yields.

The following compounds were made according to the above procedure using the appropriate chloroformate.

(2S,6R)-ethyl 2,6-dimethyl-4-(4-(quinoline-8-sulfonamido)benzoyl)piperazine-1-carboxylate (XXIV-1) (Compound 117)

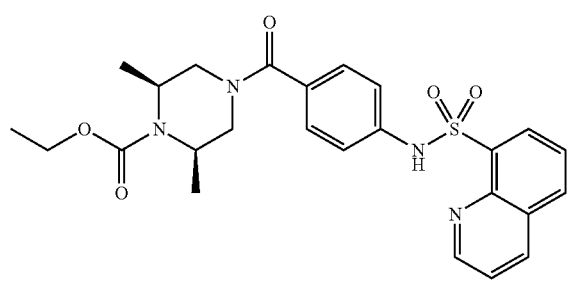 [SMILES: CCOC(=O)N1[C@H](C)CN(C(=O)c2ccc(NS(=O)(=O)c3cccc4cccnc34)cc2)C[C@@H]1C]

¹H NMR (400 MHz, CDCl₃) δ: 1.2 (t, 3H), 1.3-1.4 (d, 6H), 3.0-3.4 (m, 2H), 4.0-4.4 (m, 6H), 7.0-7.3 (m, 4H), 7.6 (m, 2H), 8.0 (m, 1H), 8.2-8.4 (m, 2H), 9.0 (m, 1H); HPLC Purity: 98.96%; Mass (M+1): 497.3.

(2S,6R)-isopropyl 2,6-dimethyl-4-(4-(quinoline-8-sulfonamido)benzoyl)piperazine-1-carboxylate (Compound 106)

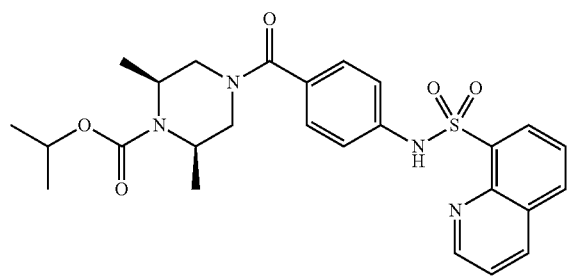 [SMILES: CC(C)OC(=O)N1[C@H](C)CN(C(=O)c2ccc(NS(=O)(=O)c3cccc4cccnc34)cc2)C[C@@H]1C]

¹H NMR (400 MHz, CDCl₃) δ: 1.2 (s, 6H), 3.0-3.4 (m, 3H), 4.0-4.4 (m, 3H), 4.9 (m, 1H), 7.0-7.3 (m, 4H), 7.6 (m, 2H), 8.0 (m, 1H), 8.2-8.4 (m, 2H), 9.0 (m, 1H); HPLC Purity: 99.96%; Mass (M+1): 511.4.

(2S,6R)-isobutyl-2,6-dimethyl-4-(4-(quinoline-8-sulfonamido)benzoyl)piperazine-1-carboxylate (Compound 105)

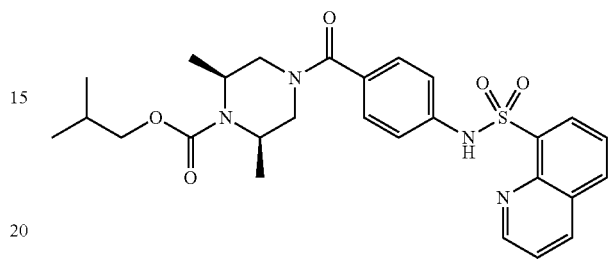

¹H NMR (400 MHz, CDCl₃) δ: 3.2-3.8 (m, 8H), 6.8-7.3 (m, 5H), 7.6 (m, 2H), 8.0 (m, 1H), 8.3-8.4 (m, 3H), 9.0 (m, 1H), 10.4 (m, 1H); HPLC Purity: 99.45%; Mass (M+1): 492.2.

Example 18

PKR Mutant Assay

Procedure:
  PKR or PKR mutant enzyme solution was diluted in assay buffer.
  2 μL of test compound was added into wells first, and then 180 μL reaction mix was added.
  Reactions mixture with test compound was assembled except for ADP, and plates were stored for 60 minutes at room temperature.
  20 uL ADP was added to start reaction at room temperature and reaction progress was measured as changes in absorbance at 340 nm wavelength at room temperature.
  Test Compound Preparation:
  Test compound stock was made at 100× concentration in 100% DMSO (10 mM)
  1 to 3 dilutions were made for 11 points (i.e. 50 μl of first concentration added to 100 μl 100% DMSO to yield 3.33 mM, 50 μl of this added to 100 μl DMSO to yield 1.11 mM, and so forth)
  1 to 100 dilution into assay (2 μl in 200 μl) yielded starting concentration of 100 μM, decreasing 3 fold for 11 points.
  Assay Buffer: 100 mM KCl, 50 mM Tris 7.5, 5 mM MgCl₂, 1 mM DTT, 0.03% BSA
  Reaction Mixture: PKR mutant enzyme: 80-400 ng/well; ADP: 0.22-1.65 mM; PEP: 0.1-0.5 mM; NADH: 180 uM; LDH: 0.5 units (Sigma#59023); DTT: 1 mM; BSA: 0.03%.

Example 19

PKR WT Single Point Percent Activation Assay

A compound described herein was diluted with DMSO and tested at 1 μM concentration. The enzyme was diluted in 1× Buffer: (100 mM KCl, 50 mM Tris 7.5, 5 mM MgCl₂, 1 mM DTT, 0.03% BSA). 2 μL of compound solution was first added into wells, and then 180 μL of enzyme solution was added. Assays were assembled except for ADP, and plates were stored for 60 minutes at RT. 20 µL ADP was added to start the assay and assay output was evaluated using OD340 at SpectraMax. The assay was run at room temperature.
Final concentration: PKR wt (100 ng/well), Tris pH 7.5 (50 mM), KCl (100 mM), MgCl$_2$ (5 mM), ADP (0.48 mM), PEP (0.15 mM), NADH (180 µM), LDH (0.5 units, Sigma 59023), DTT (1 mM) and BSA (0.03%).

Example 20

PKR R510Q Single Point Percent Activation Assay

A compound described herein was diluted with DMSO and tested at 1 µM concentration. The enzyme was diluted in 1× Buffer: (100 mM KCl, 50 mM Tris 7.5, 5 mM MgCl$_2$, 1 mM DTT, 0.03% BSA). 2 µL of compound solution was first added into wells, and then 180 µL of enzyme solution was added. Assays were assembled except for ADP, and plates were stored for 60 minutes at RT. 20 µL ADP was added to start the assay and assay output was evaluated using OD340 at SpectraMax. The assay was run at room temperature.
Final concentration: PKR R510Q (40 ng/well), Tris pH 7.5 (50 mM), KCl (100 mM), MgCl$_2$ (5 mM), ADP (0.2 mM), PEP (0.11 mM), NADH (180 µM), LDH (0.5 units, Sigma 59023), DTT (1 mM) and BSA (0.03%).

Example 21

PKR R532W Single Point Percent Activation Assay

A compound described herein was diluted with DMSO and tested at 1 µM concentration. The enzyme was diluted in 1× Buffer: (100 mM KCl, 50 mM Tris 7.5, 5 mM MgCl$_2$, 1 mM DTT, 0.03% BSA). 2 µL of compound solution was first added into wells, and then 180 µL of enzyme solution was added. Assays were assembled except for ADP, and plates were stored for 60 minutes at RT. 20 µL ADP was added to start the assay and assay output was evaluated using OD340 at SpectraMax. The assay was run at room temperature.
Final concentration: PKR R532W (100 ng/well), Tris pH 7.5 (50 mM), KCl (100 mM), MgCl2 (5 mM), ADP (0.36 mM), PEP (0.1 mM), NADH (180 µM), LDH (0.5 units, Sigma 59023), DTT (1 mM) and BSA (0.03%).

Example 22

PKR T384W Single Point Percent Activation Assay

A compound described herein was diluted with DMSO and tested at 1 µM concentration. The enzyme was diluted in 1× Buffer: (100 mM KCl, 50 mM Tris 7.5, 5 mM MgCl$_2$, 1 mM DTT, 0.03% BSA). 2 µL of compound solution was first added into wells, and then 180 µL enzyme solution was added. Assays were assembled except for ADP, and plates were stored for 60 minutes at RT. 20 µL ADP was added to start the assay and assay output was evaluated using OD340 at SpectraMax. The assay was run at room temperature.
Final concentration: PKR T384W soluble (300 ng/well), Tris pH 7.5 (50 mM), KCl (100 mM), MgCl2 (5 mM), ADP (0.08 mM), PEP (0.23 mM), NADH (180 µM), LDH (0.5 units, Sigma 59023), DTT (1 mM) and BSA (0.03%).

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:
1. A method for increasing the lifetime of red blood cells (RBCs) in need thereof comprising contacting blood with an effective amount of (1) a compound of formula I or a pharmaceutically acceptable salt thereof; (2) a composition comprising a compound of formula I or a salt thereof, and a carrier or (3) a pharmaceutically acceptable composition comprising a compound of formula I or a pharmaceutically acceptable salt thereof, and a pharmaceutically acceptable carrier, wherein:

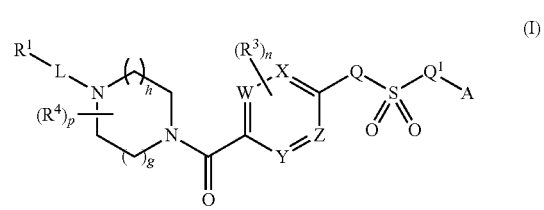

(I)

W, X, Y and Z are each independently selected from CH or N;
Q and Q$^1$ are independently selected from a bond or NR$^b$;
A is optionally substituted bicyclic aryl or optionally substituted bicyclic heteroaryl;
L is a bond, —C(O)—, —(CR$^c$R$^c$)$_m$—, —OC(O)—, —(CR$^c$R$^c$)$_m$—OC(O)—, —(CR$^c$R$^c$)$_m$—C(O)—, —NR$^b$C(S)—, or —NR$^b$C(O)— (wherein the point of the attachment to R$^1$ is on the left-hand side);
R$^1$ is selected from alkyl, carbocycle, aryl, heteroaryl, and heterocyclyl; each of which is substituted with 0-5 occurrences of R$^d$;
each R$^3$ is independently selected from halo, haloalkyl, alkyl, hydroxyl and —OR$^a$, or two adjacent R$^3$ taken together with the carbon atoms to which they are attached form an optionally substituted heterocyclyl;
each R$^4$ is independently selected from halo, haloalkyl, alkyl, hydroxyl, =O, —OR$^a$ and phenyl, or two R$^4$ taken together with the carbon atoms to which they are attached form a bridged, fused or spyro-fused carbocycle, an aryl or a heteroaryl;
each R$^a$ is independently selected from alkyl, acyl, hydroxyalkyl and haloalkyl;
each R$^b$ is independently selected from hydrogen and alkyl;
each R$^c$ is independently selected from hydrogen, halo, alkyl, alkoxy and halo alkoxy or two R$^c$ taken together with the carbon atoms to which they are attached form an optionally substituted carbocycle;
each R$^d$ is independently selected from halo, haloalkyl, haloalkoxy, alkyl, alkynyl, nitro, cyano, hydroxyl, —C(O)R$^a$, —OC(O)R$^a$, —C(O)OR$^a$, —SR$^a$, —NR$^a$R$^b$ and —OR$^a$, or two R$^d$ taken together with the carbon atoms to which they are attached form an optionally substituted heterocyclyl;
n is 0, 1, or 2;
m is 1, 2 or 3;
h is 0, 1, 2;
g is 0, 1 or 2;
the sum of g+h is equal to or greater than 2; and
p is 1 or 2.
2. The method of claim 1, wherein the compound is added directly to whole blood or packed cells extracorporeally.

3. The method of claim 1, wherein the pharmaceutical composition is administered to a subject in need thereof.

4. A method for regulating 2,3-diphosphoglycerate levels in blood in need thereof comprising contacting blood with an effective amount of (1) a compound of formula I or a pharmaceutically acceptable salt thereof; (2) a composition comprising a compound of formula I or a salt thereof, and a carrier or (3) a pharmaceutically acceptable composition comprising a compound of formula I or a pharmaceutically acceptable salt thereof, and a pharmaceutically acceptable carrier, wherein:

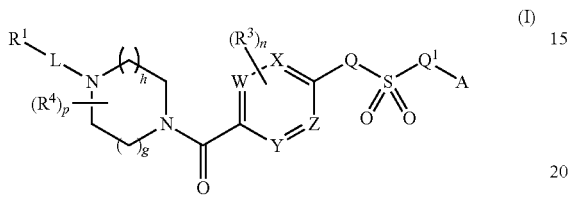

W, X, Y and Z are each independently selected from CH or N;
Q and $Q^1$ are independently selected from a bond or $NR^b$;
A is optionally substituted bicyclic aryl or optionally substituted bicyclic heteroaryl;
L is a bond, —C(O)—, —$(CR^cR^c)_m$—, —OC(O)—, —$(CR^cR^c)_m$—OC(O)—, —$(CR^cR^c)_m$—C(O)—, —$NR^bC(S)$—, or —$NR^bC(O)$— (wherein the point of the attachment to $R^1$ is on the left-hand side);
$R^1$ is selected from alkyl, carbocycle, aryl, heteroaryl, and heterocyclyl; each of which is substituted with 0-5 occurrences of $R^d$;
each $R^3$ is independently selected from halo, haloalkyl, alkyl, hydroxyl and —$OR^a$, or two adjacent $R^3$ taken together with the carbon atoms to which they are attached form an optionally substituted heterocyclyl;
each $R^4$ is independently selected from halo, haloalkyl, alkyl, hydroxyl, =O, —$OR^a$ and phenyl, or two $R^4$ taken together with the carbon atoms to which they are attached form a bridged, fused or spyro-fused carbocycle, an aryl or a heteroaryl;
each $R^a$ is independently selected from alkyl, acyl, hydroxyalkyl and haloalkyl;
each $R^b$ is independently selected from hydrogen and alkyl;
each $R^c$ is independently selected from hydrogen, halo, alkyl, alkoxy and halo alkoxy or two $R^c$ taken together with the carbon atoms to which they are attached form an optionally substituted carbocycle;
each $R^d$ is independently selected from halo, haloalkyl, haloalkoxy, alkyl, alkynyl, nitro, cyano, hydroxyl, —$C(O)R^a$, —$OC(O)R^a$, —$C(O)OR^a$, —$SR^a$, —$NR^aR^b$ and —$OR^a$, or two $R^d$ taken together with the carbon atoms to which they are attached form an optionally substituted heterocyclyl;
n is 0, 1, or 2;
m is 1, 2 or 3;
h is 0, 1, 2;
g is 0, 1 or 2;
the sum of g+h is equal to or greater than 2; and
p is 1 or 2.

5. A method for treating hemolytic anemia comprising administering to a subject in need thereof a therapeutically effective amount of (1) a compound of formula I or a pharmaceutically acceptable salt thereof; or (2) a pharmaceutically acceptable composition comprising a compound of formula I or a pharmaceutically acceptable salt thereof, and a pharmaceutically acceptable carrier, wherein:

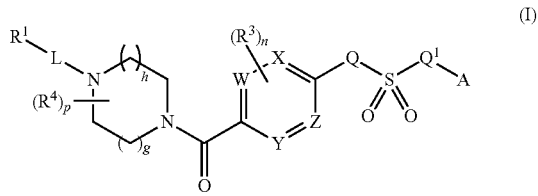

W, X, Y and Z are each independently selected from CH or N;
Q and $Q^1$ are independently selected from a bond or $NR^b$;
A is optionally substituted bicyclic aryl or optionally substituted bicyclic heteroaryl;
L is a bond, —C(O)—, —$(CR^cR^c)_m$—, —OC(O)—, —$(CR^cR^c)_m$—OC(O)—, —$(CR^cR^c)_m$—C(O)—, —$NR^bC(S)$—, or —$NR^bC(O)$— (wherein the point of the attachment to $R^1$ is on the left-hand side);
$R^1$ is selected from alkyl, carbocycle, aryl, heteroaryl, and heterocyclyl; each of which is substituted with 0-5 occurrences of $R^d$;
each $R^3$ is independently selected from halo, haloalkyl, alkyl, hydroxyl and —$OR^a$, or two adjacent $R^3$ taken together with the carbon atoms to which they are attached form an optionally substituted heterocyclyl;
each $R^4$ is independently selected from halo, haloalkyl, alkyl, hydroxyl, =O, —$OR^a$ and phenyl, or two $R^4$ taken together with the carbon atoms to which they are attached form a bridged, fused or spyro-fused carbocycle, an aryl or a heteroaryl;
each $R^a$ is independently selected from alkyl, acyl, hydroxyalkyl and haloalkyl;
each $R^b$ is independently selected from hydrogen and alkyl;
each $R^c$ is independently selected from hydrogen, halo, alkyl, alkoxy and halo alkoxy or two $R^c$ taken together with the carbon atoms to which they are attached form an optionally substituted carbocycle;
each $R^d$ is independently selected from halo, haloalkyl, haloalkoxy, alkyl, alkynyl, nitro, cyano, hydroxyl, —$C(O)R^a$, —$OC(O)R^a$, —$C(O)OR^a$, —$SR^a$, —$NR^aR^b$ and —$OR^a$, or two $R^d$ taken together with the carbon atoms to which they are attached form an optionally substituted heterocyclyl;
n is 0, 1, or 2;
m is 1, 2 or 3;
h is 0, 1, 2;
g is 0, 1 or 2;
the sum of g+h is equal to or greater than 2; and
p is 1 or 2.

6. A method for treating sickle cell anemia comprising administering to a subject in need thereof a therapeutically effective amount of (1) a compound of formula I or a pharmaceutically acceptable salt thereof; or (2) a pharmaceutically acceptable composition comprising a compound of formula I or a pharmaceutically acceptable salt thereof, and a pharmaceutically acceptable carrier, wherein:

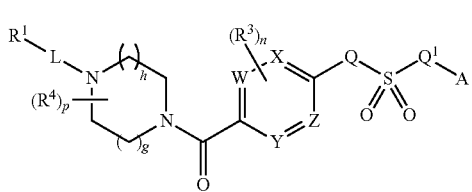

W, X, Y and Z are each independently selected from CH or N;
Q and $Q^1$ are independently selected from a bond or $NR^b$;
A is optionally substituted bicyclic aryl or optionally substituted bicyclic heteroaryl;
L is a bond, —C(O)—, —$(CR^cR^c)_m$—, —OC(O)—, —$(CR^cR^c)_m$—OC(O)—, —$(CR^cR^c)_m$—C(O)—, —$NR^bC(S)$—, or —$NR^bC(O)$— (wherein the point of the attachment to $R^1$ is on the left-hand side);
$R^1$ is selected from alkyl, carbocycle, aryl, heteroaryl, and heterocyclyl; each of which is substituted with 0-5 occurrences of $R^d$;
each $R^3$ is independently selected from halo, haloalkyl, alkyl, hydroxyl and —$OR^a$, or two adjacent $R^3$ taken together with the carbon atoms to which they are attached form an optionally substituted heterocyclyl;
each $R^4$ is independently selected from halo, haloalkyl, alkyl, hydroxyl, =O, —$OR^a$ and phenyl, or two $R^4$ taken together with the carbon atoms to which they are attached form a bridged, fused or spyro-fused carbocycle, an aryl or a heteroaryl;
each $R^a$ is independently selected from alkyl, acyl, hydroxyalkyl and haloalkyl;
each $R^b$ is independently selected from hydrogen and alkyl;
each $R^c$ is independently selected from hydrogen, halo, alkyl, alkoxy and halo alkoxy or two $R^c$ taken together with the carbon atoms to which they are attached form an optionally substituted carbocycle;
each $R^d$ is independently selected from halo, haloalkyl, haloalkoxy, alkyl, alkynyl, nitro, cyano, hydroxyl, —$C(O)R^a$, —$OC(O)R^a$, —$C(O)OR^a$, —$SR^a$, —$NR^aR^b$ and —$OR^a$, or two $R^d$ taken together with the carbon atoms to which they are attached form an optionally substituted heterocyclyl;
n is 0, 1, or 2;
m is 1, 2 or 3;
h is 0, 1, 2;
g is 0, 1 or 2;
the sum of g+h is equal to or greater than 2; and
p is 1 or 2.

7. The method of claim 1, wherein p is 2 and the compound has the formula (Ia):

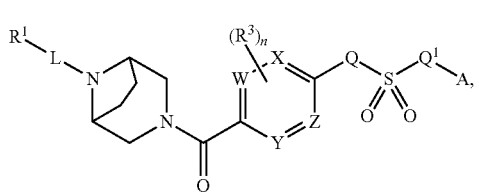

or formula (Ib):

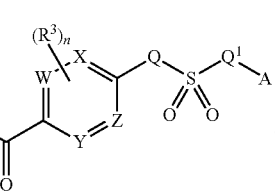

8. The method of claim 1, wherein:
each $R^4$ is independently selected from alkyl, phenyl, (S)-alkyl, (R)-alkyl, (S)-phenyl, and (R)-phenyl.

9. The method of claim 8, wherein:
g is 1;
h is 1; and
each $R^4$ is independently selected from methyl, (S)-methyl, (R)-methyl, ethyl, (S)-ethyl, (R)-ethyl, isopropyl, (S)-isopropyl, (R)-isopropyl, phenyl, (S)-phenyl, and (R)-phenyl.

10. The method of claim 1, wherein A is

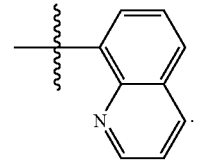 [SMILES: *c1cccc2cccnc12 ; "."]

11. The method of claim 1, wherein W, X, Y, Z and the carbons to which they are attached form a phenyl ring.

12. The method of claim 1, wherein:
n is 1; and
$R^3$ is selected from fluoro, chloro, methyl, ethyl, $CF_3$, methoxy, and $OCF_3$.

13. The method of claim 1, wherein:
Q is NH; and
$Q^1$ is a bond.

14. The method of claim 1, wherein L is selected from a bond, —C(O)—, —OC(O)—, —$CH_2$—OC(O)—, —$(CH_2)_2$—OC(O)—, —$C(CH_3)_2$—C(O)—, —$CH_2$—, —$(CH_2)_2$—, —$(CH_2)_3$—, —$CH(CH_3)$—, —$CH(CF_3)$—, —$C(CH_3)_2$—, -CHD-, -$CD_2$-,

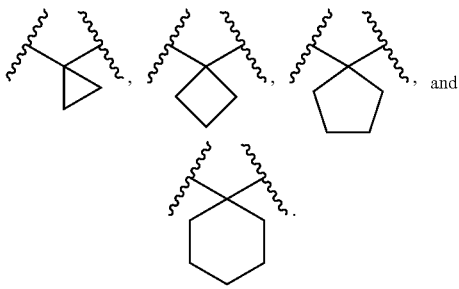

15. The method of claim 1, wherein $R^1$ is selected from the group consisting of methyl, ethyl, isopropyl, cyclopropyl, cyclobutyl, cyclopentyl, cyclohexyl, phenyl, pyridin-2-yl, pyridin-3-yl, pyridin-4-yl, 1,2,3-thiadiazol-5-yl, 1,2,3-thiadiazol-4-yl, thiazol-4-yl, thiazol-5-yl, 1H-imidazol-4-yl, 1H-imidazol-2-yl, 1H-pyrazol-3-yl, 1H-pyrazol-4-yl, 1H-pyrazol-5-yl, pyrazin-2-yl, oxazol-4-yl, isoxazol-5-yl, tetrahydrofuran-2-yl, tetrahydrofuran-3-yl, tetrahydro-2H-pyran-4-yl, tetrahydro-2H-pyran-3-yl, and tetrahydro-2H-pyran-2-yl.
16. The method of claim 1, wherein the compound is selected from.
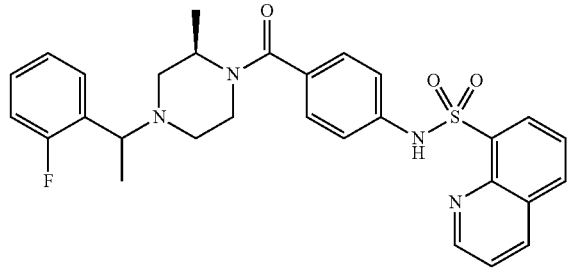
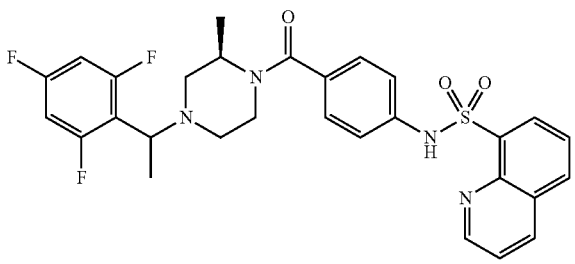
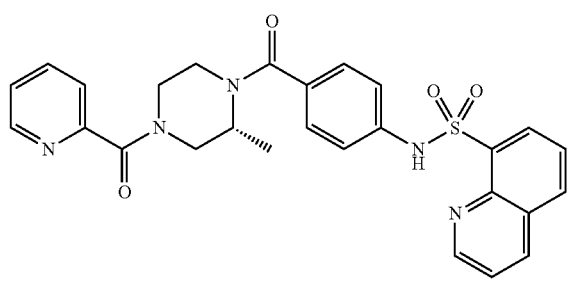
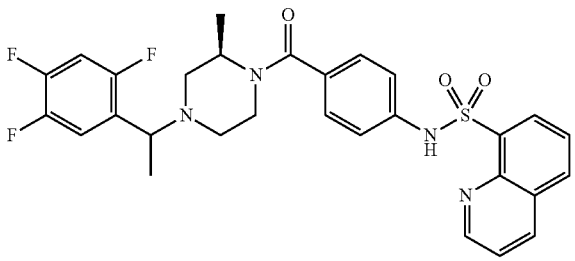
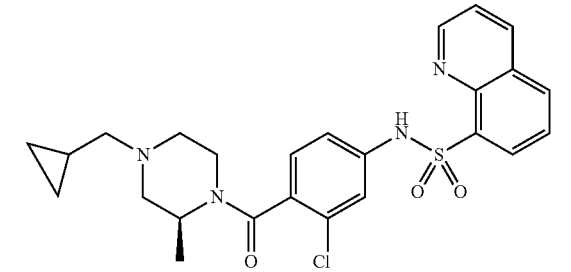
-continued
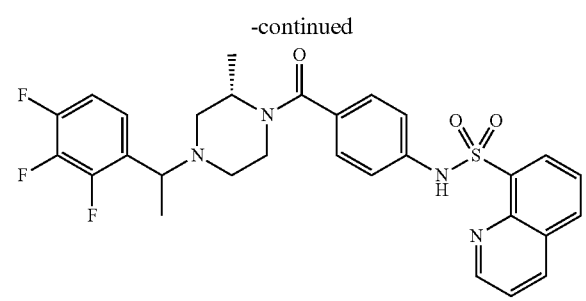
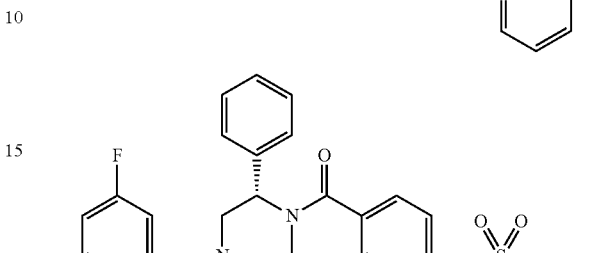
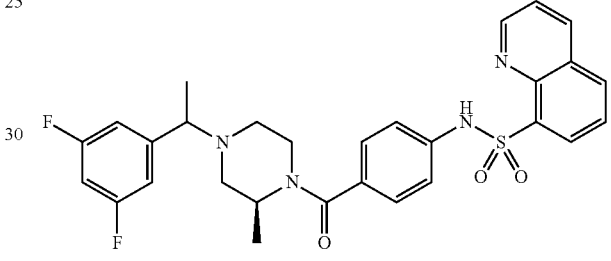
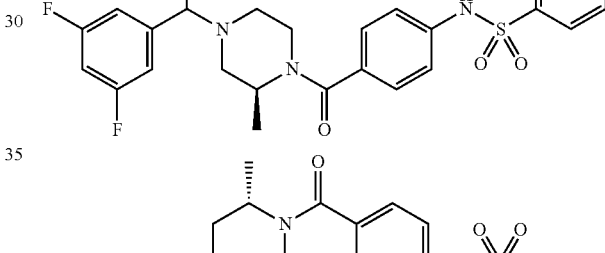
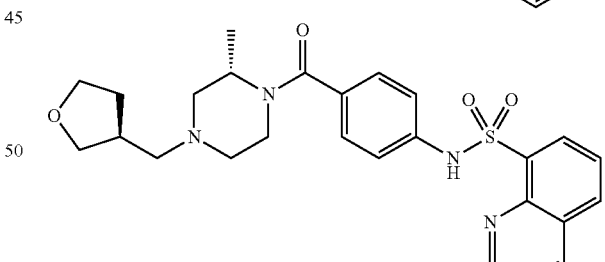
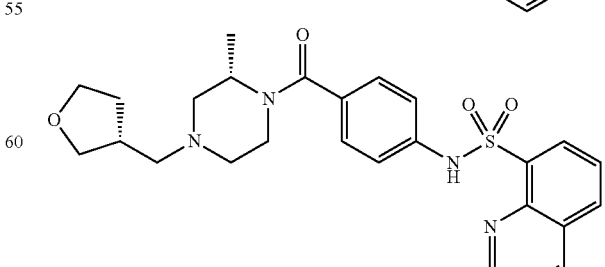

223
-continued
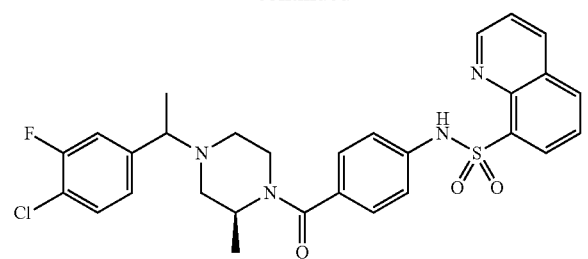
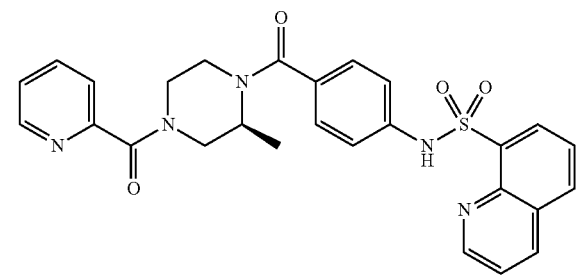
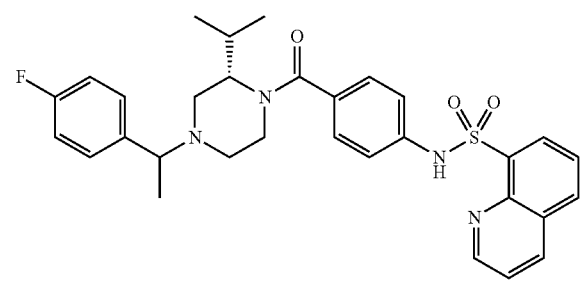
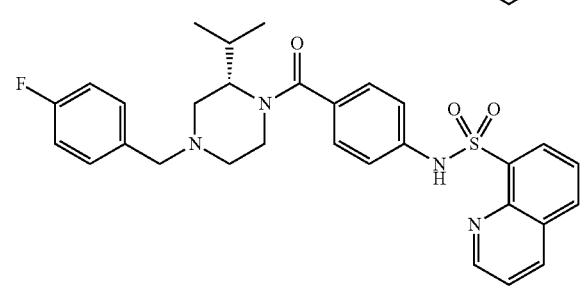
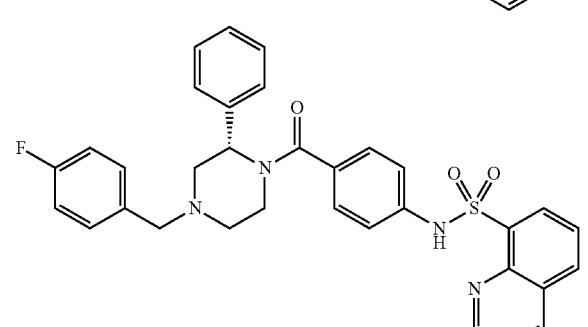
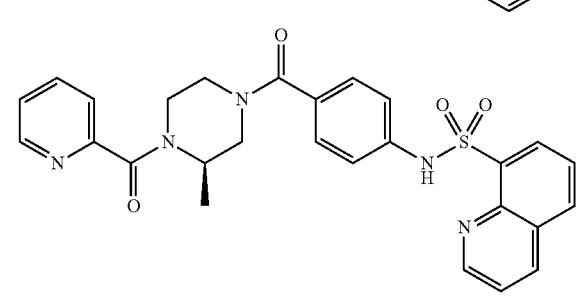
224
-continued
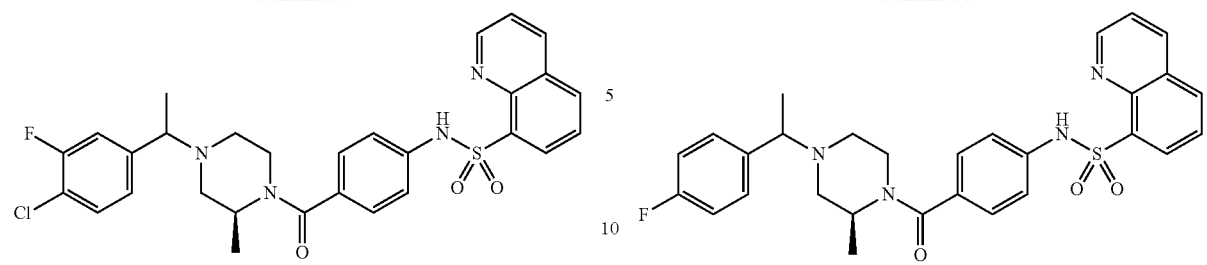
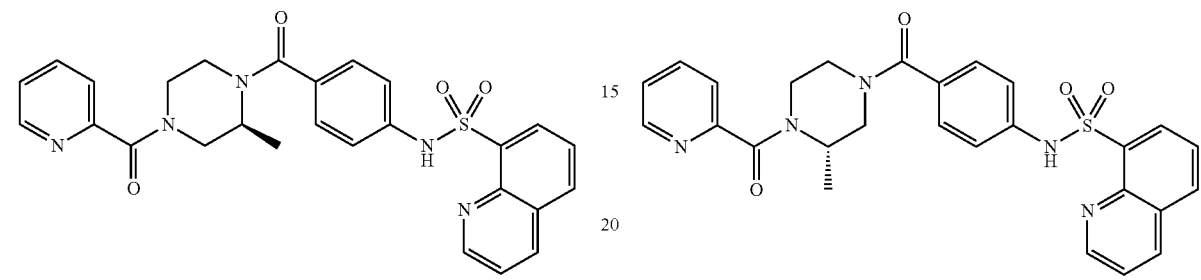
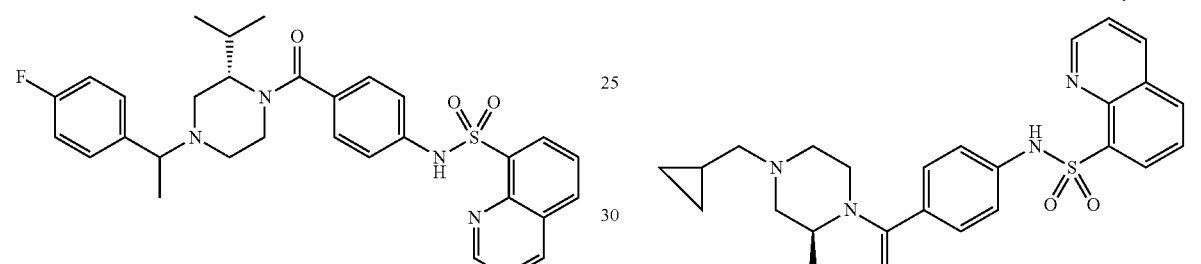
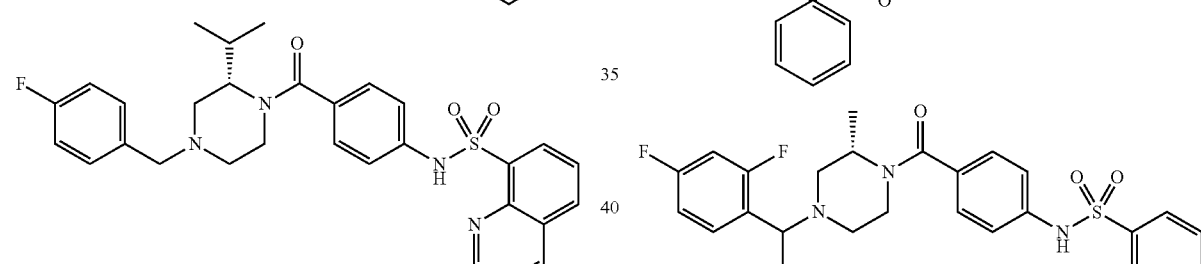
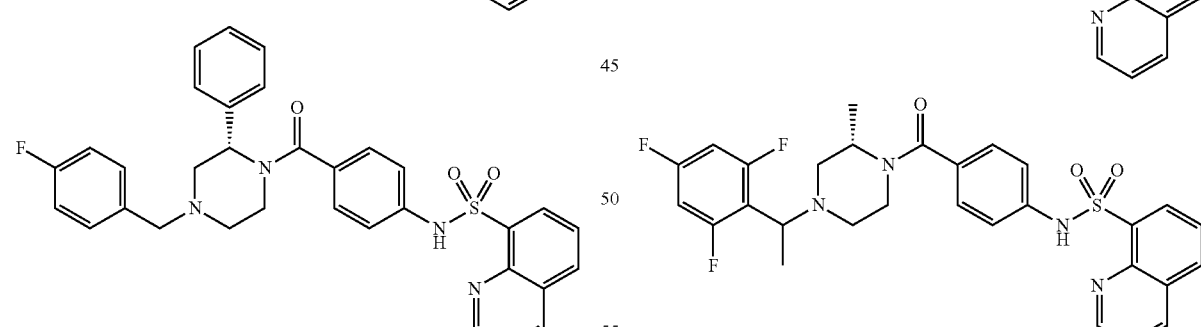
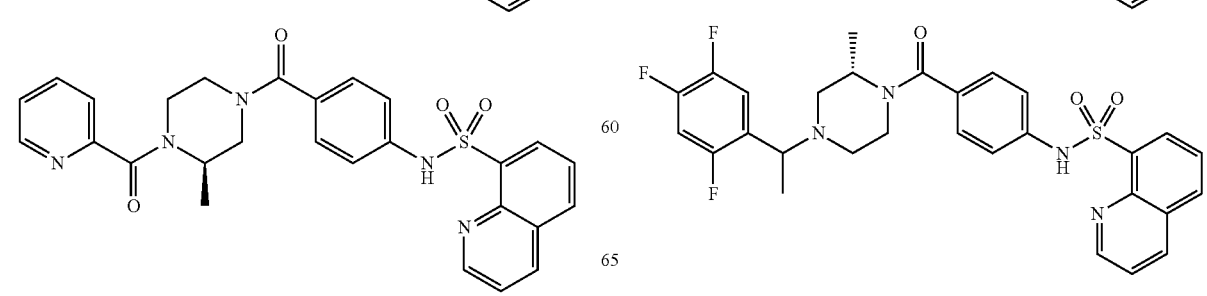

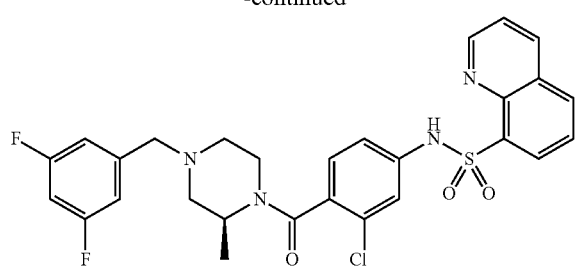
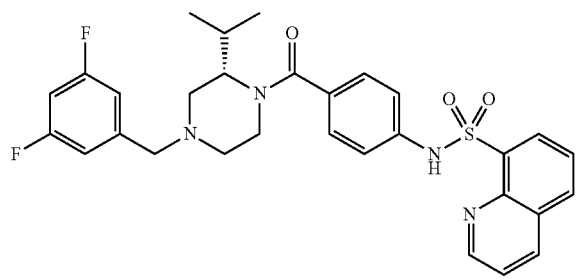
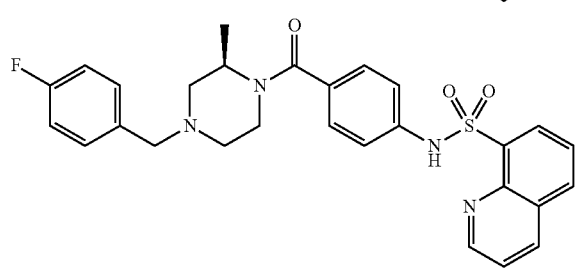
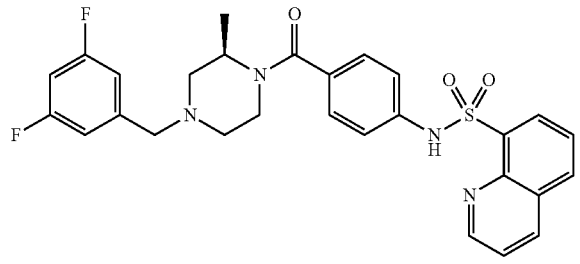
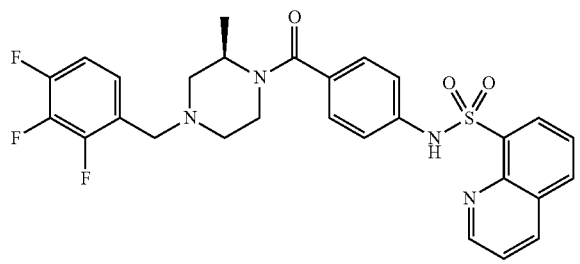
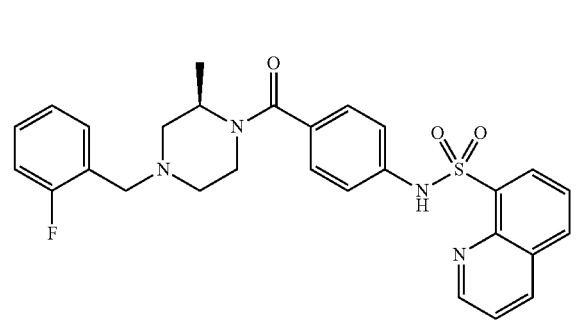
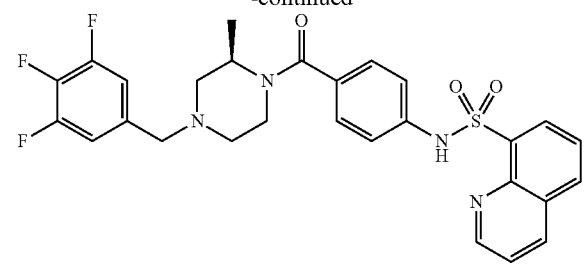
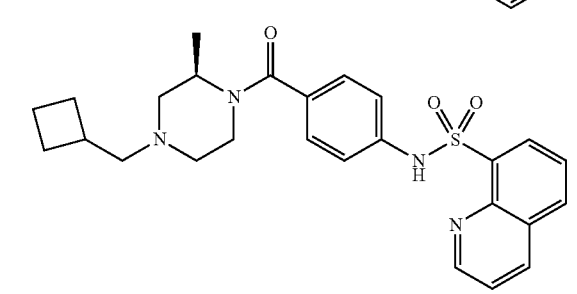
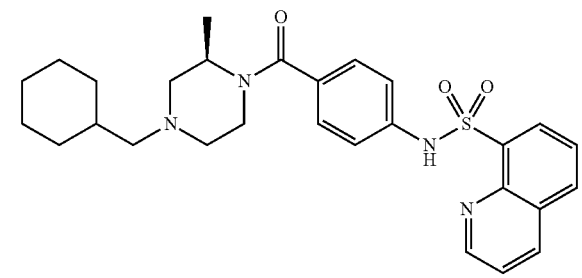
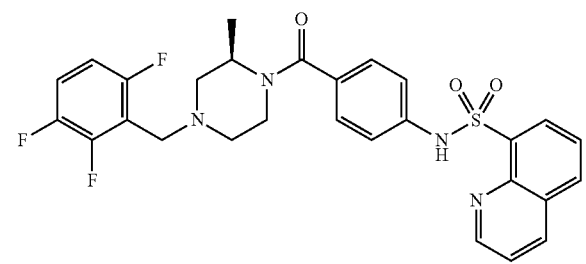
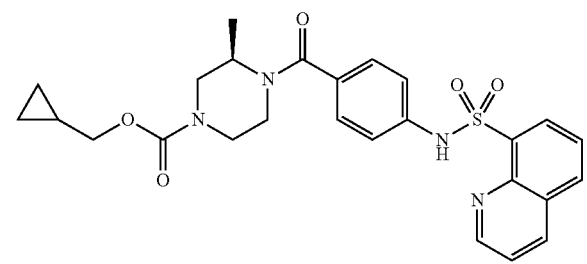
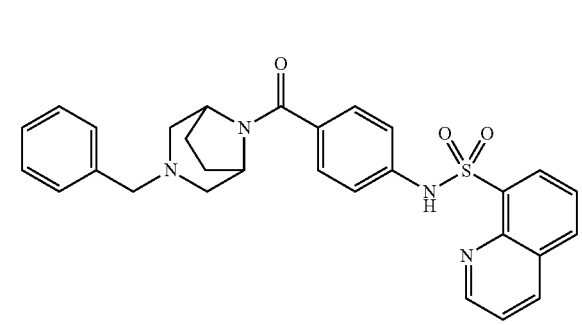

227
-continued
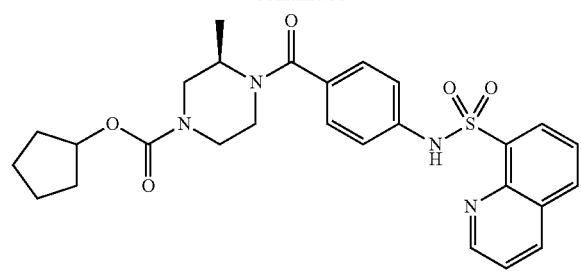
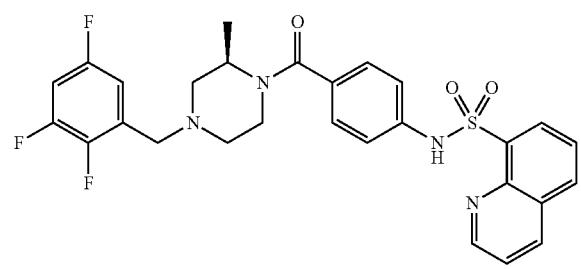
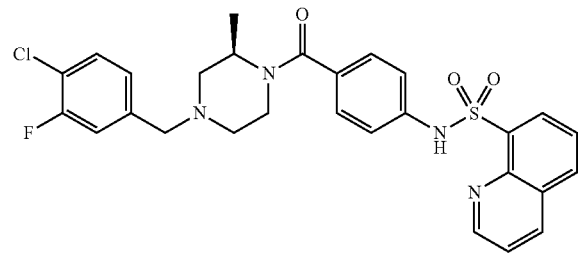
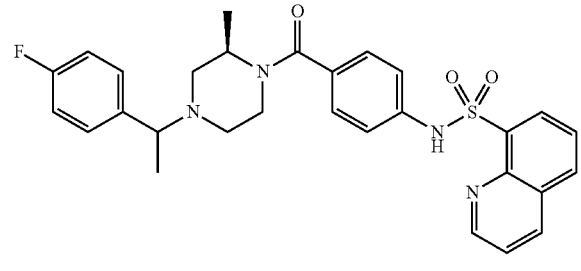
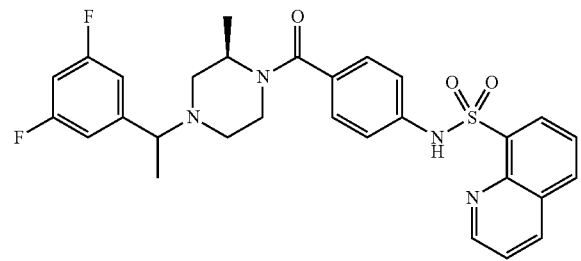
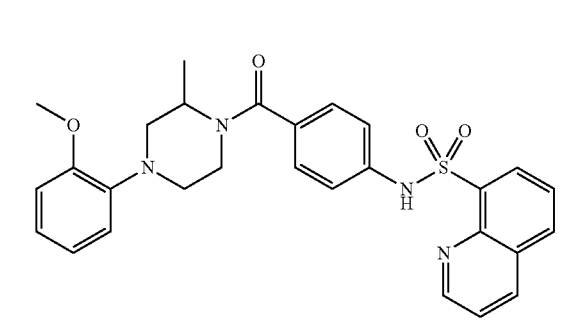
228
-continued
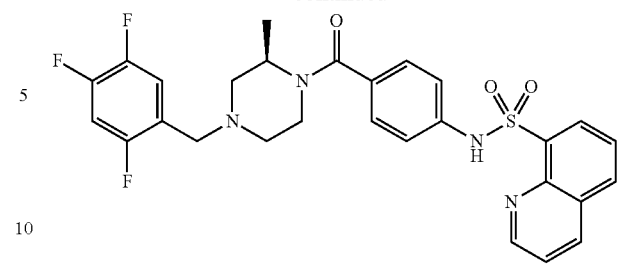
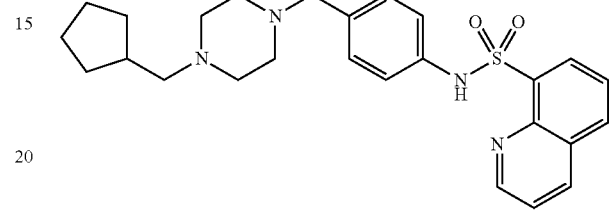
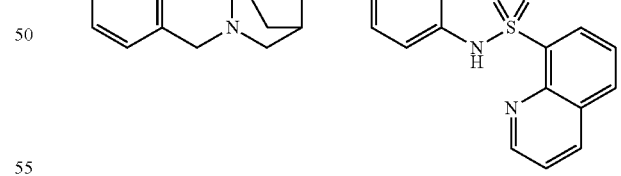
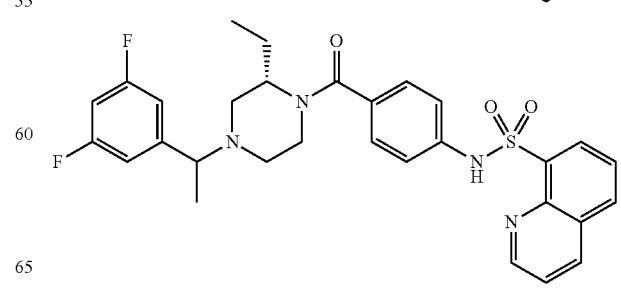

229
-continued
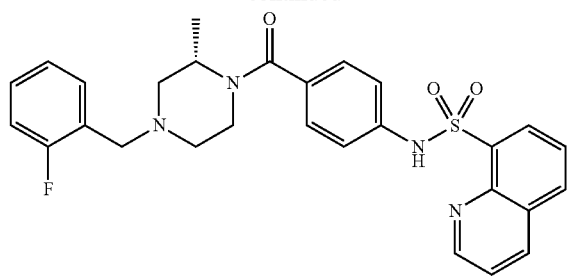
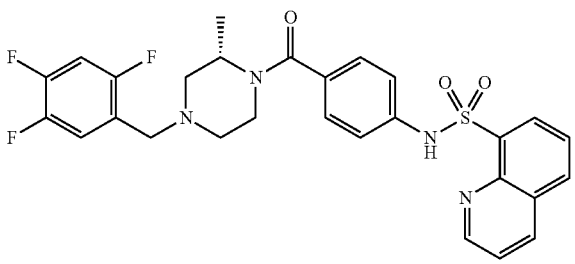
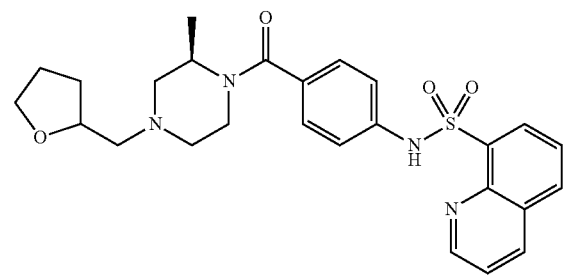
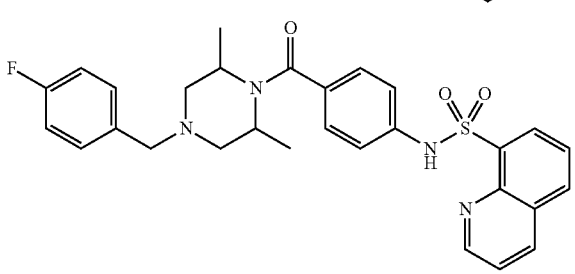
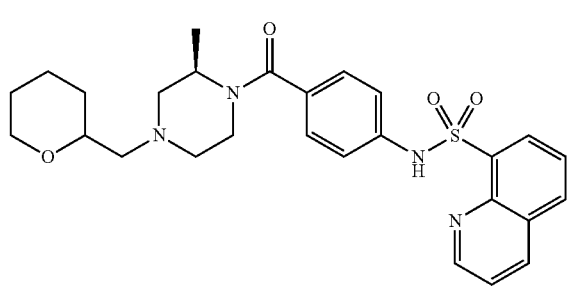
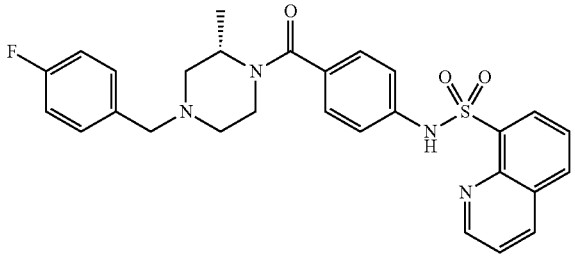
230
-continued
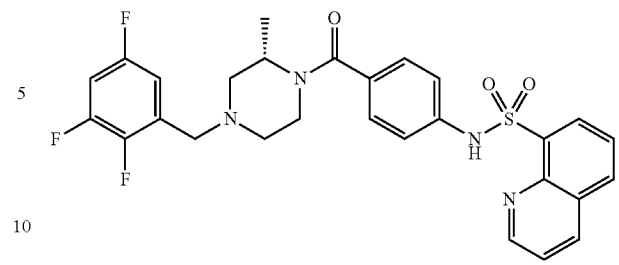
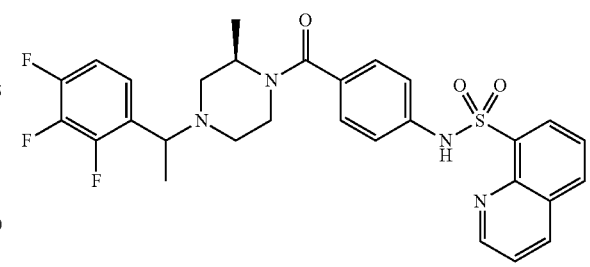
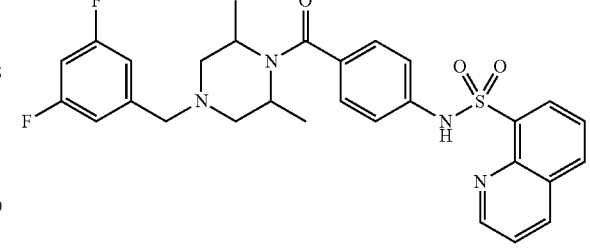
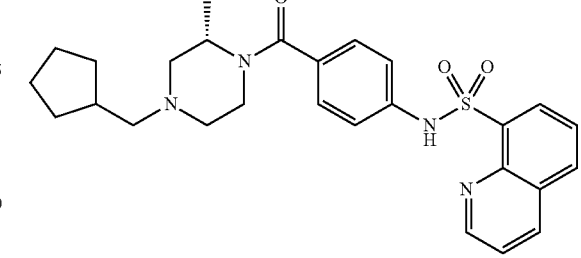
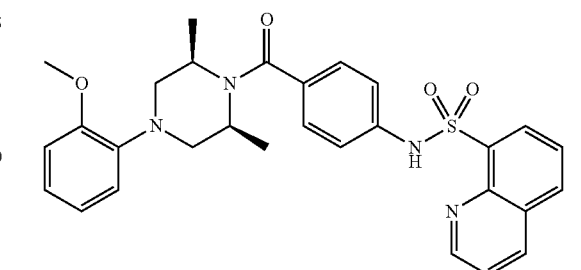
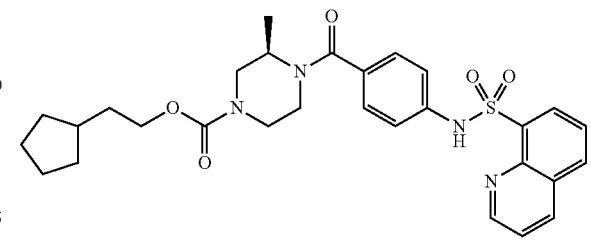

231
-continued

232
-continued

233
-continued
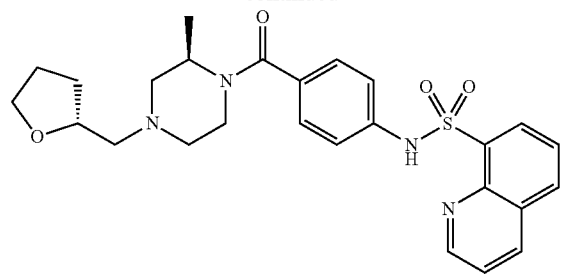
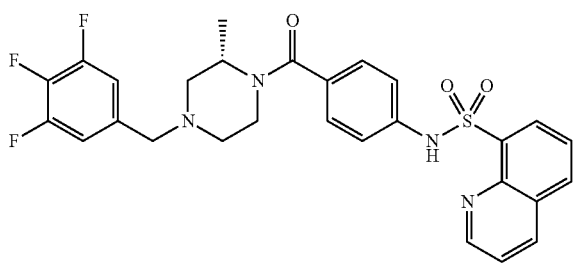
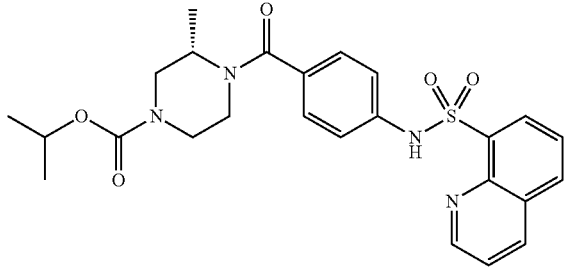
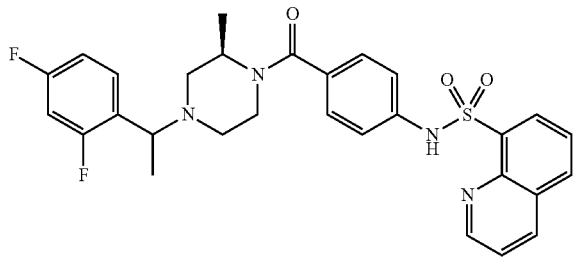
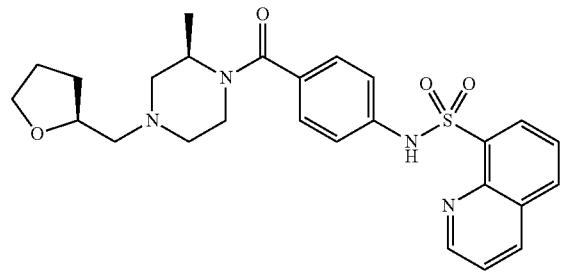
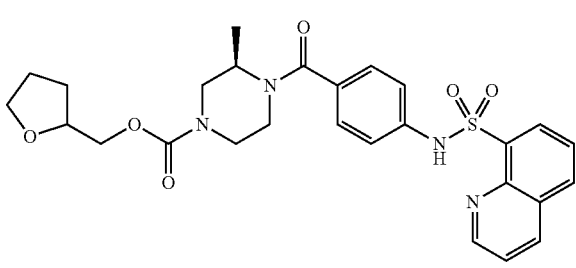
234
-continued
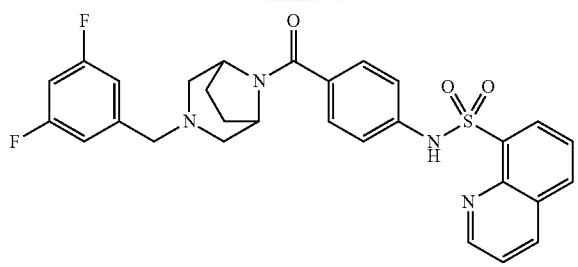
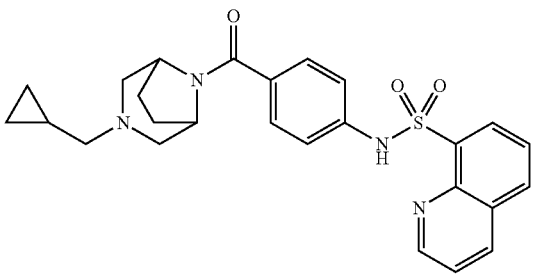
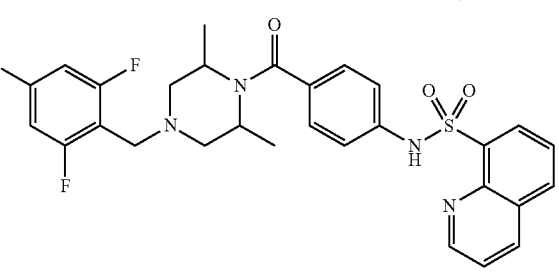
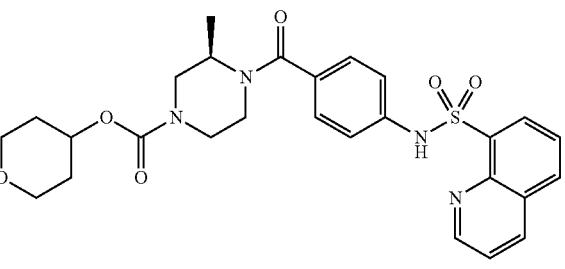
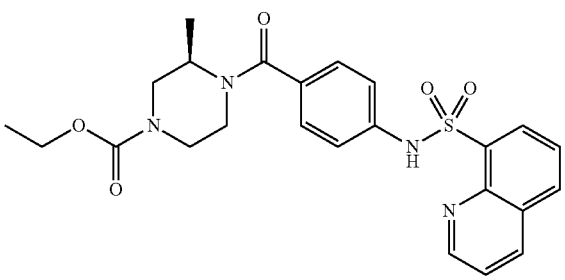
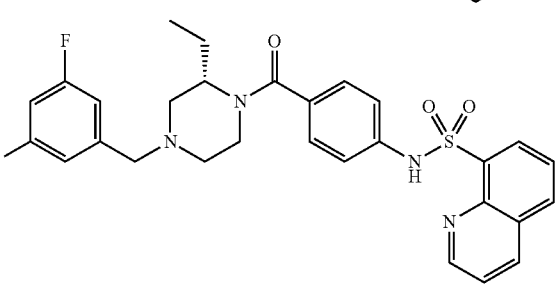

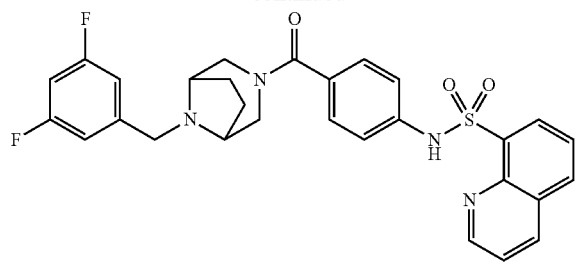
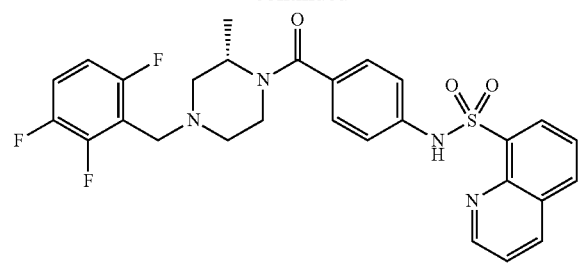
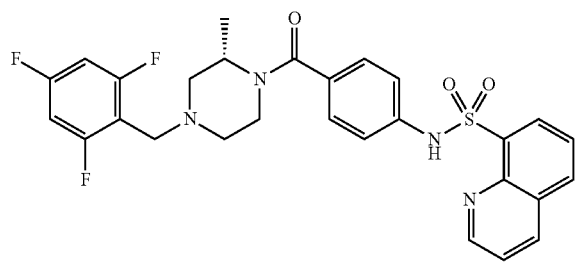
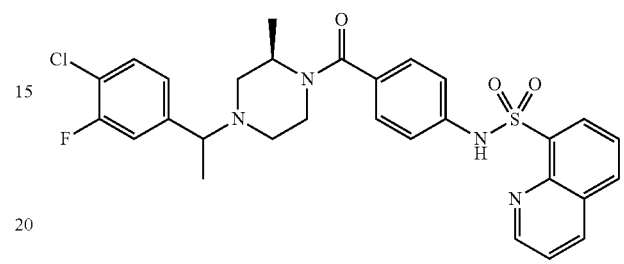
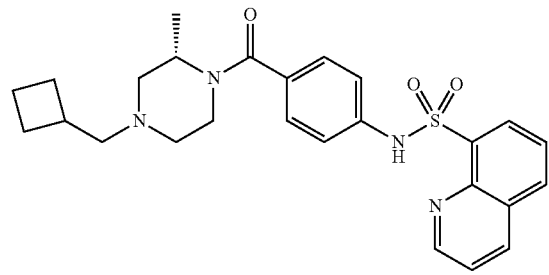
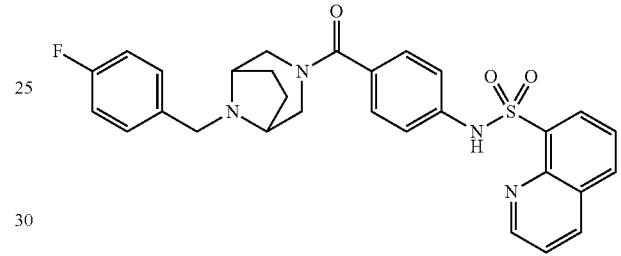
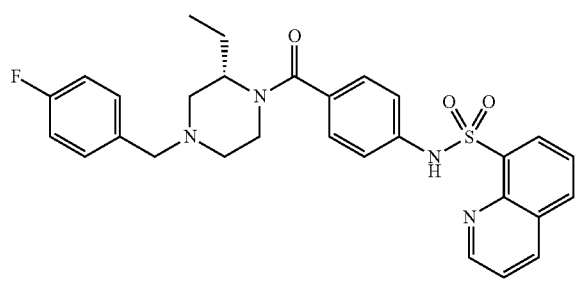
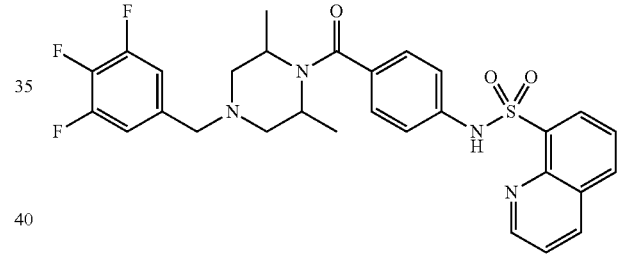
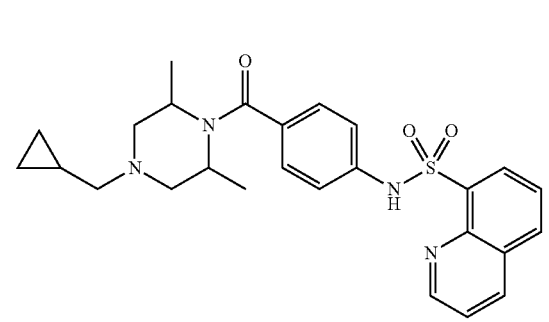
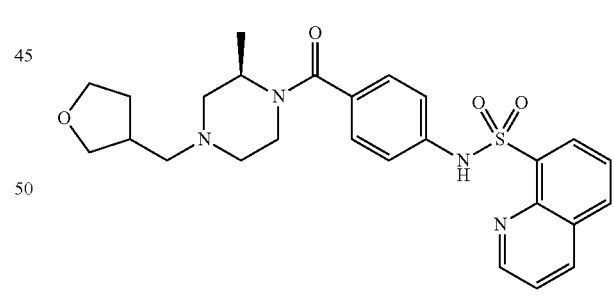
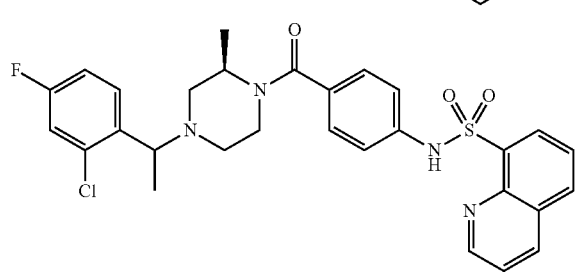
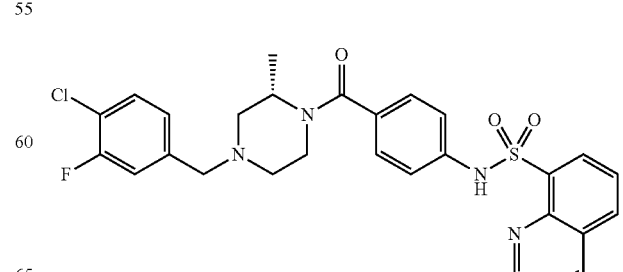

237
-continued
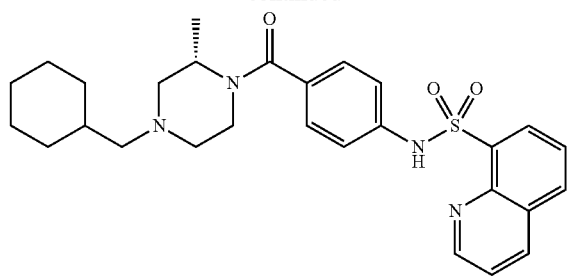
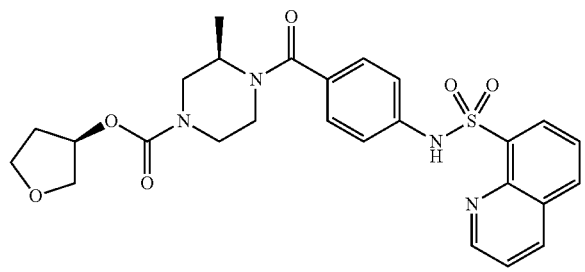
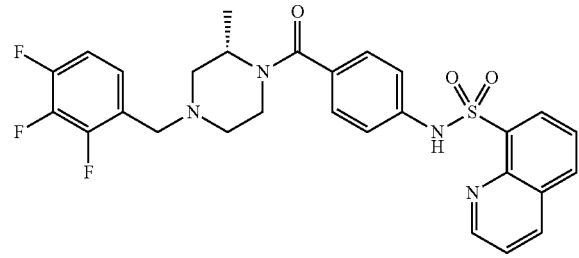
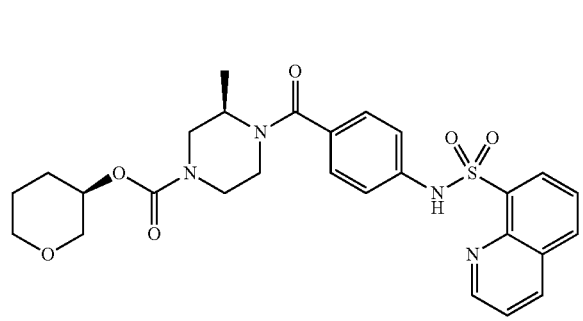
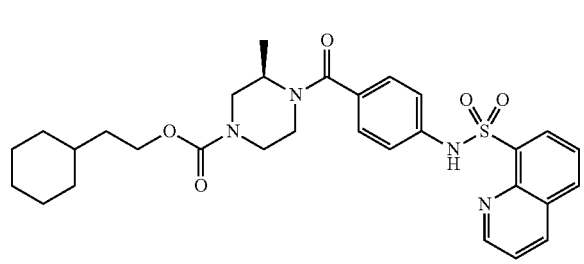
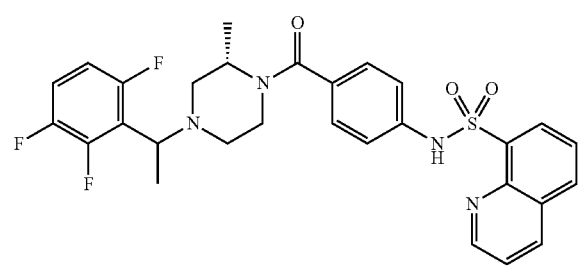
238
-continued
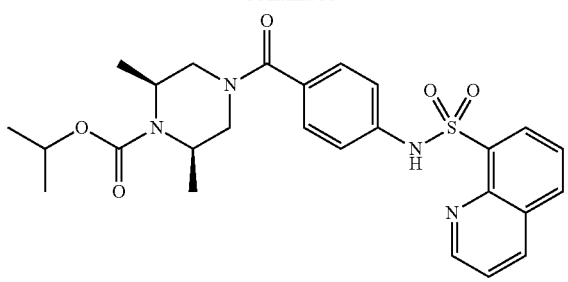
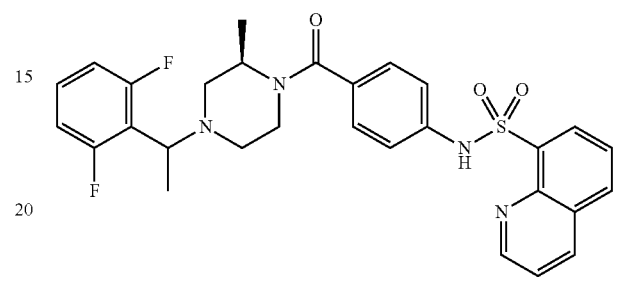
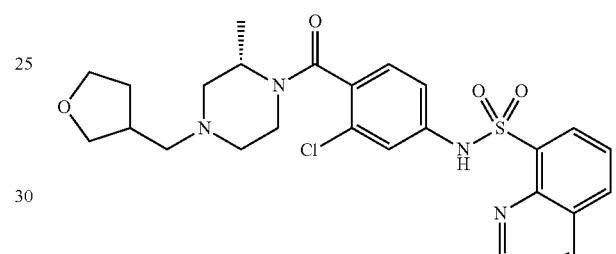
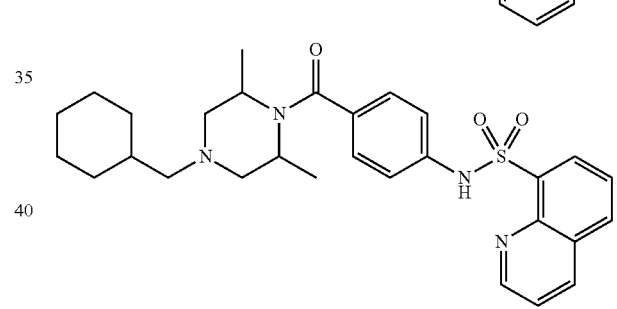
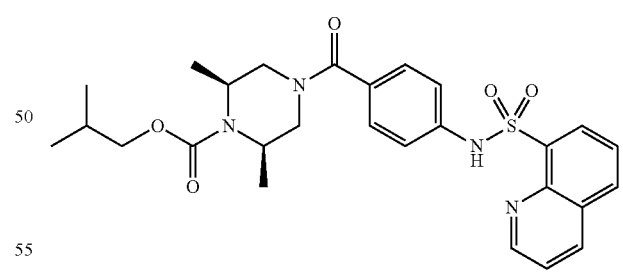
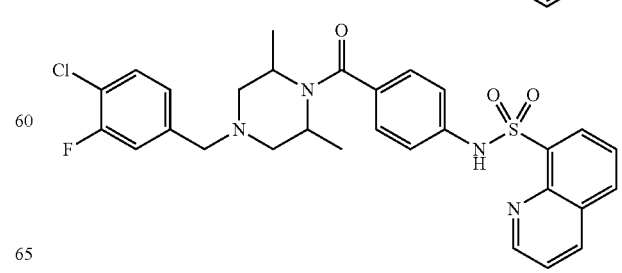

239
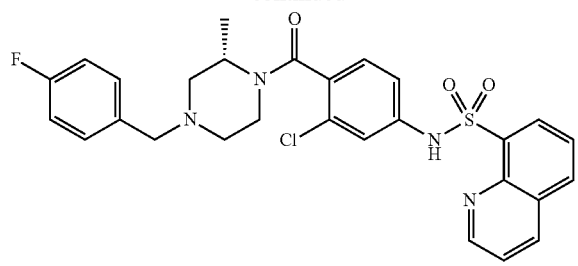
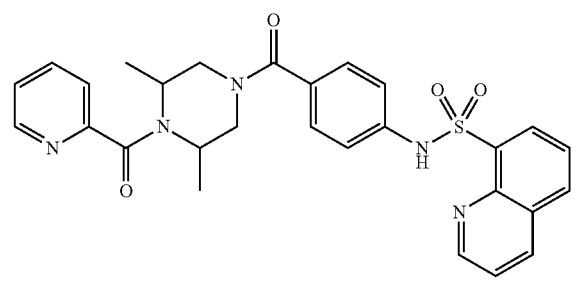
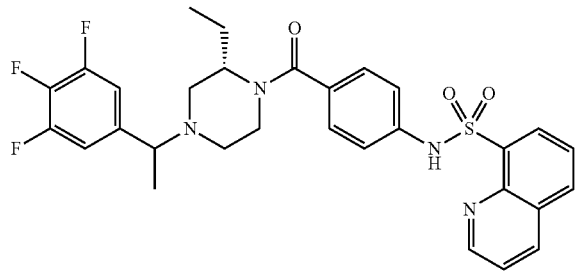
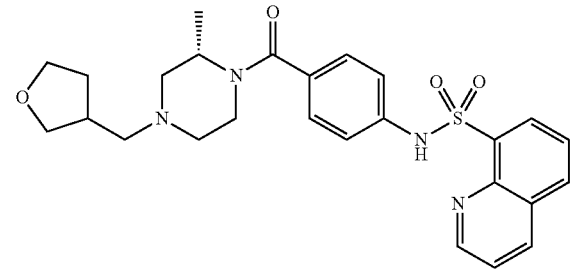
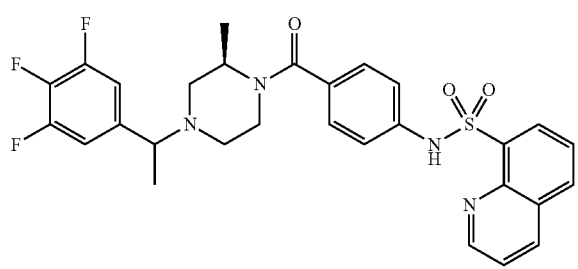
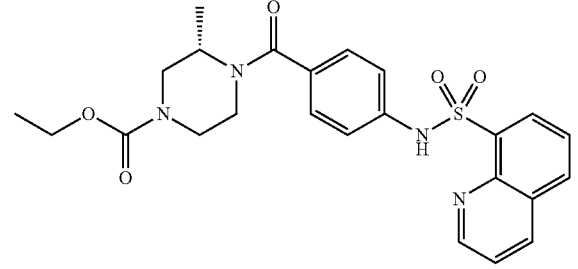
240
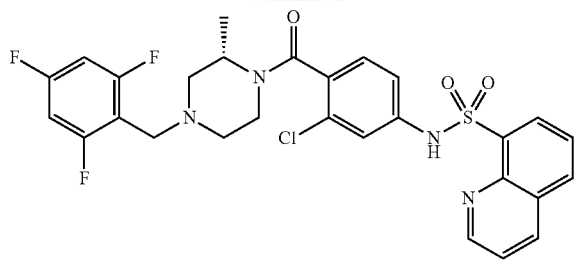
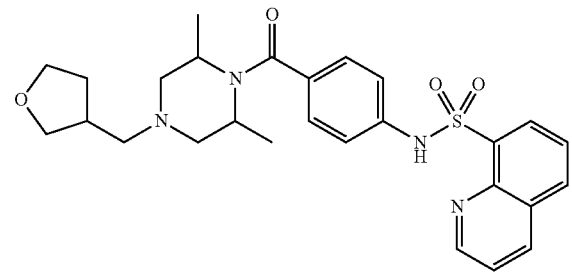
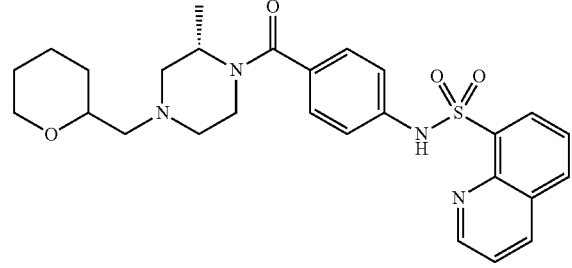
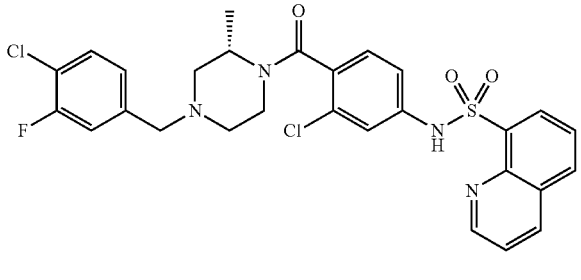
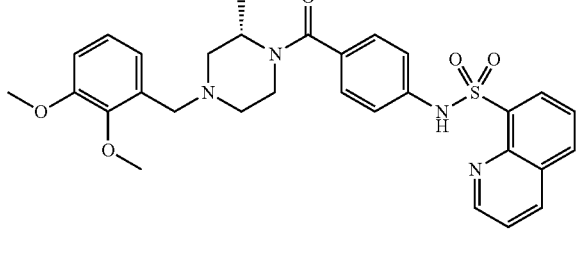
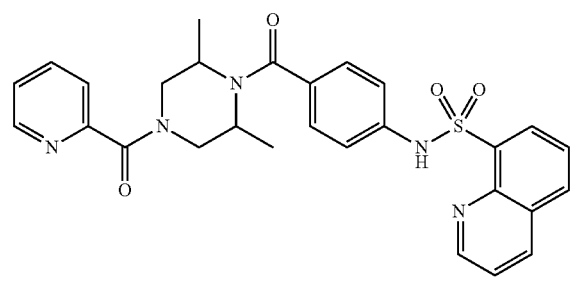

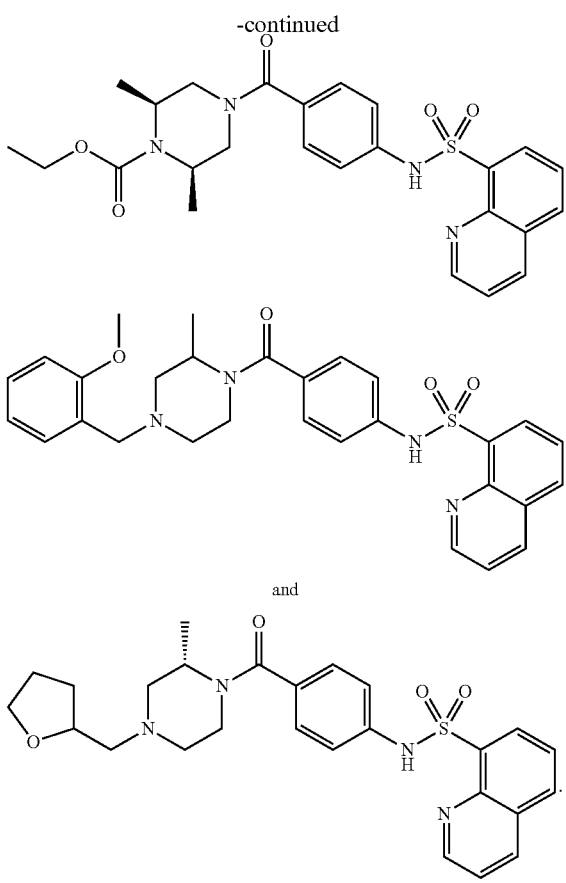

17. The method of claim 5, wherein the hemolytic anemia is hereditary non-spherocytic hemolytic anemia.

18. A method of treating pyruvate kinase deficiency (PKD) in a subject comprising administering to a subject in need thereof a therapeutically effective amount of (1) a compound of formula I or a pharmaceutically acceptable salt thereof; or (2) a pharmaceutically acceptable composition comprising a compound of formula I or a pharmaceutically acceptable salt thereof, and a pharmaceutically acceptable carrier, wherein:

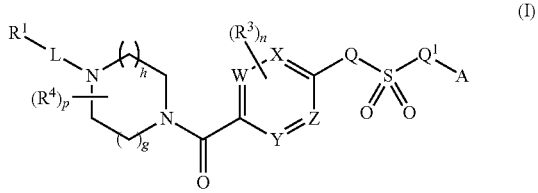

W, X, Y and Z are each independently selected from CH or N;
Q and $Q^1$ are independently selected from a bond or $NR^b$;
A is optionally substituted bicyclic aryl or optionally substituted bicyclic heteroaryl;
L is a bond, —C(O)—, —$(CR^cR^c)_m$—, —OC(O)—, —$(CR^cR^c)_m$—OC(O)—, —$(CR^cR^c)_m$—C(O)—, —$NR^bC(S)$—, or —$NR^bC(O)$— (wherein the point of the attachment to $R^1$ is on the left-hand side);
$R^1$ is selected from alkyl, carbocycle, aryl, heteroaryl, and heterocyclyl; each of which is substituted with 0-5 occurrences of $R^d$;
each $R^3$ is independently selected from halo, haloalkyl, alkyl, hydroxyl and —$OR^a$, or two adjacent $R^3$ taken together with the carbon atoms to which they are attached form an optionally substituted heterocyclyl;
each $R^4$ is independently selected from halo, haloalkyl, alkyl, hydroxyl, =O, —$OR^a$ and phenyl, or two $R^4$ taken together with the carbon atoms to which they are attached form a bridged, fused or spyro-fused carbocycle, an aryl or a heteroaryl;
each $R^a$ is independently selected from alkyl, acyl, hydroxyalkyl and haloalkyl;
each $R^b$ is independently selected from hydrogen and alkyl;
each $R^c$ is independently selected from hydrogen, halo, alkyl, alkoxy and halo alkoxy or two $R^c$ taken together with the carbon atoms to which they are attached form an optionally substituted carbocycle;
each $R^d$ is independently selected from halo, haloalkyl, haloalkoxy, alkyl, alkynyl, nitro, cyano, hydroxyl, —$C(O)R^a$, —$OC(O)R^a$, —$C(O)OR^a$, —$SR^a$, —$NR^aR^b$ and —$OR^a$, or two $R^d$ taken together with the carbon atoms to which they are attached form an optionally substituted heterocyclyl;
n is 0, 1, or 2;
m is 1, 2 or 3;
h is 0, 1, 2;
g is 0, 1 or 2;
the sum of g+h is equal to or greater than 2; and
p is 1 or 2.

19. A method for activating PKR in red blood cells comprising (1) a compound of formula I or a pharmaceutically acceptable salt thereof; or (2) a pharmaceutical composition comprising a compound of formula I or a pharmaceutically acceptable salt thereof, and a pharmaceutically acceptable carrier, wherein:

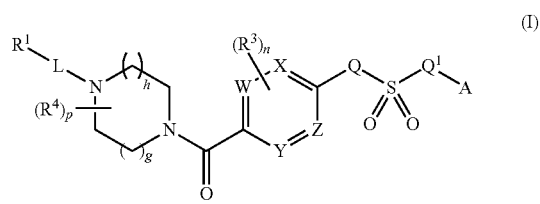

W, X, Y and Z are each independently selected from CH or N;
Q and $Q^1$ are independently selected from a bond or $NR^b$;
A is optionally substituted bicyclic aryl or optionally substituted bicyclic heteroaryl;
L is a bond, —C(O)—, —$(CR^cR^c)_m$—, —OC(O)—, —$(CR^cR^c)_m$—OC(O)—, —$(CR^cR^c)_m$—C(O)—, —$NR^bC(S)$—, or —$NR^bC(O)$— (wherein the point of the attachment to $R^1$ is on the left-hand side);
$R^1$ is selected from alkyl, carbocycle, aryl, heteroaryl, and heterocyclyl; each of which is substituted with 0-5 occurrences of $R^d$;
each $R^3$ is independently selected from halo, haloalkyl, alkyl, hydroxyl and —$OR^a$, or two adjacent $R^3$ taken together with the carbon atoms to which they are attached form an optionally substituted heterocyclyl;
each $R^4$ is independently selected from halo, haloalkyl, alkyl, hydroxyl, =O, —$OR^a$ and phenyl, or two $R^4$ taken together with the carbon atoms to which they are attached form a bridged, fused or spyro-fused carbocycle, an aryl or a heteroaryl;

each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted carbocycle;

each $R^d$ is independently selected from halo, haloalkyl, haloalkoxy, alkyl, alkynyl, nitro, cyano, hydroxyl, —C(O)$R^a$, —OC(O)$R^a$, —C(O)O$R^a$, —S$R^a$, —N$R^a R^b$ and —O$R^a$, or two $R^d$ taken together with the carbon atoms to which they are attached form an optionally substituted heterocyclyl;

n is 0, 1, or 2;

m is 1, 2 or 3;

h is 0, 1, 2;

g is 0, 1 or 2;

the sum of g+h is equal to or greater than 2; and p is 1 or 2.

20. A method for treating thalassemia; hereditary spherocytosis; hereditary elliptocytosis; abetalipoproteinemia; Bassen-Kornzweig syndrome; paroxysmal nocturnal hemoglobinuria; acquired hemolytic anemia; or anemia of chronic diseases comprising (1) a compound of formula I or a pharmaceutically acceptable salt thereof; or (2) a pharmaceutical composition comprising a compound of formula I or a pharmaceutically acceptable salt thereof, and a pharmaceutically acceptable carrier; wherein:

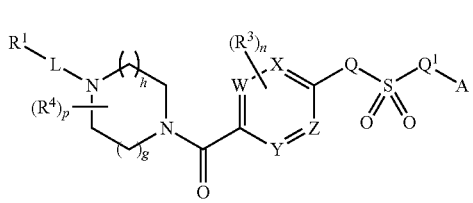

W, X, Y and Z are each independently selected from CH or N;

Q and $Q^1$ are independently selected from a bond or N$R^b$;

A is optionally substituted bicyclic aryl or optionally substituted bicyclic heteroaryl;

L is a bond, —C(O)—, —(C$R^c R^c$)$_m$—, —OC(O)—, —(C$R^c R^c$)$_m$—OC(O)—, —(C$R^c R^c$)$_m$—C(O)—, —N$R^b$C(S)—, or —N$R^b$C(O)— (wherein the point of the attachment to $R^1$ is on the left-hand side);

$R^1$ is selected from alkyl, carbocycle, aryl, heteroaryl, and heterocyclyl; each of which is substituted with 0-5 occurrences of $R^d$;

each $R^3$ is independently selected from halo, haloalkyl, alkyl, hydroxyl and —O$R^a$, or two adjacent $R^3$ taken together with the carbon atoms to which they are attached form an optionally substituted heterocyclyl;

each $R^4$ is independently selected from halo, haloalkyl, alkyl, hydroxyl, =O, —O$R^a$ and phenyl, or two $R^4$ taken together with the carbon atoms to which they are attached form a bridged, fused or spyro-fused carbocycle, an aryl or a heteroaryl;

each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted carbocycle;

each $R^d$ is independently selected from halo, haloalkyl, haloalkoxy, alkyl, alkynyl, nitro, cyano, hydroxyl, —C(O)$R^a$, —OC(O)$R^a$, —C(O)O$R^a$, —S$R^a$, —N$R^a R^b$ and —O$R^a$, or two $R^d$ taken together with the carbon atoms to which they are attached form an optionally substituted heterocyclyl;

n is 0, 1, or 2;

m is 1, 2 or 3;

h is 0, 1, 2;

g is 0, 1 or 2;

the sum of g+h is equal to or greater than 2; and p is 1 or 2.

21. The compound of claim 1 having the following structure:

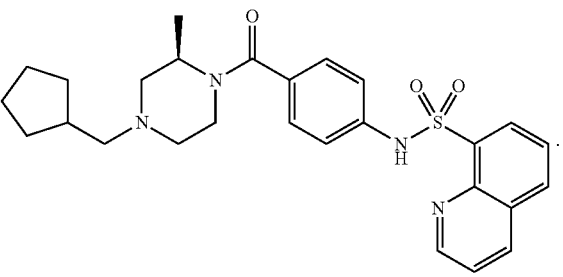 [SMILES: C[C@@H]1CN(CC2CCCC2)CCN1C(=O)c1ccc(NS(=O)(=O)c2cccc3cccnc23)cc1]

22. The compound of claim 1 having the following structure:

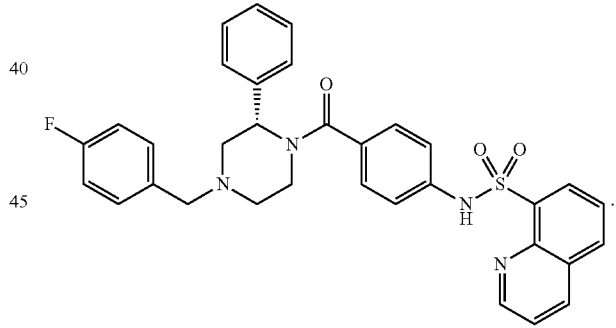

23. The compound of claim 1 having the following structure:

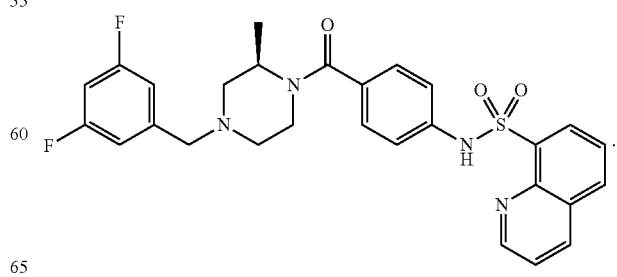

24. The compound of claim 1 having the following structure:
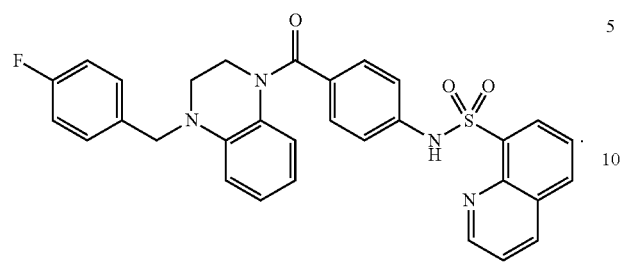
25. The compound of claim 1 having the following structure:
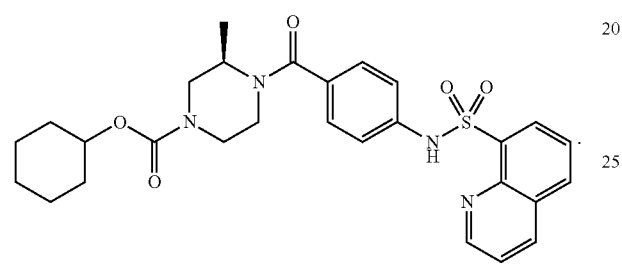
* * * * *